US011453718B2

(12) United States Patent
Arboleda-Velasquez

(10) Patent No.: US 11,453,718 B2
(45) Date of Patent: Sep. 27, 2022

(54) NOTCH3 AGONIST COMPOSITIONS AND METHODS FOR TREATING SMALL VESSEL DISEASES

(71) Applicant: The Schepens Eye Research Institute, Inc., Boston, MA (US)

(72) Inventor: Joseph F. Arboleda-Velasquez, Newton, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 279 days.

(21) Appl. No.: 16/499,225

(22) PCT Filed: Mar. 26, 2018

(86) PCT No.: PCT/US2018/024397
§ 371 (c)(1),
(2) Date: Sep. 27, 2019

(87) PCT Pub. No.: WO2018/183216
PCT Pub. Date: Oct. 4, 2018

(65) Prior Publication Data
US 2020/0102384 A1 Apr. 2, 2020

Related U.S. Application Data

(60) Provisional application No. 62/477,289, filed on Mar. 27, 2017.

(51) Int. Cl.
*C07K 16/28* (2006.01)
*C07K 14/705* (2006.01)
*C12Q 1/6883* (2018.01)
*A61K 38/00* (2006.01)

(52) U.S. Cl.
CPC ............ *C07K 16/28* (2013.01); *C07K 14/705* (2013.01); *C12Q 1/6883* (2013.01); *A61K 38/00* (2013.01); *C07K 2317/75* (2013.01)

(58) Field of Classification Search
CPC .. C07K 16/28; C07K 14/705; C07K 2317/75; A61K 38/00; C12Q 1/6883
See application file for complete search history.

(56) References Cited

U.S. PATENT DOCUMENTS

| | | |
|---|---|---|
| 7,915,390 B2 | 3/2011 | Li et al. |
| 7,935,791 B2 | 5/2011 | Fung et al. |
| 8,187,839 B2 | 5/2012 | Li et al. |
| 8,226,943 B2 | 7/2012 | Gurney et al. |
| 2002/0182733 A1 | 12/2002 | Naldini et al. |
| 2003/0186290 A1 | 10/2003 | Tournier-Lasserve et al. |
| 2008/0131908 A1 | 6/2008 | Li et al. |
| 2011/0223183 A1 | 9/2011 | Ewski et al. |
| 2012/0100536 A1 | 4/2012 | Tsuji et al. |
| 2013/0129743 A1 | 5/2013 | Wu et al. |
| 2013/0323266 A1 | 12/2013 | Hoey et al. |
| 2013/0324468 A1 | 12/2013 | Cipolla et al. |
| 2014/0045198 A1 | 2/2014 | Montaner Villalonga et al. |
| 2014/0323413 A1 | 10/2014 | Hageman et al. |
| 2015/0119278 A1 | 4/2015 | Goetzl |
| 2015/0268251 A1 | 9/2015 | Zaugg et al. |
| 2016/0115453 A1 | 4/2016 | Mummery et al. |
| 2016/0185852 A1 | 6/2016 | Okamura et al. |
| 2017/0023576 A1 | 1/2017 | Cancilla |
| 2019/0350961 A1 | 11/2019 | Arboleda-Velasquez et al. |
| 2020/0103419 A1 | 4/2020 | Arboleda-Velasquez et al. |
| 2020/0375899 A1 | 12/2020 | Kim et al. |
| 2020/0377888 A1 | 12/2020 | Kim et al. |

FOREIGN PATENT DOCUMENTS

WO 2016046053 A1 3/2016

OTHER PUBLICATIONS

Bae et al., "Regulation of IGFBP-1 in metabolic diseases," J Lifestyle Med., 2013, 3(2):73-79.
Altobelli et al., "HtrA1: Its future potential as a novel biomarker for cancer," Oncol Rep, 2015, 34(2):555-66.
Arboleda-Velasquez et al., "C455R notch3 mutation in a Colombian CADASIL kindred with early onset of stroke," Neurology, 2002, 59(2):277-279.
Arboleda-Velasquez et al., "CADASIL mutations impair Notch3 glycosylation by Fringe," Hum Mol Genet., 2005, 14(12):1631-1639.
Arboleda-Velasquez et al., "Linking Notch signaling to ischemic stroke," Proc Natl Acad Sci USA, 2008, 105(12):4856-4861.
Arboleda-Velasquez et al., "Notch Signaling Functions in Retinal Pericyte Survival," Invest Ophthalmol Vis Sci., 2014, 55(8):5191-5199.
Baudrimont et al., "Autosomal Dominant Leukoencephalopathy and Subcortical Ischemic Stroke. A Clinicopathological study," Stroke, 1993, 24:122-125.
Beaufort et al., "Cerebral small vessel disease-related protease HtrA1 processes latent TGF-β binding protein 1 and facilitates TGF-β signaling," Proc Natl Acad Sci USA, 2014, 111(46):16496-16501.
Brass et al., "Case Dec. 2009: A 46-Year-Old Man with Migraine, Aphasia, and Hemiparesis and Similarly Affected Family Members," N Engl J Med, 2009, 360(16):1656-1665.
Cade, "Diabetes-Related Microvascular and Macrovascular Diseases in the Physical therapy setting," Phys Ther, 2008, 88(11):1322-1335.
Chabriat et al., "CADASIL," Lancet Neurol., 2009, 8:643-653.
Charidimou, "Book review: 'Cerebral small vessel disease'. What's the big deal about small vessels?" Front Neurol, 2015, 6:175, 2 pages.
Damico et al., "Serum endostatin is a genetically determined predictor of survival in pulmonary arterial hypertension," Am J Respir Crit Care Med, 2015, 191(2):208-218.
Dichgans et al., "Small in-frame deletions and missense mutations in CADASIL: 3D models predict misfolding of Notch3 EGF-like repeat domains," European Journal of Human Genetics, 2000, 8:280-285.

(Continued)

*Primary Examiner* — Ruixiang Li
(74) *Attorney, Agent, or Firm* — Fish & Richardson P.C.

(57) ABSTRACT

The present subject matter provides, inter alia compositions, formulations, and methods for inhibiting, treating, and preventing small vessel diseases.

9 Claims, 6 Drawing Sheets
Specification includes a Sequence Listing.

(56) References Cited

OTHER PUBLICATIONS

Dichgans et al., "The Phenotypic Spectrum of CADASIL: Clinical Findings in 102 Cases," Annals of Neurology, 1998, 44(5):731-739.
Dotti et al., "A Novel NOTCH3 Frameshift Deletion and Mitochondrial Abnormalities in a Patient With CADASIL," Arch Neurol., 2004, 61(6):942-945.
Erro et al., "Are granular osmiophilic material deposits an epiphenomenon in CADASIL?" Folia Neuropathol., 2015, 53:168-171.
Fouillade et al., "Activating NOTCH3 Mutation in a Patient with Small-vessel-disease of the Brain," Human Mutation, 2008, 29(3):452, 9 pages.
Funatsu et al., "Outcome of vitreous surgery and the balance between vascular endothelial growth factor and endostatin," Invest Ophthalmol Vis Sci, 2003, 44(3):1042-1047.
Fung et al., "Delta-like 4 induces notch signaling in macrophages: implications for inflammation," Circulation, 2007, 115(23):2948-2956.
Ghosh et al., "Pericytes are involved in the pathogenesis of cerebral autosomal dominant arteriopathy with subcortical infarcts and leukoencephalopathy," Ann Neurol., 2015, 78(6):887-900.
Gould et al., "Role of COL4A1 in Small-Vessel Disease and Hemorrhagic Stroke," N Engl J Med, 2006, 354:1489-1496.
Gouya et al., "Association of endostatin with mortality in patients with chronic heart failure," Eur J Clin Invest, 2014, 44(2):125-35.
Hakim, "Silent, but preventable, perils," Nature, 2014, 510:S12.
Hara et al., "Association of HTRA1 Mutations and Familial Ischemic Cerebral Small-Vessel Disease," N Engl J Med, 2009, 360:1729-1739.
Henshall et al., "Notch3 Is Necessary for Blood Vessel Integrity in the Central Nervous System," Arterioscler Thromb Vase Biol., 2015, 35(2):409-420.
Iadecola, "The Pathobiology of Vascular Dementia," Neuron, 2013, 80(4):844-866.
Inagaki et al., "Upregulation of HtrA4 in the placentas of patients with severe pre-eclampsia," Placenta, 2012, 33(11):919-926.
Ishiko et al., "Notch3 ectodomain is a major component of granular osmiophilic material (GOM) in CADASIL," Acta Neuropathol, 2006, 112:333-339.
Joutel and Faraci, "Cerebral Small Vessel Disease: Insights and Opportunities From Mouse Models of Collagen IV-Related Small Vessel Disease and Cerebral Autosomal Dominant Arteriopathy With Subcortical Infarcts and Leukoencephalopathy," Stroke, 2014, 45(4):1215-1221.
Joutel et al., "Cerebrovascular dysfunction and microcirculation rarefaction precede white matter lesions in a mouse genetic model of cerebral ischemic small vessel disease," J Clin Invest., 2010, 120(2):433-445.
Joutel et al., "Notch3 mutations in CADASIL, a hereditary adult-onset condition causing stroke and dementia," Nature, 1996, 383:707-710.
Joutel et al., "Pathogenic Mutations Associated with Cerebral Autosomal Dominant Arteriopathy with Subcortical Infarcts and Leukoencephalopathy Differently Affect Jagged1 Binding and Notch3 Activity via the RBP/JK Signaling Pathway," Am J Hum Genet., 2004, 74:338-347.
Joutel et al., "Perturbations of the cerebrovascular matrisome: A convergent mechanism in small vessel disease of the brain?," J Cereb Blood Flow Metab, 2016, 36(1):143-157.
Joutel et al., "Strong clustering and stereotyped nature of Notch3 mutations in CADASIL patients," Lancet, 1997, 350(9090):1511-1515.
Kalaria, "Cerebrovascular Disease and Mechanisms of Cognitive Impairment," Stroke, 2012, 43(9):2526-2534.
Klueg and Muskavitch, "Ligand-receptor interactions and trans-endocytosis of Delta, Serrate and Notch: members of the Notch signalling pathway in *Drosophila*," J Cell Sci., 1999, 112(Pt 19):3289-3297.
Kodadek, "Protein microarrays: prospects and problems," Chem Biol., 2001, 8:105-115.
Kofler et al., "Combined deficiency of Notch1 and Notch3 causes pericyte dysfunction, models CADASIL and results in arteriovenous malformations," Sci Rep., 2015, 5:16449, 13 pages.
Kopan, "Notch signaling," Cold Spring Harb Perspect Biol., 2012, 4(10):a011213, 5 pages.
Lafkas et al., "NOTCH3 marks clonogenic mammary luminal progenitor cells in vivo," J Cell Biol., 2013, 203(1):47-56.
Li et al., "The Human Homolog of Rat Jagged1 Expressed by Marrow Stroma Inhibits Differentiation of 32D Cells through Interaction with Notch1," Immunity, 1998, 8:43-55.
Louvi et al., "CADASIL: A Critical Look at a Notch Disease," Dev Neurosci, 2006, 28:5-12.
Louvi et al., "Notch and disease: a growing field," Semin Cell Dev Biol., 2012, 23(4):473-480.
MayoClinic.org [online], "Small vessel disease," available on or before Mar. 29, 2016, via Internet Archive: Wayback Machine URL <http://web.archive.org/web/20160329050842/http://www.mayoclinic.org/diseases-conditions/small-vessel-disease/home/ovc-20198376>, retrieved on Feb. 11, 2021, URL <http://www.mayoclinic.org/diseases-conditions/small-vessel-disease/home/ovc-20198376>, 3 pages.
Meng et al., "Biochemical Characterization and Cellular Effects of CADASIL Mutants of NOTCH3," PLoS ONE, Sep. 2012, 7(9):1-13.
Moccia et al., "Hypomorphic NOTCH3 mutation in an Italian family with CADASIL features," Neurobiol Aging, 2015, 36(1):547.e5-547.e11.
Monet-Lepretre et al., "Abnormal recruitment of extracellular matrix proteins by excess Notch3ECD: a new pathomechanism in CADASIL," Brain, 2013, 136(6):1830-1845.
Navarro-Sobrino et al., "A large screening of angiogenesis biomarkers and their association with neurological outcome after ischemic stroke," Atherosclerosis, 2011, 216:205-211.
Nickoloff et al., "Jagged-1 mediated activation of notch signaling induces complete maturation of human keratinocytes through NF-κB and PPARγ," Cell Death Different., 2002, 9:842-855.
O'Reilly et al., "Endostatin: An Endogenous Inhibitor of Angiogenesis and Tumor Growth," Cell, 1997, 88(2):277-285.
PCT International Preliminary Report on Patentability in International Appln. No. PCT/US2018/024394, dated Oct. 1, 2019, 16 pages.
PCT International Preliminary Report on Patentability in International Appln. No. PCT/US2018/0243 97, dated Oct. 10, 2019, 10 pages.
PCT International Preliminary Report on Patentability in International Appln. No. PCT/US2018/024407, dated Oct. 10, 2019, 12 pages.
PCT International Search Report and Written Opinion in International Appln. No. PCT/US2018/0243 94, dated Aug. 8, 2018, 22 pages.
PCT International Search Report and Written Opinion in International Appln. No. PCT/US2018/0243 97, dated Aug. 3, 2018, 14 pages.
PCT International Search Report and Written Opinion in International Appln. No. PCT/US2018/024407, dated Sep. 18, 2018, 17 pages.
Pippucci et al., "Homozygous NOTCH3 null mutation and impaired NOTCH3 signaling in recessive early onset arteriopathy and cavitating leukoencephalopathy," EMBO Mol Med., 2015, 7(6):848-858.
Primo et al., "Blood Biomarkers inaMouse Model of CADASIL," Brain Research, 2016, 1644:118-126.
Robinson et al., "Retinal Findings in Cerebral Autosomal Dominant Arteriopathy with Subcortical Infarcts and Leukoencephalopathy (CADASIL)," Surv Ophthalmol., 2001, 45:445-448.
Rosenberg et al., "Consensus statement for diagnosis of subcortical small vessel disease," J Cereb Blood Flow Metab., 2015, 36(1):6-25.
Ruchoux and Maurage, "Cerebral autosomal dominant arteriopathy with subcortical infarcts and leukoencephalopathy," Journal of Neuropathology and Experimental Neurology, 1997, 56(9):947-964.

(56) References Cited

OTHER PUBLICATIONS

Ruchoux et al., "Systemic vascular smooth muscle cell impairment in cerebral autosomal dominant arteriopathy with subcortical infarcts and leukoencephalopathy," Acta Neuropathol., 1995, 89:500-512.

Rufa et al., "Retinal Nerve Fiber Layer Thinning in CADASIL: An Optical Coherence Tomography and MRI Study ," Cerebrovasc Dis., 2011, 31:77-82.

Rutten et al., "Hypomorphic NOTCH3 alleles do not cause CADASIL in humans," Hum Mutat., 2013, 34(11):1486-1489.

Rutten et al., "The NOTCH3 score: a pre-clinical CADASIL biomarker in a novel human genomic NOTCH3 transgenic mouse model with early progressive vascular NOTCH3 accumulation," Acta Neuropathol Commun., Dec. 2015, 3(1):89, 10 pages.

Rutten et al., "Therapeutic NOTCH3 cysteine correction in CADASIL using exon skipping: in vitro proof of concept," Brain, 2016, 139(4):1123-1135.

Silva et al., "Predictive value of vascular disease biomarkers for digital ulcers in systemic sclerosis patients," Clin Exp Rheumatol, 2015, 33(4 Suppl 91):S127-S130.

Snyder et al., "Vascular Contributions to Cognitive Impairment and Dementia Including Alzheimer's Disease," Alzheimers Dement, 2015, 11(6):710-717.

Teoh et al., "Serum HtrA1 is differentially regulated between early-onset and late-onset preeclampsia," Placenta, 2015, 36(9):990-995.

Thompson et al., "Living Beyond Our Physiological Means: Small Vessel Disease of the Brain Is an Expression of a Systemic Failure in Arteriolar Function: A Unifying Hypothesis," Stroke, 2009, 40:e322-e330.

Tikka et al., "Congruence between NOTCH3 mutations and GOM in 131 CADASIL patients," Brain, 2009, 132:933-939.

Tikka et al., "MINI-SYMPOSIUM: Pathology & Genetics of (non-CAA) Cerebral Microvascular Disease, CADASIL and CARASIL," Brain Pathology, 2014, 24(5):525-544.

Velasquez et al., "Hypomorphic Notch 3 alleles link Notch signaling to ischemic cerebral small-vessel disease," Proc Natl Acad Sci USA, 2011, 108(21):E128-E135.

Vermeer et al., "Silent brain infarcts: a systematic review," Lancet Neurol., 2007, 6(7):611-619.

Wollenweber et al., "Cysteine-sparing CADASIL mutations in NOTCH3 show proaggregatory properties in vitro," Stroke, 2015, 46(3):786-792.

Xu et al., "Insights into Autoregulation of Notch3 from Structural and Functional Studies of Its Negative Regulatory Region," Structure, 2015, 23:1227-1235.

Yamamura et al., "Activation of Notch signaling by short-term treatment with Jagged-1 enhances store-operated Ca2+ entry in human pulmonary arterial smooth muscle cells," Am J Physiol Cell Physiol., 2014, 306(9):C871-878.

Yoon et al., "NOTCH3 variants in patients with subcortical vascular cognitive impairment: a comparison with typical CADASIL patients," Neurobiol Aging, 2015, 36:2443.e1-2443.e7.

Arboleda-Velasquez , et al., "Hypomorphic Notch 3 Alleles Link Notch Signaling to Ischemic Cerebral Small-Vessel Disease", Proceedings of the National Academy of Sciences of the United States of America., May 24, 2011, 108(21):E128-E135 (8 pages).

Haque , et al., "Inhibition of Tau Aggregation by a Rosamine Derivative that Blocks Tau Intermolecular Disulfide Dross-Linking", Amyloid, The Journal of Protein Folding Disorders, vol. 21, No. 3, Sep. 2014, pp. 185-190.

Joutel , et al., "Cerebrovascular Dysfunction and Microcirculation Rarefaction Precede White Matter Lesions in a Mouse Genetic Model of Cerebral Ischemic Small Vessel Disease", Journal of Clinical Investigation, vol. 120, No. 2, Feb. 1, 2010, pp. 433-445.

Rana , et al., "Neurofilament Light Chain as an Eady and Sensitive Predictor of Long-Term Neurological Outcome in Patients after Cardiac Arrest", International Journal of Cardiology, vol. 168, Issue 2, Sep. 30, 2013, pp. 1322-1327.

Verdura , et al., "Heterozygous HTRAI Mutations are Associated with Autosomal Dominant Cerebral Small Vessel Disease", Brain, vol. 138, Aug. 2015, pp. 2347-2358.

Evans et al., "Cardiovascular comorbidities, inflammation, and cerebral small vessel disease," Cardiovasc Res, Nov. 2021, 117(13):2575-2588.

Giau et al., "Genetic factors of cerebral small vessel disease and their potential clinical outcome," Int J Mol Sci, Sep. 2019, 20(17):4298, 27 pages.

Joutel et al., "Skin biopsy immunostaining with a Notch3 monoclonal antibody for CADASIL diagnosis," Lancet, Dec. 2001, 358(9298):2049-2051.

Joutel et al., "The ectodomain of the Notch3 receptor accumulates within the cerebrovasculature of CADASIL patients," J Clin Invest, Mar. 2000, 105(5):597-605.

Tan et al., "New insights into mechanisms of small vessel disease stroke from genetics," Clin Sci, Apr. 2017, 131(7):515-531.

Wardlaw et al., "Small vessel disease: mechanisms and clinical implications," Lancet Neurol, Jul. 2019, 18(7):684-696, 13 pages.

Zaucker et al., "notch3 is essential for oligodendrocyte development and vascular integrity in zebrafish," Dis Models Meeh, Sep. 2013, 6(5):1246-1259.

FIG. 1D Retina

FIG. 1E Brain

NOTCH3 AGONIST COMPOSITIONS AND METHODS FOR TREATING SMALL VESSEL DISEASES

CROSS REFERENCE TO RELATED APPLICATIONS

This application is a national stage application filed under 35 U.S.C. § 371, of International Patent Application No. PCT/US2018/024397, filed Mar. 26, 2018, which claims the benefit of and priority to U.S. Provisional Patent Application No. 62/477,289, filed Mar. 27, 2017, the entire contents of each of which are incorporated herein by reference in its entirety.

STATEMENT AS TO FEDERALLY SPONSORED RESEARCH

This invention was made with government support under EY021624 and NS100121 awarded by the National Institutes of Health. The government has certain rights in the invention.

FIELD OF THE INVENTION

The present invention relates to small vessel diseases.

SEQUENCE LISTING

Incorporated by reference in its entirety is a computer-readable nucleotide/amino acid sequence listing submitted concurrently herewith and identified as follows: 177,092 byte text file named "36770-556001WO_Sequence_Listing_ ST25.txt" created on Mar. 26, 2018.

BACKGROUND

Cerebral small vessel disease (SVD) is characterized by progressive degeneration of the small penetrating arteries and arterioles of the brain (Rosenberg et al., 2015, *J Cereb Blood Flow Metab*). Pathological changes in the small vessels include mural cell loss, thickening of basement membranes, and accumulation of deposits in vessel walls (Iadecola, 2013, *Neuron* 80:844-866; Rosenberg et al., 2015, *J Cereb Blood Flow Metab*). SVD is responsible for the vast majority of silent brain infarcts, is the most common cause of vascular cognitive impairment and vascular dementia, and is a major risk factor for clinically overt stroke (Hakim, 2014, *Nature* 510:S12; Iadecola, 2013, *Neuron* 80:844-866; Thompson and Hakim, 2009, *Stroke* 40:e322-330). There is increasing evidence that SVD exacerbates Alzheimer's disease pathology and vice versa; indeed, it is now clear that the most common etiology of dementia in older people includes a mixture of vascular (particularly small vessel) disease and Alzheimer's pathology (Snyder et al., 2015, *Alzheimers Dement* 11:710-717). SVD is accelerated and exacerbated by cardiovascular risk factors, including high blood pressure and diabetes, but one of the strongest risk factors for SVD is age (Iadecola, 2013, *Neuron* 80:844-866). Currently, SVD is treated via modification of cardiovascular risk factors without addressing vascular degeneration directly.

New compositions and methods for the treatment of SVDs are needed.

SUMMARY OF THE INVENTION

Provided herein are, inter alia, compositions, formulations, and methods for inhibiting, treating, preventing, and/or reducing the symptoms of severity of SVDs. Aspects of the present subject matter relate to the use of NOTCH3 agonists for the treatment of a wide variety of SVDs including but not limited to cerebral small vessel disease, cerebral autosomal recessive arteriopathy with subcortical infarcts and leukoencephalopathy (CARASIL), age-related macular degeneration (AMD), cerebral autosomal-dominant arteriopathy with subcortical infarcts and leukoencephalopathy (CADASIL), NOTCH3 loss-of-function-associated SVD (e.g., a SVD associated with a mutation that reduces the expression and/or activity of NOTCH3), nephropathy, microangiopathy, heart failure, Alagille syndrome, familial tetralogy of Fallot, patent ductus arteriosus, cerebral cavernous malformation, and diabetic retinopathy.

Included herein is a method for treating or preventing a SVD in a subject. The method comprises administering to the subject an effective amount of a Neurogenic Locus Notch Homolog Protein 3 (NOTCH3) agonist such as an antibody that binds to the ectodomain (e.g., SEQ ID NO: 12). Such an antibody targets the extracellular domain and activates the receptor. In various embodiments, the SVD comprises cerebral SVD. In some embodiments, SVD comprises CADASIL. In certain embodiments, the SVD comprises CARASIL. In some embodiments, the SVD comprises diabetic retinopathy. In various embodiments, the SVD comprises a cerebral SVD, CARASIL, CADASIL, age-related macular degeneration (AMD), retinopathy, nephropathy or another SVD of the kidney, microangiopathy, proximal 19p13.12 microdeletion syndrome, myocardial ischemia, heart failure, NOTCH3 loss of function-associated SVD, Alagille syndrome, familial tetralogy of Fallot, patent ductus arteriosus, a cerebral cavernous malformation, or a HTRA1-associated small vessel disease.

Aspects provide methods of administering a NOTCH3 agonist to a person who has or is at risk of suffering from a SVD. In some embodiments, a subject who has or is at risk of suffering from a SVD has at least 1, 2, 3, or 4 grandparents, parents, aunts, uncles, cousins, or siblings who have the SVD. In various embodiments, the subject has diabetes (e.g., type 1 diabetes or type 2 diabetes). In certain embodiments, the subject is at least about 10, 20, 30, 40, 50, 60, 70, 80, or 90 years old. In some embodiments, the subject has Alzheimer's disease. In certain embodiments, the subject has dementia. In various embodiments, the subject has arterial hypertension.

In some embodiments, the subject comprises granular osmiophilic material (GOM) deposits. In certain embodiments, the subject does not comprise GOM deposits.

In certain embodiments, the lower the level of NOTCH3 activity is, the higher the dose of a NOTCH3 agonist is. In various embodiments, the lower the level of NOTCH3 protein or mRNA is, the higher the dose of a NOTCH3 agonist is.

In various embodiments, a subject who has or is at risk of suffering from a SVD has an abnormal level of NOTCH3, collagen18α1 or endostatin, insulin growth factor binding protein 1 (IGFBP-1), and/or High-Temperature Requirement A Serine Peptidase 1 (HTRA1) protein or mRNA. In some embodiments, a test sample obtained from the subject comprises a level of NOTCH3 protein or mRNA that is different than a normal control. For example, the test sample may comprise a level of NOTCH3 and/or collagen18α1 or endostatin protein or mRNA that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% lower in the test sample compared to a normal control. In some embodiments, the test sample comprises a level of collagen18α1 or endostatin and/or HTRA1 and/or IGFBP-1 protein or mRNA that is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher in the test sample compared to a normal control. In certain embodiments, a test sample comprises a level of HTRA1 protein or mRNA that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% higher in the test sample compared to a normal control. In certain embodiments, a test sample comprises a level of HTRA1 protein or mRNA that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% lower in the test sample compared to a normal control. In some embodiments, the subject (e.g., a test sample from the subject) comprises a level of NOTCH3 protein bound to collagen18α1 and/or endostatin and/or HTRA1 and/or IGFBP-1 that is different than a normal control. For example, the test sample may comprise levels of NOTCH3 protein bound to collagen18α1 and/or endostatin and/or HTRA1 and/or IGFBP-1 that is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher in the test sample compared to a normal control. Non-limiting examples of test samples include blood, serum, plasma, saliva, tears, vitreous, cerebrospinal fluid, sweat, cerebrospinal fluid, or urine.

In various embodiments, a test sample comprises a level of HTRA1 protein or mRNA that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% higher in the test sample compared to a normal control. In some embodiments, the subject has or is at risk of suffering from CADASIL.

In various embodiments, a test sample comprises a level of HTRA1 protein or mRNA that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% lower in the test sample compared to a normal control. In some embodiments, the subject has or is at risk of suffering from CARASIL.

In certain embodiments, an agonist is administered to a subject with an SVD until one or more biomarkers (e.g., NOTCH3 such as the extracellular domain thereof, a mutant thereof, or the wilt-type version thereof; GFBP-1; HTRA1; and/or collagen18α1/endostatin) reaches a level observed in a corresponding subject who does not have the SVD. In certain embodiments, the dose of the agonist is increased until one or more biomarkers (e.g., NOTCH3 such as the extracellular domain thereof, a mutant thereof, or the wilt-type version thereof; GFBP-1; HTRA1; and/or collagen18α1/endostatin) reaches a level observed in a corresponding subject who does not have the SVD.

In certain embodiments, the subject expresses NOTCH3 with any of the following CADASIL mutations: C43G, C49F, C49Y, R54C, S60C, C65S, C67Y, W71C, C76R, C76W, 77-82del, 80-84del, C87R, C87Y, R90C, C93F, C93Y, C106W, C108W, C108Y, R110C, 114-120del, C117F, S118C, C123F, C123Y, C128Y, R133C, C134W, R141C, F142C, C144S, C144Y, S145C, C146R, G149C, Y150C, 153-155del, R153C, C155S, C162S, R169C, G171C, C174F, C174R, C174Y, S180C, R182C, C183F, C183R, C183S, C185G, C185R, Y189C, C194F, C194R, C194S, C194Y, C201Y, C206Y, R207C, C212S, R213K, C222G, C222Y, C224Y, C233S, C233Y, 239-253del, C240S, C245R, C251R, Y258C, C260Y, C311G, A319C, R332C, S335C, Y337C, C349S, C379S, C395R, G420C, R421C, C428S, C428Y, C440G, C440R, C446S, R449C, C455R, C484F, C484Y, C495Y, C511R, C542Y, R544C, C549Y, R558C, R578C, R587C, R607C, C608Y, C624S, R635C, R640C, R717C, Y710C, R728C, C775S, G942C, R951C, G953C, F984C, R985C, R1006C, C1015R, Y1021C, R1031C, R1143C, D1063C, R1190C, R1201C, C1202S, R1210C, C1222G, R1231C, R1242C, C1261R, and C1261Y. In certain embodiments, the subject expresses NOTCH3 with a mutation that results in an extracellular domain of NOTCH3 having an odd number of cysteines according to the formula CnX or XnC where C stands for cysteine, n for an amino acid number in the NOTCH3 extracellular domain and X any amino replacing cysteine (for CnX) or replaced by cysteine (for XnC). In certain embodiments, n is the amino acid number (i.e., position) of any amino acid in the extracellular domain of NOTCH3. In certain embodiments, n is any one of positions 40-1643 of SEQ ID NO: 10. In certain embodiments, n is any one of positions 40-100, 100-250, 250-500, 500-750, 750-1000, 1000-1250, 1250-1500, or 1500-1643 of SEQ ID NO: 10. In certain embodiments, the subject express NOTCH3 with cysteine-sparing mutations either of the following: R61W, R75P, D80G 88-91del. See, e.g., Wollenweber et al., (2015) Cysteine-sparing CADASIL mutations in NOTCH3 show proaggregatory properties in vitro. Stroke 46(3):786-92, the entire content of which is incorporated herein by reference. In certain embodiments, the subject carries loss of function mutations in NOTCH 3 including frame shift, premature stop codon, out of frame insertions or deletions, or splicing mutations including any of the following mutations: p.R113Ter, p.R103Ter, p.R156Ter, p.Y220Ter, c.1951+2delT, p.C729Ter, p.R735Ter, p.C966Ter, p.G2035RfsTer60, p.T1816ITer3, c.2566+1G>C, p.C1110Ter, p.E1125Ter, p.Y1453Ter, p.R1851VfsTer60, c.5667+1G>A, p.R1893Ter, c.5914-2_5914-linsT, p.G2035RfsTer60, p.G2035VfsTer50. See, e.g., Pippucci et al., (2015) Homozygous NOTCH3 null mutation and impaired NOTCH3 signaling in recessive early-onset arteriopathy and cavitating leukoencephalopathy. EMBO Mol Med. 7(6):848-58; Moccia et al., (2015) Hypomorphic NOTCH3 mutation in an Italian family with CADASIL features. Neurobiol Aging 36(1):547.e5-11, the entire contents of each of which are incorporated herein by reference.

In some embodiments, a NOTCH3 agonist is administered as a monotherapy. In certain embodiments, especially where the SVD is CADASIL, the subject is not administered a thrombolytic agent.

Aspects include a NOTCH3 agonist, as well methods and compositions comprising a NOTCH3 agonist, where the NOTCH3 agonist comprises a polypeptide, an antibody or a fragment thereof, an aptamer, or a small molecule.

In various embodiments, the NOTCH3 agonist comprises a polypeptide. In some embodiments, the polypeptide comprises a fragment of a NOTCH3 ligand. In certain embodiments, the ligand comprises JAGGED1 or a fragment thereof, JAGGED2 or a fragment thereof, or DELTA-LIKE1 or a fragment thereof.

In certain embodiments, the NOTCH3 agonist comprises a fragment of JAGGED1. In some embodiments, the fragment of JAGGED1 is the extracellular domain of JAGGED1 or a fragment thereof comprising a stretch of amino acids having the sequence CDDYYYGFGCNKFCRPR (SEQ ID NO:1). In various embodiments, the fragment of JAGGED1 comprises a stretch of amino acids having the sequence CDDYYYGFGCNKFCRPRDDFFGH (SEQ ID NO:2).

In some embodiments, the NOTCH3 agonist comprises a fragment of JAGGED2. In various embodiments, the fragment of JAGGED2 is the extracellular domain of JAGGED2 or a fragment thereof comprising a stretch of amino acids having the sequence CDENYYSATCNKFCRPR (SEQ ID NO:3). In certain embodiments, the fragment of JAGGED2 comprises a stretch of amino acids having the sequence CDENYYSATCNKFCRPRNDFFGH (SEQ ID NO:4).

In various embodiments, the NOTCH3 agonist comprises a fragment of DELTA-LIKE1. In some embodiments, the fragment of DELTA-LIKE1 is the extracellular domain of DELTA-LIKE1 or a fragment thereof comprising a stretch of amino acids having the sequence CDEHYYGEGCSVF CRPR (SEQ ID NO:5). In various embodiments, the fragment of DELTA-LIKE1 comprises a stretch of amino acids having the sequence CDEHYYGEGCSVFCRPRDDAFGH (SEQ ID NO:6).

In certain embodiments, the polypeptide comprises a fragment of DELTA-LIKE3. In some embodiments, the fragment of DELTA-LIKE3 is the extracellular domain of DELTA-LIKE3 or a fragment thereof comprising a stretch of amino acids having the sequence CEPPAVGTACTRLCRPR (SEQ ID NO:7).

In various embodiments, the polypeptide comprises a fragment of DELTA-LIKE4. In certain embodiments, the fragment of DELTA-LIKE4 is the extracellular domain of DELTA-LIKE4 or a fragment thereof comprising a stretch of amino acids having the sequence CSDNYYGDNCS RLCKKR (SEQ ID NO:8). In some embodiments, the fragment of DELTA-LIKE4 comprises a stretch of amino acids having the sequence CSDNYYGDNCSRLCKK RNDHFGH (SEQ ID NO:9).

In certain embodiments, the NOTCH3 agonist increases or decreases the expression or activity of a known modulator of NOTCH3 signaling. Non-limiting examples of NOTCH3 signaling modulators are described in Hicks et al. (2000) Nature Cell Biology 2, 515-520; Moloney et al. (2000) Nature 406(6794):369-75; and Matsuno et al. (1998) Nat Genet. 19(1):74-8, the entire contents of each of which are incorporated herein by reference. In some embodiments, the NOTCH3 agonist increases the expression or activity of a protein encoded by a gene within the fringe family of genes. In various embodiments, the NOTCH3 agonist increases the expression or activity of Lunatic fringe (LFNG). In certain embodiments, the NOTCH3 agonist increases the expression or activity of a Fringe protein that has glycosyltransferase activity. In various embodiments, the NOTCH3 agonist increases the expression or activity of a Fringe protein that has fucose-specific beta1,3 N-acetylglucosaminyltransferase activity. In some embodiments, the protein initiates elongation of O-linked fucose residues attached to a epidermal growth factor-like sequence repeat of NOTCH3. In some embodiments, the NOTCH3 agonist decreases the expression or activity of a protein encoded by a gene within the fringe family of genes. In various embodiments, the NOTCH3 agonist decreases the expression or activity of Lunatic fringe (LFNG). In certain embodiments, the NOTCH3 agonist decreases the expression or activity of a Fringe protein that has glycosyltransferase activity. In various embodiments, the NOTCH3 agonist decreases the expression or activity of a Fringe protein that has fucose-specific beta1,3 N-acetylglucosaminyltransferase activity. In some embodiments, the protein initiates elongation of O-linked fucose residues attached to an epidermal growth factor-like sequence repeat of NOTCH3. In certain embodiments, the NOTCH3 agonist increases the expression or activity of suppressor of hairless [Su(H)] or deltex (dx). In certain embodiments, the NOTCH3 agonist increases the expression or activity of RBPJ (recombining binding protein suppressor of hairless; UniProt No. Q06330) or DELTEX. In certain embodiments, the NOTCH3 agonist decreases the expression or activity of suppressor of hairless [Su(H)] or deltex (dx).

Aspects also include compositions comprising a NOTCH3 agonist and a pharmaceutically acceptable carrier for treating or preventing a SVD in a subject. Uses of a NOTCH3 agonist in the manufacture of a medicament for treating or preventing a SVD in a subject are also disclosed herein.

Also provided are compositions comprising an effective amount of a NOTCH3 agonist and an ophthalmically acceptable vehicle. In some embodiments, the composition is in the form of an aqueous solution comprising an osmolality of about 200 to about 400 milliosmoles/kilogram water.

Each embodiment disclosed herein is contemplated as being applicable to each of the other disclosed embodiments. Thus, all combinations of the various elements described herein are within the scope of the invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

DESCRIPTION OF THE DRAWINGS

(FIG. 1A) Schematic representation of four mouse strains utilized to study genetic rescue of Notch 3 signaling: wild type Notch 3 (N3WT, white), Notch 3 knockout (N3KO, light gray), mice N3KO conditionally expressing wild type human Notch 3 (hN3WT, dark gray) and N3KO mice conditionally expressing a human CADASIL mutant Notch 3 (C455R, black).

(FIG. 3B) Graph shows quantification of leakage events in the listed genotypes: N3WT (n=6), N3KO (n=6), hN3WT (n=5), C455R (n=3), C455R/hN3WT (n=5). ** $p<0.05$. NS means non significant.

DETAILED DESCRIPTION

Figure 1A:
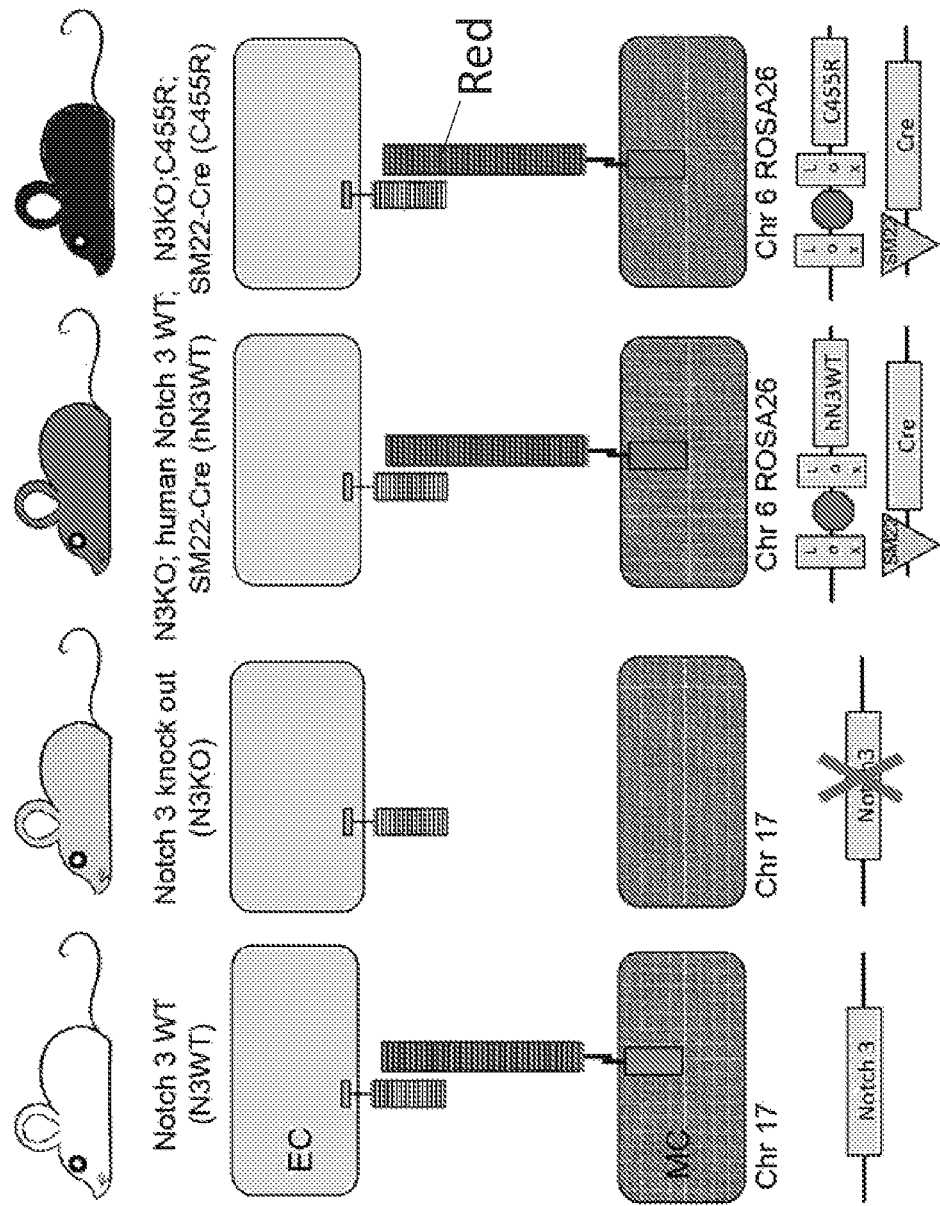
FIG. 1A is a cartoon.

Provided are methods of treating SVD, including CADASIL and NOTCH3 loss of function-associated SVD, with a Notch agonist. Exemplary agonists include antibodies, e.g., monoclonal antibodies that bind to the ectodomain (SEQ ID NO: 12) of NOTCH3. Such antibodies activate the receptor. Exemplary antibodies are described in U.S. Pat. No. 8,513,388, hereby incorporated by reference. Cerebral SVD affects about a third of individuals over 80 years of age, and is a leading cause of stroke, cognitive impairment, and dementia. No disease modifying therapies are available and most treatments focus on managing cardiovascular risk factors known to contribute to the disease. Loss of mural cells, which encompass pericytes and vascular smooth muscle cells, is a hallmark of SVD resulting in vascular instability. NOTCH3 signaling is both necessary and sufficient to support mural cell coverage in arteries using genetic rescue, and SVD may be treated by modulating NOTCH3 signaling. Additionally, the levels of NOTCH3 ectodomain and/or endostatin/collagen 18α1 in patient-derived tissue or bodily fluid samples can be used as surrogate markers of NOTCH3 activity in vivo.

Small vessel diseases are highly prevalent and impact highly vascularized tissues such as the brain, retina, and the kidney. In the brain, small vessel disease is the most prevalent neurological condition and a strong contributor to the susceptibility to stroke, vascular cognitive impairment, and dementia. In the retina, small vessel disease plays a critical role in early stage diabetic retinopathy, which is characterized by mural cell loss. Prior to the methods and compositions provided herein, there were no specific treatments to prevent mural cell degeneration in small vessel disease. Included herein are methods of treating SVD with Notch signaling activators. In some embodiments, mural cell degeneration is reduced or prevented in SVD, e.g., in vascularized tissues such as retina and brain.

CADASIL is a monogenic cause of cerebral small vessel disease associated with mutations in the NOTCH3 gene. There are no specific treatments for small vessels disease in general or CADASIL in particular. Methods and compositions provided herein solve this practical problem by using NOTCH3 signaling in mural cells as a therapeutic target to prevent mural cell loss in small vessel diseases. Prior to the present invention, there were no methods to address mural cell loss in SVD.

NOTCH3 loss of function-associated SVD is distinct from CADASIL because it lacks the characteristic accumulation of Notch 3 extracellular domain in vessels and it lacks granular osmiophilic deposits (GOMs). Prior to the present invention, there were no methods to address mural cell loss in NOTCH3 loss of function-associated SVD. In embodiments, a subject with such a SVD has symptoms that are similar to CADASIL. See, e.g., Moccia et al., (2015) Hypomorphic NOTCH3 mutation in an Italian family with CADASIL features. Neurobiol Aging 36(1):547.e5-11; the entire contents of which is incorporated herein by reference. In various embodiments, the subject has migraines. In some embodiments, the subject has migraines with aura. In certain embodiments, the skin of the subject comprises vascular damage. In various embodiments, the subject has cerebral SVD. A non-limiting example of a mutation that may result in a SVD symptoms similar to CADASIL is a C to U substitution at position 307 of the open reading frame of NOTCH3-encoding mRNA (a cDNA sequence is provided as SEQ ID NO: 11), which results in a truncation of the protein such that amino acids from position R103 to the wild-type C-terminus are missing.

In some embodiments, the subject comprises a R103X substitution mutation. In certain embodiments, the mutation results in a substitution or a truncation within an Epidermal Growth-Factor-like Repeat of NOTCH3. In various embodiments, the mutation is within one of exons 2-24 of the NOTCH3 gene. In some embodiments, the mutation is a missense mutation in exon 25 of NOTCH3. In some embodiments, the substitution is not a conservative substitution. In certain embodiments, the subject comprises an autosomal mutation in NOTCH3. In some embodiments, the mutation results in reduced NOTCH3 function. In some embodiments, the mutation comprises substitution in the extracellular domain of NOTCH3 that adds or removes a cysteine compared to wild-type NOTCH3. In certain embodiments, the mutation comprises a truncation beginning in the extracellular domain of the NOTCH3 protein. In embodiments, the subject is heterozygous for the mutation. In embodiments, the subject is homozygous for the mutation.

Without being bound by any scientific theory, the non-limiting data herein show for the first time that NOTCH3 signaling is both necessary and sufficient to sustain mural cell coverage in arteries via a cell autonomous effect. This finding is demonstrated, e.g. by rescuing mural degeneration in a NOTCH3 knockout by expressing the human NOTCH3 protein specifically in mural cells. This finding is demonstrated, e.g. by rescuing vascular leakage events in a NOTCH3 knockout by expressing the human NOTCH3 protein specifically in mural cells. This finding is demonstrated, e.g. by rescuing vascular leakage events in a NOTCH3 knockout expressing the C455R CADASIL mutation by also expressing the wild type human NOTCH3 protein specifically in mural cells. This finding is demonstrated, e.g. by the observation of indistinguishable levels of mural cell loss and frequency of vascular leakage events between NOTCH3 knockouts and NOTCH3 knockouts expressing the C455R CADASIL mutation. This finding shows that a gene replacement approach, in which a defective NOTCH3 is replaced by a wild-type NOTCH3 specifically in mural cells, results in a functional rescue. This is surprising because NOTCH3 is expressed in other cell types including monocytes/macrophages, other immune cells, and stem cells all of which have been shown to play roles in the vasculatures. See, e.g., Fung et al., (2007) Delta-like 4 induces notch signaling in macrophages: implications for inflammation. Circulation 115(23):2948-56; and Lafkas et al., (2013) NOTCH3 marks clonogenic mammary luminal progenitor cells in vivo. *J Cell Biol.* 203(1):47-56, the entire contents of which are hereby incorporated herein by reference. This is surprising because the predominant view is that CADASIL mutations in NOTCH3 operate via neomorphic toxic gain of function effects. It is therefore unexpected and surprising that by increasing NOTCH3 signaling in mural cells one can rescue vascular degeneration and thus bypass the neomorphic effects.

The following findings were unexpected:
(i) The discovery was made using a NOTCH3 mutation associated with the human small vessel disease called CADASIL (cerebral autosomal dominant arteriopathy with subcortical infarcts and leukoencephalopathy) (Arboleda-Velasquez et al., Neurology 59:277-279, 2002; Arboleda-Velasquez et al., Proc Natl Acad Sci USA 105:4856-4861, 2008; Arboleda-Velasquez et al., Proc Natl Acad Sci USA 108:E128-135, 2011). In that condition, the most widely accepted pathobiological mechanism is that of toxic neomorphism via accumulation of the NOTCH3 receptor extracellular domain whereas NOTCH3 signaling defects due to the mutations are not considered to be primary drivers of the disease (Joutel et al., J Cereb Blood Flow Metab, 36(1):143-57, 2016). In a challenge to this paradigm, the data herein shows that mural cell loss and vascular leakage in a model carrying the CADASIL mutation was similar to that of the mice lacking NOTCH3 (knockout), suggesting a negligible contribution of the toxic neomorphic effects. It is also surprising that the expression of the WT human Notch3 in the presence of a CADASIL mutant Notch 3 rescues the phenotype. This further supports the idea of a negligible contribution of the toxic neomorphic effects.

(ii) The discovery was made using a NOTCH3 knockout mouse model. NOTCH3 loss of function mutations including premature stop codons and frame shifts have been reported in individuals with SVD. See, e.g., Pippucci et al., (2015) Homozygous NOTCH3 null mutation and impaired NOTCH3 signaling in recessive early-onset arteriopathy and cavitating leukoencephalopathy. EMBO Mol Med. 7(6):848-58; Moccia et al., (2015) Hypomorphic NOTCH3 mutation in an Italian family with CADASIL features. Neurobiol Aging 36(1):547.e5-11, the entire contents of each of which are incorporated herein by reference. However, the clinical significance of these mutations has been highly debated and the most widely accepted view is that they represent variants of polymorphic nature. See, e.g., Rutten et al., (2013) Hypomorphic NOTCH3 alleles do not cause CADASIL in humans Hum Mutat. 34(11): 1486-9, the entire content of which is incorporated herein by reference. In a challenge to this paradigm, the data herein shows that a NOTCH3 knockout develops an SVD phenotype that can be rescued by expression of wild type NOTCH3 in mural cells, unambiguously linking NOTCH3 deficiency to SVD in an experimental model.

(iii) Because Notch signaling regulates a developmental program, it is unexpected that a process resulting from defective signaling could be corrected or prevented from being fulfilled. Accordingly, the ability of NOTCH3 agonism to prevent or treat mural cell loss is surprising.

NOTCH3

The NOTCH3 gene encodes the third discovered human homologue of the *Drosophila melanogaster* type I membrane protein notch. In *Drosophila*, notch's interaction with its cell-bound ligands (delta, serrate) establishes an intercellular signaling pathway that plays a key role in neural development. Homologues of the notch-ligands have also been identified in humans, but precise interactions between these ligands and the human notch homologues remains to be determined. NOTCH3 functions as a receptor for membrane-bound ligands such as JAGGED1, JAGGED2 and DELTA-LIKE1 to regulate cell-fate determination. NOTCH3 has been proposed to affect the implementation of differentiation, proliferation and apoptotic programs. Mutations in NOTCH3 have been identified as the underlying cause of cerebral autosomal dominant arteriopathy with subcortical infarcts and leukoencephalopathy (CADASIL) and other SVD conditions similar to CADASIL.

The cytogenetic band of the NOTCH3 gene has been reported to be 19p13.12 by Ensembl, 19p13.12 by Entrez Gene, and 19p13.12 by the HUGO Gene Nomenclature Committee. According to Ensemble, the location of the NOTCH3 gene is Chromosome 19: 15,159,038-15,200,981 reverse strand (Ensembl release 87—December 2016). Additionally, this gene maps to 15,269,849-15,311,792 in GRCh37 coordinates. Non-limiting examples of NOTCH3 genomic sequences are available from public databases such as Genbank (see, e.g., Accession Nos. NC_000019.10 and AH006054.2).

An amino acid sequence for human NOTCH3 is publically available in the UniProt database under accession number Q9UM47 (SEQ ID NO: 10) and is as follows (exemplary sites that may be substituted in subjects with SVD including CADASIL, cysteine-sparing mutations and Notch 3 loss of function mutations are bolded and underlined):

MGPGARGRRRRRRPMSPPPPPPPVRALPLLLLLAGPGAAAPPCLDGSPCANGGRCTQ

LPSREAACLCPPGWVGERCQLEDPCHSGPCAGRGVCQSSVVAGTARFSCRCPRGF

RGPDCSLPDPCLSSPCAHGARCSVGPDGRFLCSCPPGYQGRSCRSDVDECRVGEPC

RHGGTCLNTPGSFRCQCPAGYTGPLCENPAVPCAPSPCRNGGTCRQSGDLTYDCA

CLPGFEGQNCEVNVDDCPGHRCLNGGTCVDGVNTYNCQCPPEWTGQFCTEDVDE

CQLQPNACHNGGTCFNTLGGHSCVCVNGWTGESCSQNIDDCATAVCFHGATCHDR

VASFYCACPMGKTGLLCHLDDACVSNPCHEDAICDTNPVNGRAICTCPPGFTGGAC

DQDVDECSIGANPCEHLGRCVNTQGSFLCQCGRGYTGPRCETDVNECLSGPCRNQA

TCLDRIGQFTCICMAGFTGTYCEVDIDECQSSPCVNGGVCKDRVNGFSCTCPSGFSG

STCQLDVDECASTPCRNGAKCVDQPDGYECRCAEGFEGTLCDRNVDDCSPDPCHH

GRCVDGIASFSCACAPGYTGTRCESQVDECRSQPCRHGGKCLDLVDKYLCRCPSGT

-continued

TGVNCEVNIDDCASNPCTFGVCRDGINRYDCVCQPGFTGPLCNVEINECASSPCGEG

GSCVDGENGFRCLCPPGSLPPLCLPPSHPCAHEPCSHGICYDAPGGFRCVCEPGWSGP

RCSQSLARDACESQPCRAGGTCSSDGMGFHCTCPPGVQGRQCELLSPCTPNPCEHG

GRCESAPGQLPVCSCPQGWQGPRCQQDVDECAGPAPCGPHGICTNLAGSFSCTCHG

GYTGPSCDQDINDCDPNPCLNGGSCQDGVGSFSCSCLPGFAGPRCARDVDECLSNPC

GPGTCTDHVASFTCTCPPGYGGFHCEQDLPDCSPSSCFNGGTCVDGVNSFSCLCRPG

YTGAHCQHEADPCLSRPCLHGGVCSAAHPGFRCTCLESFTGPQCQTLVDWCSRQPC

QNGGRCVQTGAYCLCPPGWSGRLCDIRSLPCREAAAQIGVRLEQLCQAGGQCVDED

SSHYCVCPEGRTGSHCEQEVDPCLAQPCQHGGTCRGYMGGYMCCLPGYNGDNCE

DDVDECASQPCQHGGSCIDLVARYLCSCPPGTLGVLCEINEDDCGPGPPLDSGPRCL

HNGTCVDLVGGFRCTCPPGYTGLRCEADINECRSGACHAAHTRDCLQDPGGGFRCL

CHAGFSGPRCQTVLSPCESQPCQHGGQCLRPSPGPGGGLTFTCHCAQPFWGPRCERVA

RSCRELQCPVGVPCQQTPRGPRCACPPGLSGPSCRSFPGSPPGASNASCAAAPCLHGG

SCRPAPLAPFFRCACAQGWTGPRCEAPAAAPEVSEEPRCPRAACQAKRGDQRCDRE

CNSPGCGWDGGDCSLSVGDPWRQCEALQCWRLFNNSRCDPACSSPACLYDNFDCH

AGGRERTCNPVYEKYCADHFADGRCDQGCNTEECGWDGLDCASEVPALLARGVLV

LTVLLPPEELLRSSADFLQRLSAILRTSLRFRLDAHGQAMVFPYHRPSPGSEPRARREL

APEVIGSVVMLEIDNRLCLQSPENDHCFPDAQSAADYLGALSAVERLDFPYPLRDVR

GEPLEPPEPSVPLLPLLVAGAVLLLVILVLGVMVARRKREHSTLWFPEGFSLHKDVAS

GHKGRREPVGQDALGMKNMAKGESLMGEVATDWMDTECPEAKRLKVEEPGMGA

EEAVDCRQWTQHHLVAADIRVAPAMALTPPQGDADADGMDVNVRGPDGFTPLML

ASFCGGALEPMPTEEDEADDTSASIISDLICQGAQLGARTDRTGETALHLAARYARA

DAAKRLLDAGADTNAQDHSGRTPLHTAVTADAQGVFQILIRNRSTDLDARMADGST

ALILAARLAVEGMVEELIASHADVNAVDELGKSALHWAAAVNNVEATLALLKNGA

NKDMQDSKEETPLFLAAREGSYEAAKLLLDHFANREITDHLDRLPRDVAQERLHQDI

VRLLDQPSGPRSPPGPHGLGPLLCPPGAFLPGLKAAQSGSKKSRRPPGKAGLGPQGPR

GRGKKLTLACPGPLADSSVTLSPVDSLDSPRPFGGPPASPGGFPLEGPYAAATATAVS

LAQLGGPGRAGLGRQPPGGCVLSLGLLNPVAVPLDWARLPPPAPPGPSFLLPLAPGP

QLLNPGTPVSPQERPPPYLAVPGHGEEYPAAGAHSSPPKARFLRVPSEHPYLTPSPESP

EHWASPSPPSLSDWSESTPSPATATGAMATTTGALPAQPLPLSVPSSLAQAQTQLGPQ

PEVTPKRQVLA

A nucleotide sequence that encodes human NOTCH3 is publically available in the GenBank database under accession number NM_000435.2 and is as follows (the start and stop codons are underlined and bolded):

(SEQ ID No. 32)

GCGGCGCGGAGGCTGGCCCGGGACGCGCCCGGAGCCCAGGGAAGGAGGGAGGA

GGGGAGGGTCGCGGCCGGCCGCCATGGGGCCGGGGGCCCGTGGCCGCCGCCGC

CGCCGTCGCCCGATGTCGCCGCCACCGCCACCGCCACCCGTGCGGGCGCTGCCCC

TGCTGCTGCTGCTAGCGGGGCCGGGGCTGCAGCCCCCCCTTGCCTGGACGGAA

GCCCGTGTGCAAATGGAGGTCGTTGCACCCAGCTGCCCTCCCGGGAGGCTGCCTG

-continued

```
CCTGTGCCCGCCTGGCTGGGTGGGTGAGCGGTGTCAGCTGGAGGACCCCTGTCAC
TCAGGCCCCTGTGCTGGCCGTGGTGTCTGCCAGAGTTCAGTGGTGGCTGGCACCG
CCCGATTCTCATGCCGGTGCCCCCGTGGCTTCCGAGGCCCTGACTGCTCCCTGCC
AGATCCCTGCCTCAGCAGCCCTTGTGCCCACGGTGCCCGCTGCTCAGTGGGGCCC
GATGGACGCTTCCTCTGCTCCTGCCCACCTGGCTACCAGGGCCGCAGCTGCCGAA
GCGACGTGGATGAGTGCCGGGTGGGTGAGCCCTGCCGCCATGGTGGCACCTGCC
TCAACACACCTGGCTCCTTCCGCTGCCAGTGTCCAGCTGGCTACACAGGGCCACT
ATGTGAGAACCCCGCGGTGCCCTGTGCACCCTCACCATGCCGTAACGGGGGCAC
CTGCAGGCAGAGTGGCGACCTCACTTACGACTGTGCCTGTCTTCCTGGGTTTGAG
GGTCAGAATTGTGAAGTGAACGTGGACGACTGTCCAGGACACCGATGTCTCAAT
GGGGGGACATGCGTGGATGGCGTCAACACCTATAACTGCCAGTGCCCTCCTGAG
TGGACAGGCCAGTTCTGCACGGAGGACGTGGATGAGTGTCAGCTGCAGCCCAAC
GCCTGCCACAATGGGGGTACCTGCTTCAACACGCTGGGTGGCCACAGCTGCGTGT
GTGTCAATGGCTGGACAGGCGAGAGCTGCAGTCAGAATATCGATGACTGTGCCA
CAGCCGTGTGCTTCCATGGGGCCACCTGCCATGACCGCGTGGCTTCTTTCTACTGT
GCCTGCCCCATGGGCAAGACTGGCCTCCTGTGTCACCTGGATGACGCCTGTGTCA
GCAACCCCTGCCACGAGGATGCTATCTGTGACACAAATCCGGTGAACGGCCGGG
CCATTTGCACCTGTCCTCCCGGCTTCACGGGTGGGGCATGTGACCAGGATGTGGA
CGAGTGCTCTATCGGCGCCAACCCCTGCGAGCACTTGGGCAGGTGCGTGAACAC
GCAGGGCTCCTTCCTGTGCCAGTGCGGTCGTGGCTACACTGGACCTCGCTGTGAG
ACCGATGTCAACGAGTGTCTGTCGGGGCCCTGCCGAAACCAGGCCACGTGCCTC
GACCGCATAGGCCAGTTCACCTGTATCTGTATGGCAGGCTTCACAGGAACCTATT
GCGAGGTGGACATTGACGAGTGTCAGAGTAGCCCCTGTGTCAACGGTGGGGTCT
GCAAGGACCGAGTCAATGGCTTCAGCTGCACCTGCCCCTCGGGCTTCAGCGGCTC
CACGTGTCAGCTGGACGTGGACGAATGCGCCAGCACGCCCTGCAGGAATGGCGC
CAAATGCGTGGACCAGCCCGATGGCTACGAGTGCCGCTGTGCCGAGGGCTTTGA
GGGCACGCTGTGTGATCGCAACGTGGACGACTGCTCCCCTGACCCATGCCACCAT
GGTCGCTGCGTGGATGGCATCGCCAGCTTCTCATGTGCCTGTGCTCCTGGCTACA
CGGGCACACGCTGCGAGAGCCAGGTGGACGAATGCCGCAGCCAGCCCTGCCGCC
ATGGCGGCAAATGCCTAGACCTGGTGGACAAGTACCTCTGCCGCTGCCCTTCTGG
GACCACAGGTGTGAACTGCGAAGTGAACATTGACGACTGTGCCAGCAACCCCTG
CACCTTTGGAGTCTGCCGTGATGGCATCAACCGCTACGACTGTGTCTGCCAACCT
GGCTTCACAGGGCCCCTTTGTAACGTGGAGATCAATGAGTGTGCTTCCAGCCCAT
GCGGCGAGGGAGGTTCCTGTGTGGATGGGAAATGGCTTCCGCTGCCTCTGCCC
GCCTGGCTCCTTGCCCCCACTCTGCCTCCCCCGAGCCATCCCTGTGCCCATGAG
CCCTGCAGTCACGGCATCTGCTATGATGCACCTGGCGGGTTCCGCTGTGTGTGTG
AGCCTGGCTGGAGTGGCCCCGCTGCAGCCAGAGCCTGGCCCGAGACGCCTGTG
AGTCCCAGCCGTGCAGGGCCGGTGGGACATGCAGCAGCGATGGAATGGGTTTCC
ACTGCACCTGCCCGCCTGGTGTCCAGGGACGTCAGTGTGAACTCCTCTCCCCCTG
CACCCCGAACCCCTGTGAGCATGGGGGCCGCTGCGAGTCTGCCCCTGGCCAGCT
```

-continued
```
GCCTGTCTGCTCCTGCCCCAGGGCTGGCAAGGCCCACGATGCCAGCAGGATGT

GGACGAGTGTGCTGGCCCCGCACCCTGTGGCCCTCATGGTATCTGCACCAACCTG

GCAGGGAGTTTCAGCTGCACCTGCCATGGAGGGTACACTGGCCCTTCCTGCGATC

AGGACATCAATGACTGTGACCCCAACCCATGCCTGAACGGTGGCTCGTGCCAAG

ACGGCGTGGGCTCCTTTTCCTGCTCCTGCCTCCCTGGTTTCGCCGGCCCACGATGC

GCCCGCGATGTGGATGAGTGCCTGAGCAACCCCTGCGGCCCGGGCACCTGTACC

GACCACGTGGCCTCCTTCACCTGCACCTGCCCGCCAGGCTACGGAGGCTTCCACT

GCGAACAGGACCTGCCCGACTGCAGCCCCAGCTCCTGCTTCAATGGCGGGACCT

GTGTGGACGGCGTGAACTCGTTCAGCTGCCTGTGCCGTCCCGGCTACACAGGAGC

CCACTGCCAACATGAGGCAGACCCCTGCCTCTCGCGGCCCTGCCTACACGGGGG

CGTCTGCAGCGCCGCCCACCCTGGCTTCCGCTGCACCTGCCTCGAGAGCTTCACG

GGCCCGCAGTGCCAGACGCTGGTGGATTGGTGCAGCCGCCAGCCTTGTCAAAAC

GGGGGTCGCTGCGTCCAGACTGGGGCCTATTGCCTTTGTCCCCCTGGATGGAGCG

GACGCCTCTGTGACATCCGAAGCTTGCCCTGCAGGGAGGCCGCAGCCCAGATCG

GGGTGCGGCTGGAGCAGCTGTGTCAGGCGGGTGGGCAGTGTGTGGATGAAGACA

GCTCCCACTACTGCGTGTGCCCAGAGGGCCGTACTGGTAGCCACTGTGAGCAGG

AGGTGGACCCCTGCTTGGCCCAGCCCTGCCAGCATGGGGGGACCTGCCGTGGCT

ATATGGGGGGCTACATGTGTGAGTGTCTTCCTGGCTACAATGGTGATAACTGTGA

GGACGACGTGGACGAGTGTGCCTCCCAGCCCTGCCAGCACGGGGGTTCATGCAT

TGACCTCGTGGCCCGCTATCTCTGCTCCTGTCCCCCAGGAACGCTGGGGGTGCTC

TGCGAGATTAATGAGGATGACTGCGGCCCAGGCCCACCGCTGGACTCAGGGCCC

CGGTGCCTACACAATGGCACCTGCGTGGACCTGGTGGGTGGTTTCCGCTGCACCT

GTCCCCCAGGATACACTGGTTTGCGCTGCGAGGCAGACATCAATGAGTGTCGCTC

AGGTGCCTGCCACGCGGCACACACCCGGGACTGCCTGCAGGACCCAGGCGGAGG

TTTCCGTTGCCTTTGTCATGCTGGCTTCTCAGGTCCTCGCTGTCAGACTGTCCTGT

CTCCCTGCGAGTCCCAGCCATGCCAGCATGGAGGCCAGTGCCGTCCTAGCCCGG

GTCCTGGGGGTGGGCTGACCTTCACCTGTCACTGTGCCCAGCCGTTCTGGGGTCC

GCGTTGCGAGCGGGTGGCGCGCTCCTGCCGGGAGCTGCAGTGCCCGGTGGGCGT

CCCATGCCAGCAGACGCCCCGCGGGCCGCGCTGCGCCTGCCCCCCAGGGTTGTC

GGGACCCTCCTGCCGCAGCTTCCCGGGGTCGCCGCCGGGGGCCAGCAACGCCAG

CTGCGCGGCCGCCCCCTGTCTCCACGGGGGCTCCTGCCGCCCCGCGCCGCTCGCG

CCCTTCTTCCGCTGCGCTTGCGCGCAGGGCTGGACCGGGCCGCGCTGCGAGGCGC

CCGCCGCGGCACCCGAGGTCTCGGAGGAGCCGCGGTGCCCGCGCGCCGCCTGCC

AGGCCAAGCGCGGGGACCAGCGCTGCGACCGCGAGTGCAACAGCCCAGGCTGC

GGCTGGGACGGCGGCGACTGCTCGCTGAGCGTGGGCGACCCCTGGCGGCAATGC

GAGGCGCTGCAGTGCTGGCGCCTCTTCAACAACAGCCGCTGCGACCCCGCCTGC

AGCTCGCCCGCCTGCCTCTACGACAACTTCGACTGCCACGCCGGTGGCCGCGAGC

GCACTTGCAACCCGGTGTACGAGAAGTACTGCGCCGACCACTTTGCCGACGGCC

GCTGCGACCAGGGCTGCAACACGGAGGAGTGCGGCTGGGATGGGCTGGATTGTG

CCAGCGAGGTGCCGGCCCTGCTGGCCCGCGGCGTGCTGGTGCTCACAGTGCTGCT

GCCGCCAGAGGAGCTACTGCGTTCCAGCGCCGACTTTCTGCAGCGGCTCAGCGCC
```

-continued

```
ATCCTGCGCACCTCGCTGCGCTTCCGCCTGGACGCGCACGGCCAGGCCATGGTCT

TCCCTTACCACCGGCCAGTCCTGGCTCCGAACCCCGGGCCCGTCGGGAGCTGGC

CCCCGAGGTGATCGGCTCGGTAGTAATGCTGGAGATTGACAACCGGCTCTGCCTG

CAGTCGCCTGAGAATGATCACTGCTTCCCCGATGCCCAGAGCGCCGCTGACTACC

TGGGAGCGTTGTCAGCGGTGGAGCGCCTGGACTTCCCGTACCCACTGCGGGACGT

GCGGGGGAGCCGCTGGAGCCTCCAGAACCCAGCGTCCCGCTGCTGCCACTGCT

AGTGGCGGGCGCTGTCTTGCTGCTGGTCATTCTCGTCCTGGGTGTCATGGTGGCC

CGGCGCAAGCGCGAGCACAGCACCCTCTGGTTCCCTGAGGGCTTCTCACTGCACA

AGGACGTGGCCTCTGGTCACAAGGGCCGGCGGGAACCCGTGGGCCAGGACGCGC

TGGGCATGAAGAACATGGCCAAGGGTGAGAGCCTGATGGGGGAGGTGGCCACA

GACTGGATGGACACAGAGTGCCCAGAGGCCAAGCGGCTAAAGGTAGAGGAGCC

AGGCATGGGGGCTGAGGAGGCTGTGGATTGCCGTCAGTGGACTCAACACCATCT

GGTTGCTGCTGACATCCGCGTGGCACCAGCCATGGCACTGACACCACCACAGGG

CGACGCAGATGCTGATGGCATGGATGTCAATGTGCGTGGCCCAGATGGCTTCACC

CCGCTAATGCTGGCTTCCTTCTGTGGGGGGGCTCTGGAGCCAATGCCAACTGAAG

AGGATGAGGCAGATGACACATCAGCTAGCATCATCTCCGACCTGATCTGCCAGG

GGGCTCAGCTTGGGGCACGGACTGACCGTACTGGCGAGACTGCTTTGCACCTGGC

TGCCCGTTATGCCCGTGCTGATGCAGCCAAGCGGCTGCTGGATGCTGGGGCAGAC

ACCAATGCCCAGGACCACTCAGGCCGCACTCCCCTGCACACAGCTGTCACAGCC

GATGCCCAGGGTGTCTTCCAGATTCTCATCCGAAACCGCTCTACAGACTTGGATG

CCCGCATGGCAGATGGCTCAACGGCACTGATCCTGGCGGCCCGCCTGGCAGTAG

AGGGCATGGTGGAAGAGCTCATCGCCAGCCATGCTGATGTCAATGCTGTGGATG

AGCTTGGGAAATCAGCCTTACACTGGGCTGCGGCTGTGAACAACGTGGAAGCCA

CTTTGGCCCTGCTCAAAAATGGAGCCAATAAGGACATGCAGGATAGCAAGGAGG

AGACCCCCCTATTCCTGGCCGCCCGCGAGGGCAGCTATGAGGCTGCCAAGCTGCT

GTTGGACCACTTTGCCAACCGTGAGATCACCGACCACCTGGACAGGCTGCCGCG

GGACGTAGCCCAGGAGAGACTGCACCAGGACATCGTGCGCTTGCTGGATCAACC

CAGTGGGCCCCGCAGCCCCCCCGGTCCCCACGGCCTGGGGCCTCTGCTCTGTCCT

CCAGGGGCCTTCCTCCCTGGCCTCAAAGCGGCACAGTCGGGGTCCAAGAAGAGC

AGGAGGCCCCCGGGAAGGCGGGGCTGGGGCCGCAGGGGCCCCGGGGCGGGG

CAAGAAGCTGACGCTGGCCTGCCCGGGCCCCCTGGCTGACAGCTCGGTCACGCT

GTCGCCCGTGGACTCGCTGGACTCCCCGCGGCCTTTCGGTGGGCCCCCTGCTTCC

CCTGGTGGCTTCCCCCTTGAGGGGCCCTATGCAGCTGCCACTGCCACTGCAGTGT

CTCTGGCACAGCTTGGTGGCCCAGGCCGGGCGGGTCTAGGGCGCCAGCCCCCTG

GAGGATGTGTACTCAGCCTGGGCCTGCTGAACCCTGTGGCTGTGCCCCTCGATTG

GGCCCGGCTGCCCCCACCTGCCCCTCCAGGCCCCTCGTTCCTGCTGCCACTGGCG

CCCGGGACCCCAGCTGCTCAACCCAGGGACCCCCGTCTCCCCGCAGGAGCGGCCC

CCGCCTTACCTGGCAGTCCCAGGACATGGCGAGGAGTACCCGGCGGCTGGGGCA

CACAGCAGCCCCCAAAGGCCCGCTTCCTGCGGGTTCCCAGTGAGCACCCTTACC

TGACCCCATCCCCCGAATCCCCTGAGCACTGGGCCAGCCCCTCACCTCCCTCCCT
```

```
CTCAGACTGGTCCGAATCCACGCCTAGCCCAGCCACTGCCACTGGGGCCATGGCC

ACCACCACTGGGGCACTGCCTGCCCAGCCACTTCCCTTGTCTGTTCCCAGCTCCCT

TGCTCAGGCCCAGACCCAGCTGGGGCCCCAGCCGGAAGTTACCCCCAAGAGGCA

AGTGTTGGCCTGAGACGCTCGTCAGTTCTTAGATCTTGGGGGCCTAAAGAGACCC

CCGTCCTGCCTCCTTTCTTTCTCTGTCTCTTCCTTCCTTTTAGTCTTTTTCATCCTCT

TCTCTTTCCACCAACCCTCCTGCATCCTTGCCTTGCAGCGTGACCGAGATAGGTC

ATCAGCCCAGGGCTTCAGTCTTCCTTTATTTATAATGGGTGGGGGCTACCACCCA

CCCTCTCAGTCTTGTGAAGAGTCTGGGACCTCCTTCTTCCCCACTTCTCTCTTCCC

TCATTCCTTTCTCTCTCCTTCTGGCCTCTCATTTCCTTACACTCTGACATGAATGAA

TTATTATTATTTTTATTTTTCTTTTTTTTTTACATTTTGTATAGAAACAAATTCATT

TAAACAAACTTATTATTATTATTTTTTACAAAATATATATATGGAGATGCTCCCTC

CCCCTGTGAACCCCCCAGTGCCCCCGTGGGGCTGAGTCTGTGGGCCCATTCGGCC

AAGCTGGATTCTGTGTACCTAGTACACAGGCATGACTGGGATCCCGTGTACCGAG

TACACGACCCAGGTATGTACCAAGTAGGCACCCTTGGGCGCACCCACTGGGGCC

AGGGGTCGGGGAGTGTTGGGAGCCTCCTCCCCACCCCACCTCCCTCACTTCACT

GCATTCCAGATGGGACATGTTCCATAGCCTTGCTGGGGAAGGGCCCACTGCCAAC

TCCCTCTGCCCCAGCCCCACCCTTGGCCATCTCCCTTTGGGAACTAGGGGGCTGC

TGGTGGGAAATGGGAGCCAGGGCAGATGTATGCATTCCTTTGTGTCCCTGTAAAT

GTGGGACTACAAGAAGAGGAGCTGCCTGAGTGGTACTTTCTCTTCCTGGTAATCC

TCTGGCCCAGCCTCATGGCAGAATAGAGGTATTTTTAGGCTATTTTTGTAATATG

GCTTCTGGTCAAAATCCCTGTGTAGCTGAATTCCCAAGCCCTGCATTGTACAGCC

CCCCACTCCCCTCACCACCTAATAAAGGAATAGTTAACACTCAAAAAAAAAAAA

AAAAAAA
```

In a NOTCH3-encoding mRNA sequence, each "T" in the sequence above would be a "U".

Another amino acid sequence for human NOTCH3 is publically available in the GenBank database under accession number AAB91371.1 and is as follows:

(SEQ ID No. 33)
```
MGPGARGRRRRRRPMSPPPPPPPVRALPLLLLLAGPGAAAPPCLDGSPCANGGRCTQ

LPSREAACLCPPGWVGERCQLEDPCHSGPCAGRGVCQSSVVAGTARFSCRCPRGFR

GPDCSLPDPCLSSPCAHGARCSVGPDGRFLCSCPPGYQGRSCRSDVDECRVGEPCRH

GGTCLNTPGSFRCQCPAGYTGPLCENPAVPCAPSPCRNGGTCRQSGDLTYDCACLPG

FEGQNCEVNVDDCPGHRCLNGGTCVDGVNTYNCQCPPEWTGQFCTEDVDECQLQP

NACHNGGTCFNTLGGHSCVCVNGWTGESCSQNIDDCATAVCFHGATCHDRVASFY

CACPMGKTGLLCHLDDACVSNPCHEDAICDTNPVNGRAICTCPPGFTGGACDQDVD

ECSIGANPCEHLGRCVNTQGSFLCQCGRGYTGPRCETDVNECLSGPCRNQATCLDRI

GQFTCICMAGFTGTYCEVDIDECQSSPCVNGGVCKDRVNGFSCTCPSGFSGSTCQLD

VDECASTPCRNGAKCVDQPDGYECRCAEGFEGTLCDRNVDDCSPDPCHHGRCVDGI

ASFSCACAPGYTGTRCESQVDECRSQPCRHGGKCLDLVDKYLCRCPSGTTGVNCEV

NIDDCASNPCTFGVCRDGINRYDCVCQPGFTGPLCNVEINECASSPCGEGGSCVDGE

NGFRCLCPPGSLPPLCLPPSHPCAHEPCSHGICYDAPGGFRCVCEPGWSGPRCSQSLA
```

-continued

RDACESQPCRAGGTCSSDGMGFHCTCPPGVQGRQCELLSPCTPNPCEHGGRCESAPG

QLPVCSCPQGWQGPRCQQDVDECAGPAPCGPHGICTNLAGSFSCTCHGGYTGPSCD

QDINDCDPNPCLNGGSCQDGVGSFSCSCLPGFAGPRCARDVDECLSNPCGPGTCTDH

VASFTCTCPPGYGGFHCEQDLPDCSPSSCFNGGTCVDGVNSFSCLCRPGYTGAHCQH

EADPCLSRPCLHGGVCSAAHPGFRCTCLESFTGPQCQTLVDWCSRQPCQNGGRCVQ

TGAYCLCPPGWSGRLCDIRSLPCREAAAQIGVRLEQLCQAGGQCVDEDSSHYCVCPE

GRTGSHCEQEVDPCLAQPCQHGGTCRGYMGGYMCECLPGYNGDNCEDDVDECAS

QPCQHGGSCIDLVARYLCSCPPGTLGVLCEINEDDCGPGPPLDSGPRCLHNGTCVDL

VGGFRCTCPPGYTGLRCEADINECRSGACHAAHTRDCLQDPGGGFRCLCHAGFSGP

RCQTVLSPCESQPCQHGGQCRPSPGPGGGLTFTCHCAQPFWGPRCERVARSCRELQC

PVGVPCQQTPRGPRCACPPGLSGPSCRSFPGSPPGASNASCAAAPCLHGGSCRPAPLA

PFFRCACAQGWTGPRCEAPAAAPEVSEEPRCPRAACQAKRGDQRCDRECNSPGCGW

DGGDCSLSVGDPWRQCEALQCWRLFNNSRCDPACSSPACLYDNFDCHAGGRERTC

NPVYEKYCADHFADGRCDQGCNTEECGWDGLDCASEVPALLARGVLVLTVLLPPEE

LLRSSADFLQRLSAILRTSLRFRLDAHGQAMVFPYHRPSPGSEPRARRELAPEVIGSV

VMLEIDNRLCLQSPENDHCFPDAQSAADYLGALSAVERLDFPYPLRDVRGEPLEPPE

PSVPLLPLLVAGAVLLLVILVLGVMVARRKREHSTLWFPEGFSLHKDVASGHKGRRE

PVGQDALGMKNMAKGESLMGEVATDWMDTECPEAKRLKVEEPGMGAEEAVDCR

QWTQHHLVAADIRVAPAMALTPPQGDADADGMDVNVRGPDGFTPLMLASFCGGA

LEPMPTEEDEADDTSASIISDLICQGAQLGARTDRTGETALHLAARYARADAAKRLL

DAGADTNAQDHSGRTPLHTAVTADAQGVFQILIRNRSTDLDARMADGSTALILAAR

LAVEGMVEELIASHADVNAVDELGKSALHWAAAVNNVEATLALLKNGANKDMQD

SKEETPLFLAAREGSYEAAKLLLDHFANREITDHLDRLPRDVAQERLHQDIVRLLDQP

SGPRSPPGPHGLGPLLCPPGAFLPGLKAAQSGSKKSRRPPGKAGLGPQGPRGRGKKL

TLACPGPLADSSVTLSPVDSLDSPRPFGGPPASPGGFPLEGPYAAATATAVSLAQLGG

PGRAGLGRQPPGGCVLSLGLLNPVAVPLDWARLPPPAPPGPSFLLPLAPGPQLLNPGT

PVSPQERPPPYLAVPGHGEEYPVAGAHSSPPKARFLRVPSEHPYLTPSPESPEHWASPS

PPSLSDWSESTPSPATATGAMATTTGALPAQPLPLSVPSSLAQAQTQLGPQPEVTPKR

QVLA

A nucleotide sequence that encodes human NOTCH3 is publically available in the GenBank database under accession number U97669.1 (SEQ ID NO: 11) and is as follows (the start and stop codons are underlined and bolded):

ACGCGGCGCGGAGGCTGGCCCGGGACGCGCCCGGAGCCCAGGGAAGGAGGGAG

GAGGGGAGGGTCGCGGCCGGCCGCCATGGGGCCGGGGCCCGTGGCCGCCGCC

GCCGCCGTCGCCCGATGTCGCCGCCACCGCCACCGCCACCCGTGCGGGCGCTGCC

CCTGCTGCTGCTGCTAGCGGGGCCGGGGCTGCAGCCCCCCCTTGCCTGGACGGA

AGCCCGTGTGCAAATGGAGGTCGTTGCACCCAGCTGCCCTCCCGGGAGGCTGCCT

GCCTGTGCCCGCCTGGCTGGGTGGGTGAGCGGTGTCAGCTGGAGGACCCCTGTCA

CTCAGGCCCCTGTGCTGGCCGTGGTGTCTGCCAGAGTTCAGTGGTGGCTGGCACC

GCCCGATTCTCATGCCGGTGCCCCCGTGGCTTCCGAGGCCCTGACTGCTCCCTGC

-continued

```
CAGATCCCTGCCTCAGCAGCCCTTGTGCCCACGGTGCCCGCTGCTCAGTGGGCC

CGATGGACGCTTCCTCTGCTCCTGCCCACCTGGCTACCAGGGCCGCAGCTGCCGA

AGCGACGTGGATGAGTGCCGGGTGGGTGAGCCCTGCCGCCATGGTGGCACCTGC

CTCAACACACCTGGCTCCTTCCGCTGCCAGTGTCCAGCTGGCTACACAGGGCCAC

TATGTGAGAACCCCGCGGTGCCCTGTGCGCCCTCACCATGCCGTAACGGGGCA

CCTGCAGGCAGAGTGGCGACCTCACTTACGACTGTGCCTGTCTTCCTGGGTTTGA

GGGTCAGAATTGTGAAGTGAACGTGGACGACTGTCCAGGACACCGATGTCTCAA

TGGGGGGACATGCGTGGATGGCGTCAACACCTATAACTGCCAGTGCCCTCCTGA

GTGGACAGGCCAGTTCTGCACGGAGGACGTGGATGAGTGTCAGCTGCAGCCCAA

CGCCTGCCACAATGGGGGTACCTGCTTCAACACGCTGGGTGGCCACAGCTGCGT

GTGTGTCAATGGCTGGACAGGTGAGAGCTGCAGTCAGAATATCGATGACTGTGC

CACAGCCGTGTGCTTCCATGGGGCCACCTGCCATGACCGCGTGGCTTCTTTCTAC

TGTGCCTGCCCCATGGGCAAGACTGGCCTCCTGTGTCACCTGGATGACGCCTGTG

TCAGCAACCCCTGCCACGAGGATGCTATCTGTGACACAAATCCGGTGAACGGCC

GGGCCATTTGCACCTGTCCTCCCGGCTTCACGGGTGGGGCATGTGACCAGGATGT

GGACGAGTGCTCTATCGGCGCCAACCCCTGCGAGCACTTGGGCAGGTGCGTGAA

CACGCAGGGCTCCTTCCTGTGCCAGTGCGGTCGTGGCTACACTGGACCTCGCTGT

GAGACCGATGTCAACGAGTGTCTGTCGGGGCCCTGCCGAAACCAGGCCACGTGC

CTCGACCGCATAGGCCAGTTCACCTGTATCTGTATGGCAGGCTTCACAGGAACC

TATTGCGAGGTGGACATTGACGAGTGTCAGAGTAGCCCCTGTGTCAACGGTGGG

GTCTGCAAGGACCGAGTCAATGGCTTCAGCTGCACCTGCCCCTCGGGCTTCAGCG

GCTCCACGTGTCAGCTGGACGTGGACGAATGCGCCAGCACGCCCTGCAGGAATG

GCGCCAAATGCGTGGACCAGCCCGATGGCTACGAGTGCCGCTGTGCCGAGGGCT

TTGAGGGCACGCTGTGTGATCGCAACGTGGACGACTGCTCCCCTGACCCATGCCA

CCATGGTCGCTGCGTGGATGGCATCGCCAGCTTCTCATGTGCCTGTGCTCCTGGC

TACACGGGCACACGCTGCGAGAGCCAGGTGGACGAATGCCGCAGCCAGCCCTGC

CGCCATGGCGGCAAATGCCTAGACCTGGTGGACAAGTACCTCTGCCGCTGCCCTT

CTGGGACCACAGGTGTGAACTGCGAAGTGAACATTGACGACTGTGCCAGCAACC

CCTGCACCTTTGGAGTCTGCCGTGATGGCATCAACCGCTACGACTGTGTCTGCCA

ACCTGGCTTCACAGGGCCCCTTTGTAACGTGGAGATCAATGAGTGTGCTTCCAGC

CCATGCGGCGAGGGAGGTTCCTGTGTGGATGGGGAAAATGGCTTCCGCTGCCTCT

GCCCGCCTGGCTCCTTGCCCCCACTCTGCCTCCCCCCGAGCCATCCCTGTGCCCAT

GAGCCCTGCAGTCACGGCATCTGCTATGATGCACCTGGCGGGTTCCGCTGTGTGT

GTGAGCCTGGCTGGAGTGGCCCCCGCTGCAGCCAGAGCCTGGCCCGAGACGCCT

GTGAGTCCCAGCCGTGCAGGGCCGGTGGGACATGCAGCAGCGATGGAATGGGTT

TCCACTGCACCTGCCCGCCTGGTGTCCAGGGACGTCAGTGTGAACTCCTCTCCCC

CTGCACCCCGAACCCCTGTGAGCATGGGGGCCGCTGCGAGTCTGCCCCTGGCCA

GCTGCCTGTCTGCTCCTGCCCCCAGGGCTGGCAAGGCCCACGATGCCAGCAGGAT

GTGGACGAGTGTGCTGGCCCCGCACCCTGTGGCCCTCATGGTATCTGCACCAACC

TGGCAGGGAGTTTCAGCTGCACCTGCCATGGAGGGTACACTGGCCCTTCCTGTGA

TCAGGACATCAATGACTGTGACCCCAACCCATGCCTGAACGGTGGCTCGTGCCA
```

-continued

```
AGACGGCGTGGGCTCCTTTTCCTGCTCCTGCCTCCCTGGTTTCGCCGGCCCACGAT
GCGCCCGCGATGTGGATGAGTGCCTGAGCAACCCCTGCGGCCCGGGCACCTGTA
CCGACCACGTGGCCTCCTTCACCTGCACCTGCCCGCCGGGCTACGGAGGCTTCCA
CTGCGAACAGGACCTGCCCGACTGCAGCCCCAGCTCCTGCTTCAATGGCGGGAC
CTGTGTGGACGGCGTGAACTCGTTCAGCTGCCTGTGCCGTCCCGGCTACACAGGA
GCCCACTGCCAACATGAGGCAGACCCCTGCCTCTCGCGGCCCTGCCTACACGGG
GGCGTCTGCAGCGCCGCCCACCCTGGCTTCCGCTGCACCTGCCTCGAGAGCTTCA
CGGGCCCGCAGTGCCAGACGCTGGTGGATTGGTGCAGCCGCCAGCCTTGTCAAA
ACGGGGGTCGCTGCGTCCAGACTGGGGCCTATTGCCTTTGTCCCCCTGGATGGAG
CGGACGCCTCTGTGACATCCGAAGCTTGCCCTGCAGGGAGGCCGCAGCCCAGAT
CGGGGTGCGGCTGGAGCAGCTGTGTCAGGCGGGTGGGCAGTGTGTGGATGAAGA
CAGCTCCCACTACTGCGTGTGCCCAGAGGGCCGTACTGGTAGCCACTGTGAGCA
GGAGGTGGACCCCTGCTTGGCCCAGCCCTGCCAGCATGGGGGACCTGCCGTGG
CTATATGGGGGCTACATGTGTGAGTGTCTTCCTGGCTACAATGGTGATAACTGT
GAGGACGACGTGGACGAGTGTGCCTCCCAGCCCTGCCAGCACGGGGGTTCATGC
ATTGACCTCGTGGCCCGCTATCTCTGCTCCTGTCCCCCAGGAACGCTGGGGGTGC
TCTGCGAGATTAATGAGGATGACTGCGGCCCAGGCCCACCGCTGGACTCAGGGC
CCCGGTGCCTACACAATGGCACCTGCGTGGACCTGGTGGGTGGTTTCCGCTGCAC
CTGTCCCCCAGGATACACTGGTTTGCGCTGCGAGGCAGACATCAATGAGTGTCGC
TCAGGTGCCTGCCACGCGGCACACACCCGGGACTGCCTGCAGGACCCAGGCGGA
GGTTTCCGTTGCCTTTGTCATGCTGGCTTCTCAGGTCCTCGCTGTCAGACTGTCCT
GTCTCCCTGCGAGTCCCAGCCATGCCAGCATGGAGGCCAGTGCCGTCCTAGCCCG
GGTCCTGGGGGTGGGCTGACCTTCACCTGTCACTGTGCCCAGCCGTTCTGGGGTC
CGCGTTGCGAGCGGGTGGCGCGCTCCTGCCGGGAGCTGCAGTGCCCGGTGGGCG
TCCCATGCCAGCAGACGCCCCGCGGGCCGCGCTGCGCCTGCCCCCCAGGGTTGTC
GGGACCCTCCTGCCGCAGCTTCCCGGGGTCGCCGCCGGGGGCCAGCAACGCCAG
CTGCGCGGCCGCCCCCTGTCTCCACGGGGGCTCCTGCCGCCCCGCGCCGCTCGCG
CCCTTCTTCCGCTGCGCTTGCGCGCAGGGCTGGACCGGGCCGCGCTGCGAGGCG
CCCGCCGCGGCACCCGAGGTCTCGGAGGAGCCGCGGTGCCCGCGCGCCGCCTGC
CAGGCCAAGCGCGGGGACCAGCGCTGCGACCGCGAGTGCAACAGCCCAGGCTGC
GGCTGGGACGGCGGCGACTGCTCGCTGAGCGTGGGCGACCCCTGGCGGCAATGC
GAGGCGCTGCAGTGCTGGCGCCTCTTCAACAACAGCCGCTGCGACCCCGCCTGC
AGCTCGCCCGCCTGCCTCTACGACAACTTCGACTGCCACGCCGGTGGCCGCGAGC
GCACTTGCAACCCGGTGTACGAGAAGTACTGCGCCGACCACTTTGCCGACGGCC
GCTGCGACCAGGGCTGCAACACGGAGGAGTGCGGCTGGGATGGGCTGGATTGTG
CCAGCGAGGTGCCGGCCCTGCTGGCCCGCGGCGTGCTGGTGCTCACAGTGCTGCT
GCCGCCGGAGGAGCTACTGCGTTCCAGCGCCGACTTTCTGCAGCGGCTCAGCGCC
ATCCTGCGCACCTCGCTGCGCTTCCGCCTGGACGCGCACGGCCAGGCCATGGTCT
TCCCTTACCACCGGCCTAGTCCTGGCTCCGAACCCCGGGCCCGTCGGGAGCTGGC
CCCCGAGGTGATCGGCTCGGTAGTAATGCTGGAGATTGACAACCGGCTCTGCCTG
```

-continued

```
CAGTCGCCTGAGAATGATCACTGCTTCCCCGATGCCCAGAGCGCCGCTGACTACC

TGGGAGCGTTGTCAGCGGTGGAGCGCCTGGACTTCCCGTACCCACTGCGGGACGT

GCGGGGGGAGCCGCTGGAGCCTCCAGAACCCAGCGTCCCGCTGCTGCCACTGCT

AGTGGCGGGCGCTGTCTTGCTGCTGGTCATTCTCGTCCTGGGTGTCATGGTGGCC

CGGCGCAAGCGCGAGCACAGCACCCTCTGGTTCCCTGAGGGCTTCTCACTGCACA

AGGACGTGGCCTCTGGTCACAAGGGCCGGCGGGAACCCGTGGGCCAGGACGCGC

TGGGCATGAAGAACATGGCCAAGGGTGAGAGCCTGATGGGGGAGGTGGCCACA

GACTGGATGGACACAGAGTGCCCAGAGGCCAAGCGGCTAAAGGTAGAGGAGCC

AGGCATGGGGGCTGAGGAGGCTGTGGATTGCCGTCAGTGGACTCAACACCATCT

GGTTGCTGCTGACATCCGCGTGGCACCAGCCATGGCACTGACACCACCACAGGG

CGACGCAGATGCTGATGGCATGGATGTCAATGTGCGTGGCCCAGATGGCTTCACC

CCGCTAATGCTGGCTTCCTTCTGTGGGGGGGCTCTGGAGCCAATGCCAACTGAAG

AGGATGAGGCAGATGACACATCAGCTAGCATCATCTCCGACCTGATCTGCCAGG

GGGCTCAGCTTGGGGCACGGACTGACCGTACTGGCGAGACTGCTTTGCACCTGGC

TGCCCGTTATGCCCGTGCTGATGCAGCCAAGCGGCTGCTGGATGCTGGGGCAGAC

ACCAATGCCCAGGACCACTCAGGCCGCACTCCCCTGCACACAGCTGTCACAGCC

GATGCCCAGGGTGTCTTCCAGATTCTCATCCGAAACCGCTCTACAGACTTGGATG

CCCGCATGGCAGATGGCTCAACGGCACTGATCCTGGCGGCCCGCCTGGCAGTAG

AGGGCATGGTGGAAGAGCTCATCGCCAGCCATGCTGATGTCAATGCTGTGGATG

AGCTTGGGAAATCAGCCTTACACTGGGCTGCGGCTGTGAACAACGTGGAAGCCA

CTTTGGCCCTGCTCAAAAATGGAGCCAATAAGGACATGCAGGATAGCAAGGAGG

AGACCCCCCTATTCCTGGCCGCCCGCGAGGGCAGCTATGAGGCTGCCAAGCTGCT

GTTGGACCACTTTGCCAACCGTGAGATCACCGACCACCTGGACAGGCTGCCGCG

GGACGTAGCCCAGGAGAGACTGCACCAGGACATCGTGCGCTTGCTGGATCAACC

CAGTGGGCCCCGCAGCCCCCCGGTCCCCACGGCCTGGGGCCTCTGCTCTGTCCT

CCAGGGGCCTTCCTCCCTGGCCTCAAAGCGGCACAGTCGGGGTCCAAGAAGAGC

AGGAGGCCCCCGGGAAGGCGGGGCTGGGGCCGCAGGGGCCCCGGGGCGGGG

CAAGAAGCTGACGCTGGCCTGCCCGGGCCCCTGGCTGACAGCTCGGTCACGCT

GTCGCCCGTGGACTCGCTGGACTCCCCGCGGCCTTTCGGTGGGCCCCTGCTTCC

CCTGGTGGCTTCCCCCTTGAGGGGCCCTATGCAGCTGCCACTGCCACTGCAGTGT

CTCTGGCACAGCTTGGTGGCCCAGGCCGGGCAGGTCTAGGGCGCCAGCCCCCTG

GAGGATGTGTACTCAGCCTGGGCCTGCTGAACCCTGTGGCTGTGCCCCTCGATTG

GGCCCGGCTGCCCCCACCTGCCCCTCCAGGCCCCTCGTTCCTGCTGCCACTGGCG

CCGGGACCCCAGCTGCTCAACCCAGGGACCCCCGTCTCCCCGCAGGAGCGGCCC

CCGCCTTACCTGGCAGTCCCAGGACATGGCGAGGAGTACCCGGTGGCTGGGGCA

CACAGCAGCCCCCAAAGGCCCGCTTCCTGCGGGTTCCCAGTGAGCACCCTTACC

TGACCCCATCCCCCGAATCCCCTGAGCACTGGGCCAGCCCCTCACCTCCCTCCCT

CTCAGACTGGTCCGAATCCACGCCTAGCCCAGCCACTGCCACTGGGGCCATGGCC

ACCACCACTGGGGCACTGCCTGCCCAGCCACTTCCCTTGTCTGTTCCCAGCTCCCT

TGCTCAGGCCCAGACCCAGCTGGGGCCCCAGCCGGAAGTTACCCCCAAGAGGCA

AGTGTTGGCCTGAGACGCTCGTCAGTTCTTAGATCTTGGGGGCCTAAAGAGACCC
```

-continued

```
CCGTCCTGCCTCCTTTCTTTCTCTGTCTCTTCCTTCCTTTTAGTCTTTTTCATCCTCT

TCTCTTTCCACCAACCCTCCTGCATCCTTGCCTTGCAGCGTGACCGAGATAGGTC

ATCAGCCCAGGGCTTCAGTCTTCCTTTATTTATAATGGGTGGGGGCTACCACCCA

CCCTCTCAGTCTTGTGAAGAGTCTGGGACCTCCTTCTTCCCCACTTCTCTCTTCCC

TCATTCCTTTCTCTCTCCTTCTGGCCTCTCATTTCCTTACACTCTGACATGAATGAA

TTATTATTATTTTTCTTTTTCTTTTTTTTTTACATTTTGTATAGAAACAAATTCATT

TAAACAAACTTATTATTATTATTTTTTACAAAATATATATATGGAGATGCTCCCTC

CCCCTGTGAACCCCCCAGTGCCCCCGTGGGGCTGAGTCTGTGGGCCCATTCGGCC

AAGCTGGATTCTGTGTACCTAGTACACAGGCATGACTGGGATCCCGTGTACCGAG

TACACGACCCAGGTATGTACCAAGTAGGCACCCTTGGGCGCACCCACTGGGGCC

AGGGGTCGGGGGAGTGTTGGGAGCCTCCTCCCCACCCCACCTCCCTCACTTCACT

GCATTCCAGATTGGACATGTTCCATAGCCTTGCTGGGGAAGGGCCCACTGCCAAC

TCCCTCTGCCCCAGCCCCACCCTTGGCCATCTCCCTTTGGGAACTAGGGGCTGC

TGGTGGGAAATGGGAGCCAGGGCAGATGTATGCATTCCTTTATGTCCCTGTAAAT

GTGGGACTACAAGAAGAGGAGCTGCCTGAGTGGTACTTTCTCTTCCTGGTAATCC

TCTGGCCCAGCCTTATGGCAGAATAGAGGTATTTTTAGGCTATTTTTGTAATATG

GCTTCTGGTCAAAATCCCTGTGTAGCTGAATTCCCAAGCCCTGCATTGTACAGCC

CCCCACTCCCCTCACCACCTAATAAAGGAATAGTTAACACTCAAAAAAAAAAAA

AAAAAAA
```

In a NOTCH3-encoding mRNA sequence, each "T" in the sequence above would be a "U".

The human NOTCH3 ectodomain sequence comprises amino acid positions 40 to 1571 of accession number Q9UM47. With respect to embodiments relating to CADASIL, the ectodomain comprises the extracellular domain until the furin cleavage site. This excludes the signal peptide from positions 1 to 39 and also excludes the 1572 to 2321 amino acid region encompassing a small portion that is extracellular, the transmembrane domain, and the intracellular domain.

An amino acid sequence for human N3ECD is:

```
                                                    (SEQ ID NO: 12)
APPCLDGSPC ANGGRCTQLP SREAACLCPP GWVGERCQLE DPCHSGPCAG

RGVCQSSVVAGTARFSCRCP RGFRGPDCSL PDPCLSSPCA HGARCSVGPD

GRFLCSCPPG YQGRSCRSDVDECRVGEPCR HGGTCLNTPG SFRCQCPAGY

TGPLCENPAV PCAPSPCRNG GTCRQSGDLTYDCACLPGFE GQNCEVNVDD

CPGHRCLNGG TCVDGVNTYN CQCPPEWTGQ FCTEDVDECQLQPNACHNGG

TCFNTLGGHS CVCVNGWTGE SCSQNIDDCA TAVCFHGATC HDRVASFYCA

CPMGKTGLLC HLDDACVSNP CHEDAICDTN PVNGRAICTC PPGFTGGACD

QDVDECSIGANPCEHLGRCV NTQGSFLCQCGRGYTGPRCE TDVNECLSGP

CRNQATCLDR IGQFTCICMAGFTGTYCEVD IDECQSSPCV NGGVCKDRVN

GFSCTCPSGF SGSTCQLDVD ECASTPCRNGAKCVDQPDGY ECRCAEGFEG

TLCDRNVDDC SPDPCHHGRC VDGIASFSCA CAPGYTGTRCESQVDECRSQ

PCRHGGKCLD LVDKYLCRCP SGTTGVNCEV NIDDCASNPC TFGVCRDGIN

RYDCVCQPGF TGPLCNVEIN ECASSPCGEG GSCVDGENGF RCLCPPGSLP

PLCLPPSHPCAHEPCSHGIC YDAPGGFRCV CEPGWSGPRC SQSLARDACE

SQPCRAGGTC SSDGMGFHCTCPPGVQGRQC ELLSPCTPNP CEHGGRCESA
```

-continued

```
PGQLPVCSCP QGWQGPRCQQ DVDECAGPAPCGPHGICTNL AGSFSCTCHG

GYTGPSCDQD INDCDPNPCL NGGSCQDGVG SFSCSCLPGFAGPRCARDVD

ECLSNPCGPG TCTDHVASFT CTCPPGYGGF HCEQDLPDCS PSSCFNGGTC

VDGVNSFSCL CRPGYTGAHC QHEADPCLSR PCLHGGVCSA AHPGFRCTCL

ESFTGPQCQTLVDWCSRQPC QNGGRCVQTG AYCLCPPGWS GRLCDIRSLP

CREAAAQIGV RLEQLCQAGG QCVDEDSSHY CVCPEGRTGSHCEQEVDPCL

AQPCQHGGTC RGYMGGYMCE CLPGYNGDNCEDDVDECASQ PCQHGGSCID

LVARYLCSCP PGTLGVLCEI NEDDCGPGPP LDSGPRCLHNGTCVDLVGGF

RCTCPPGYTG LRCEADINEC RSGACHAAHT RDCLQDPGGG FRCLCHAGFS

GPRCQTVLSP CESQPCQHGG QCRPSPGPGG GLTFTCHCAQ PFWGPRCERV

ARSCRELQCPVGVPCQQTPR GPRCACPPGL SGPSCRSFPG SPPGASNASC

AAAPCLHGGS CRPAPLAPFFRCACAQGWTG PRCEAPAAAP EVSEEPRCPR

AACQAKRGDQ RCDRECNSPG CGWDGGDCSLSVGDPWRQCE ALQCWRLFNN

SRCDPACSSP ACLYDNFDCH AGGRERTCNP VYEKYCADHFADGRCDQGCN

TEECGWDGLD CASEVPALLA RGVLVLTVLL PPEELLRSSA DFLQRLSAILR

TSLRFRLDAHGQAMVFPYHR PSPGSEPRARR
```

The amino acid sequence for mouse N3ECD runs from positions 40 to 1572 of the amino acid sequence that is available in the UniProt database under accession number Q61982 (SEQ ID NO: 13), and is as follows:

```
                                                  (SEQ ID NO: 13)
APPCLDGSPC ANGGRCTHQQ PSLEAACLCL PGWVGERCQL EDPCHSGPCA

GRGVCQSSVVAGTARFSCRC LRGFQGPDCS QPDPCVSRPC VHGAPCSVGP

DGRFACACPP GYQGQSCQSDIDECRSGTTC RHGGTCLNTP GSFRCQCPLG

YTGLLCENPV VPCAPSPCRN GGTCRQSSDVTYDCACLPGF EGQNCEVNVD

DCPGHRCLNG GTCVDGVNTY NCQCPPEWTG QFCTEDVDECQLQPNACHNG

GTCFNLLGGH SCVCVNGWTG ESCSQNIDDC ATAVCFHGAT CHDRVASFYC

ACPMGKTGLL CHLDDACVSN PCHEDAICDT NPVSGRAICT CPPGFTGGAC

DQDVDECSIGANPCEHLGRC VNTQGSFLCQ CGRGYTGPRC ETDVNECLSG

PCRNQATCLD RIGQFTCICMAGFTGTYCEV DIDECQSSPC VNGGVCKDRV

NGFSCTCPSG FSGSMCQLDV DECASTPCRNGAKCVDQPDG YECRCAEGIth

GTLCERNVDD CSPDPCHHGR CVDGIASFSC ACAPGYTGIRCESQVDECRS

QPCRYGGKCL DLVDKYLCRC PPGTTGVNCE VNIDDCASNP CTFGVCRDGI

NRYDCVCQPG FTGPLCNVEI NECASSPCGE GGSCVDGENG FHCLCPPGSL

PPLCLPANHPCAHKPCSHGV CHDAPGGFRC VCEPGWSGPR CSQSLAPDAC

ESQPCQAGGT CTSDGIGFRCTCAPGFQGHQ CEVLSPCTPSLCEHGGHCES

DPDRLTVCSC PPGWQGPRCQ QDVDECAGASPCGPHGTCTN LPGNFRCICH

RGYTGPFCDQ DIDDCDPNPC LHGGSCQDGV GSFSCSCLDGFAGPRCARDV

DECLSSPCGP GTCTDHVASF TCACPPGYGG FHCEIDLPDC SPSSCFNGGT

CVDGVSSFSC LCRPGYTGTH CQYEADPCFS RPCLHGGICN PTHPGFECTC

REGFTGSQCQNPVDWCSQAP CQNGGRCVQT GAYCICPPGW SGRLCDIQSL

PCTEAAAQMG VRLEQLCQEGGKCIDKGRSH YCVCPEGRTG SHCEHEVDPC
```

-continued

```
TAQPCQHGGT CRGYMGGYVC ECPAGYAGDSCEDNIDECAS QPCQNGGSCI

DLVARYLCSC PPGTLGVLCE INEDDCDLGP SLDSGVQCLHNGTCVDLVGG

FRCNCPPGYT GLHCEADINE CRPGACHAAH TRDCLQDPGG HFRCYCHPGF

TGPRCQIALS PCESQPCQHG GQCRHSLGRG GGLTFTCHCV PPFWGLRCER

VARSCRELQCPVGIPCQQTA RGPRCACPPG LSGPSCRVSR ASPSGATNAS

CASAPCLHGG SCLPVQSVPFFRCVCAPGWG GPRCETPSAA PEVPEEPRCP

RAACQAKRGD QNCDRECNTP GCGWDGGDCSLNVDDPWRQC EALQCWRLFN

NSRCDPACSS PACLYDNFDC YSGGRDRTCN PVYEKYCADHFADGRCDQGC

NTEECGWDGL DCASEVPALL ARGVLVLTVL LPPEELLRSS ADFLQRLSAIL

RTSLRFRLDARGQAMVFPYH RPSPGSESRV RR
```

Endostatin

Endostatin is a naturally-occurring, 20-kDa C-terminal fragment derived collagen18α1 (which is encoded by the COL18A1 gene). Endostatin is cleaved off collagen18α1. It is reported to serve as an anti-angiogenic agent, similar to angiostatin and thrombospondin. Endostatin is a broad-spectrum angiogenesis inhibitor and may interfere with the pro-angiogenic action of growth factors such as basic fibroblast growth factor (bFGF/FGF-2) and vascular endothelial growth factor (VEGF).

A binding agent (e.g., an antibody) that specifically binds endostatin may also bind full-length collagen18α1. In various embodiments, it is not necessary to distinguish endostatin that is detected from collagen18α1 (i.e., it is not necessary to rule out or determine that a portion of the endostatin detected is full-length collagen18α1).

An amino acid sequence for human endostatin is publically available in the UniProt database as positions 1572-1754 of accession number P39060 (SEQ ID NO: 24) and is as follows:

```
HSHRDFQPVLHLVALNSPLSGGMRGIRGADFQCFQQARAVGLAGTFRAF

LSSRLQDLYSIVRRADRAAVPIVNLKDELLFPSWEALFSGSEGPLKPGA

RIFSFDGKDVLRHPTWPQKSVWHGSDPNGRRLTESYCETWRTEAPSATG

QASSLLGGRLLGQSAASCHHAYIVLCIENSFMTASK
```

A nucleotide sequence that encodes human endostatin is publically available in the GenBank database as positions 4021-4569 of accession number NM_030582.3 (SEQ ID NO: 25) and is as follows:

```
CACAGCCACC GCGACTTCCA GCCGGTGCTC CACCTGGTTG

CGCTCAACAG CCCCCTGTCA GGCGGCATGC GGGGCATCCG

CGGGGCCGAC TTCCAGTGCT TCCAGCAGGC GCGGGCCGTG GGGCTGG

CGG GCACCTTCCG CGCCTTCCTG TCCTCGCGCC TGCAGGACCT

GTACAGCATCGTGCGCCGTG CCGACCGCGC AGCCGTGCCC

ATCGTCAACC TCAAGGACGA GCTGCTGTTT CCCAGCTGGG

AGGCTCTGTT CTCAGGCTCT GAGGGTCCGC TGAAGCCCGG

GGCACGCAT CTTCTCCTTTG ACGGCAAGGA CGTCCTGAGG

CACCCCACCT GGCCCCAGAA GAGCGTGTGG CATGGCTCGG

ACCCCAACGG GCGCAGGCTG ACCGAGAGCT ACTGTGAGAC

GTGGCGGACGGAGGCTCCCT CGGCCACGGG CCAGGCCTCC

TCGCTGCTGG GGGGCAGGCT CCTGGGGCAG AGTGCCGCGA

GCTGCCATCA CGCCTACATC GTGCTCTGCA TTGAGAACAG

CTTCATGACTGCCTCCAAG
```

IGFBP-1

IGFBP-1 is a member of the insulin-like growth factor binding protein (IGFBP) family and encodes a protein with an IGFBP domain and a thyroglobulin type-I domain. The protein binds both insulin-like growth factors (IGFs) I and II and circulates in the plasma. Binding of this protein prolongs the half-life of the IGFs and alters their interaction with cell surface receptors.

An amino acid sequence for human IGFBP-1 is publically available in the UniProt database under accession number P08833 (SEQ ID NO: 26) and is as follows:

```
MSEVPVARVWLVLLLLTVQVGVTAGAPWQCAPCSAEKLALCPPVSASCSE

VTRSAGCGCCPMCALPLGAACGVATARCARGLSCRALPGEQQPLHALTRG

QGACVQESDASAPHAAEAGSPESPESTEITEEELLDNFHLMAPSEEDHSI

LWDAISTYDGSKALHVTNIKKWKEPCRIELYRVVESLAKAQETSGEEISK

FYLPNCNKNGFYHSRQCETSMDGEAGLCWCVYPWNGKRIPGSPEIRGDPN

CQIYFNVQN
```

A nucleotide sequence that encodes human IGFBP-1 is publically available in the GenBank database under accession number NM_000596.2 (SEQ ID NO: 27) and is as follows (the start and stop codons are underlined and bolded):

```
GGTGCACTAGCAAAACAAACTTATTTTGAACACTCAGCTCCTAGCGTGCGGCGCT

GCCAATCATTAACCTCCTGGTGCAAGTGGCGCGGCCTGTGCCCTTTATAAGGTGC
```

```
-continued
GCGCTGTGTCCAGCGAGCATCGGCCACCGCCATCCCATCCAGCGAGCATCTGCCG

CCGCGCCGCCGCCACCCTCCCAGAGAGCACTGGCCACCGCTCCACCATCACTTGC

CCAGAGTTTGGGCCACCGCCCGCCGCCACCAGCCCAGAGAGCATCGGCCCCTGT

CTGCTGCTCGCGCCTGGAGATGTCAGAGGTCCCCGTTGCTCGCGTCTGGCTGGTA

CTGCTCCTGCTGACTGTCCAGGTCGGCGTGACAGCCGGCGCTCCGTGGCAGTGCG

CGCCCTGCTCCGCCGAGAAGCTCGCGCTCTGCCCGCCGGTGTCCGCCTCGTGCTC

GGAGGTCACCCGGTCCGCCGGCTGCGGCTGTTGCCCGATGTGCGCCCTGCCTCTG

GGCGCCGCGTGCGGCGTGGCGACTGCACGCTGCGCCCGGGGACTCAGTTGCCGC

GCGCTGCCGGGGGAGCAGCAACCTCTGCACGCCCTCACCCGCGGCCAAGGCGCC

TGCGTGCAGGAGTCTGACGCCTCCGCTCCCCATGCTGCAGAGGCAGGGAGCCCT

GAAAGCCCAGAGAGCACGGAGATAACTGAGGAGGAGCTCCTGGATAATTTCCAT

CTGATGGCCCCTTCTGAAGAGGATCATTCCATCCTTTGGGACGCCATCAGTACCT

ATGATGGCTCGAAGGCTCTCCATGTCACCAACATCAAAAAATGGAAGGAGCCCT

GCCGAATAGAACTCTACAGAGTCGTAGAGAGTTTAGCCAAGGCACAGGAGACAT

CAGGAGAAGAAATTTCCAAATTTTACCTGCCAAACTGCAACAAGAATGGATTTTA

TCACAGCAGACAGTGTGAGACATCCATGGATGGAGAGGCGGGACTCTGCTGGTG

CGTCTACCCTTGGAATGGGAAGAGGATCCCTGGGTCTCCAGAGATCAGGGGAGA

CCCCAACTGCCAGATATATTTTAATGTACAAAACTGAAACCAGATGAAATAATG

TTCTGTCACGTGAAATATTTAAGTATATAGTATATTTATACTCTAGAACATGCAC

ATTTATATATATATGTATATGTATATATATATAGTAACTACTTTTTATACTCCATA

CATAACTTGATATAGAAAGCTGTTTATTTATTCACTGTAAGTTTATTTTTTCTACA

CAGTAAAAACTTGTACTATGTTAATAACTTGTCCTATGTCAATTTGTATATCATGA

AACACTTCTCATCATATTGTATGTAAGTAATTGCATTTCTGCTCTTCCAAAGCTCC

TGCGTCTGTTTTTAAAGAGCATGGAAAAATACTGCCTAGAAAATGCAAAATGAA

ATAAGAGAGAGTAGTTTTTCAGCTAGTTTGAAGGAGGACGGTTAACTTGTATATT

CCACCATTCACATTTGATGTACATGTGTAGGGAAAGTTAAAAGTGTTGATTACAT

AATCAAAGCTACCTGTGGTGATGTTGCCACCTGTTAAAATGTACACTGGATATGT

TGTTAAACACGTGTCTATAATGGAAACATTTACAATAAATATTCTGCATGGAAAT

ACTGTTAAAAAAAAAAA
```

HTRA1

HTRA1 is a serine protease with a variety of targets, including extracellular matrix proteins such as fibronectin. HTRA1-generated fibronectin fragments further induce synovial cells to up-regulate matrix metalloproteinase-1 (MMP1) and matrix metalloproteinase-3 (MMP3) production. HTRA1 may also degrade proteoglycans, such as aggrecan, decorin and fibromodulin. Through cleavage of proteoglycans, HTRA1 may release soluble fibroblast growth factor (FGF)-glycosaminoglycan complexes that promote the range and intensity of FGF signals in the extracellular space. HTRA1 is also thought to regulate the availability of insulin-like growth factors (IGFs) by cleaving IGF-binding proteins. HTRA1 is further believed to inhibit signaling mediated by transforming growth factor beta (TGF-β) family members. This activity requires the integrity of the catalytic site, although it is unclear whether TGF-τ3 proteins are themselves degraded. By acting on TGF-τ3 signaling, HTRA1 may regulate many physiological processes, including retinal angiogenesis and neuronal survival and maturation during development. Intracellularly, HTRA1 degrades Tuberous Sclerosis Complex 2 (TSC2), leading to the activation of TSC2 downstream targets.

An amino acid sequence for human HTRA1 is publically available in the UniProt database under accession number Q92743 (SEQ ID NO: 28) and is as follows:

```
MQIPRAALLPLLLLLLAAPASAQLSRAGRSAPLAAGCPDRCEPARCPPQP

EHCEGGRARDACGCCEVCGAPEGAACGLQEGPCGEGLQCVVPFGVPASAT

VRRRAQAGLCVCASSEPVCGSDANTYANLCQLRAASRRSERLHRPPVIVL

QRGACGQGQEDPNSLRHKYNFIADVVEKIAPAVVHIELFRKLPFSKREVP

VASGSGFIVSEDGLIVTNAHVVTNKHRVKVELKNGATYEAKIKDVDEKAD
```

-continued
IALIKIDHQGKLPVLLLGRSSELRPGEFVVAIGSPFSLQNTVTTGIVSTT

QRGGKELGLRNSDMDYIQTDAIINYGNSGGPLVNLDGEVIGINTLKVTAG

ISFAIPSDKIKKFLTESHDRQAKGKAITKKKYIGIRMMSLTSSKAKELKD

RHRDFPDVISGAYIIEVIPDTPAEAGGLKENDVIISINGQSVVSANDVSD

VIKRESTLNMVVRRGNEDIMITVIPEEIDP

In the sequence shown above, positions 1-22 (SEQ ID NO: 29) correspond to the signal peptide, positions 204-364 (SEQ ID NO: 30) correspond to a serine protease domain.

A nucleotide sequence that encodes human HTRA1 is publically available in the GenBank database under accession number NM_002775.4 (SEQ ID NO: 31) and is as follows (the start and stop codons are underlined and bolded):

CAATGGGCTGGGCCGCGCGGCCGCGCGCACTCGCACCCGCTGCCCCCGAGGCCC

TCCTGCACTCTCCCCGGCGCCGCTCTCCGGCCCTCGCCCTGTCCGCCGCCACCGC

CGCCGCCGCCAGAGTCGCCATGCAGATCCCGCGCGCCGCTCTTCTCCCGCTGCTG

CTGCTGCTGCTGGCGGCGCCCGCCTCGGCGCAGCTGTCCCGGGCCGGCCGCTCGG

CGCCTTTGGCCGCCGGGTGCCCAGACCGCTGCGAGCCGGCGCGCTGCCCGCCGC

AGCCGGAGCACTGCGAGGGCGGCCGGGCCCGGGACGCGTGCGGCTGCTGCGAG

GTGTGCGGCGCGCCCGAGGGCGCCGCGTGCGGCCTGCAGGAGGGCCCGTGCGGC

GAGGGGCTGCAGTGCGTGGTGCCCTTCGGGGTGCCAGCCTCGGCCACGGTGCGG

CGGCGCGCGCAGGCCGGCCTCTGTGTGTGCGCCAGCAGCGAGCCGGTGTGCGGC

AGCGACGCCAACACCTACGCCAACCTGTGCCAGCTGCGCGCCGCCAGCCGCCGC

TCCGAGAGGCTGCACCGGCCGCCGGTCATCGTCCTGCAGCGCGGAGCCTGCGGC

CAAGGGCAGGAAGATCCCAACAGTTTGCGCCATAAATATAACTTTATCGCGGAC

GTGGTGGAGAAGATCGCCCCTGCCGTGGTTCATATCGAATTGTTTCGCAAGCTTC

CGTTTTCTAAACGAGAGGTGCCGGTGGCTAGTGGGTCTGGGTTTATTGTGTCGGA

AGATGGACTGATCGTGACAAATGCCCACGTGGTGACCAACAAGCACCGGGTCAA

AGTTGAGCTGAAGAACGGTGCCACTTACGAAGCCAAAATCAAGGATGTGGATGA

GAAAGCAGACATCGCACTCATCAAAATTGACCACCAGGGCAAGCTGCCTGTCCT

GCTGCTTGGCCGCTCCTCAGAGCTGCGGCCGGGAGAGTTCGTGGTCGCCATCGGA

AGCCCGTTTTCCCTTCAAAACACAGTCACCACCGGGATCGTGAGCACCACCCAGC

GAGGCGGCAAAGAGCTGGGGCTCCGCAACTCAGACATGGACTACATCCAGACCG

ACGCCATCATCAACTATGGAAACTCGGGAGGCCCGTTAGTAAACCTGGACGGTG

AAGTGATTGGAATTAACACTTTGAAAGTGACAGCTGGAATCTCCTTTGCAATCCC

ATCTGATAAGATTAAAAAGTTCCTCACGGAGTCCCATGACCGACAGGCCAAAGG

AAAAGCCATCACCAAGAAGAAGTATATTGGTATCCGAATGATGTCACTCACGTC

CAGCAAAGCCAAAGAGCTGAAGGACCGGCACCGGGACTTCCCAGACGTGATCTC

AGGAGCGTATATAATTGAAGTAATTCCTGATACCCCAGCAGAAGCTGGTGGTCTC

AAGGAAAACGACGTCATAATCAGCATCAATGGACAGTCCGTGGTCTCCGCCAAT

GATGTCAGCGACGTCATTAAAAGGGAAAGCACCCTGAACATGGTGGTCCGCAGG

GGTAATGAAGATATCATGATCACAGTGATTCCCGAAGAAATTGACCCATAGGCA

GAGGCATGAGCTGGACTTCATGTTTCCCTCAAAGACTCTCCCGTGGATGACGGAT

GAGGACTCTGGGCTGCTGGAATAGGACACTCAAGACTTTTGACTGCCATTTTGTT

TGTTCAGTGGAGACTCCCTGGCCAACAGAATCCTTCTTGATAGTTTGCAGGCAAA

ACAAATGTAATGTTGCAGATCCGCAGGCAGAAGCTCTGCCCTTCTGTATCCTATG

TATGCAGTGTGCTTTTTCTTGCCAGCTTGGGCCATTCTTGCTTAGACAGTCAGCAT

```
                        -continued
TTGTCTCCTCCTTTAACTGAGTCATCATCTTAGTCCAACTAATGCAGTCGATACAA

TGCGTAGATAGAAGAAGCCCCACGGGAGCCAGGATGGGACTGGTCGTGTTTGTG

CTTTTCTCCAAGTCAGCACCCAAAGGTCAATGCACAGAGACCCCGGGTGGGTGA

GCGCTGGCTTCTCAAACGGCCGAAGTTGCCTCTTTTAGGAATCTCTTTGGAATTG

GGAGCACGATGACTCTGAGTTTGAGCTATTAAAGTACTTCTTACACATTGCAAAA

AAAAAAAAAAAAAA
```

Exemplary SVDs and the Treatment Thereof

Aspects of the present subject matter relate to the treatment of SVDs. Non-limiting examples of SVDs are discussed below.

Cerebral Small Vessel Disease

As used herein, the term "cerebral small vessel disease" or "cerebral SVD" refers to a group of pathological processes with various aetiologies that affect the small arteries, arterioles, venules, and capillaries of the brain. See, e.g., Pantoni (2010) Lancet Neurol, 9(7):689-701, the entire contents of which are incorporated herein by reference. Age-related and hypertension-related SVDs and cerebral amyloid angiopathy are the most common forms. The consequences of small vessel disease on the brain parenchyma are mainly lesions located in the subcortical structures such as lacunar infarcts, white matter lesions, large hemorrhages, and microbleeds. Small vessel disease has an important role in cerebrovascular disease and is a leading cause of cognitive decline and functional loss in the elderly.

Cerebral SVD may lead to vascular dementia (also known as vascular cognitive impairment). In vascular dementia, changes in thinking skills sometimes occur suddenly following strokes that block major brain blood vessels. See, e.g., Alzheimer's Association, Alzheimer's & Dementia, available at www.alz.org/dementia/vascular-dementia-symptoms.asp, the entire contents of which are incorporated herein by reference. Thinking problems also may begin as mild changes that worsen gradually as a result of multiple minor strokes or other conditions that affect smaller blood vessels, leading to cumulative damage. Symptoms can vary widely, depending on the severity of the blood vessel damage and the part of the brain affected. Memory loss may or may not be a significant symptom depending on the specific brain areas where blood flow is reduced. Vascular dementia symptoms may be most obvious when they happen soon after a major stroke. Sudden post-stroke changes in thinking and perception may include, e.g., (i) confusion; (ii) disorientation; (iii) trouble speaking or understanding speech; and/or (iv) vision loss. These changes may happen at the same time as stroke symptoms such as a sudden headache, difficulty walking, or numbness or paralysis on one side of the face or the body.

Multiple small strokes or other conditions that affect blood vessels and nerve fibers deep inside the brain may cause more gradual thinking changes as damage accumulates. Common early signs of widespread small vessel disease include impaired planning and judgment; uncontrolled laughing and crying; declining ability to pay attention; impaired function in social situations; and difficulty finding the right words.

The present subject matter provides methods for treating each subtype, symptom, and/or complication of cerebral SVD.

HTRA1-Associated Small Vessel Disease

As used herein, an "HTRA1-associated small vessel disease" or HTRA1-associated SVD is a SVD that results from a dominant HTRA1 mutation. In various embodiments, a subject is heterozygous for the mutation. Descriptions of exemplary heterozygous mutations of the HTRA1 gene in patients with familial cerebral small vessel disease are included in Donato et al. 2017 "Heterozygous mutations of HTRA1 gene in patients with familial cerebral small vessel disease" *CNS Neurosci Ther.* 23(9):759-765; and Verdura et al. (2015) "Heterozygous HTRA1 mutations are associated with autosomal dominant cerebral small vessel disease" *Brain* 138; 2347-2358, the entire contents of each of which are incorporated herein by reference.

Cerebral Autosomal Recessive Arteriopathy with Subcortical Infarcts and Leukoencephalopathy Cerebral autosomal recessive arteriopathy with subcortical infarcts and leukoencephalopathy, commonly known as CARASIL, is an inherited condition that causes stroke and other impairments. As its name suggests, this condition is inherited in an autosomal recessive pattern. Autosomal recessive inheritance means both copies of the gene in each cell have mutations. The parents of an individual with an autosomal recessive condition each carry one copy of the mutated gene, but they typically do not show signs and symptoms of the condition. See, e.g., the U.S. National Library of Medicine Genetics Home Reference, CARASIL, available at ghr.nlm.nih.gov/condition/cerebral-autosomal-recessive-arteriopathy-with-subcortical-infarcts-and-leuko-encephalopathy # inheritance, the entire contents of which are incorporated herein by reference.

Abnormalities affecting the brain and other parts of the nervous system become apparent in an affected person's twenties or thirties. Often, muscle stiffness (spasticity) in the legs and problems with walking are the first signs of the disorder. About half of affected individuals have a stroke or similar episode before age 40. As the disease progresses, most people with CARASIL also develop mood and personality changes, a decline in thinking ability (dementia), memory loss, and worsening problems with movement.

Other characteristic features of CARASIL include premature hair loss (alopecia) and attacks of low back pain. The hair loss often begins during adolescence and is limited to the scalp. Back pain, which develops in early to mid-adulthood, results from the breakdown (degeneration) of the discs that separate the bones of the spine (vertebrae) from one another.

The signs and symptoms of CARASIL worsen slowly with time. Over the course of several years, affected individuals become less able to control their emotions and communicate with others. They increasingly require help with personal care and other activities of daily living; after a few years, they become unable to care for themselves. Most affected individuals die within a decade after signs and symptoms first appear, although few people with the disease have survived for 20 to 30 years.

The present subject matter provides methods for treating each subtype, symptom, and/or complication of CARASIL.

Cerebral Autosomal-Dominant Arteriopathy with Subcortical Infarcts and Leukoencephalopathy Cerebral autosomal dominant arteriopathy with subcortical infarcts and leukoencephalopathy, usually called CADASIL, is an inherited condition that causes stroke and other impairments. This condition affects blood flow in small blood vessels, particularly cerebral vessels within the brain. The muscle cells surrounding these blood vessels (vascular smooth muscle cells) are abnormal and gradually die. In the brain, the resulting blood vessel damage (arteriopathy) can cause migraines, often with visual sensations or auras, or recurrent seizures (epilepsy). See, e.g., the U.S. National Library of Medicine Genetics Home Reference, CADASIL, available at ghr.nlm.nih.gov/condition/cerebral-autosomal-dominant-arteriopathy-with-subcortical-infarcts-and-leukoencephalopathy #genes, the entire contents of which are incorporated herein by reference.

Damaged blood vessels reduce blood flow and can cause areas of tissue death (infarcts) throughout the body. An infarct in the brain can lead to a stroke. In individuals with CADASIL, a stroke can occur at any time from childhood to late adulthood, but typically happens during mid-adulthood. People with CADASIL often have more than one stroke in their lifetime. Recurrent strokes can damage the brain over time. Strokes that occur in the subcortical region of the brain, which is involved in reasoning and memory, can cause progressive loss of intellectual function (dementia) and changes in mood and personality.

Many people with CADASIL also develop leukoencephalopathy, which is a change in a type of brain tissue called white matter that can be seen with magnetic resonance imaging (MRI).

The age at which the signs and symptoms of CADASIL first begin varies greatly among affected individuals, as does the severity of these features.

CADASIL is not associated with the common risk factors for stroke and heart attack, such as high blood pressure and high cholesterol, although some affected individuals might also have these health problems.

Prior to the present invention, no specific treatment was available for CADASIL. However, anti-platelet agents such as aspirin, dipyridamole, ticlopidine, and clopidogrel are used to slow down the disease and help prevent strokes. Aspects of the present invention relate to administering an anti-platelet agent to a subject who is diagnosed with or determined to be at risk of developing CADASIL. In some embodiments, the subject receives therapy for primary or secondary prevention of stroke and myocardial infarction. Risk-reduction measures in primary stroke prevention may include the use of antihypertensive medications; platelet antiaggregants; 3-hydroxy-3-methylglutaryl coenzyme A (HMG-CoA) reductase inhibitors (statins); smoking cessation; dietary intervention; weight loss; and exercise. Secondary prevention may include the use of antiaggregants (aspirin, clopidogrel, extended-release dipyridamole, ticlopidine), cholesterol-reducing medications, and/or blood pressure-lowering medications, as well as the cessation of cigarette smoking, improving the diet (e.g., reducing red meat consumption and/or increasing vegetable consumption), and increased exercise.

The present subject matter provides methods for treating each subtype, symptom, and/or complication of CADASIL.

NOTCH3 Loss of Function-Associated Small Vessel Disease

NOTCH3 loss of function mutations cause an SVD phenotype strikingly similar to CADASIL but with key differences including the lack of accumulation of the NOTCH3 extracellular domain and the lack of GOM deposits. Typical mutations include changes leading to NOTCH 3 frame shifts, premature stop codons, or splicing defects. Partial or complete gene deletions or promoter or enhancer mutations leading to lower than normal NOTCH3 expression are also included. It has been reported that in some patients, typical CADASIL mutations also lead to NOTCH3 loss of function and in these, NOTCH3 loss of function contributes to SVD pathology. In most cases, patients with NOTCH3 loss of function are heterozygotes although a homozygote patient has been reported with earlier age at onset of SVD. This indicates that NOTCH3 is haploinsufficient in humans because one wild type copy of the gene is not sufficient to produce a wild type phenotype. Conditions that may indirectly lead to a decrease in NOTCH3 expression or function in the absence of mutations include cardiovascular, metabolic disease, disease, environmental factor, and aging.

Age-Related Macular Degeneration

Age-related macular degeneration (AMD) is an eye disease that is a leading cause of vision loss in older people in developed countries. The vision loss usually becomes noticeable in a person's sixties or seventies and tends to worsen over time. See, e.g., the U.S. National Library of Medicine Genetics Home Reference, Age-Related Macular Degeneration, available at ghr.nlm.nih.gov/condition/age-related-macular-degeneration, the entire contents of which are incorporated herein by reference.

AMD mainly affects central vision, which is needed for detailed tasks such as reading, driving, and recognizing faces. The vision loss in this condition results from a gradual deterioration of light-sensing cells in the tissue at the back of the eye that detects light and color (the retina). Specifically, age-related macular degeneration affects a small area near the center of the retina, called the macula, which is responsible for central vision. Side (peripheral) vision and night vision are generally not affected.

There are two major types of AMD, known as the dry form and the wet form. The dry form is much more common, accounting for 85 to 90 percent of all cases of age-related macular degeneration. It is characterized by a buildup of yellowish deposits called drusen beneath the retina and slowly progressive vision loss. The condition typically affects vision in both eyes, although vision loss often occurs in one eye before the other.

The wet form of AMD is associated with severe vision loss that can worsen rapidly. This form of the condition is characterized by the growth of abnormal, fragile blood vessels underneath the macula. These vessels leak blood and fluid, which damages the macula and makes central vision appear blurry and distorted.

AMD results from a combination of genetic and environmental factors. Many of these factors have been identified, but some remain unknown.

Without wishing to be bound by any scientific theory, changes in many genes may be risk factors for age-related macular degeneration. The best-studied of these genes are involved in a part of the body's immune response known as the complement system. This system is a group of proteins that work together to destroy foreign invaders (such as bacteria and viruses), trigger inflammation, and remove debris from cells and tissues. Genetic changes in and around several complement system genes, including the complement factor H (CFH) gene, contribute to a person's risk of developing age-related macular degeneration. It is unclear how these genetic changes are related to the retinal damage and vision loss characteristic of this condition. Changes on the long (q) arm of chromosome 10 in a region known as 10q26 are also associated with an increased risk of age-related macular degeneration. The 10q26 region contains two genes of interest, age-related maculopathy susceptibility 2 (ARMS2) and high-temperature requirement A serine peptidase 1 (HTRA1). Changes in both genes have been studied as possible risk factors for the disease. However, because the two genes are so close together, it is difficult to tell which gene is associated with age-related macular degeneration risk, or whether increased risk results from variations in both genes. An estimated 15 to 20 percent of people with age-related macular degeneration have at least one first-degree relative (such as a sibling) with the condition. Other genes that are associated with age-related macular degeneration include genes involved in transporting and processing high-density lipoprotein (HDL) and genes that have been associated with other forms of macular disease.

Nongenetic factors that contribute to the risk of age-related macular degeneration are also known. Age appears to be the most important risk factor; the chance of developing the condition increases significantly as a person gets older. Smoking is another established risk factor for age-related macular degeneration.

Aspects of the present subject matter relate to administering a treatment for AMD to a subject who is diagnosed with or determined to be at risk of developing AMD. In some embodiments, the subject is administered a statin. In some embodiments relating to neovascular AMD, the subject is administered an antiangiogenic steroid such as anecortave acetate or triamcinolone acetonide. In various embodiments relating to wet AMD, the subject can be treated with laser coagulation or a medication that stops and sometimes reverses the growth of blood vessels. In certain embodiments, the subject is treated with bevacizumab, ranibizumab, pegaptanib, or aflibercept. In some embodiments, photodynamic therapy is administered to the subject. For example, the drug verteporfin is administered intravenously and light of a certain wavelength (e.g., 689 nm) is then applied to the abnormal blood vessels, which activates the verteporfin to destroy the vessels.

The present subject matter provides diagnostic, prognostic, treatment, and monitoring methods, as well as related compositions, kits, and systems, for each subtype, symptom, and/or complication of AMD.

Retinopathy

Retinopathy is persistent or acute damage to the retina of the eye. Ongoing inflammation and vascular remodeling may occur over periods of time where the patient is not fully aware of the extent of the disease. Frequently, retinopathy is an ocular manifestation of systemic disease as seen in diabetes or hypertension. Diabetic retinopathy is the leading cause of blindness in working-aged people.

Causes of retinopathy include but are not limited to: (i) diabetes mellitus, which can cause diabetic retinopathy; (ii) arterial hypertension, which can cause hypertensive retinopathy; (iii) retinopathy of prematurity due to prematurity of a newborn (under the 9 months of human pregnancy); (iv) radiation retinopathy due to exposure to ionizing radiation; (v) solar retinopathy due to direct sunlight exposure; (vi) sickle cell disease; (vii) retinal vascular disease such as retinal vein or artery occlusion; (viii) trauma, especially to the head, and several diseases may cause Purtscher's retinopathy; and (ix) hyperviscosity-related retinopathy as seen in disorders which cause paraproteinemia.

Many types of retinopathy are proliferative, most often resulting from neovascularization or blood vessel overgrowth. Angiogenesis is the hallmark precursor that may result in blindness or severe vision loss, particularly if the macula becomes affected. Retinopathy may also be a symptom or complication of a ciliopathic genetic disorder such as Alström syndrome or Bardet-Biedl syndrome.

Aspects of the present subject matter relate to administering a treatment for retinopathy to a subject who is diagnosed with or determined to be at risk of developing retinopathy. Treatment may include laser therapy to the retina and/or the administration of a vascular endothelial growth factor (VEGF) inhibitor.

The present subject matter provides methods for the treatment of each subtype, symptom, and/or complication of retinopathy.

Microangiopathy

Microangiopathy (or microvascular disease, or small vessel disease) is an angiopathy (i.e. disease of blood vessels) affecting small blood vessels in the body. The condition can occur in any organ of the body. One cause of microangiopathy is long-term diabetes mellitus. In this case, high blood glucose levels cause the endothelial cells lining the blood vessels to take in more glucose than normal (these cells do not depend on insulin). They then form more glycoproteins on their surface than normal, and also cause the basement membrane in the vessel wall to grow abnormally thicker and weaker. Mural cell loss is also a hallmark of microangiopathy and is associated with hyperglycemia. Therefore vessels bleed, leak protein, and slow the flow of blood through the body. As a result, some organs and tissues do not get enough blood (carrying oxygen & nutrients) and are damaged, for example, the retina (diabetic retinopathy) or kidney (diabetic nephropathy). Nerves and neurons, if not sufficiently supplied with blood, are also damaged, which leads to loss of function (diabetic neuropathy, especially peripheral neuropathy).

Massive microangiopathy may cause microangiopathic hemolytic anemia (MAHA).

The present subject matter provides methods for the treatment of each subtype, symptom, and/or complication of microangiopathy.

Nephropathy and Small Vessel Diseases of the Kidney

SVD can occur in the kidneys during or as part of nephropathy. For example, diabetic nephropathy (or diabetic kidney disease) is a progressive kidney disease caused by damage to the capillaries in the kidneys' glomeruli. It is characterized by nephrotic syndrome and diffuse scarring of the glomeruli. It is due to longstanding diabetes mellitus, and is a prime reason for dialysis in many developed countries. It is classified as a small blood vessel complication of diabetes. During its early course, diabetic nephropathy often has no symptoms. Symptoms can take 5 to 10 years to appear after the kidney damage begins. These late symptoms include severe tiredness, headaches, a general feeling of illness, nausea, vomiting, frequent voiding, lack of appetite, itchy skin, and leg swelling.

The present subject matter provides methods for the treatment of each subtype, symptom, and/or complication of nephropathy.

Proximal 19p13.12 Microdeletion Syndrome

In embodiments, the SVD comprises proximal 19p13.12 microdeletion syndrome. Non-limiting descriptions relating to this syndrome are provided in Huynh et al. (2018) "First prenatal case of proximal 19p13.12 microdeletion syndrome: New insights and new delineation of the syndrome"

*Eur J Med Genet.* S1769-7212(17)30466-4, the entire content of which is incorporated herein by reference.

In certain embodiments, proximal 19p13.12 microdeletion syndrome comprises intellectual disability, facial dysmorphism, and/or branchial arch defects. In some embodiments, proximal 19p13.12 microdeletion syndrome comprises hypertrichosis-synophrys-protruding front teeth. In various embodiments, a subject with proximal 19p13.12 microdeletion syndrome comprises a heterozygous interstitial deletion at 19p13.12 chromosome region. In certain embodiments, the deletion is a deletion of about 350 kb to about 750 kb. In some embodiments, the deletion is a deletion of about 745 kb. In various embodiments, the deletion includes at least a portion of the NOTCH3 gene. In certain embodiments, the deletion includes the entire NOTCH3 gene. In some embodiments, the deletion comprises (e.g., in addition to a mutation in part of all of the NOTCH3 gene) a portion of, or the entirety of any one of, any combination of the following genes: SYDE1, AKAP8, AKAP8L, WIZ and BRD4.

The present subject matter provides methods for the treatment of each subtype, symptom, and/or complication of proximal 19p13.12 microdeletion syndrome.

Myocardial Ischemia

NOTCH3 deficiency impairs coronary microvascular maturation and reduces cardiac recovery after myocardial ischemia. See, e.g., Tao et al. (2017) "Notch3 deficiency impairs coronary microvascular maturation and reduces cardiac recovery after myocardial ischemia" Int J Cardiol. 2017 Jun. 1; 236:413-422, the entire content of which is incorporated herein by reference. In various embodiments, a subject with myocardial ischemia has myocardial infarction.

In certain embodiments, reduced NOTCH3 results in a reduction of pericytes and small arterioles. In some embodiments, the reduction in pericytes and small arterioles increases the severity of myocardial ischemia, and/or reduces cardiac recovery after myocardial ischemia. In various embodiments, a subject with reduced NOTCH3 function (e.g., due to a mutation) is prone to ischemic injury with larger infarcted size and higher rates of mortality. In certain embodiments, the expression of CXCR-4 and VEGF/Ang-1 is decreased in a subject with reduced NOTCH3 function. In some embodiments, a subject with reduced NOTCH3 function has fewer NG2+/Sca1+ and NG2+/c-kit+ progenitor cells in an ischemic area and exhibits worse cardiac function recovery at 2 weeks after myocardial ischemia compared to a corresponding subject with a normal level of NOTCH3 function. In certain embodiments, a subject with reduced NOTCH3 function has a significant reduction of pericyte/capillary coverage and arteriolar maturation compared to a corresponding subject with a normal level of NOTCH3 function. In various embodiments, a subject with a reduced level of NOTCH3 function and who has had myocardial ischemia has increased intracellular adhesion molecule-2 (ICAM-2) expression and CD11b+ macrophage infiltration into ischemic areas compared to that of a corresponding subject with a normal level of NOTCH3 function. In embodiments, a subject has a NOTCH3 mutation that impairs recovery of cardiac function post-myocardial ischemia by the mechanisms involving the pre-existing coronary microvascular dysfunction conditions, and impairment of pericyte/progenitor cell recruitment and microvascular maturation.

The present subject matter provides methods for the treatment of each subtype, symptom, and/or complication of myocardial ischemia.

Heart Failure

Heart failure is a chronic, progressive condition in which the heart muscle is unable to pump enough blood through to meet the body's needs for blood and oxygen. Loss of NOTCH3 signaling in vascular smooth muscle cells promotes severe heart failure upon hypertension. See, e.g., Ragot et al., (2016) Hypertension. 68(2):392-400; and the American Heart Association, What is Heart Failure? available at www.heart.org/HEARTORG/Conditions/HeartFailure/AboutHeartFailure/About-Heart-Failure_UCM_002-044_ Article.jsp #.WM16W_7lva8, the entire contents of each of which are incorporated herein by reference.

The heart tries to make up for this by enlarging, developing more muscle mass, and/or pumping faster. When the heart chamber enlarges, it stretches more and can contract more strongly, so it pumps more blood. With an enlarged heart, the body starts to retain fluid, the lungs get congested with fluid and the heart begins to beat irregularly. An increase in muscle mass occurs because the contracting cells of the heart get bigger. This lets the heart pump more strongly, at least initially. Increased heartrate helps to increase the heart's output.

The body also tries to compensate in other ways: (i) The blood vessels narrow to keep blood pressure up, trying to make up for the heart's loss of power; and (ii) The body diverts blood away from less important tissues and organs (like the kidneys), the heart and brain.

These temporary measures mask the problem of heart failure, but they do not solve it. Heart failure continues and worsens until these substitute processes no longer work. Eventually the subject experiences the fatigue, breathing problems or other symptoms that usually prompt a trip to the doctor.

Heart failure can involve the heart's left side, right side or both sides. However, it usually affects the left side first.

The present subject matter provides methods for the treatment of each subtype, symptom, and/or complication of heart failure.

Alagille Syndrome and Familial Tetralogy of Fallot

Alagille syndrome is a genetic disorder that can affect the liver, heart, and other parts of the body. See, e.g., the U.S. National Library of Medicine Genetics Home Reference, Alagille syndrome, available at ghr.nlm.nih.gov/condition/alagille-syndrome, the entire contents of which are incorporated herein by reference.

One of the major features of Alagille syndrome is liver damage caused by abnormalities in the bile ducts. These ducts carry bile (which helps to digest fats) from the liver to the gallbladder and small intestine. In Alagille syndrome, the bile ducts may be narrow, malformed, and reduced in number (bile duct paucity). As a result, bile builds up in the liver and causes scarring that prevents the liver from working properly to eliminate wastes from the bloodstream. Signs and symptoms arising from liver damage in Alagille syndrome may include a yellowish tinge in the skin and the whites of the eyes (jaundice), itchy skin, and deposits of cholesterol in the skin (xanthomas).

Alagille syndrome is also associated with several heart problems, including impaired blood flow from the heart into the lungs (pulmonic stenosis). Pulmonic stenosis may occur along with a hole between the two lower chambers of the heart (ventricular septal defect) and other heart abnormalities. This combination of heart defects is called tetralogy of Fallot.

People with Alagille syndrome may have distinctive facial features including a broad, prominent forehead; deep-set eyes; and a small, pointed chin. The disorder may also affect the blood vessels within the brain and spinal cord (central nervous system) and the kidneys. Affected individuals may have an unusual butterfly shape of the bones of the spinal column (vertebrae) that can be seen in an x-ray.

Problems associated with Alagille syndrome generally become evident in infancy or early childhood. The severity of the disorder varies among affected individuals, even within the same family Symptoms range from so mild as to go unnoticed to severe heart and/or liver disease requiring transplantation.

Some people with Alagille syndrome may have isolated signs of the disorder, such as a heart defect like tetralogy of Fallot, or a characteristic facial appearance. These individuals do not have liver disease or other features typical of the disorder.

In more than 90 percent of cases, mutations in the JAGGED1 gene cause Alagille syndrome. Another 7 percent of individuals with Alagille syndrome have small deletions of genetic material on chromosome 20 that include the JAG1 gene, which encodes JAGGED1. A few people with Alagille syndrome have mutations in a different gene, called NOTCH2. The JAG1 and NOTCH2 genes provide instructions for making proteins that fit together to trigger interactions called Notch signaling between neighboring cells during embryonic development. This signaling influences how the cells are used to build body structures in the developing embryo. Changes in either the JAG1 gene or NOTCH2 gene probably disrupt the Notch signaling pathway. As a result, errors may occur during development, especially affecting the bile ducts, heart, spinal column, and certain facial features.

The present subject matter provides methods for the treatment of each subtype, symptom, and/or complication of Alagille syndrome and/or familial tetralogy of Fallot.

Patent Ductus Arteriosus

Patent ductus arteriosus (PDA) is a condition wherein the ductus arteriosus fails to close after birth. Early symptoms are uncommon, but in the first year of life include increased work of breathing and poor weight gain. An uncorrected PDA may lead to congestive heart failure with increasing age.

The ductus arteriosus is a fetal blood vessel that closes soon after birth. In a PDA, the vessel does not close and remains "patent" (open), resulting in irregular transmission of blood between the aorta and the pulmonary artery. PDA is common in newborns with persistent respiratory problems such as hypoxia, and has a high occurrence in premature newborns. Premature newborns are more likely to be hypoxic and have PDA due to underdevelopment of the heart and lungs.

A PDA allows a portion of the oxygenated blood from the left heart to flow back to the lungs by flowing from the aorta (which has higher pressure) to the pulmonary artery. If this shunt is substantial, the neonate becomes short of breath: the additional fluid returning to the lungs increases lung pressure, which in turn increases the energy required to inflate the lungs. This uses more calories than normal and often interferes with feeding in infancy. This condition, as a constellation of findings, is called congestive heart failure.

In some congenital heart defects (such as in transposition of the great vessels) a PDA may need to remain open, as it is the only way that oxygenated blood can mix with deoxygenated blood. In these cases, prostaglandins are used to keep the DA open until surgical correction of the heart defect is completed.

PDA is associated with NOTCH3 loss of function. See, e.g., Baeten et al., (2015) Genesis 53(12):738-48, the entire content of which is incorporated herein by reference.

The present subject matter provides methods for the treatment of each subtype, symptom, and/or complication of PDA.

Cerebral Cavernous Malformations

Cerebral cavernous malformations are collections of small blood vessels (capillaries) in the brain that are enlarged and irregular in structure. These capillaries have abnormally thin walls, and they lack other support tissues, such as elastic fibers, which normally make them stretchy. See, e.g., the U.S. National Library of Medicine Genetics Home Reference, Cerebral Cavernous Malformation, available at ghr.nlm.nih.gov/condition/cerebral-cavernous-malformation, the entire contents of which are incorporated herein by reference. As a result, the blood vessels are prone to leakage, which can cause the health problems related to this condition. Cavernous malformations can occur anywhere in the body, but usually produce serious signs and symptoms only when they occur in the brain and spinal cord (which are described as cerebral).

Approximately 25 percent of individuals with cerebral cavernous malformations never experience any related health problems. Other people with this condition may experience serious signs and symptoms such as headaches, seizures, paralysis, hearing or vision loss, and bleeding in the brain (cerebral hemorrhage). Severe brain hemorrhages can result in death. The location and number of cerebral cavernous malformations determine the severity of this disorder. These malformations can change in size and number over time.

There are two forms of the condition: familial and sporadic. The familial form is passed from parent to child, and affected individuals typically have multiple cerebral cavernous malformations. The sporadic form occurs in people with no family history of the disorder. These individuals typically have only one malformation.

Defective NOTCH3 signaling is associated with cerebral cavernous malformations. See, e.g., Schultz et al. (2015) Stroke 46(5):1337-43, the entire content of which is incorporated herein by reference.

The present subject matter provides methods for the treatment of each subtype, symptom, and/or complication of cerebral cavernous malformation.

Lacunar Strokes and Hemorrhagic Strokes

As disclosed herein, the consequences of SVD on the brain parenchyma are mainly lesions located in the subcortical structures such as lacunar infarcts (also termed "lacunar strokes"), white matter lesions, large hemorrhages, and microbleeds. Strokes, such as lacunar strokes and hemorrhagic strokes, are signs of (e.g., may result from) a SVD. A lacunar stroke is the most common type of stroke, and results from the occlusion of one or more small penetrating arteries that provide blood to the brain's deep structures. In some embodiments, a lacunar stroke comprises a small infarct (2-20 mm in diameter) in the deep cerebral white matter, basal ganglia, or pons, presumed to result from the occlusion of a single small perforating artery supplying the subcortical areas of the brain. Hemorrhagic strokes (bleeds) result from a weakened vessel that ruptures and bleeds into the surrounding brain. Pericytes have been reported to play different roles during the different phases of ischemic stroke (e.g., lacunar stroke). See, e.g., Yang et al. (2017), *Curr Neuropharmacol* 15(6): 892-905, the entire content of which is incorporated herein by reference. In some embodiments, pericyte constriction and death may be a cause of the no-reflow phenomenon in brain capillaries during the hyperacute phase of stroke. In certain embodiments, during the acute phase, pericytes detach from microvessels and participate in inflammatory-immunological response, resulting in blood brain barrier (BBB) damage and brain edema. In various embodiments, pericytes are neuroprotective by protecting endothelium, stabilizing BBB and releasing neurotrophins. In some embodiments, pericytes contribute to angiogenesis and neurogenesis, and thereby promote neurological recovery during the recovery phase of stroke.

In certain embodiments, a subject with a SVD has more difficulty recovering from a lacunar stroke. In some embodiments, a subject with a SVD has more difficulty recovering from a hemorrhagic stroke. In various embodiments, a treatment herein improves (e.g., the rate or degree of) treatment in a subject with a SVD who has had a lacunar stroke or a hemorrhagic stroke. In certain embodiments, a treatment herein reduces the likelihood that a subject who has a SVD will have a lacunar stroke or a hemorrhagic stroke. In various embodiments, NOTCH3 signaling manipulation (e.g., increasing NOTCH3 signaling) can stabilize mural cells after stroke (e.g., during the different phases after stroke).

The present subject matter provides methods for the treatment of each subtype, symptom, and/or complication of lacunar strokes and hemorrhagic strokes.

Subjects at Risk of Developing a Small Vessel Disease or a Symptom or Complication of a Small Vessel Disease Aspects of the present subject matter relate to inhibiting or preventing a SVD (or a complication or symptom thereof) in a subject who is at risk of developing the SVD (or a symptom or complication thereof). In some embodiments, a subject at risk of developing an SVD or a symptom or complication thereof is administered a therapeutic treatment for the SVD prior to the subject's diagnosis or perception of the SVD or a symptom or complication of the SVD.

Risk factors may vary from SVD to SVD. However, a subject may generally be considered to be at risk of suffering from a SVD or a symptom or complication thereof if the subject has at least 1 grandparent, parent, aunt, uncle, cousin, and/or sibling who suffers from the SVD or the symptom or complication thereof. Additional non-limiting examples of risk factors for SVDs are discussed below.

Cerebral SVD has frequently been found on computed tomography (CT) and magnetic resonance imaging (MRI) scans of elderly people. See, e.g., van Norden et al., (2011) BMC NeurologyBMC series 11:29, the entire contents of which are incorporated herein by reference. In various embodiments, an elderly subject (e.g., a subject who is at least about 70, 75, 80, 85, 90, or 95 years old) is deemed to be at risk of and treated and/or screened for (e.g., using a diagnostic or prognostic method disclosed herein) cerebral SVD and/or a complication or symptom of cerebral SVD. Symptoms and complications of cerebral SVD are disclosed herein and include, e.g., vascular cognitive impairment, hemorrhages and microbleeds, neuropathy, strokes, dementia, and/or parkinsonism. In various embodiments, a subject at risk of developing cerebral SVD or a complication or symptom thereof is a subject who has suffered from at least one stroke. In certain embodiments, a subject is at risk of developing cerebral SVD or a complication or symptom thereof if the subject has hypertension (e.g., a systolic pressure of at least 140 mmHg or a diastolic pressure of at least 90 mmHg) and/or amyloid deposits in the walls of the blood vessels of the central nervous system. There are also hereditary risk factors for cerebral SVD. See, e.g., Plancher et al. Case Rep Neurol. 2015 May-August; 7(2): 142-147, the entire contents of which are incorporated herein by reference. In some embodiments, the subject has a mutated gene that is associated with cerebral SVD. In certain embodiments, a subject is at risk of developing cerebral SVD if the subject has at least 1 grandparent, parent, aunt, uncle, cousin, or sibling who suffers or has suffered from cerebral SVD or a complication or symptom thereof, and/or who has a gene mutation that is associated with cerebral SVD.

In some embodiments, the subject (or at least 1 grandparent, parent, aunt, uncle, cousin, and/or sibling thereof) has a mutation in a COL4A1 gene (which encodes the type IV collagen alpha-1 chain). COL4A1-related brain SVD is part of a group of conditions called the COL4A1-related disorders. See, e.g., the U.S. National Library of Medicine Genetics Home Reference, COL4A1-related brain small-vessel disease, available at ghr.nlm.nih.gov/condition/col4a1-related-brain-small-vessel-disease #genes, the entire contents of which are incorporated herein by reference. The conditions in this group have a range of signs and symptoms that involve fragile blood vessels. COL4A1-related brain small-vessel disease is characterized by weakening of the blood vessels in the brain. Stroke is often the first symptom of this condition, typically occurring in mid-adulthood. In affected individuals, stroke is usually caused by bleeding in the brain (hemorrhagic stroke) rather than a lack of blood flow in the brain (ischemic stroke), although either type can occur. Individuals with this condition are at increased risk of having more than one stroke in their lifetime. People with COL4A1-related brain small vessel disease also have leukoencephalopathy, which is a change in a type of brain tissue called white matter that can be seen with MRI. Affected individuals may also experience seizures and migraine headaches accompanied by visual sensations known as auras. In various embodiments, a subject with a COL4A1 mutation is at risk of and treated and/or screened for (e.g., using a diagnostic or prognostic method disclosed herein) for a symptom or complication such as a ischemic stroke, a hemorrhagic stroke, a migraine, a seizure, leukomalacia, nephropathy, hematuria, chronic muscle cramps, and/or a ocular anterior segment disease.

In some embodiments, a subject is at risk of cerebral SVD (e.g., sporadic cerebral SVD). In certain embodiments, the subject (or at least 1 grandparent, parent, aunt, uncle, cousin, and/or sibling thereof) has a mutation in a COL4A2 gene. COL4A2 is associated with lacunar ischemic stroke and deep intracerebral hemorrhage (ICH). See, e.g., Rannikmae et al. (2017) "COL4A2 is associated with lacunar ischemic stroke and deep ICH: Meta-analyses among 21,500 cases and 40,600 controls" Neurology October 24; 89(17):1829-1839.

In embodiments, subjects at risk of ICH (e.g., deep or lobar ICH) and/or ischemic stroke (IS) (e.g., lacunar, cardioembolic, or large vessel disease) include subjects with a mutation in a COL4A1 or COL4A2 gene.

Subjects at risk of developing CARASIL or CADASIL and/or a symptom or complication thereof include subjects with at least 1 or 2 grandparents, parents, or siblings who suffer from CARASIL, or CADASIL, and/or the symptom or complication thereof. Subjects at risk of developing CARASIL also include subjects who carry a mutation in the HTRA1 gene, or who have a grandparent, parent, or sibling who carries such a mutation. Subjects at risk of developing CADASIL also include subjects who carry a mutation in the NOTCH3 gene, or who have a grandparent, parent, or sibling who carries such a mutation.

Subjects at risk of developing AMD (such as wet or dry AMD) and/or a symptom or complication thereof include subjects with high blood pressure, heart disease, a high-fat diet or one that is low in certain nutrients (such as antioxidants and zinc), obesity, repeated and/or prolonged exposure to ultraviolet (UV) rays from sunlight, or who smoke or have smoked for at least about 1, 5, 10, or more years. Subjects at risk of developing AMD and/or a symptom or complication thereof also include subjects with at least 1 or 2 grandparents, parents, or siblings who suffer from AMD, and/or the symptom or complication thereof. In various embodiments, a subject who carries a mutation in a CFH, ARMS2, HTRA1 gene, or a gene involved in transporting or processing HDL.

Subjects at risk of developing retinopathy include subjects with diabetes, arterial hypertension, sickle cell disease, a retinal vascular disease such as retinal vein or artery occlusion, Alström syndrome, or Bardet-Biedl syndrome. Subjects at risk of developing retinopathy also include premature human newborns (infants about 0, 1, 2, 3, 4, 5, 6, 7, 8, 9, 10 or more weeks old who were born after less than about 9, 8, or 7, months of pregnancy), subjects who have been exposed to ionizing radiation, and subjects whose retinas have been exposed to direct sunlight. In some embodiments, the retinopathy is diabetic retinopathy. Subjects at risk of developing diabetic retinopathy include, e.g., subjects with type 1 or type 2 diabetes. In various embodiments, the retinopathy is proliferative (e.g., proliferative diabetic retinopathy).

Subjects at risk of developing heart failure include subjects with high blood pressure, coronary artery disease, diabetes, sleep apnea, a congenital heart defect, valvular heart disease, or irregular heartbeats. Subjects at risk of heart failure also include alcoholics and former alcoholics, subjects who have used tobacco (e.g., who have smoked cigarettes for at least about 5, 10, 15, or 20 years), subjects who are obese, and subjects who have had a heart attack. Subjects who have taken rosiglitazone, pioglitazone, and nonsteroidal anti-inflammatory drugs (NSAIDs) [e.g., regularly (such as 1, 2, 3, 4, 5, 6, or 7 times per week) for at least about 1, 2, 3, 4, or 5 years] are also at risk for heart failure.

Subjects at risk of developing nephropathy (especially diabetic nephropathy) include subjects who have hyperglycemia, hypertension, at least 1 grandparent, parent, aunt, uncle, cousin, or sibling with nephropathy or hypertension. Additional non-limiting examples include subjects who smoke or have smoked for at least about 1, 5, 10, or more years.

Such subjects may be treated using the methods, agonists, and compositions disclosed herein.

Exemplary Agonists

Non-limiting examples of NOTCH3 agonists include any molecule, e.g., an antibody, that can produce an activated signaling form of the receptor, including soluble ligands of the receptor, antibodies and fragments thereof, small molecules that bind NOTCH3 extracellularly or that can enter the cell and act intracellularly, molecules that have enzymatic activity in cleaving the receptor to release the activated form, and molecules with the ability to destabilize the negative regulatory region of the receptor. In various embodiments, an agonist of NOTCH3, in addition to binding a NOTCH3 receptor, has a direct effect on a cell that comprises the NOTCH3 receptor. In embodiments, the NOTCH3 agonist will bind NOTCH3 receptor, and as well, initiate or mediate the signaling event associated with the NOTCH3 receptor, such as, for example, to cause the intracellular domain of NOTCH3 to be released for nuclear translocation.

In some embodiments (e.g., relating to CADASIL), a mechanism for reduced NOTCH3 function (e.g. inhibition) includes aberrant protein-protein interaction mediated by cysteine residues. In certain embodiments, a NOTCH3 agonist may operate by inhibiting the formation of these aberrant disulfide bridges, e.g., using small molecules or peptides or nucleic acids that neutralize disulfide bridges. See, e.g., Hague et al. (2014) "Inhibition of tau aggregation by a rosamine derivative that blocks tau intermolecular disulfide cross-linking" *Amyloid* 21(3):185-90, the entire content of which is incorporated herein by reference.

Small Molecules

In some embodiments, the NOTCH3 agonist is a small molecule.

In some embodiments, the small molecule comprises an Amaryllidaceae alkaloid. Non-limiting examples or small molecules include N-methylhemeanthidine chloride (NMHC), and pharmaceutically acceptable salts thereof. NMHC is an Amaryllidaceae alkaloid that may be isolated from *Zephyranthes candida*. See, e.g., Ye et al. (2016) Sci. Rep. 6, 26510; and Luo et al. (2012) J Nat Prod. 75, 2113-20, the entire contents of each of which are hereby incorporated herein by reference. The structure of NMHC is:

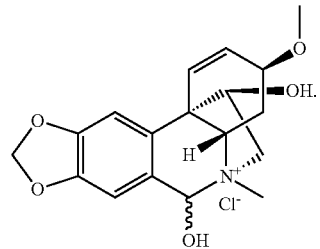 [SMILES: CO[C@@H]1C=C[C@@]23c4cc5c(cc4C(O)[N@@+](C)(C[C@@H]2O)[C@H]3C1)OCO5 ; [Cl-]]

In certain embodiments, the small molecule comprises a rosamine derivative bearing mild thiol reactivity. See, e.g., Hague et al. (2014) "Inhibition of tau aggregation by a rosamine derivative that blocks tau intermolecular disulfide cross-linking" Amyloid 21(3):185-90, the entire contents of which are incorporated herein by reference. In embodiments, the small molecule has the following structure:

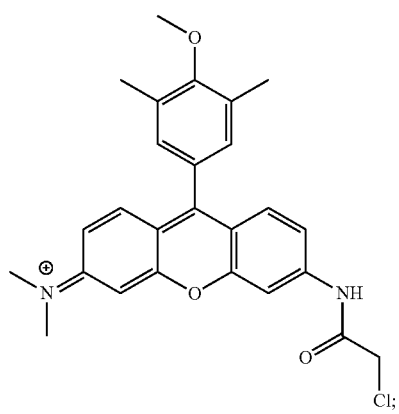

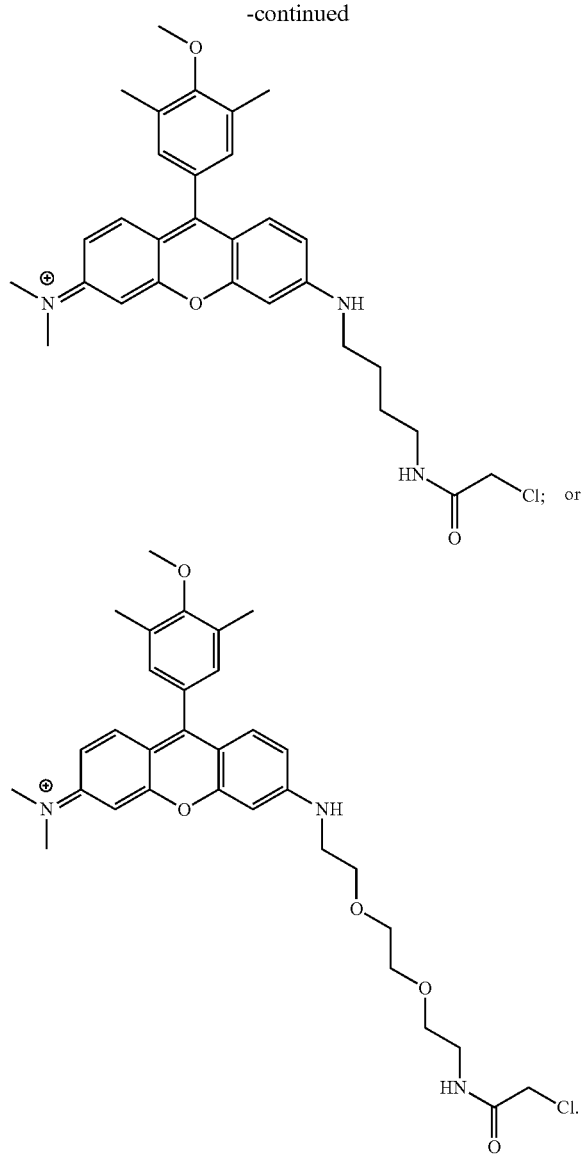

Antibodies

In some embodiments, the NOTCH3 agonist is an antibody or a fragment thereof.

As used herein, the term "antibody" refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, an $F_{ab}$ expression library, single-chain antibody molecules (e.g., scFv), and multispecific antibodies formed from antibody fragments. By "specifically bind" or "immunoreacts with" is meant that the antibody reacts with one or more antigenic determinants of the desired antigen and does not react (i.e., bind) with other polypeptides or binds at much lower affinity ($K_d > 10^{-6}$) with other polypeptides.

An "antibody fragment" refers to a molecule other than an intact antibody that comprises a portion of an intact antibody that binds the antigen to which the intact antibody binds. The terms "full length antibody," "intact antibody," and "whole antibody" are used herein interchangeably to refer to an antibody having a structure substantially similar to a native antibody structure or having heavy chains that contain an Fc region.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ea., 2nd ed. Raven Press, N.Y. (1989)). The variable regions of each light/heavy chain pair form the antibody binding site.

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs." Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three hypervariable regions (HVRs) of each variable domain interact to define an antigen binding site on the surface of the VH-VL dimer. Collectively, the six HVRs or a subset thereof confer antigen binding specificity to the antibody. However, even a single variable domain (or half of an Fv comprising only three HVRs specific for an antigen) has the ability to recognize and bind antigen, although usually at a lower affinity than the entire binding site.

A "Fab" fragment contains a variable and constant domain of the light chain and a variable domain and the first constant domain (CHI) of the heavy chain. F(ab') 2 antibody fragments comprise a pair of Fab fragments which are generally covalently linked near their carboxy termini by hinge cysteines between them. Other chemical couplings of antibody fragments are also known in the art, "Single-chain Fv" or "scFv" antibody fragments comprise the VH and VL domains of an antibody, wherein these domains are present in a single polypeptide chain. Generally the Fv polypeptide further comprises a polypeptide linker between the VH and L domains, which enables the scFv to form the desired structure for antigen binding. For a review of scFv, see Pluckthun in The Pharmacology of Monoclonal Antibodies, Vol 113, Rosenburg and Moore eds. Springer-Verlag, New York, pp. 269-31S (1994).

The term "diabodies" refers to small antibody fragments with two antigen-binding sites, which fragments comprise a heavy chain variable domain (VH) connected to a light chain variable domain (VL) in the same polypeptide chain (VH and VL). By using a linker that is too short to allow pairing between the two domains on the same chain, the domains are forced to pair with the complementary domains of another chain and create two antigen-binding sites. Diabodies are described more fully in, for example, BP 404,097; WO 93/11161; and Hollinger et al., Proc. Natl. Acad. Sci. USA, 90:6444-6448 (1993).

The expression "linear antibodies" refers to antibodies as described in Zapata et al., Protein Eng., 8 (10): 1057-1062 (1995). Briefly, these antibodies comprise a pair of tandem segments which, together with complementary light chain polypeptides, form a pair of antigen binding regions. Linear antibodies can be bispecific or monospecific.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

As used herein, the term "epitope" includes any protein determinant capable of specific binding to an antibody, an antibody fragment, or a T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is ≤1 µM; preferably ≤100 nM and most preferably ≤10 nM.

Antibodies can be produced according to various methods known in the art.

Methods of preparing monoclonal antibodies are known in the art. For example, monoclonal antibodies may be prepared using hybridoma methods, such as those described by Kohler and Milstein (1975) Nature 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include a full length protein or a fragment thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (see pp. 59-103 in Goding (1986) Monoclonal Antibodies: Principles and Practice Academic Press) Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In some examples, the antibodies to an epitope for an interested protein as described herein or a fragment thereof are humanized antibodies. Humanized forms of non-human (e.g., murine) antibodies are chimeric molecules of immunoglobulins, immunoglobulin chains or fragments thereof (such as Fv, $F_{ab}$, $F_{ab'}$, $F_{(ab')2}$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al. 1986. Nature 321:522-525; Riechmann et al. 1988. Nature 332:323-329; Presta. 1992. Curr. Op. Struct. Biol. 2:593-596). Humanization can be essentially performed following methods of Winter and co-workers (see, e.g., Jones et al. 1986. Nature 321:522-525; Riechmann et al. 1988. Nature 332:323-327; and Verhoeyen et al. 1988. Science 239:1534-1536), by substituting rodent CDRs or CDR sequences for the corresponding sequences of a human antibody. Accordingly, such humanized antibodies are chimeric antibodies (e.g., U.S. Pat. No. 4,816,567), wherein substantially less than an intact human variable domain has been substituted by the corresponding sequence from a non-human species.

In various examples the antibodies to an epitope of an interested protein as described herein or a fragment thereof are human antibodies. Human antibodies can also be produced using various techniques known in the art, including phage display libraries (Hoogenboom and Winter. 1991. J. Mol. Biol. 227:381-388; Marks et al. 1991. J. Mol. Biol. 222:581-597) or the preparation of human monoclonal antibodies [e.g., Cole et al. 1985. Monoclonal Antibodies and Cancer Therapy Liss; Boerner et al. 1991. J. Immunol. 147(1):86-95]. Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in most respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al. 1992. Bio/Technology 10:779-783; Lonberg et al. 1994. Nature 368:856-859; Morrison. 1994. Nature 368: 812-13; Fishwild et al. 1996. Nature Biotechnology 14:845-51; Neuberger. 1996. Nature Biotechnology 14:826; Lonberg and Huszar. 1995. Intern. Rev. Immunol. 13:65-93. U.S. Pat. No. 6,719,971 also provides guidance to methods of generating humanized antibodies.

Aptamers

Aptamers are small, single stranded biomolecules, typically oligonucleotides (either DNA or RNA) or peptides, that bind to a specific target molecule (e.g. a protein or small molecule such as a steroid). They can be considered analogous to antibodies in their specificity but, unlike antibodies, aptamers are have a relatively low molecular weight. Peptide-based aptamers are generally less than thirty residues long while nucleotide-based aptamers are typically less than one hundred residues long.

Non-limiting examples of methods that are useful for designing aptamers that bind to a particular protein, such as NOTCH3, are described in U.S. Pat. Nos. 8,484,010; 5,582,981; PCT International Patent Application No. WO 2015/049356; Blackwell et al., (1993) Science 250:1104-1110; Blackwell, et al., (1990) Science 250:1149-1152; Tuerk and Gold (1990) Science 249:505-510; and Joyce (1989) Gene 82:83-87, the entire contents of each of which are incorporated herein by reference.

Peptides

Additional non-limiting examples of NOTCH3 agonists include NOTCH3 ligands and fragments (e.g., soluble fragments) thereof.

In some embodiments, the NOTCH3 agonist is a fragment of JAGGED1, JAGGED2, DELTA-LIKE1, DELTA-LIKE3, or DELTA-LIKE4.

In certain embodiments, the agonist comprises a fragment of JAGGED1 having the amino acid sequence CDDYYYGFGCNKFCRPR (SEQ ID NO:1) or CDDYYYGFGCNKFCRPRDDFFGH (SEQ ID NO:2). See, e.g., Li et al. (1998) Immunity 1998, 8, 43-55; Nickoloff et al. (2002) Cell Death Different. 9, 842; and Yamamura et al., (2014) Am J Physiol Cell Physiol. 306(9): C871-8, the entire contents of each of which are incorporated herein by reference. A polypeptide comprising the sequence CDDYYYGFGCNKFCRPR (SEQ ID NO:1) is commercially available from AnaSpec Inc. (Fremont, Calif., USA). Additional non-limiting examples of NOTCH3 agonists include larger fragments of JAGGED1 that comprise CDDYYYGFGCNKFCRPR (SEQ ID NO:1), with the proviso that such fragments do not comprise the transmembrane domain (positions 1068-1093) or cytoplasmic domain (positions 1094-1218) of JAGGED1. Thus, in some embodiments, the NOTCH3 agonist comprises the extracellular domain of JAGGED1 (positions 34-1067; SEQ ID NO: 15) or a fragment thereof that comprises the amino acid sequence CDDYYYGFGCNKFCRPR (SEQ ID NO:1). In certain embodiments, the fragment of the JAGGED1 extracellular domain is a fragment that comprises the amino acid sequence of CDDYYYGFGCNKFCRPRDDFFGH (SEQ ID NO:2).

The amino acid sequence for full-length human JAGGED1 is publically available in the UniProt database under accession number P78504 (SEQ ID NO: 14) and is as follows (an exemplary functional fragment that agonizes NOTCH3 is bolded and underlined):

MRSPRTRGRSGRPLSLLLALLCALRAKVCGASGQFELEILSMQNVNGELQ

NGNCCGGARNPGDRKCTRDECDTYFKVCLKEYQSRVTAGGPCSFGSGSTP

VIGGNTFNLKASRGNDRNRIVLPFSFAWPRSYTLLVEAWDSSNDTVQPDS

IIEKASHSGMINPSRQWQTLKQNTGVAHFEYQIRVTCDDYYYGFGCNKFC

RPRDDFIGHYACDQNGNKTCMEGWMGPECNRAICRQGCSPKHGSCKLPGD

CRCQYGWQGLYCDKCIPHPGCVHGICNEPWQCLCETNWGGQLCDKDLNYC

GTHQPCLNGGTCSNTGPDKYQCSCPEGYSGPNCEIAEHACLSDPCHNRGS

CKETSLGFECECSPGWTGPTCSTNIDDCSPNNCSHGGTCQDLVNGFKCVC

PPQWTGKTCQLDANECEAKPCVNAKSCKNLIASYYCDCLPGWMGQNCDIN

INDCLGQCQNDASCRDLVNGYRCICPPGYAGDHCERDIDECASNPCLNGG

HCQNEINRFQCLCPTGFSGNLCQLDIDYCEPNPCQNGAQCYNRASDYFCK

CPEDYEGKNCSHLKDHCRTTPCEVIDSCTVAMASNDTPEGVRYISSNVCG

PHGKCKSQSGGKFTCDCNKGFTGTYCHENINDCESNPCRNGGTCIDGVNS

YKCICSDGWEGAYCETNINDCSQNPCHNGGTCRDLVNDFYCDCKNGWKGK

TCHSRDSQCDEATCNNGGTCYDEGDAFKCMCPGGWEGTTCNIARNSSCLP

NPCHNGGTCVVNGESFTCVCKEGWEGPICAQNTNDCSPHPCYNSGTCVDG

DNWYRCECAPGFAGPDCRININECQSSPCAFGATCVDEINGYRCVCPPGH

SGAKCQEVSGRPCITMGSVIPDGAKWDDDCNTCQCLNGRIACSKVWCGPR

PCLLHKGHSECPSGQSCIPILDDQCFVHPCTGVGECRSSSLQPVKTKCTS

DSYYQDNCANITFTFNKEMMSPGLTTEHICSELRNLNILKNVSAEYSIYI

ACEPSPSANNEIHVAISAEDIRDDGNPIKEITDKIIDLVSKRDGNSSLIA

AVAEVRVQRRPLKNRTDFLVPLLSSVLTVAWICCLVTAFYWCLRKRRKPG

SHTHSASEDNTTNNVREQLNQIKNPIEKHGANTVPIKDYENKNSKMSKIR

THNSEVEEDDMDKHQQKARFAKQPAYTLVDREEKPPNGTPTKHPNWTNKQ

DNRDLESAQSLNRMEYIV

The amino acid sequence for the extracellular domain of human JAGGED1 is as follows (SEQ ID NO: 15):

QFELEILSMQNVNGELQNGNCCGGARNPGDRKCTRDECDTYFKVCLKEYQ

SRVTAGGGPCSFGSGSTPVIGGNTFNLKASRGNDRNRIVLPFSFAWPRSYT

LLVEAWDSSNDTVQPDSIIEKASHSGMINPSRQWQTLKQNTGVAHFEYQI

RVTCDDYYYGFGCNKFCRPRDDFFGHYACDQNGNKTCMEGWMGPECNRAI

CRQGCSPKHGSCKLPGDCRCQYGWQGLYCDKCIPHPGCVHGICNEPWQCL

CETNWGGQLCDKDLNYCGTHQPCLNGGTCSNTGPDKYQCSCPEGYSGPNC

EIAEHACLSDPCHNRGSCKETSLGFECECSPGWTGPTCSTNIDDCSPNNC

SHGGTCQDLVNGFKCVCPPQWTGKTCQLDANECEAKPCVNAKSCKNLIAS

YYCDCLPGWMGQNCDININDCLGQCQNDASCRDLVNGYRCICPPGYAGDH

CERDIDECASNPCLNGGHCQNEINRFQCLCPTGFSGNLCQLDIDYCEPNP

CQNGAQCYNRASDYFCKCPEDYEGKNCSHLKDHCRTTPCEVIDSCTVAMA

SNDTPEGVRYISSNVCGPHGKCKSQSGGKFTCDCNKGFTGTYCHENINDC

ESNPCRNGGTCIDGVNSYKCICSDGWEGAYCETNINDCSQNPCHNGGTCR

DLVNDFYCDCKNGWKGKTCHSRDSQCDEATCNNGGTCYDEGDAFKCMCPG

GWEGTTCNIARNSSCLPNPCHNGGTCVVNGESFTCVCKEGWEGPICAQNT

NDCSPHPCYNSGTCVDGDNWYRCECAPGFAGPDCRININECQSSPCAFGA

TCVDEINGYRCVCPPGHSGAKCQEVSGRPCITMGSVIPDGAKWDDDCNTC

QCLNGRIACSKVWCGPRPCLLHKGHSECPSGQSCIPILDDQCFVHPCTGV

GECRSSSLQPVKTKCTSDSYYQDNCANITFTFNKEMMSPGLTTEHICSEL

RNLNILKNVSAEYSIYIACEPSPSANNEIHVAISAEDIRDDGNPIKEITD

KIIDLVSKRDGNSSLIAAVAEVRVQRRPLKNRTD

In some embodiments, the agonist comprises a fragment of JAGGED2 comprising the amino acid sequence CDE-NYYSATCNKFCRPR (SEQ ID NO:3) or CDE-NYYSATCNKFCRPRNDFFGH (SEQ ID NO:4). Additional non-limiting examples of NOTCH3 agonists include larger fragments of JAGGED2 that comprise CDE-NYYSATCNKFCRPR (SEQ ID NO:3), with the proviso that such fragments do not comprise the transmembrane domain (positions 1081-1101) or cytoplasmic domain (positions 1102-1238) of JAGGED2. Thus, in some embodiments, the NOTCH3 agonist comprises the extracellular domain of JAGGED2 (positions 27-1080; SEQ ID NO: 17) or a fragment thereof that comprises the amino acid sequence CDENYYSATCNKFCRPR (SEQ ID NO:3). In certain embodiments, the fragment of the JAGGED2 extracellular domain is a fragment that comprises the amino acid sequence of CDENYYSATCNKFCRPRNDFFGH (SEQ ID NO:4).

The amino acid sequence for full-length human JAGGED2 is publically available in the UniProt database under accession number Q9Y219 (SEQ ID NO: 16) and is as follows (an exemplary functional fragment that agonizes NOTCH3 is bolded and underlined):

MRAQGRGRLPRRLLLLLALWVQAARPMGYFELQLSALRNVNGELLSGACC

DGDGRTTRAGGCGHDECDTYVRVCLKEYQAKVTPTGPCSYGHGATPVLGG

NSFYLPPAGAAGDRARARARAGGDQDPGLVVIPFQFAWPRSFTLIVEAWD

WDNDTTPNEELLIERVSHAGMINPEDRWKSLHFSGHVAHLELQIRVRCDE

NYYSATCNKFCRPRNDFFGHYTCDQYGNKACMDGWMGKECKEAVCKQGCN

LLHGGCTVPGECRCSYGWQGRFCDECVPYPGCVHGSCVEPWQCNCETNWG

GLLCDKDLNYCGSHHPCTNGGTCINAEPDQYRCTCPDGYSGRNCEKAEHA

CTSNPCANGGSCHEVPSGFECHCPSGWSGPTCALDIDECASNPCAAGGTC

VDQVDGFECICPEQWVGATCQLDANECEGKPCLNAFSCKNLIGGYYCDCI

PGWKGINCHINVNDCRGQCQHGGTCKDLVNGYQCVCPRGFGGRHCELERD

ECASSPCHSGGLCEDLADGFHCHCPQGFSGPLCEVDVDLCEPSPCRNGAR

CYNLEGDYYCACPDDFGGKNCSVPREPCPGGACRVIDGCGSDAGPGMPGT

AASGVCGPHGRCVSQPGGNFSCICDSGFTGTYCHENIDDCLGQPCRNGGT

CIDEVDAFRCFCPSGWEGELCDTNPNDCLPDPCHSRGRCYDLVNDFYCAC

DDGWKGKTCHSREFQCDAYTCSNGGTCYDSGDTFRCACPPGWKGSTCAVA

KNSSCLPNPCVNGGTCVGSGASFSCICRDGWEGRTCTHNTNDCNPLPCYN

GGICVDGVNWFRCECAPGFAGPDCRINIDECQSSPCAYGATCVDEINGYR

CSCPPGRAGPRCQEVIGFGRSCWSRGTPFPHGSSWVEDCNSCRCLDGRRD

CSKVWCGWKPCLLAGQPEALSAQCPLGQRCLEKAPGQCLRPPCEAWGECG

AEEPPSTPCLPRSGHLDNNCARLTLHFNRDHVPQGTTVGAICSGIRSLPA

TRAVARDRLLVLLCDRASSGASAVEVAVSFSPARDLPDSSLIQGAAHAIV

AAITQRGNSSLLLAVTEVKVETVVTGGSSTGLLVPVLCGAFSVLWLACVV

LCVWWTRKRRKERERSRLPREESANNQWAPLNPIRNPIERPGGHKDVLYQ

CKNFTPPPRRADEALPGPAGHAAVREDEEDEDLGRGEEDSLEAEKFLSHK

FTKDPGRSPGRPAHWASGPKVDNRAVRSINEARYAGKE

The amino acid sequence for the extracellular domain of human JAGGED2 is as follows (SEQ ID NO: 17):

MGYFELQLSALRNVNGELLSGACCDGDGRTTRAGGCGHDECDTYVRVCLK

EYQAKVTPTGPCSYGHGATPVLGGNSFYLPPAGAAGDRARARARAGGDQD

PGLVVIPFQFAWPRSFTLIVEAWDWDNDTTPNEELLIERVSHAGMINPED

RWKSLHFSGHVAHLELQIRVRCDENYYSATCNKFCRPRNDFFGHYTCDQY

GNKACMDGWMGKECKEAVCKQGCNLLHGGCTVPGECRCSYGWQGRFCDEC

VPYPGCVHGSCVEPWQCNCETNWGGLLCDKDLNYCGSHHPCTNGGTCINA

EPDQYRCTCPDGYSGRNCEKAEHACTSNPCANGGSCHEVPSGFECHCPSG

WSGPTCALDIDECASNPCAAGGTCVDQVDGFECICPEQWVGATCQLDANE

CEGKPCLNAFSCKNLIGGYYCDCIPGWKGINCHINVNDCRGQCQHGGTCK

DLVNGYQCVCPRGFGGRHCELERDECASSPCHSGGLCEDLADGFHCHCPQ

GFSGPLCEVDVDLCEPSPCRNGARCYNLEGDYYCACPDDFGGKNCSVPRE

PCPGGACRVIDGCGSDAGPGMPGTAASGVCGPHGRCVSQPGGNFSCICDS

GFTGTYCHENIDDCLGQPCRNGGTCIDEVDAFRCFCPSGWEGELCDTNPN

DCLPDPCHSRGRCYDLVNDFYCACDDGWKGKTCHSREFQCDAYTCSNGGT

CYDSGDTFRCACPPGWKGSTCAVAKNSSCLPNPCVNGGTCVGSGASFSCI

CRDGWEGRTCTHNTNDCNPLPCYNGGICVDGVNWFRCECAPGFAGPDCRI

NIDECQSSPCAYGATCVDEINGYRCSCPPGRAGPRCQEVIGFGRSCWSRG

```
TPFPHGSSWVEDCNSCRCLDGRRDCSKVWCGWKPCLLAGQPEALSAQCPL

GQRCLEKAPGQCLRPPCEAWGECGAEEPPSTPCLPRSGHLDNNCARLTLH

FNRDHVPQGTTVGAICSGIRSLPATRAVARDRLLVLLCDRASSGASAVEV

AVSFSPARDLPDSSLIQGAAHAIVAAITQRGNSSLLLAVTEVKVETVVTG

GSST
```

In some embodiments, the agonist comprises a fragment of DELTA-LIKE1 comprising the amino acid sequence CDEHYYGEGCSVFCRPR (SEQ ID NO:5) or CDEHYYGEGCSVFCRPRDDAFGH (SEQ ID NO:6). Additional non-limiting examples of NOTCH3 agonists include larger fragments of DELTA-LIKE1 that comprise CDEHYYGEGCSVFCRPR (SEQ ID NO:5), with the proviso that such fragments do not comprise the transmembrane domain (positions 546-568) or cytoplasmic domain (positions 569-723) of DELTA-LIKE1. Thus, in some embodiments, the NOTCH3 agonist comprises the extracellular domain of DELTA-LIKE1 (positions 18-545; SEQ ID NO: 19) or a fragment thereof that comprises the amino acid sequence CDEHYYGEGCSVFCRPR (SEQ ID NO:5). In certain embodiments, the fragment of the DELTA-LIKE1 extracellular domain is a fragment that comprises the amino acid sequence of CDEHYYGEGCSVFCRPRDDAFGH (SEQ ID NO:6).

The amino acid sequence for full-length human DELTA-LIKE1 is publically available in the UniProt database under accession number 000548 (SEQ ID NO: 18) and is as follows (an exemplary functional fragment that agonizes NOTCH3 is bolded and underlined):

```
MGSRCALALAVLSALLCQVWSSGVFELKLQEFVNKKGLLGNRNCCRGGAG

PPPCACRTFFRVCLKHYQASVSPEPPCTYGSAVTPVLGVDSFSLPDGGGA

DSAFSNPIRFPFGFTWPGTFSLIIEALHTDSPDDLATENPERLISRLATQ

RHLTVGEEWSQDLHSSGRTDLKYSYRFVCDEHYYGEGCSVFCRPRDDAFG

HFTCGERGEKVCNPGWKGPYCTEPICLPGCDEQHGFCDKPGECKCRVGWQ

GRYCDECIRYPGCLHGTCQQPWQCNCQEGWGGLFCNQDLNYCTHHKPCKN

GATCTNTGQGSYTCSCRPGYTGATCELGIDECDPSPCKNGGSCTDLENSY

SCTCPPGFYGKICELSAMTCADGPCFNGGRCSDSPDGGYSCRCPVGYSGF

NCEKKIDYCSSSPCSNGAKCVDLGDAYLCRCQAGFSGRHCDDNVDDCASS

PCANGGTCRDGVNDFSCTCPPGYTGRNCSAPVSRCEHAPCHNGATCHERG

HRYVCECARGYGGPNCQFLLPELPPGPAVVDLTEKLEGQGGPFPWVAVCA

GVILVLMLLLGCAAVVVCVRLRLQKHRPPADPCRGETETMNNLANCQREK

DISVSIIGATQIKNTNKKADFHGDHSADKNGFKARYPAVDYNLVQDLKGD

DTAVRDAHSKRDTKCQPQGSSGEEKGTPTTLRGGEASERKRPDSGCSTSK

DTKYQSVYVISEEKDECVIATEV
```

The amino acid sequence for the extracellular domain of human DELTA-LIKE1 is as follows (SEQ ID NO: 19):

```
QVWSSGVFELKLQEFVNKKGLLGNRNCCRGGAGPPPCACRTFFRVCLKHY

QASVSPEPPCTYGSAVTPVLGVDSFSLPDGGGADSAFSNPIRFPFGFTWP

GTFSLIIEALHTDSPDDLATENPERLISRLATQRHLTVGEEWSQDLHSSG

RTDLKYSYRFVCDEHYYGEGCSVFCRPRDDAFGHFTCGERGEKVCNPGWK

GPYCTEPICLPGCDEQHGFCDKPGECKCRVGWQGRYCDECIRYPGCLHGT

CQQPWQCNCQEGWGGLFCNQDLNYCTHHKPCKNGATCTNTGQGSYTCSCR

PGYTGATCELGIDECDPSPCKNGGSCTDLENSYSCTCPPGFYGKICELSA

MTCADGPCFNGGRCSDSPDGGYSCRCPVGYSGFNCEKKIDYCSSSPCSNG

AKCVDLGDAYLCRCQAGFSGRHCDDNVDDCASSPCANGGTCRDGVNDFSC

TCPPGYTGRNCSAPVSRCEHAPCHNGATCHERGHRYVCECARGYGGPNCQ

FLLPELPPGPAVVDLTEKLEGQGGPFPW
```

In some embodiments, the agonist comprises a fragment of DELTA-LIKE3 comprising the amino acid sequence CEPPAVGTACTRLCRPR (SEQ ID NO:7). Additional non-limiting examples of NOTCH3 agonists include larger fragments of DELTA-LIKE3 that comprise CEPPAVGTACTRLCRPR (SEQ ID NO:7), with the proviso that such fragments do not comprise the transmembrane domain (positions 493-513) or cytoplasmic domain (positions 514-618) of DELTA-LIKE3. Thus, in some embodiments, the NOTCH3 agonist comprises the extracellular domain of DELTA-LIKE3 (positions 27-492; SEQ ID NO: 21) or a fragment thereof that comprises the amino acid sequence CEPPAVGTACTRLCRPR (SEQ ID NO:7).

The amino acid sequence for full-length human DELTA-LIKE3 is publically available in the UniProt database under accession number Q9NYJ7 (SEQ ID NO: 20) and is as follows (an exemplary functional fragment that agonizes NOTCH3 is bolded and underlined):

```
MVSPRMSGLLSQTVILALIFLPQTRPAGVFELQIHSFGPGPGPAPRSPC

SARLPCRLFFRVCLKPGLSEEAAESPCALGAALSARGPVYTEQPGAPAPD

LPLPDGLLQVPFRDAWPGTFSFIIETWREELGDQIGGPAWSLLARVAGRR

RLAAGGPWARDIQRAGAWELRFSYRARCEPPAVGTACTRLCRPRSAPSRC

GPGLRPCAPLEDECEAPLVCRAGCSPEHGFCEQPGECRCLEGWTGPLCTV

PVSTSSCLSPRGPSSATTGCLVPGPGPCDGNPCANGGSCSETPRSFECTC

PRGFYGLRCEVSGVTCADGPCFNGGLCVGGADPDSAYICHCPPGFQGSNC

EKRVDRCSLQPCRNGGLCLDLGHALRCRCRAGFAGPRCEHDLDDCAGRAC

ANGGTCVEGGGAHRCSCALGFGGRDCRERADPCAARPCAHGGRCYAHFSG

LVCACAPGYMGARCEFPVHPDGASALPAAPPGLRPGDPQRYLLPPALGLL

VAAGVAGAALLLVHVRRRGHSQDAGSRLLAGTPEPSVHALPDALNNLRTQ

EGSGDGPSSSVDWNRPEDVDPQGIYVISAPSIYAREVATPLFPPLHTGRA

GQRQHLLFPYPSSILSVK
```

The amino acid sequence for the extracellular domain of human DELTA-LIKE3 is as follows (SEQ ID NO: 21):

```
AGVFELQIHSFGPGPGPAPRSPCSARLPCRLFIRVCLKPGLSEEAAESP

CALGAALSARGPVYTEQPGAPAPDLPLPDGLLQVPFRDAWPGTFSFIIET

WREELGDQIGGPAWSLLARVAGRRRLAAGGPWARDIQRAGAWELRFSYRA

RCEPPAVGTACTRLCRPRSAPSRCGPGLRPCAPLEDECEAPLVCRAGCSP
```

```
EHGFCEQPGECRCLEGWTGPLCTVPVSTSSCLSPRGPSSATTGCLVPGPG

PCDGNPCANGGSCSETPRSFECTCPRGFYGLRCEVSGVTCADGPCFNGGL

CVGGADPDSAYICHCPPGFQGSNCEKRVDRCSLQPCRNGGLCLDLGHALR

CRCRAGFAGPRCEHDLDDCAGRACANGGTCVEGGGAHRCSCALGFGGRDC

RERADPCAARPCAHGGRCYAHFSGLVCACAPGYMGARCEFPVHPDGASAL

PAAPPGLRPGDPQRYL
```

In some embodiments, the agonist comprises a fragment of DELTA-LIKE4 comprising the amino acid sequence CSDNYYGDNCSRLCKKR (SEQ ID NO:8) or CSDNYYGDNCSRLCKKRNDHFGH (SEQ ID NO:9). Additional non-limiting examples of NOTCH3 agonists include larger fragments of DELTA-LIKE4 that comprise CSDNYYGDNCSRLCKKR (SEQ ID NO:8), with the proviso that such fragments do not comprise the transmembrane domain (positions 530-550) or cytoplasmic domain (positions 551-685) of DELTA-LIKE4. Thus, in some embodiments, the NOTCH3 agonist comprises the extracellular domain of DELTA-LIKE4 (positions 27-529; SEQ ID NO: 23) or a fragment thereof that comprises the amino acid sequence CSDNYYGDNCSRLCKKR (SEQ ID NO:8). In certain embodiments, the fragment of the DELTA-LIKE4 extracellular domain is a fragment that comprises the amino acid sequence of CSDNYYGDNCSRLCKKRNDHFGH (SEQ ID NO:9).

The amino acid sequence for full-length human DELTA-LIKE4 is publically available in the UniProt database under accession number Q9NR61 (SEQ ID NO: 22) and is as follows (an exemplary functional fragment that agonizes NOTCH3 is bolded and underlined):

```
MAAASRSASGWALLLLVALWQQRAAGSGVFQLQLQEFINERGVLASGRPC

EPGCRTFFRVCLKHFQAVVSPGPCTFGTVSTPVLGTNSFAVRDDSSGGGR

NPLQLPFNFTWPGTFSLIIEAWHAPGDDLRPEALPPDALISKIAIQGSLA

VGQNWLLDEQTSTLTRLRYSYRVICSDNYYGDNCSRLCKKRNDHFGHYVC

QPDGNLSCLPGWTGEYCQQPICLSGCHEQNGYCSKPAECLCRPGWQGRLC

NECIPHNGCRHGTCSTPWQCTCDEGWGGLFCDQDLNYCTHHSPCKNGATC

SNSGQRSYTCTCRPGYTGVDCELELSECDSNPCRNGGSCKDQEDGYHCLC

PPGYYGLHCEHSTLSCADSPCFNGGSCRERNQGANYACECPPNFTGSNCE

KKVDRCTSNPCANGGQCLNRGPSRMCRCRPGFTGTYCELHVSDCARNPCA

HGGTCHDLENGLMCTCPAGFSGRRCEVRTSIDACASSPCFNRATCYTDLS

TDTFVCNCPYGFVGSRCEFPVGLPPSFPWVAVSLGVGLAVLLVLLGMVAV

AVRQLRLRRPDDGSREAMNNLSDFQKDNLIPAAQLKNTNQKKELEVDCGL

DKSNCGKQQNHTLDYNLAPGPLGRGTMPGKFPHSDKSLGEKAPLRLHSEK

PECRISAICSPRDSMYQSVCLISEERNECVIATEV
```

The amino acid sequence for the extracellular domain of human DELTA-LIKE4 is as follows (SEQ ID NO: 23):

```
SGVFQLQLQEFINERGVLASGRPCEPGCRTFFRVCLKHFQAVVSPGPCTF

GTVSTPVLGTNSFAVRDDSSGGGRNPLQLPFNFTWPGTFSLIIEAWHAPG

DDLRPEALPPDALISKIAIQGSLAVGQNWLLDEQTSTLTRLRYSYRVICS

DNYYGDNCSRLCKKRNDHFGHYVCQPDGNLSCLPGWTGEYCQQPICLSGC

HEQNGYCSKPAECLCRPGWQGRLCNECIPHNGCRHGTCSTPWQCTCDEGW

GGLFCDQDLNYCTHHSPCKNGATCSNSGQRSYTCTCRPGYTGVDCELELS

ECDSNPCRNGGSCKDQEDGYHCLCPPGYYGLHCEHSTLSCADSPCFNGGS

CRERNQGANYACECPPNFTGSNCEKKVDRCTSNPCANGGQCLNRGPSRMC

RCRPGFTGTYCELHVSDCARNPCAHGGTCHDLENGLMCTCPAGFSGRRCE

VRTSIDACASSPCFNRATCYTDLSTDTFVCNCPYGFVGSRCEFPVGLPPS

FPW
```

Pharmaceutical Formulations and Delivery

Dosages, formulations, dosage volumes, regimens, and methods for administering a NOTCH3 agonist may vary. Thus, minimum and maximum effective dosages vary depending on the method of administration.

"Administering" an agonist described herein can be effected or performed using any of the various methods and delivery systems known to those skilled in the art. The administering can be, for example, intravenous, oral, ocular (e.g., subconjunctival, intravitreal, retrobulbar, or intracameral), intramuscular, intravascular, intra-arterial, intracoronary, intramyocardial, intraperitoneal, subcutaneous, inhaled, or intrathecal. Other non-limiting examples include topical administration, or coating of a device to be placed within the subject. In embodiments, administration is effected by injection or via a catheter.

As used herein, "effective" when referring to an amount of a therapeutic compound refers to the quantity of the compound that is sufficient to yield a desired therapeutic response without undue adverse side effects (such as toxicity, irritation, or allergic response) commensurate with a reasonable benefit/risk ratio when used in the manner of this disclosure.

As used herein, "pharmaceutically acceptable" carrier or excipient refers to a carrier or excipient that is suitable for use with humans and/or animals without undue adverse side effects (such as toxicity, irritation, and allergic response) commensurate with a reasonable benefit/risk ratio. It can be, e.g., a pharmaceutically acceptable solvent, suspending agent or vehicle, for delivering the instant compounds to the subject.

As used herein, a "monotherapy" is therapy that is administered to inhibit, treat, or prevent a disorder, such as a SVD, without any other therapy that is used to treat the disorder. A monotherapy for treating a disorder may optionally be combined with another treatment that is used to ameliorate a symptom of the disorder while not being directed against the disorder, for example an analgesic compound, an anti-pyretic compound, and/or an anti-inflammatory compound (e.g., aspirin, ibuprofen, naproxen, or acetaminophen) may be administered concurrently with the monotherapy.

In various embodiments, a composition comprising a NOTCH3 agonist may be administered only once or multiple times. For example, a NOTCH3 agonist may be administered using a method disclosed herein at least about once, twice, three times, four times, five times, six times, or seven times per day, week, month, or year. In some embodiments, a composition comprising a NOTCH3 agonist is administered once per month. In certain embodiments, the composition is administered once per month via intravitreal injection. In various embodiments, such as embodiments involving eye drops, a composition is self-administered.

For the treatment of an ocular disorder, a NOTCH3 agonist (e.g., a pharmaceutical composition comprising a NOTCH3 agonist) may be administered locally, e.g., as a topical eye drop, peri-ocular injection (e.g., sub-tenon), intraocular injection, intravitreal injection, retrobulbar injection, intraretinal injection, subretinal injection, subconjunctival injection, or using iontophoresis, or peri-ocular devices which can actively or passively deliver drug.

Sustained release of drug may be achieved by the use of technologies such as implants (e.g., solid implants) (which may or may not be bio-degradable) or bio-degradable polymeric matrices (e.g., micro-particles). These may be administered, e.g., peri-ocularly or intravitreally.

Pharmaceutical formulations adapted for topical administration may be formulated as aqueous solutions, ointments, creams, suspensions, lotions, powders, solutions, pastes, gels, sprays, aerosols, liposomes, microcapsules, microspheres, or oils.

For treatments of the eye or other external tissues, such as the mouth or skin, the formulations (e.g., a pharmaceutical composition comprising a NOTCH3 agonist) may be applied as a topical ointment or cream. When formulated in an ointment, a NOTCH3 agonist may be employed with either a paraffinic or a water-miscible ointment base. Alternatively, a NOTCH3 agonist may be formulated in a cream with an oil-in-water cream base or a water-in-oil base.

The present subject matter provides compositions comprising a NOTCH3 agonist and a carrier or excipient suitable for administration to ocular tissue. Such carriers and excipients are suitable for administration to ocular tissue (e.g., sclera, lens, iris, cornea, uvea, retina, macula, or vitreous tissue) without undue adverse side effects (such as toxicity, irritation, and allergic response) commensurate with a reasonable benefit/risk ratio.

Pharmaceutical formulations adapted for topical administrations to the eye include eye drops wherein a NOTCH3 agonist is dissolved or suspended in a suitable carrier, especially an aqueous solvent. Formulations to be administered to the eye will have ophthalmically compatible pH and osmolality. The term "ophthalmically acceptable vehicle" means a pharmaceutical composition having physical properties (e.g., pH and/or osmolality) that are physiologically compatible with ophthalmic tissues.

In some embodiments, an ophthalmic composition of the present invention is formulated as sterile aqueous solutions having an osmolality of from about 200 to about 400 milliosmoles/kilogram water ("mOsm/kg") and a physiologically compatible pH. The osmolality of the solutions may be adjusted by means of conventional agents, such as inorganic salts (e.g., NaCl), organic salts (e.g., sodium citrate), polyhydric alcohols (e.g., propylene glycol or sorbitol) or combinations thereof.

In various embodiments, the ophthalmic formulations may be in the form of liquid, solid or semisolid dosage form. The ophthalmic formulations may comprise, depending on the final dosage form, suitable ophthalmically acceptable excipients. In some embodiments, the ophthalmic formulations are formulated to maintain a physiologically tolerable pH range. In certain embodiments, the pH range of the ophthalmic formulation is in the range of from about 5 to about 9. In some embodiments, pH range of the ophthalmic formulation is in the range of from about 6 to about 8, or is about 6.5, about 7, or about 7.5.

In some embodiments, the composition is in the form of an aqueous solution, such as one that can be presented in the form of eye drops. By means of a suitable dispenser, a desired dosage of the active agent can be metered by administration of a known number of drops into the eye, such as by one, two, three, four, or five drops.

One or more ophthalmically acceptable pH adjusting agents and/or buffering agents can be included in a composition, including acids such as acetic, boric, citric, lactic, phosphoric, and hydrochloric acids; bases such as sodium hydroxide, sodium phosphate, sodium borate, sodium citrate, sodium acetate, and sodium lactate; and buffers such as citrate/dextrose, sodium bicarbonate, and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium, or ammonium cations and chloride, citrate, ascorbate, borate, phosphate, bicarbonate, sulfate, thiosulfate, or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g., poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition, and polymeric coatings that will enhance drug diffusion, erosion, dissolution, and osmosis.

Formulations for drug delivery using ocular devices may combine one or more active agents and adjuvants appropriate for the indicated route of administration. For example, a NOTCH3 agonist (optionally with another agent) may be admixed with any pharmaceutically acceptable excipient, lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, tableted or encapsulated for conventional administration. Alternatively, the compounds may be dissolved in polyethylene glycol, propylene glycol, carboxymethyl cellulose colloidal solutions, ethanol, corn oil, peanut oil, cottonseed oil, sesame oil, tragacanth gum, and/or various buffers. The compounds may also be mixed with compositions of both biodegradable and non-biodegradable polymers, and a carrier or diluent that has a time delay property. Representative examples of biodegradable compositions can include albumin, gelatin, starch, cellulose, dextrans, polysaccharides, poly (D,L-lactide), poly (D,L-lactide-co-glycolide), poly (glycolide), poly (hydroxybutyrate), poly (alkylcarbonate) and poly (orthoesters), and mixtures thereof. Representative examples of non-biodegradable polymers can include EVA copolymers, silicone rubber and poly (methylacrylate), and mixtures thereof.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig, Adv. Drug Deliv. Rev. 3; 57:1595-639 (2005), the entire content of which is incorporated herein by reference.

Biocompatible implants for placement in the eye have been disclosed in a number of patents, such as U.S. Pat. Nos. 4,521,210; 4,853,224; 4,997,652; 5,164,188; 5,443,505; 5,501,856; 5,766,242; 5,824,072; 5,869,079; 6,074,661; 6,331,313; 6,369,116; 6,699,493; and 8,293,210, the entire contents of each of which are incorporated herein by reference.

The implants may be monolithic, i.e. having the active agent (e.g., a NOTCH3 agonist) or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated, reservoir-type implant may be of benefit in some circumstances, where the therapeutic level of the drug falls within a narrow window. In addition, the therapeutic component, including a NOTCH3 agonist, may be distributed in a non-homogenous pattern in the matrix. For example, the implant may include a portion that has a greater concentration of a NOTCH3 agonist relative to a second portion of the implant.

The intraocular implants disclosed herein may have a size of between about 5 um and about 2 mm, or between about 10 um and about 1 mm for administration with a needle, greater than 1 mm, or greater than 2 mm, such as 3 mm or up to 10 mm, for administration by surgical implantation. The vitreous chamber in humans is able to accommodate relatively large implants of varying geometries, having lengths of, for example, 1 to 10 mm. The implant may be a cylindrical pellet (e.g., rod) with dimensions of about 2 mm×0.75 mm diameter. The implant may be a cylindrical pellet with a length of about 7 mm to about 10 mm, and a diameter of about 0.75 mm to about 1.5 mm.

The implants may also be at least somewhat flexible so as to facilitate both insertion of the implant in the eye, such as in the vitreous, and accommodation of the implant. The total weight of the implant is usually about 250-5000 µg, more preferably about 500-1000 µg. For example, an implant may be about 500 µg, or about 1000 µg. For non-human subject, the dimensions and total weight of the implant(s) may be larger or smaller, depending on the type of subject. For example, humans have a vitreous volume of approximately 3.8 ml, compared with approximately 30 ml for horses, and approximately 60-100 ml for elephants. An implant sized for use in a human may be scaled up or down accordingly for other animals, for example, about 8 times larger for an implant for a horse, or about, for example, 26 times larger for an implant for an elephant.

Implants can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The implants may be of any geometry including fibers, sheets, films, microspheres, spheres, circular discs, plaques, and the like. The upper limit for the implant size will be determined by factors such as toleration for the implant, size limitations on insertion, ease of handling, etc. Where sheets or films are employed, the sheets or films will be in the range of at least about 0.5 mm×0.5 mm, usually about 3-10 mm×5-10 mm with a thickness of about 0.1-1.0 mm for ease of handling. Where fibers are employed, the fiber diameter will generally be in the range of about 0.05 to 3 mm and the fiber length will generally be in the range of about 0.5-10 mm Spheres may be in the range of 0.5 µm to 4 mm in diameter, with comparable volumes for other shaped particles.

The size and form of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the site of implantation.

Microspheres for ocular delivery are described, for example, in U.S. Pat. Nos. 5,837,226; 5,731,005; 5,641,750; 7,354,574; and U.S. Pub. No. 2008-0131484, the entire contents of each of which are incorporated herein by reference.

For oral or enteral formulations for use with the present invention, tablets can be formulated in accordance with conventional procedures employing solid carriers well-known in the art. Capsules employed for oral formulations to be used with the methods of the present invention can be made from any pharmaceutically acceptable material, such as gelatin or cellulose derivatives. Sustained release oral delivery systems and/or enteric coatings for orally administered dosage forms are also contemplated, such as those described in U.S. Pat. Nos. 4,704,295; 4, 556,552; 4,309, 404; and 4,309,406, the entire contents of each of which are incorporated herein by reference.

General Definitions

Unless specifically defined otherwise, all technical and scientific terms used herein shall be taken to have the same meaning as commonly understood by one of ordinary skill in the art (e.g., in cell culture, molecular genetics, and biochemistry).

As used herein, the term "about" in the context of a numerical value or range means±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (RNA or DNA) is free of the genes or sequences that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

The term "sample" as used herein refers to a biological sample obtained for the purpose of evaluation in vitro. In embodiments, the sample may comprise a body fluid. In some embodiments, the body fluid includes, but is not limited to, whole blood, plasma, serum, lymph, breast milk, saliva, mucous, semen, cellular extracts, inflammatory fluids, cerebrospinal fluid, vitreous humor, tears, vitreous, aqueous humor, or urine obtained from the subject. In some aspects, the sample is a composite panel of two or more body fluids. In exemplary aspects, the sample comprises blood or a fraction thereof (e.g., plasma, serum, or a fraction obtained via leukapheresis). In embodiments, the sample is a tissue sample, such as a biopsy.

A "control" sample or value refers to a sample that serves as a reference, usually a known reference, for comparison to a test sample. For example, a test sample can be taken from a test subject, e.g., a subject with a small vessel disease or in need of diagnosis for a small vessel disease, and compared to samples from known conditions, e.g., a subject (or subjects) that does not have the small vessel disease (a negative or normal control), or a subject (or subjects) who does have the small vessel disease (positive control). A control can also represent an average value gathered from a number of tests or results. One of skill in the art will recognize that controls can be designed for assessment of any number of parameters. One of skill in the art will understand which controls are valuable in a given situation and be able to analyze data based on comparisons to control values. Controls are also valuable for determining the significance of data. For example, if values for a given parameter are variable in controls, variation in test samples will not be considered as significant.

The term, "normal amount" with respect to a compound (e.g., a protein or mRNA) refers to a normal amount of the compound in an individual who does not have a SVD or in a healthy or general population. The amount of a compound can be measured in a test sample and compared to the "normal control" level, utilizing techniques such as reference limits, discrimination limits, or risk defining thresholds to define cutoff points and abnormal values (e.g., for a particular SVD or a symptom thereof). The normal control level means the level of one or more compounds or combined compounds typically found in a subject known not suffering from an SVD. Such normal control levels and cutoff points may vary based on whether a compounds is used alone or in a formula combining with other compounds into an index. Alternatively, the normal control level can be a database of compounds patterns from previously tested subjects who did not develop a SVD or a particular symptom thereof (e.g., in the event the SVD develops or a subject already having the SVD is tested) over a clinically relevant time horizon.

The level that is determined may be the same as a control level or a cut off level or a threshold level, or may be increased or decreased relative to a control level or a cut off level or a threshold level. In some aspects, the control subject is a matched control of the same species, gender, ethnicity, age group, smoking status, body mass index (BMI), current therapeutic regimen status, medical history, or a combination thereof, but differs from the subject being diagnosed in that the control does not suffer from the disease (or a symptom thereof) in question or is not at risk for the disease.

Relative to a control level, the level that is determined may an increased level. As used herein, the term "increased" with respect to level (e.g., protein or mRNA level) refers to any % increase above a control level. In various embodiments, the increased level may be at least or about a 5% increase, at least or about a 10% increase, at least or about a 15% increase, at least or about a 20% increase, at least or about a 25% increase, at least or about a 30% increase, at least or about a 35% increase, at least or about a 40% increase, at least or about a 45% increase, at least or about a 50% increase, at least or about a 55% increase, at least or about a 60% increase, at least or about a 65% increase, at least or about a 70% increase, at least or about a 75% increase, at least or about a 80% increase, at least or about a 85% increase, at least or about a 90% increase, at least or about a 95% increase, relative to a control level.

Relative to a control level, the level that is determined may a decreased level. As used herein, the term "decreased" with respect to level (e.g., protein or mRNA level) refers to any % decrease below a control level. In various embodiments, the decreased level may be at least or about a 5% decrease, at least or about a 10% decrease, at least or about a 15% decrease, at least or about a 20% decrease, at least or about a 25% decrease, at least or about a 30% decrease, at least or about a 35% decrease, at least or about a 40% decrease, at least or about a 45% decrease, at least or about a 50% decrease, at least or about a 55% decrease, at least or about a 60% decrease, at least or about a 65% decrease, at least or about a 70% decrease, at least or about a 75% decrease, at least or about a 80% decrease, at least or about a 85% decrease, at least or about a 90% decrease, at least or about a 95% decrease, relative to a control level.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The terms "subject," "patient," "individual," and the like as used herein are not intended to be limiting and can be generally interchanged. An individual described as a "subject," "patient," "individual," and the like does not necessarily have a given disease, but may be merely seeking medical advice. The terms "subject," "patient," "individual," and the like as used herein include all members of the animal kingdom that may suffer from the indicated disorder. In some aspects, the subject is a mammal, and in some aspects, the subject is a human.

As used herein, the singular forms "a," "an," and "the" include the plural reference unless the context clearly dictates otherwise. Thus, for example, a reference to "a disease," "a disease state", or "a nucleic acid" is a reference to one or more such embodiments, and includes equivalents thereof known to those skilled in the art and so forth.

As used herein, "treating" encompasses, e.g., inhibition, regression, or stasis of the progression of a disorder. For purposes of this disclosure, beneficial or desired clinical results include, but are not limited to, alleviation or amelioration of any symptom or symptoms, diminishment of extent of disease, stabilized (i.e., not worsening) state of disease, preventing spread of disease, delay or slowing of disease progression, amelioration or palliation of the disease state, and recovery (whether partial or total), whether detectable or undetectable. As used herein, "inhibition" of disease progression or a disease complication in a subject means preventing or reducing the disease progression and/or disease complication in the subject.

As used herein, a "symptom" associated with a disorder includes any clinical or laboratory manifestation associated with the disorder, and is not limited to what the subject can feel or observe.

Embodiments and examples are provided below to facilitate a more complete understanding of the invention. The following embodiments and examples illustrate the exemplary modes of making and practicing the invention. However, the scope of the invention is not limited to specific embodiments disclosed in these embodiments and examples, which are for purposes of illustration only, since alternative methods can be utilized to obtain similar results.

EMBODIMENTS

Embodiments include Embodiments P1 to P48 following.

Embodiment P1

A method for treating or preventing a small vessel disease (SVD) in a subject, comprising administering to the subject an effective amount of a Neurogenic Locus NOTCH Homolog Protein 3 (NOTCH3) agonist.

Embodiment P2

The method of Embodiment P1, wherein the SVD comprises cerebral SVD.

Embodiment P3

The method of Embodiment P1, wherein the SVD comprises cerebral autosomal-dominant arteriopathy with subcortical infarcts and leukoencephalopathy (CADASIL).

Embodiment P4

The method of Embodiment P1, wherein the SVD comprises cerebral autosomal recessive arteriopathy with subcortical infarcts and leukoencephalopathy (CARASIL).

Embodiment P5

The method of Embodiment P1, wherein the SVD comprises a NOTCH3 loss-of-function associated SVD.

Embodiment P6

The method of Embodiment P1, wherein the SVD comprises diabetic retinopathy.

Embodiment P7

The method of Embodiment P1, wherein the SVD comprises age-related macular degeneration (AMD), nephropathy, microangiopathy, heart failure, Alagille syndrome, familial tetralogy of Fallot, patent ductus arteriosus, or a cerebral cavernous malformation.

Embodiment P8

The method of any one of Embodiments P1-P7, wherein the subject has at least 1, 2, 3, or 4 grandparents, parents, aunts, uncles, cousins, or siblings who comprise the SVD.

Embodiment P9

The method of any one of Embodiments P1-P8, wherein the subject comprises diabetes.

Embodiment P10

The method of Embodiment P9, wherein the diabetes is type 1 diabetes or type 2 diabetes.

Embodiment P11

The method of any one of Embodiments P1-P10, wherein the subject is at least about 80 years old.

Embodiment P12

The method of any one of Embodiments P1-P11, wherein a test sample obtained from the subject comprises a level of NOTCH3 protein or mRNA that is different than a normal control.

Embodiment P13

The method of Embodiment P12, wherein the test sample comprises a level of NOTCH3 protein or mRNA that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% lower in the test sample compared to a normal control.

Embodiment P14

The method of Embodiment P12, wherein the test sample comprises a level of NOTCH3 activity that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% lower in the test sample compared to a normal control.

Embodiment P15

The method of Embodiment P12, wherein the test sample comprises blood, serum, or plasma.

Embodiment P16

The method of Embodiment P12, wherein the test sample comprises saliva, tears, vitreous, cerebrospinal fluid, sweat, cerebrospinal fluid, or urine.

Embodiment P17

The method of any one of Embodiments P1-P16, wherein a test sample obtained from the subject comprises a level of collagen18α1, endostatin, NOTCH3, N3ECD, insulin-like growth factor binding protein 1 (IGFBP-1), and/or High-Temperature Requirement A Serine Peptidase 1 (HTRA1) protein or mRNA that is different than a normal control.

Embodiment P18

The method of any one of Embodiments P12-P17, wherein the test sample comprises a level of collagen18α1, endostatin, IGFBP-1, and/or HTRA1 protein or mRNA that is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher in the test sample compared to a normal control.

Embodiment P19

The method of any one of Embodiments P12-P17, wherein the test sample comprises a level of HTRA1 protein or mRNA that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% lower in the test sample compared to a normal control.

Embodiment P20

The method of any one of Embodiments P1-P19, wherein the NOTCH3 agonist is administered as a monotherapy.

Embodiment P21

The method of Embodiment P3, wherein the subject is not administered a thrombolytic agent.

Embodiment P22

The method of any one of Embodiments P1-P21, wherein the NOTCH3 agonist comprises a polypeptide, an antibody or a fragment thereof, an aptamer, or a small molecule.

Embodiment P23

The method of any one of Embodiments P1-P22, wherein the NOTCH3 agonist comprises a polypeptide.

Embodiment P24

The method of any one of Embodiments P1-P3, wherein the polypeptide comprises a fragment of a NOTCH3 ligand.

Embodiment P25

The method of Embodiment P24, wherein the ligand comprises JAGGED1 or a fragment thereof, JAGGED2 or a fragment thereof, or DELTA-LIKE1 or a fragment thereof.

Embodiment P26

The method of Embodiment P25, wherein the polypeptide comprises a fragment of JAGGED1.

Embodiment P27

The method of Embodiment P26, wherein the fragment of JAGGED1 is the extracellular domain of JAGGED1 or a fragment thereof comprising a stretch of amino acids having the sequence CDDYYYGFGCNKFCRPR (SEQ ID NO:1).

Embodiment P28

The method of Embodiment P26, wherein the fragment of JAGGED1 comprises a stretch of amino acids having the sequence or CDDYYYGFGCNKFCRPRDDFFGH (SEQ ID NO:2).

Embodiment P29

The method of Embodiment P25, wherein the polypeptide comprises a fragment of JAGGED2.

Embodiment P30

The method of Embodiment P29, wherein the fragment of JAGGED2 is the extracellular domain of JAGGED2 or a fragment thereof comprising a stretch of amino acids having the sequence CDENYYSATCNKFCRPR (SEQ ID NO:3).

Embodiment P31

The method of Embodiment P29, wherein the fragment of JAGGED2 comprises a stretch of amino acids having the sequence CDENYYSATCNKFCRPRNDFFGH (SEQ ID NO:4).

Embodiment P32

The method of Embodiment P25, wherein the polypeptide comprises a fragment of DELTA-LIKE1.

Embodiment P33

The method of Embodiment P32, wherein the fragment of DELTA-LIKE1 is the extracellular domain of DELTA-LIKE1 or a fragment thereof comprising a stretch of amino acids having the sequence CDEHYYGEGCSVFCRPR (SEQ ID NO:5).

Embodiment P34

The method of Embodiment P32, wherein the fragment of DELTA-LIKE1 comprises a stretch of amino acids having the sequence CDEHYYGEGCSVFCRPRDDAFGH (SEQ ID NO:6).

Embodiment P35

The method of Embodiment P25, wherein the polypeptide comprises a fragment of DELTA-LIKE3.

Embodiment P36

The method of Embodiment P35, wherein the fragment of DELTA-LIKE3 is the extracellular domain of DELTA-LIKE1 or a fragment thereof comprising a stretch of amino acids having the sequence CEPPAVGTACTRLCRPR (SEQ ID NO:7).

Embodiment P37

The method of Embodiment P25, wherein the polypeptide comprises a fragment of DELTA-LIKE4.

Embodiment P38

The method of Embodiment P37, wherein the fragment of DELTA-LIKE4 is the extracellular domain of DELTA-LIKE1 or a fragment thereof comprising a stretch of amino acids having the sequence CSDNYYGDNCSRLCKKR (SEQ ID NO:8).

Embodiment P39

The method of Embodiment P37, wherein the fragment of DELTA-LIKE4 comprises a stretch of amino acids having the sequence CSDNYYGDNCSRLCKKRNDHFGH (SEQ ID NO:9).

Embodiment P40

The method of any one of Embodiments P1-P21, wherein the NOTCH3 agonist comprises an antibody or a fragment thereof.

Embodiment P41

The method of any one of Embodiments P1-P40, wherein the NOTCH3 agonist increases or decreases the expression or activity of a known modulator of NOTCH3 signaling.

Embodiment P42

A composition comprising an effective amount of a NOTCH3 agonist and an ophthalmically acceptable vehicle.

Embodiment P43

The composition of Embodiment P42, which is in the form of an aqueous solution comprising an osmolality of about 200 to about 400 milliosmoles/kilogram water.

Embodiment P44

The composition of Embodiment P42 or P43, wherein the NOTCH3 agonist comprises a polypeptide, an antibody or a fragment thereof, an aptamer, or a small molecule.

Embodiment P45

The composition of Embodiment P44, wherein the polypeptide comprises a fragment of a NOTCH3 ligand.

Embodiment P46

The composition of Embodiment P44, wherein the NOTCH3 agonist comprises an antibody or a fragment thereof.

Embodiment P47

A composition comprising a NOTCH3 agonist and a pharmaceutically acceptable carrier for treating or preventing a SVD in a subject.

Embodiment P48

Use of a NOTCH3 agonist in the manufacture of a medicament for treating or preventing a SVD in a subject.

Additional embodiments include Embodiments 1 to 60 following.

Embodiment 1

A method for treating or preventing a small vessel disease (SVD) in a subject, comprising administering to the subject an effective amount of a Neurogenic Locus Notch Homolog Protein 3 (NOTCH3) agonist.

Embodiment 2

The method of Embodiment 1, wherein the NOTCH3 agonist comprises an antibody that binds to the NOTCH3 ectodomain (N3ECD) and increases NOTCH3 activity, wherein said N3ECD comprises SEQ ID NO: 12.

Embodiment 3

The method of Embodiment 1, wherein the NOTCH3 agonist comprises a polypeptide, an antibody or a fragment thereof, an aptamer, or a small molecule.

Embodiment 4

The method of Embodiment 3, wherein the NOTCH3 agonist comprises a polypeptide.

Embodiment 5

The method of Embodiment 4, wherein the polypeptide comprises a fragment of a NOTCH3 ligand.

Embodiment 6

The method of Embodiment 5, wherein the ligand comprises JAGGED1 or a fragment thereof, JAGGED2 or a fragment thereof, or DELTA-LIKE1 or a fragment thereof.

Embodiment 7

The method of Embodiment 6, wherein the polypeptide comprises a fragment of JAGGED1.

Embodiment 8

The method of Embodiment 7, wherein the fragment of JAGGED1 is the extracellular domain of JAGGED1 or a fragment thereof comprising a stretch of amino acids having the sequence CDDYYYGFGCNKFCRPR (SEQ ID NO:1).

Embodiment 9

The method of Embodiment 7, wherein the fragment of JAGGED1 comprises a stretch of amino acids having the sequence or CDDYYYGFGCNKFCRPRDDFFGH (SEQ ID NO:2).

Embodiment 10

The method of Embodiment 6, wherein the polypeptide comprises a fragment of JAGGED2.

Embodiment 11

The method of Embodiment 10, wherein the fragment of JAGGED2 is the extracellular domain of JAGGED2 or a fragment thereof comprising a stretch of amino acids having the sequence CDENYYSATCNKFCRPR (SEQ ID NO:3).

Embodiment 12

The method of Embodiment 10, wherein the fragment of JAGGED2 comprises a stretch of amino acids having the sequence CDENYYSATCNKFCRPRNDFFGH (SEQ ID NO:4).

Embodiment 13

The method of Embodiment 6, wherein the polypeptide comprises a fragment of DELTA-LIKE1.

Embodiment 14

The method of Embodiment 13, wherein the fragment of DELTA-LIKE1 is the extracellular domain of DELTA-LIKE1 or a fragment thereof comprising a stretch of amino acids having the sequence CDEHYYGEGCSVFCRPR (SEQ ID NO:5).

Embodiment 15

The method of Embodiment 13, wherein the fragment of DELTA-LIKE1 comprises a stretch of amino acids having the sequence CDEHYYGEGCSVFCRPRDDAFGH (SEQ ID NO:6).

Embodiment 16

The method of Embodiment 6, wherein the polypeptide comprises a fragment of DELTA-LIKE3.

Embodiment 17

The method of Embodiment 16, wherein the fragment of DELTA-LIKE3 is the extracellular domain of DELTA-LIKE1 or a fragment thereof comprising a stretch of amino acids having the sequence CEPPAVGTACTRLCRPR (SEQ ID NO:7).

Embodiment 18

The method of Embodiment 6, wherein the polypeptide comprises a fragment of DELTA-LIKE4.

Embodiment 19

The method of Embodiment 18, wherein the fragment of DELTA-LIKE4 is the extracellular domain of DELTA-LIKE1 or a fragment thereof comprising a stretch of amino acids having the sequence CSDNYYGDNCSRLCKKR (SEQ ID NO:8).

Embodiment 20

The method of Embodiment 18, wherein the fragment of DELTA-LIKE4 comprises a stretch of amino acids having the sequence CSDNYYGDNCSRLCKKRNDHFGH (SEQ ID NO:9).

Embodiment 21

The method of Embodiment 3, wherein the NOTCH3 agonist comprises an antibody or a fragment thereof.

Embodiment 22

The method of any one of Embodiments 1-21, wherein the NOTCH3 agonist increases or decreases the expression or activity of a known modulator of NOTCH3 signaling.

Embodiment 23

The method of any one of Embodiments 1-22, wherein the SVD comprises cerebral SVD.

Embodiment 24

The method of any one of Embodiments 1-22, wherein the SVD comprises cerebral autosomal-dominant arteriopathy with subcortical infarcts and leukoencephalopathy (CADASIL).

Embodiment 25

The method of any one of Embodiments 1-22, wherein the SVD comprises cerebral autosomal recessive arteriopathy with subcortical infarcts and leukoencephalopathy (CARASIL).

Embodiment 26

The method of any one of Embodiments 1-22, wherein the SVD comprises a NOTCH3 loss-of-function associated SVD.

Embodiment 27

The method of any one of Embodiments 1-22, wherein the SVD comprises diabetic retinopathy.

Embodiment 28

The method of any one of Embodiments 1-22, wherein the SVD comprises age-related macular degeneration (AMD), nephropathy, microangiopathy, heart failure, Alagille syndrome, familial tetralogy of Fallot, patent ductus arteriosus, or a cerebral cavernous malformation.

Embodiment 29

The method of any one of Embodiments 1-28, wherein the subject has at least 1, 2, 3, or 4 grandparents, parents, aunts, uncles, cousins, or siblings who comprise the SVD.

Embodiment 30

The method of any one of Embodiments 1-29, wherein the subject comprises diabetes.

Embodiment 31

The method of Embodiment 30, wherein the diabetes is type 1 diabetes or type 2 diabetes.

Embodiment 32

The method of any one of Embodiments 1-31, wherein the subject is at least about 80 years old.

Embodiment 33

The method of any one of Embodiments 1-32, wherein the subject comprises a level of NOTCH3 protein or mRNA that is different than a normal control.

Embodiment 34

The method of Embodiment 33, wherein the subject comprises a level of NOTCH3 protein or mRNA that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% lower compared to a normal control.

Embodiment 35

The method of any one of Embodiments 1-34, wherein the subject comprises a level of collagen18alpha1 or endostatin protein or mRNA that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% lower compared to a normal control.

Embodiment 36

The method of any one of Embodiments 1-35, wherein the subject comprises a level of NOTCH3 protein bound to collagen18α1 and/or endostatin and/or HTRA1 and/or IGFBP-1 that is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher compared to a normal control.

Embodiment 37

The method of any one of Embodiments 1-36, wherein the subject comprises a white mater hyperintensity and/or a lacunar stroke as observed by magnetic resonance imaging.

Embodiment 38

The method of any one of Embodiments 1-37, wherein the subject comprises a level of neurofilament light chain (NF-L) protein or activity that is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher compared to a normal control.

Embodiment 39

The method of any one of Embodiments 1-38, wherein the subject comprises a level of NOTCH3 activity that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% lower compared to a normal control.

Embodiment 40

The method of any one of Embodiments 33-39, wherein the level is in a test sample obtained from the subject.

Embodiment 41

The method of Embodiment 40, wherein the test sample comprises blood, serum, or plasma.

Embodiment 42

The method of Embodiment 40, wherein the test sample comprises saliva, tears, vitreous, cerebrospinal fluid, sweat, cerebrospinal fluid, or urine.

Embodiment 43

The method of any one of Embodiments 1-42, wherein the subject comprises a level of collagen18α1, endostatin, NOTCH3, N3ECD, IGFBP-1, HTRA1, and/or NF-L protein or mRNA that is different than a normal control.

Embodiment 44

The method of any one of Embodiments 1-43, wherein the subject comprises a level of collagen18α1, endostatin, IGFBP-1, HTRA1, and/or NF-L protein or mRNA that is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher compared to a normal control.

Embodiment 45

The method of any one of Embodiments 1-44, wherein the subject comprises a level of HTRA1 protein or mRNA that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% lower compared to a normal control.

Embodiment 46

The method of any one of Embodiments 1-45, wherein the subject comprises a protein-protein complex comprising NOTCH3 bound to collagen18α1/endostatin, HTRA1, IGFBP-1, and/or NOTCH3.

Embodiment 47

The method of Embodiment 46, wherein NOTCH3 is the NOTCH3 extracellular domain (N3ECD).

Embodiment 48

The method of any one of Embodiments 1-47, wherein the subject comprises a N3ECD homodimer.

Embodiment 49

The method of any one of Embodiments 1-48, wherein the NOTCH3 agonist is administered as a monotherapy.

Embodiment 50

The method of Embodiment 24, wherein the subject is not administered a thrombolytic agent.

Embodiment 51

The method of any one of Embodiments 1-50, wherein the subject has had a lacunar stroke.

Embodiment 52

The method of any one of Embodiments 1-51, wherein the subject has had a hemorrhagic stroke.

Embodiment 53

A composition comprising an effective amount of a NOTCH3 agonist and an ophthalmically acceptable vehicle.

Embodiment 54

The composition of Embodiment 53, which is in the form of an aqueous solution comprising an osmolality of about 200 to about 400 milliosmoles/kilogram water.

Embodiment 55

The composition of Embodiment 53 or 54, wherein the NOTCH3 agonist comprises a polypeptide, an antibody or a fragment thereof, an aptamer, or a small molecule.

Embodiment 56

The composition of Embodiment 55, wherein the small molecule comprises the following structure

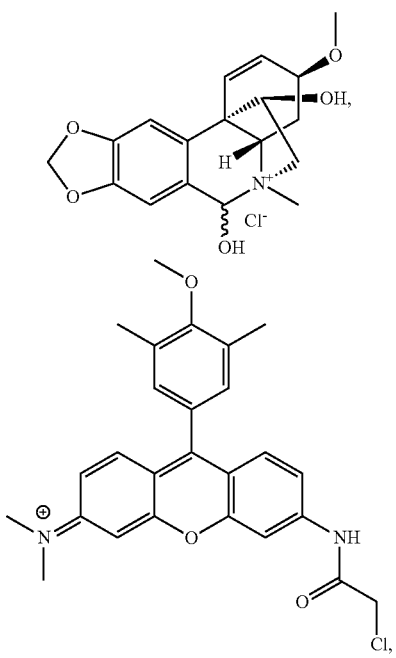

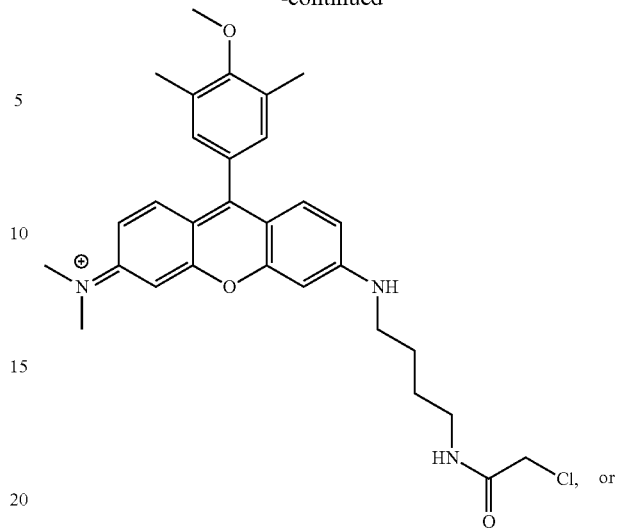

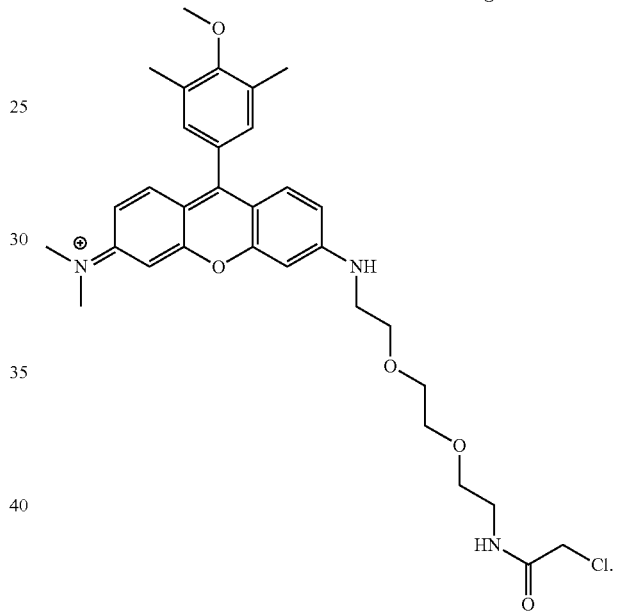

Embodiment 57

The composition of Embodiment 55, wherein the polypeptide comprises a fragment of a NOTCH3 ligand.

Embodiment 58

The composition of Embodiment 55, wherein the NOTCH3 agonist comprises an antibody or a fragment thereof.

Embodiment 59

A composition comprising a NOTCH3 agonist and a pharmaceutically acceptable carrier for treating or preventing a SVD in a subject.

Embodiment 60

Use of a NOTCH3 agonist in the manufacture of a medicament for treating or preventing a SVD in a subject.

Example 1: Therapeutic Targeting of NOTCH3 Signaling Prevents Mural Cell Loss in Small Vessel Disease The present disclosure is not limited by any particular scientific theory. However, discussions regarding the potential role of NOTCH3 in SVD are provided to facilitate the understanding of possible mechanisms involved with SVD in various embodiments described herein.

This Example discloses the characterization of a mouse model of SVD in which mural cell coverage in arteries depends upon human NOTCH3 function, a cell signaling mechanism associated with SVD and mural cell pathology in humans. The data presented herein shows that arteriolar degeneration linked to Notch mutations is suppressed by Notch signaling activation. Without being bound by any scientific theory, the data herein show Notch loss-of-function (and not Notch toxic gain-of-function or neomorphism) as the relevant mechanism in SVD.

A modality of treatment focused on preventing mural cell loss (a mechanistic cause of SVD) was tested. For that purpose mouse models of NOTCH3 were utilized. NOTCH3 is a gene strongly associated to SVD in humans (Arboleda-Velasquez et al., 2011, *Proc Natl Acad Sci USA* 108:E128-135; Arboleda-Velasquez et al., 2008, *Proc Natl Acad Sci USA* 105:4856-4861; Chabriat et al., 2009, Cadasil. *Lancet Neurol* 8:643-653; Henshall et al., 2015, *Arterioscler Thromb Vasc Biol* 35:409-420; Joutel et al., 1996, *Nature* 383:707-710). In mammalian cells, Notch receptors at the plasma membrane are heterodimers resulting from an S1 proteolytic cleavage mediated by Furin (Louvi and Artavanis-Tsakonas, 2012, *Semin Cell Dev Biol* 23:473-480). In the absence of the ligand, a Negative Regulatory Region (NRR) comprising the Lin12-Notch repeats (LNR) and the heterodimerization domain keep the receptor in an autoinhibited configuration stabilized via non-covalent bonds (Xu et al., 2015, *Structure* 23:1227-1235). Interactions with Notch ligands (DELTA-LIKE or JAGGED) expose an S2 cleavage site within the NRR to proteolysis by ADAM (A Disintegrin And Metalloproteinase Domain) (Louvi and Artavanis-Tsakonas, 2012, *Semin Cell Dev Biol* 23:473-480). Presenilin-containing gamma secretase constitutively cuts S-2 cleaved Notch receptors at a transmembrane site (S3) leading to nuclear translocation of the Notch intracellular domain and regulation of transcriptional downstream targets (Kopan, 2012, *Cold Spring Harb Perspect Biol* 4(10). pii: a011213).

Mutations in NOTCH3 leading to a NOTCH3 receptor with unpaired cysteines in the extracellular domain are a cause of CADASIL, the most common monogenic cause of cerebral SVD (Joutel et al., 1996, *Nature* 383:707-710). It has been proposed that CADASIL mutations trigger aggregation of the NOTCH3 extracellular domain and aberrant interactions between it and other proteins, leading to neomorphic effects (Arboleda-Velasquez et al., 2005, *Hum Mol Genet* 14:1631-1639; Chabriat et al., 2009, *Lancet Neurol* 8:643-653; Joutel et al., 2015, *J Cereb Blood Flow Metab* 36(1):143-57). CADASIL mutations located in the ligand-binding domain of the NOTCH3 receptor and those that impair plasma membrane localization overtly impair NOTCH3 downstream signaling (Arboleda-Velasquez et al., 2002, *Neurology* 59:277-279; Arboleda-Velasquez et al., 2011, *Proc Natl Acad Sci USA* 108:E128-135; Joutel et al., 2004, *Am J Hum Genet* 74:338-347). A distinct class of NOTCH3 mutations including premature stop codons or frame shift mutations in NOTCH3 are also associated with cerebral SVD; patients with these loss-of-function mutations in NOTCH3 develop symptoms later in life, show incomplete penetrance compared to CADASIL patients, and lack CADASIL's characteristic vascular deposits (e.g. NOTCH3 extracellular domain and granular osmiophilic material, GOM)(Dotti et al., 2004, *Arch Neurol* 61:942-945; Erro et al., 2015, *Folia Neuropathol* 53:168-171; Moccia et al., 2015, *Neurobiol Aging* 36:547 e545-511; Pippucci et al., 2015, *EMBO Mol Med* 7(6):848-58; Rutten et al., 2013, *Hum Mutat* 34:1486-1489; Yoon et al., 2015, *Neurobiol Aging* 36:2443 e2441-2447). Consistent with the pathobiology of these human conditions, CADASIL and NOTCH3 knockout mice develop progressive loss of mural cells (Arboleda-Velasquez et al., 2011, *Proc Natl Acad Sci USA* 108:E128-135; Ghosh et al., 2015, *Ann Neurol* 78(6):887-900; Henshall et al., 2015, *Arterioscler Thromb Vasc Biol* 35:409-420; Kofler et al., 2015, *Sci Rep* 5:16449).

The data herein show that targeting NOTCH3 signaling in mural cells is a useful therapeutic modality in SVD. To examine efficacy of treatment, a roster of morphological and biomarkers and retinal vascular leakage were leveraged.

Results and Discussion

Mural Cell Coverage in Vessels is Mechanistically Linked to Notch 3 Signaling

To investigate cell autonomous effects of Notch 3 signaling in mural cells, mural cell coverage was examined in retinal vessels from NOTCH3 knockout (N3KO) mice and N3KO mice conditionally expressing wild type (hN3WT) or CADASIL mutant (C455R) alleles of human Notch 3 in mural cells (FIG. 1A). Morphometric software separated main and branching vessel analyses, quantifying α-smooth muscle actin (SMA) coverage in both (FIG. 4). SMA staining was chosen to detect mural cells because expression of this marker is not impacted by changes in NOTCH3 activity (Arboleda-Velasquez et al., 2014, *Invest Ophthalmol Vis Sci* 55:5191-5199; Arboleda-Velasquez et al., 2008, *Proc Natl Acad Sci USA* 105:4856-4861). The retina has a very stereotypic vessel distribution and therefore offers unique advantages for quantitative assessments of changes in vascular structure. Moreover, there is clinical evidence for retinal changes in CADASIL patients (Robinson et al., 2001, *Surv Ophthalmol* 45:445-448; Rufa et al., 2011, *Cerebrovasc Dis* 31:77-82).

Figure 1B:
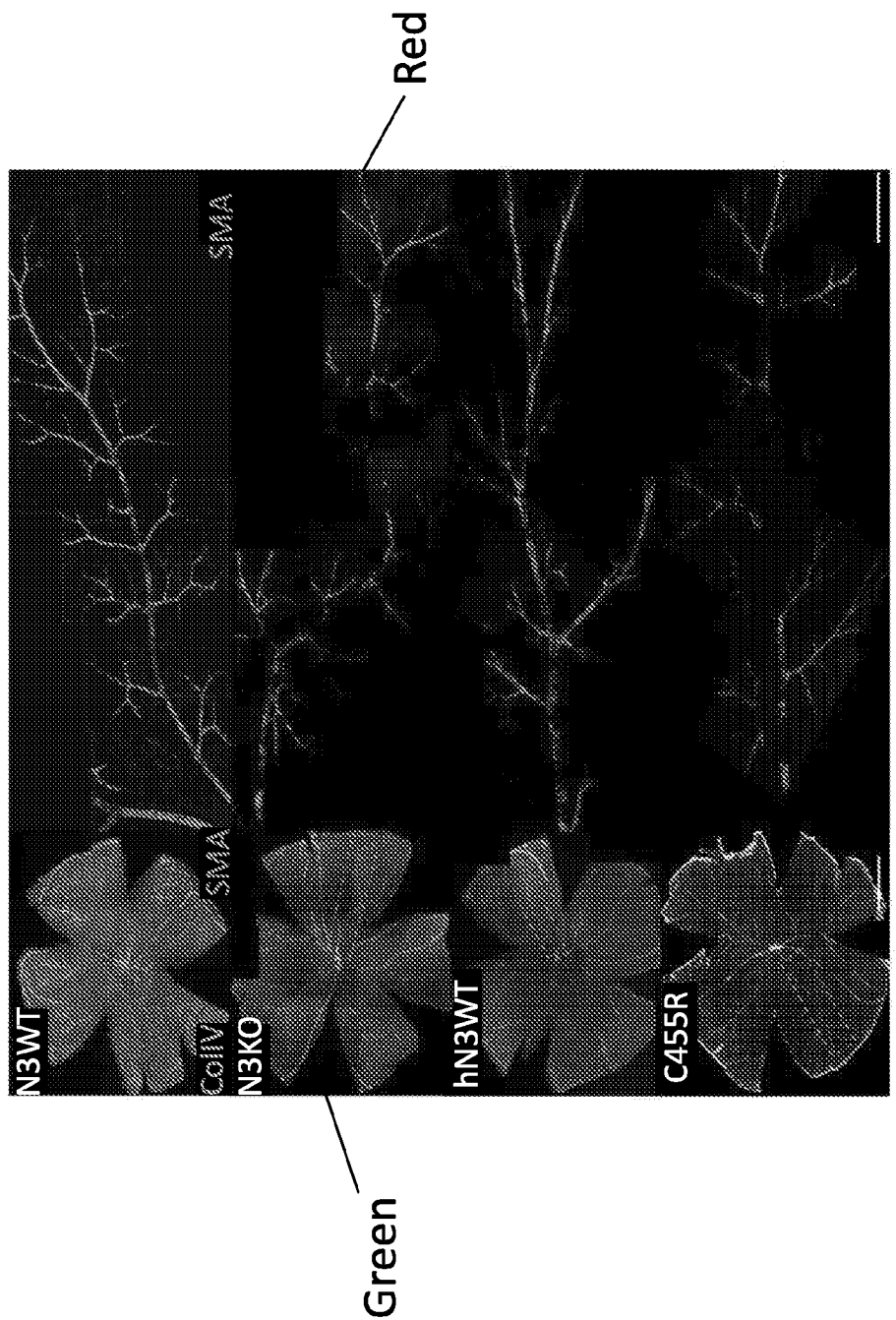
(FIG. 1B) Representative immunofluorescence images of retinal whole mounts showing SMA staining in red and collagen IV (ColIV) in green (left, scale bar=2.5 mm). Red dashed rectangles in left panels indicate regions displayed in center panels. (right, scale bar=250 µm) (FIG. 1C) Quantification of SMA coverage in main retinal arteries and branching arterioles. n=5 for each group, *p<0.05,**p<0.01, statistical analysis was done via ANOVA.
Figure 1C:
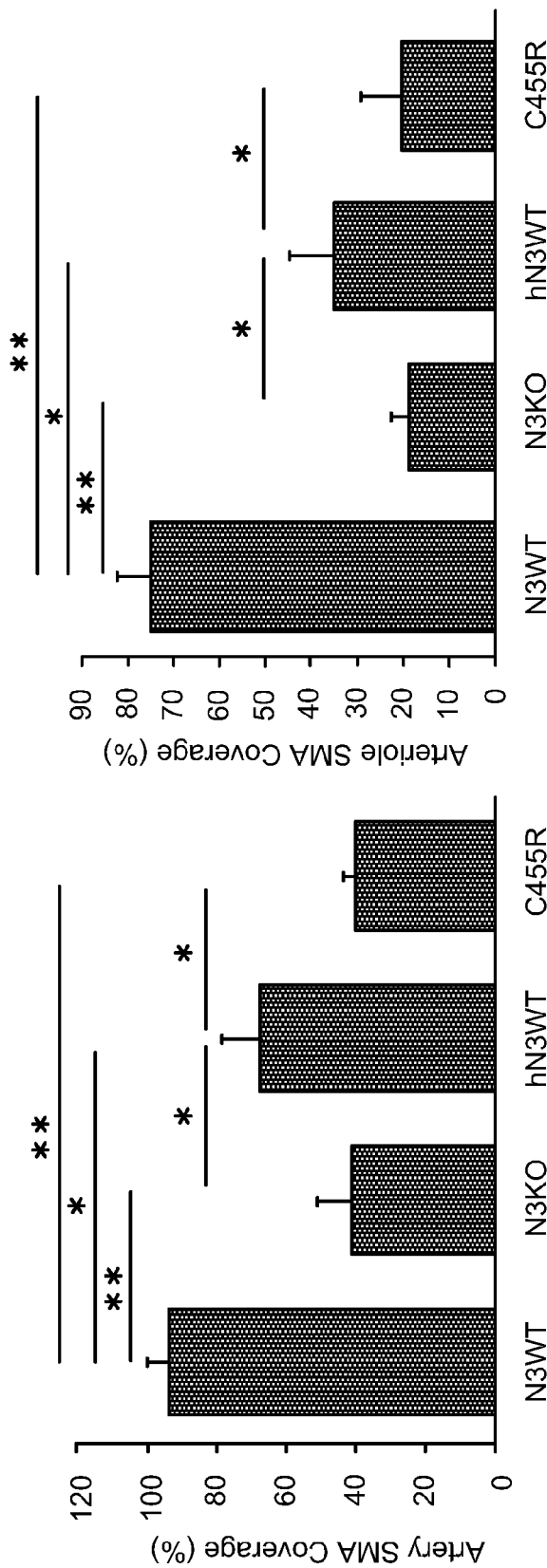
FIG. 1C is a set of graphs and FIGS. 1D, E, F, and G are images showing human Notch 3 rescue of mural cell loss in N3KO mice.
Figure 1F:
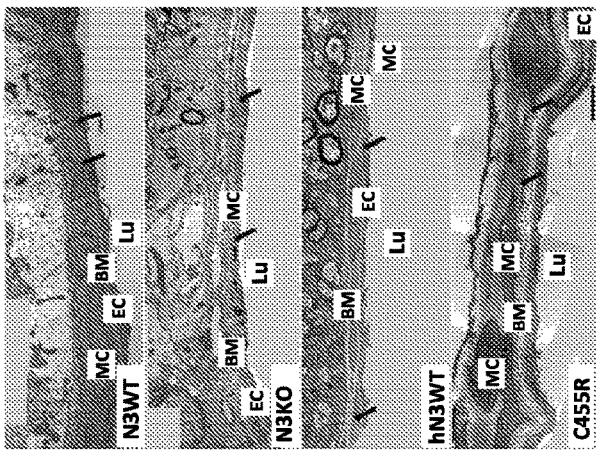
(FIG. 1D) Representative ultra structural images of retinal vessels (scale bar=200 µm) and cerebral vessels from the left hemisphere of the cerebral cortex cut at the bregma, (scale bar=2 µm) (FIG. 1E) obtained by transmission electron microscopy. Lumen (Lu), vascular endothelial cell (EC), basement membrane (BM), mural cell (MC), gaps in MC (black arrows) and apoptotic bodies (white arrows). Similarly, six features, listed above are highlighted on each image from retina (FIG. 1F) and brain (FIG. 1G). The N3WT mice exhibit large block-like MC that are in contact or are closely associated whereas the N3KO and C455R mice exhibit large gaps and elongated MCs. hN3WT exhibits elongated MCs juxtaposed to each other. Scale bar=1 µm.
Figure 1F:
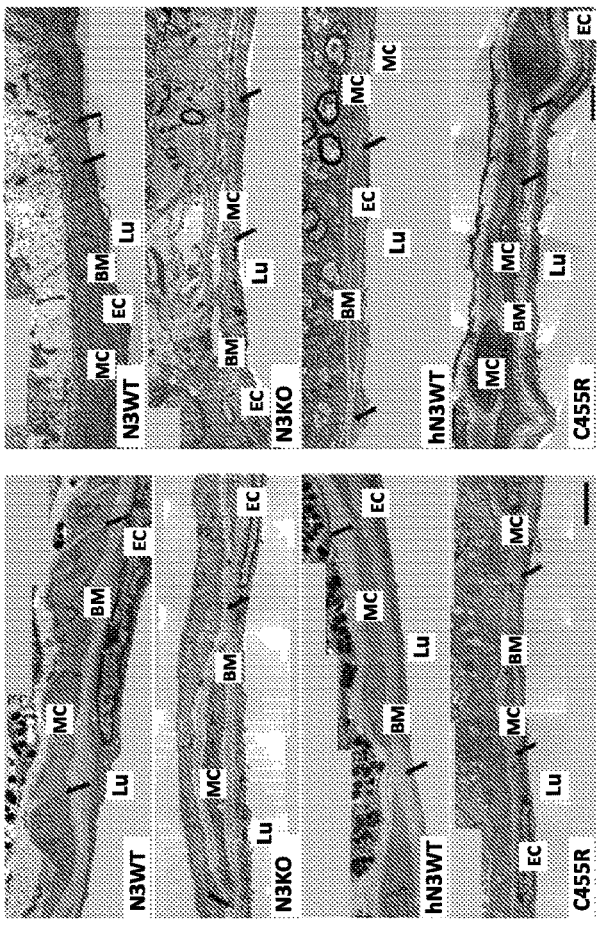
Figure 1F:
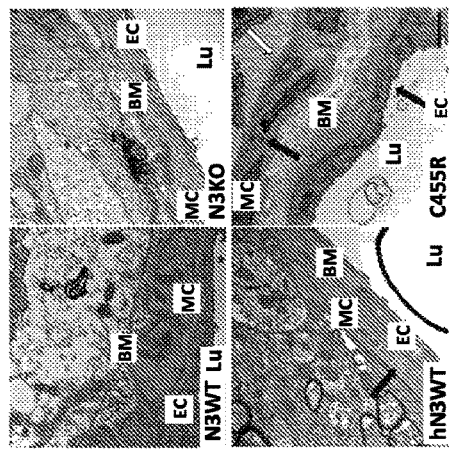
Figure 1G:
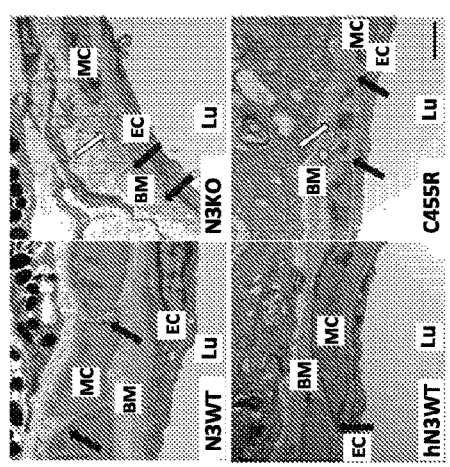
Figure 2:
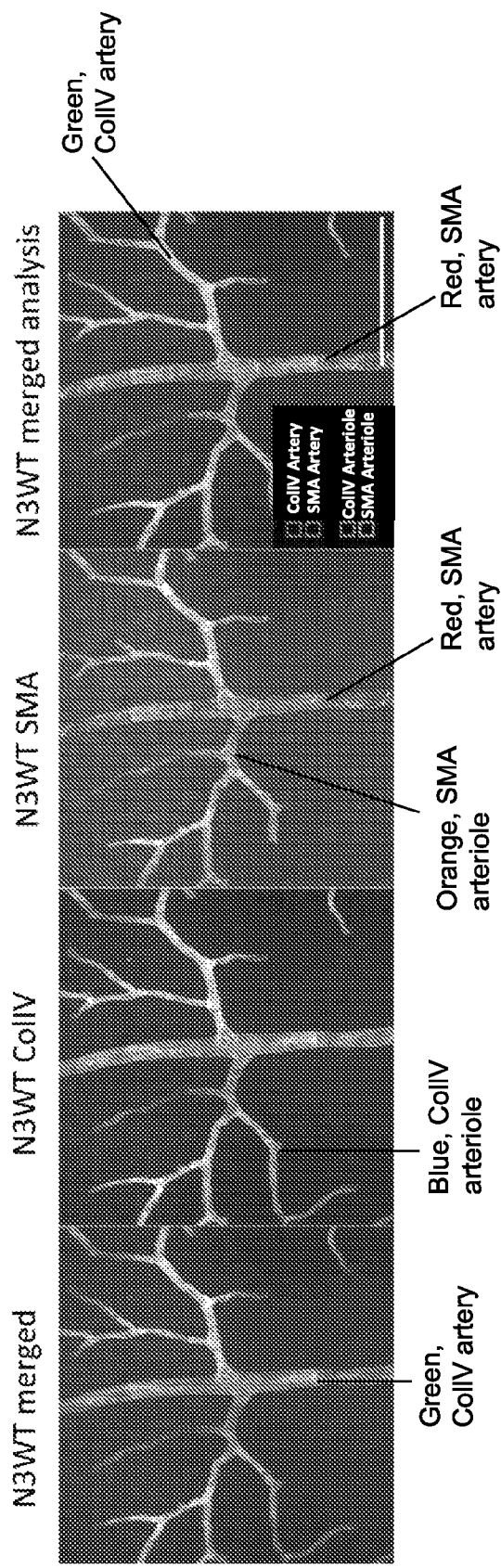
FIG. 2 is a set of images showing image processing of vessels via FIJI-based macro. Images of retinal whole mounts stained with collagen IV (Col IV) in green and smooth muscle actin (SMA) in red were processed. Seven images tracing a single vessel from optic nerve to periphery were stitched together using FIJI's MosaicJ macro. This was done for three vessels per retina/animal. The vascular analysis macro generates an outline of the vascularized area based on the Col IV silhouette, and is then cut up into small rectangles, each of which is identified as part of the main vessel, shown as green rectangles, or as part of branching vessels, shown as blue rectangles. The squares are then superimposed onto the red, SMA binary image and determined to have or not to have SMA staining. Rectangles containing a value of 0, having no SMA staining are qualified as gaps. The SMA positive areas are analyzed and qualified as main vessel coverage, shown as red outlined areas, or branching vessels, shown as orange outlined areas. The macro then saves parameters for each of the vessel types as an excel spreadsheet. Scale bar=200 µm FIG. 3A are images of fluorescein angiography (FA) of the retina.
Figure 3A:
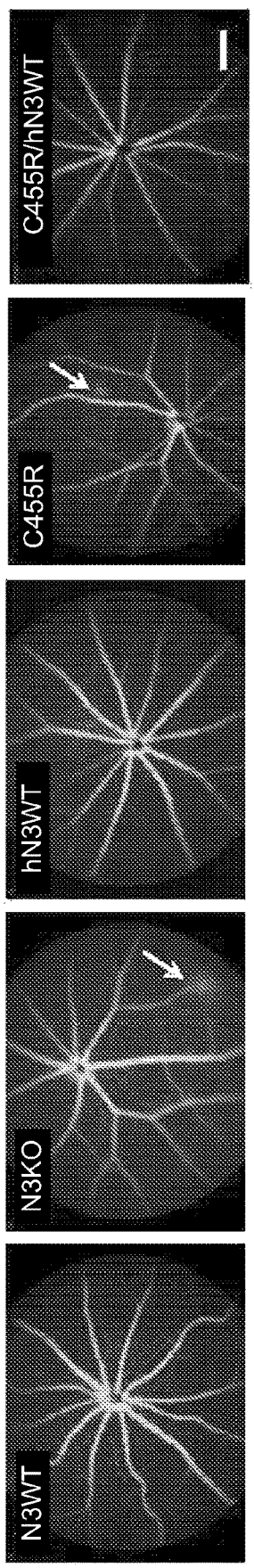
(FIG. 3A) Representative FA images from wild type Notch 3 (N3WT), Notch 3 knockout (N3KO), N3KO mice conditionally expressing wild type human Notch 3 (hN3WT), N3KO mice conditionally expressing a human CADASIL mutant Notch 3 (C455R), and N3KO mice conditionally expressing a human CADASIL mutant Notch 3 and a wild type human Notch 3 (C455R/hN3WT). Arrows indicate leakage events.
Figure 3B:
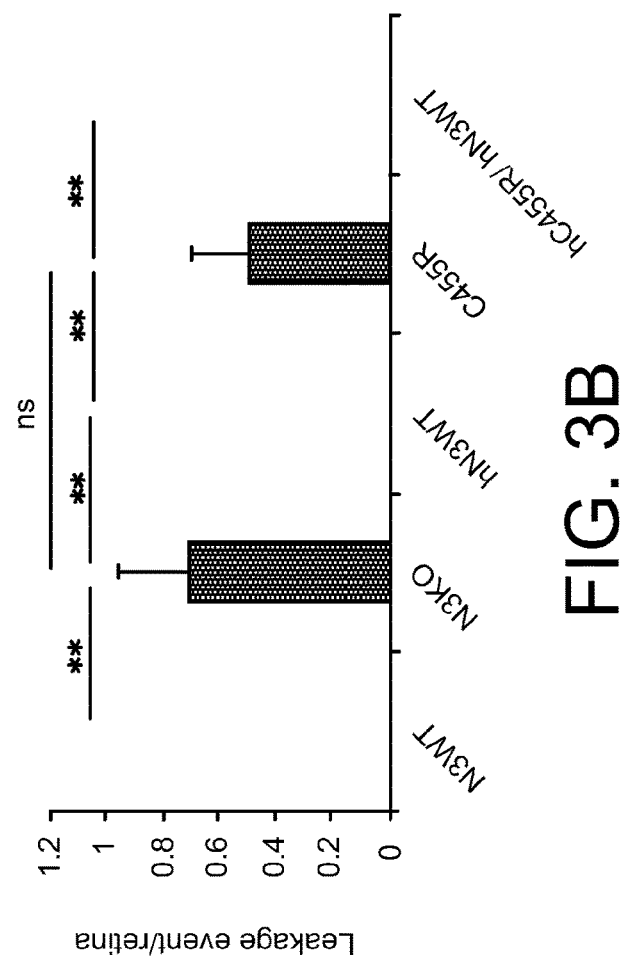
FIG. 3B is a graph relating to leakage events.

Absence of NOTCH3 expression was found to dramatically reduce mural cell coverage in retinal arteries and arterioles of six-month old animals (FIG. 1B, C). Furthermore, expression of hN3WT was sufficient to rescue mural cell loss in both large vessels and smaller caliber arteriole branches of N3KO mice (FIG. 1B, C). Indicative of a systemic phenotype, electron microscopy showed large gaps in mural cell coverage in vessels from the brain cortex and the retina in N3KO mice, whereas mural cells were juxtaposed to each other in knockout animals expressing human NOTCH3 in mural cells (FIG. 1D, E). Mural cells undergoing apoptosis were detected within the arterial gaps in N3KO animals (FIG. 1F, G). Altogether, these findings indicate that NOTCH3 signaling is both necessary and sufficient to support mural cell coverage in arteries and is indicative of a cell autonomous effect.

The impact of human NOTCH3 receptor with the C455R mutation was further investigated, because this mutation was identified in a family with early age at onset of CADASIL and can impair ligand-mediated Notch 3 signaling (Arboleda-Velasquez et al., 2002, *Neurology* 59:277-279; Arboleda-Velasquez et al., 2011, *Proc Natl Acad Sci USA* 108:E128-135). The C455R mutant did not rescue nor did it worsen mural cell loss in the N3KO animals (FIG. 1C). It was concluded that the C455R is a loss-of-function mutation and neomorphic effects, previously reported for CADASIL mutations, likely do not contribute to mural cell loss in this SVD model.

Additionally, genetic rescue of mural cell loss in N3KO mice by hN3WT supports the notion that patients with SVD due to reduced NOTCH3 signaling may benefit from therapeutic approaches leading to NOTCH3 signaling normalization.

Consistent with the morphological observations, wild type mice showed no evidence of vascular leakage in the retina using fluorescein angiography whereas Notch 3 knockout mice and Notch 3 knockout mice expressing the C455R CADASIL mutation in Notch 3 showed equally high number of leakage events in the retina. Expression of the human wild type Notch 3 was able to significantly reduce the frequency of leakage events in Notch 3 knockout animals and in Notch 3 knockout mice expressing the C455R CADASIL mutation.

Abbreviations

SVD: small vessel disease
NRR: negative regulatory region
SMA: α-smooth muscle actin
Materials and Methods
Statistical Analyses.

Pairwise comparisons were assessed using an unpaired two-tailed Student's t-test. One way ANOVA was used to compare more than two experimental groups. Results were considered significant for P<0.05. Analyses were performed and displayed using Prism software (GraphPad).

Animal Models.

All mouse models used in this study were previously described and were in a C57BL/6 (Arboleda-Velasquez et al., 2011, *Proc Natl Acad Sci USA* 108:E128-135; Arboleda-Velasquez et al., 2008, *Proc Natl Acad Sci USA* 105:4856-4861; Mitchell et al., 2001, *Nat Genet* 28:241-249). Both male and female littermates were included in the study. Briefly, mice are either wild type (N3WT), lacking endogenous mouse Notch 3 (N3KO), or express either a wild type human NOTCH3 transgene (hN3WT, MMRRC:032998 B6; 129 Gt(ROSA)26Sor$^{tm1(NOTCH3)Sat}$/Mmjax;) or a mutated human NOTCH3 transgene (C455R, MMRRC:033000 129-Gt(ROSA)26Sor$^{tm2(NOTCH3*C455R)Sat}$/Mmjax) in a N3KO background. Transgenes were inserted into the ROSA26 locus (Soriano, 1999, *Nat Genet* 21:70-71) and expression of this transgene occurs through Cre-mediated recombination under the smooth muscle cell promoter SM22 (Holtwick et al., 2002, *Proc Natl Acad Sci USA* 99:7142-7147). The hN3WT and C455R mouse models are available from the Jackson Laboratory under the auspices of the Mutant Mouse Regional Resource Centers program and National Institutes of Health (NIH).

Immunofluorescence.

Eyes were harvested and fixed in 4% paraformaldehyde overnight at 4° C. The eyes were then washed three times in phosphate buffered saline (Sigma, D5652-10x1L), at which point retinas were dissected out of each eye and washed as described above. Retinas were then placed in borosilicate glass vials (VWR, 16218-126) and 300 µl of blocking buffer for 6 hrs. Blocking buffer was prepared as previously described (Primo et al., 2016, *Brain Res* 1644:118-126). Retinas were washed again as above, and double stained with primary antibodies against; goat anti-mouse, smooth muscle actin (Novus, NB300-978) at 1:100 concentration and rabbit anti-mouse collagen IV (Abcam, ab6586) in blocking buffer overnight at 4° C. on a rocker. Retinas were then washed as described above, and immersed for four h at room temperature in secondary antibodies; Donkey Anti-Goat IgG H&L (Cy3 ®) preadsorbed (Abcam, ab6949), Donkey Anti-Rabbit IgG H&L (Alexa Fluor® 488) (Abcam, ab150073), all at a 1:100 concentration in blocking buffer. Retinas were then washed as described above and whole mounted on glass slides, (Azer Scientific, EMSC200L), coated with 50% Glycerol in PBS under a rectangular cover slip (Fisher Scientific, 12-545-F) and sealed with nail polish (REVLON, 8435-76). Entire retinas were imaged at 5×1.25 magnification and three vessels from each retina were imaged at 20×1.25 magnification with an Axioscope 2 Mot Plus (Zeiss).

Electron Microscopy (EM).

Tissue was fixed in 2.5% glutaraldehyde and 2% paraformaldehyde (PFA) in 0.1 M sodium cacodylate buffer (pH 7.4), rinsed, dehydrated in a series of ethanol dilutions (50-100%), and embedded in epoxy resin (Embed 812; Electron Microscopy Sciences). Ultrathin sections (60 nm) were cut on a Reichert ultramicrotome and collected on Formvar- and carboncoated grids. Samples were stained with 2% uranyl acetate and lead citrate and examined on a Philips Tecnai 12 BioTWIN electron microscope. Images were captured digitally using a CCD camera (Morada; Soft Imaging Systems).

Fluorescein Angiography.

A Micron III (Phoenix Research) system was used to take fundus photographs in anesthetized mice according to manufacturers instructions. The animals' pupils were dilated using a drop of 1% Tropicamide followed by a drop of 1% cyclopentolate hydrochloride applied on the corneal surface. Eyes were kept moist with ocular lubricant (Genteal). The mice were placed in front of the Fundus camera and pictures of the retina taken. FA was performed after intraperitoneal injection of 0.05 ml of 25% fluorescein sodium (Akron, pharmaceutical grade). Photographs were taken with a preset 20D lens appositioned to the camera lens at regular time (from 1 min to 4 min post IP injection). Fluorescein leakage was noted as diffuse opacity in the vitreous over-time.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for treating a small vessel disease (SVD) in a subject, comprising administering to the subject an effective amount of a Neurogenic Locus Notch Homolog Protein 3 (NOTCH3) agonist, wherein the NOTCH3 agonist comprises a polypeptide comprising a JAGGED1 extracellular domain or fragment thereof that comprises a stretch of amino acids having the sequence set forth in SEQ ID NO: 1.

2. The method of claim 1, wherein
the polypeptide comprises a stretch of amino acids having the sequence or set forth in SEQ ID NO:2.

3. The method of claim 1, wherein the subject has diabetic retinopathy, age-related macular degeneration (AMD), nephropathy, microangiopathy, heart failure, Alagille syndrome, familial tetralogy of Fallot, patent ductus arteriosus, or a cerebral cavernous malformation.

4. The method of claim 1, wherein the NOTCH3 agonist is administered as a monotherapy.

5. The method of claim 1, wherein the subject has a loss-of-function mutation in NOTCH3.

6. The method of claim 1, wherein the SVD is cerebral SVD.

7. The method of claim 6, wherein the cerebral SVD is cerebral autosomal-dominant arteriopathy with subcortical infarcts and leukoencephalopathy (CADASIL) or cerebral autosomal recessive arteriopathy with subcortical infarcts and leukoencephalopathy (CARASIL).

8. The method of claim 6, wherein the cerebral SVD is cerebral autosomal-dominant arteriopathy with subcortical infarcts and leukoencephalopathy (CADASIL).

9. The method of claim 6, wherein the cerebral SVD is cerebral autosomal recessive arteriopathy with subcortical infarcts and leukoencephalopathy (CARASIL).

* * * * *

UNITED STATES PATENT AND TRADEMARK OFFICE
CERTIFICATE OF CORRECTION

PATENT NO. : 11,453,718 B2
APPLICATION NO. : 16/499225
DATED : September 27, 2022
INVENTOR(S) : Joseph F. Arboleda-Velasquez Page 1 of 1

It is certified that error appears in the above-identified patent and that said Letters Patent is hereby corrected as shown below:

In the Specification

In Column 1, Lines 12-13 (approx.), delete "reference in its entirety." and insert -- reference. --

Signed and Sealed this
Twenty-fourth Day of January, 2023

Katherine Kelly Vidal
*Director of the United States Patent and Trademark Office*

SEQUENCE LISTING

<160> NUMBER OF SEQ ID NOS: 33

<210> SEQ ID NO 1
<211> LENGTH: 17
<212> TYPE: PRT
<213> ORGANISM: Artificial Sequence
<220> FEATURE:
<223> OTHER INFORMATION: Extracellular domain of JAGGED1

<400> SEQUENCE: 1

Cys Asp Asp Tyr Tyr Tyr Gly Phe Gly Cys Asn Lys Phe Cys Arg Pro
1               5                   10                  15

Arg

<210> SEQ ID NO 2
<211> LENGTH: 23
<212> TYPE: PRT
<213> ORGANISM: Artificial Sequence
<220> FEATURE:
<223> OTHER INFORMATION: fragment of JAGGED1

<400> SEQUENCE: 2

Cys Asp Asp Tyr Tyr Tyr Gly Phe Gly Cys Asn Lys Phe Cys Arg Pro
1               5                   10                  15

Arg Asp Asp Phe Phe Gly His
            20

<210> SEQ ID NO 3
<211> LENGTH: 17
<212> TYPE: PRT
<213> ORGANISM: Artificial Sequence
<220> FEATURE:
<223> OTHER INFORMATION: extracellular domain of JAGGED2 or fragment
      thereof

<400> SEQUENCE: 3

Cys Asp Glu Asn Tyr Tyr Ser Ala Thr Cys Asn Lys Phe Cys Arg Pro
1               5                   10                  15

Arg

<210> SEQ ID NO 4
<211> LENGTH: 23
<212> TYPE: PRT
<213> ORGANISM: Artificial Sequence
<220> FEATURE:
<223> OTHER INFORMATION: fragment of JAGGED2

<400> SEQUENCE: 4

Cys Asp Glu Asn Tyr Tyr Ser Ala Thr Cys Asn Lys Phe Cys Arg Pro
1               5                   10                  15

Arg Asn Asp Phe Phe Gly His
            20

<210> SEQ ID NO 5
<211> LENGTH: 17
<212> TYPE: PRT
<213> ORGANISM: Artificial Sequence
<220> FEATURE:
<223> OTHER INFORMATION: extracellular domain of DELTA-LIKE1

<400> SEQUENCE: 5

Cys Asp Glu His Tyr Tyr Gly Glu Gly Cys Ser Val Phe Cys Arg Pro
1               5                   10                  15

Arg

```
<210> SEQ ID NO 6
<211> LENGTH: 23
<212> TYPE: PRT
<213> ORGANISM: Artificial Sequence
<220> FEATURE:
<223> OTHER INFORMATION: DELTA-LIKE1 fragment

<400> SEQUENCE: 6

Cys Asp Glu His Tyr Tyr Gly Glu Gly Cys Ser Val Phe Cys Arg Pro
1               5                   10                  15

Arg Asp Asp Ala Phe Gly His
            20

<210> SEQ ID NO 7
<211> LENGTH: 17
<212> TYPE: PRT
<213> ORGANISM: Artificial Sequence
<220> FEATURE:
<223> OTHER INFORMATION: xtracellular domain of DELTA-LIKE3

<400> SEQUENCE: 7

Cys Glu Pro Pro Ala Val Gly Thr Ala Cys Thr Arg Leu Cys Arg Pro
1               5                   10                  15

Arg

<210> SEQ ID NO 8
<211> LENGTH: 17
<212> TYPE: PRT
<213> ORGANISM: Artificial Sequence
<220> FEATURE:
<223> OTHER INFORMATION: extracellular domain of DELTA-LIKE4

<400> SEQUENCE: 8

Cys Ser Asp Asn Tyr Tyr Gly Asp Asn Cys Ser Arg Leu Cys Lys Lys
1               5                   10                  15

Arg

<210> SEQ ID NO 9
<211> LENGTH: 23
<212> TYPE: PRT
<213> ORGANISM: Artificial Sequence
<220> FEATURE:
<223> OTHER INFORMATION: fragment of DELTA-LIKE4

<400> SEQUENCE: 9

Cys Ser Asp Asn Tyr Tyr Gly Asp Asn Cys Ser Arg Leu Cys Lys Lys
1               5                   10                  15

Arg Asn Asp His Phe Gly His
            20

<210> SEQ ID NO 10
<211> LENGTH: 2321
<212> TYPE: PRT
<213> ORGANISM: Homo sapiens

<400> SEQUENCE: 10

Met Gly Pro Gly Ala Arg Gly Arg Arg Arg Arg Arg Pro Met Ser
1               5                   10                  15

Pro Pro Pro Pro Pro Pro Val Arg Ala Leu Pro Leu Leu Leu Leu
            20                  25                  30

Leu Ala Gly Pro Gly Ala Ala Ala Pro Pro Cys Leu Asp Gly Ser Pro
        35                  40                  45
```

-continued

```
Cys Ala Asn Gly Gly Arg Cys Thr Gln Leu Pro Ser Arg Glu Ala Ala
    50                  55                  60
Cys Leu Cys Pro Pro Gly Trp Val Gly Glu Arg Cys Gln Leu Glu Asp
65                  70                  75                  80
Pro Cys His Ser Gly Pro Cys Ala Gly Arg Gly Val Cys Gln Ser Ser
                85                  90                  95
Val Val Ala Gly Thr Ala Arg Phe Ser Cys Arg Cys Pro Arg Gly Phe
            100                 105                 110
Arg Gly Pro Asp Cys Ser Leu Pro Asp Pro Cys Leu Ser Ser Pro Cys
        115                 120                 125
Ala His Gly Ala Arg Cys Ser Val Gly Pro Asp Gly Arg Phe Leu Cys
    130                 135                 140
Ser Cys Pro Pro Gly Tyr Gln Gly Arg Ser Cys Arg Ser Asp Val Asp
145                 150                 155                 160
Glu Cys Arg Val Gly Glu Pro Cys Arg His Gly Gly Thr Cys Leu Asn
                165                 170                 175
Thr Pro Gly Ser Phe Arg Cys Gln Cys Pro Ala Gly Tyr Thr Gly Pro
            180                 185                 190
Leu Cys Glu Asn Pro Ala Val Pro Cys Ala Pro Ser Pro Cys Arg Asn
        195                 200                 205
Gly Gly Thr Cys Arg Gln Ser Gly Asp Leu Thr Tyr Asp Cys Ala Cys
    210                 215                 220
Leu Pro Gly Phe Glu Gly Gln Asn Cys Glu Val Asn Val Asp Asp Cys
225                 230                 235                 240
Pro Gly His Arg Cys Leu Asn Gly Gly Thr Cys Val Asp Gly Val Asn
                245                 250                 255
Thr Tyr Asn Cys Gln Cys Pro Pro Glu Trp Thr Gly Gln Phe Cys Thr
            260                 265                 270
Glu Asp Val Asp Glu Cys Gln Leu Gln Pro Asn Ala Cys His Asn Gly
        275                 280                 285
Gly Thr Cys Phe Asn Thr Leu Gly Gly His Ser Cys Val Cys Val Asn
    290                 295                 300
Gly Trp Thr Gly Glu Ser Cys Ser Gln Asn Ile Asp Asp Cys Ala Thr
305                 310                 315                 320
Ala Val Cys Phe His Gly Ala Thr Cys His Asp Arg Val Ala Ser Phe
                325                 330                 335
Tyr Cys Ala Cys Pro Met Gly Lys Thr Gly Leu Leu Cys His Leu Asp
            340                 345                 350
Asp Ala Cys Val Ser Asn Pro Cys His Glu Asp Ala Ile Cys Asp Thr
        355                 360                 365
Asn Pro Val Asn Gly Arg Ala Ile Cys Thr Cys Pro Pro Gly Phe Thr
    370                 375                 380
Gly Gly Ala Cys Asp Gln Asp Val Asp Glu Cys Ser Ile Gly Ala Asn
385                 390                 395                 400
Pro Cys Glu His Leu Gly Arg Cys Val Asn Thr Gln Gly Ser Phe Leu
                405                 410                 415
Cys Gln Cys Gly Arg Gly Tyr Thr Gly Pro Arg Cys Glu Thr Asp Val
            420                 425                 430
Asn Glu Cys Leu Ser Gly Pro Cys Arg Asn Gln Ala Thr Cys Leu Asp
        435                 440                 445
Arg Ile Gly Gln Phe Thr Cys Ile Cys Met Ala Gly Phe Thr Gly Thr
    450                 455                 460
```

```
Tyr Cys Glu Val Asp Ile Asp Glu Cys Gln Ser Pro Cys Val Asn
465                 470                 475                 480

Gly Gly Val Cys Lys Asp Arg Val Asn Gly Phe Ser Cys Thr Cys Pro
            485                 490                 495

Ser Gly Phe Ser Gly Ser Thr Cys Gln Leu Asp Val Asp Glu Cys Ala
            500                 505                 510

Ser Thr Pro Cys Arg Asn Gly Ala Lys Cys Val Asp Gln Pro Asp Gly
            515                 520                 525

Tyr Glu Cys Arg Cys Ala Glu Gly Phe Glu Gly Thr Leu Cys Asp Arg
            530                 535                 540

Asn Val Asp Asp Cys Ser Pro Asp Pro Cys His His Gly Arg Cys Val
545                 550                 555                 560

Asp Gly Ile Ala Ser Phe Ser Cys Ala Cys Ala Pro Gly Tyr Thr Gly
                565                 570                 575

Thr Arg Cys Glu Ser Gln Val Asp Glu Cys Arg Ser Gln Pro Cys Arg
                580                 585                 590

His Gly Gly Lys Cys Leu Asp Leu Val Asp Lys Tyr Leu Cys Arg Cys
            595                 600                 605

Pro Ser Gly Thr Thr Gly Val Asn Cys Glu Val Asn Ile Asp Asp Cys
            610                 615                 620

Ala Ser Asn Pro Cys Thr Phe Gly Val Cys Arg Asp Gly Ile Asn Arg
625                 630                 635                 640

Tyr Asp Cys Val Cys Gln Pro Gly Phe Thr Gly Pro Leu Cys Asn Val
                645                 650                 655

Glu Ile Asn Glu Cys Ala Ser Ser Pro Cys Gly Glu Gly Gly Ser Cys
            660                 665                 670

Val Asp Gly Glu Asn Gly Phe Arg Cys Leu Cys Pro Pro Gly Ser Leu
            675                 680                 685

Pro Pro Leu Cys Leu Pro Pro Ser His Pro Cys Ala His Glu Pro Cys
            690                 695                 700

Ser His Gly Ile Cys Tyr Asp Ala Pro Gly Gly Phe Arg Cys Val Cys
705                 710                 715                 720

Glu Pro Gly Trp Ser Gly Pro Arg Cys Ser Gln Ser Leu Ala Arg Asp
            725                 730                 735

Ala Cys Glu Ser Gln Pro Cys Arg Ala Gly Gly Thr Cys Ser Ser Asp
            740                 745                 750

Gly Met Gly Phe His Cys Thr Cys Pro Pro Gly Val Gln Gly Arg Gln
            755                 760                 765

Cys Glu Leu Leu Ser Pro Cys Thr Pro Asn Pro Cys Glu His Gly Gly
770                 775                 780

Arg Cys Glu Ser Ala Pro Gly Gln Leu Pro Val Cys Ser Cys Pro Gln
785                 790                 795                 800

Gly Trp Gln Gly Pro Arg Cys Gln Gln Asp Val Asp Glu Cys Ala Gly
            805                 810                 815

Pro Ala Pro Cys Gly Pro His Gly Ile Cys Thr Asn Leu Ala Gly Ser
            820                 825                 830

Phe Ser Cys Thr Cys His Gly Gly Tyr Thr Gly Pro Ser Cys Asp Gln
            835                 840                 845

Asp Ile Asn Asp Cys Asp Pro Asn Pro Cys Leu Asn Gly Gly Ser Cys
            850                 855                 860

Gln Asp Gly Val Gly Ser Phe Ser Cys Ser Cys Leu Pro Gly Phe Ala
865                 870                 875                 880

Gly Pro Arg Cys Ala Arg Asp Val Asp Glu Cys Leu Ser Asn Pro Cys
```

```
                885                 890                 895
Gly Pro Gly Thr Cys Thr Asp His Val Ala Ser Phe Thr Cys Thr Cys
            900                 905                 910
Pro Pro Gly Tyr Gly Gly Phe His Cys Glu Gln Asp Leu Pro Asp Cys
            915                 920                 925
Ser Pro Ser Ser Cys Phe Asn Gly Gly Thr Cys Val Asp Gly Val Asn
            930                 935                 940
Ser Phe Ser Cys Leu Cys Arg Pro Gly Tyr Thr Gly Ala His Cys Gln
945                 950                 955                 960
His Glu Ala Asp Pro Cys Leu Ser Arg Pro Cys Leu His Gly Gly Val
                965                 970                 975
Cys Ser Ala Ala His Pro Gly Phe Arg Cys Thr Cys Leu Glu Ser Phe
            980                 985                 990
Thr Gly Pro Gln Cys Gln Thr Leu Val Asp Trp Cys Ser Arg Gln Pro
            995                1000                1005
Cys Gln Asn Gly Gly Arg Cys Val Gln Thr Gly Ala Tyr Cys Leu
    1010                1015                1020
Cys Pro Pro Gly Trp Ser Gly Arg Leu Cys Asp Ile Arg Ser Leu
    1025                1030                1035
Pro Cys Arg Glu Ala Ala Ala Gln Ile Gly Val Arg Leu Glu Gln
    1040                1045                1050
Leu Cys Gln Ala Gly Gly Gln Cys Val Asp Glu Asp Ser Ser His
    1055                1060                1065
Tyr Cys Val Cys Pro Glu Gly Arg Thr Gly Ser His Cys Glu Gln
    1070                1075                1080
Glu Val Asp Pro Cys Leu Ala Gln Pro Cys Gln His Gly Gly Thr
    1085                1090                1095
Cys Arg Gly Tyr Met Gly Gly Tyr Met Cys Glu Cys Leu Pro Gly
    1100                1105                1110
Tyr Asn Gly Asp Asn Cys Glu Asp Asp Val Asp Glu Cys Ala Ser
    1115                1120                1125
Gln Pro Cys Gln His Gly Gly Ser Cys Ile Asp Leu Val Ala Arg
    1130                1135                1140
Tyr Leu Cys Ser Cys Pro Pro Gly Thr Leu Gly Val Leu Cys Glu
    1145                1150                1155
Ile Asn Glu Asp Asp Cys Gly Pro Gly Pro Pro Leu Asp Ser Gly
    1160                1165                1170
Pro Arg Cys Leu His Asn Gly Thr Cys Val Asp Leu Val Gly Gly
    1175                1180                1185
Phe Arg Cys Thr Cys Pro Pro Gly Tyr Thr Gly Leu Arg Cys Glu
    1190                1195                1200
Ala Asp Ile Asn Glu Cys Arg Ser Gly Ala Cys His Ala Ala His
    1205                1210                1215
Thr Arg Asp Cys Leu Gln Asp Pro Gly Gly Gly Phe Arg Cys Leu
    1220                1225                1230
Cys His Ala Gly Phe Ser Gly Pro Arg Cys Gln Thr Val Leu Ser
    1235                1240                1245
Pro Cys Glu Ser Gln Pro Cys Gln His Gly Gly Gln Cys Arg Pro
    1250                1255                1260
Ser Pro Gly Pro Gly Gly Gly Leu Thr Phe Thr Cys His Cys Ala
    1265                1270                1275
Gln Pro Phe Trp Gly Pro Arg Cys Glu Arg Val Ala Arg Ser Cys
    1280                1285                1290
```

```
Arg Glu Leu Gln Cys Pro Val Gly Val Pro Cys Gln Gln Thr Pro
1295                1300                1305

Arg Gly Pro Arg Cys Ala Cys Pro Pro Gly Leu Ser Gly Pro Ser
1310                1315                1320

Cys Arg Ser Phe Pro Gly Ser Pro Pro Gly Ala Ser Asn Ala Ser
1325                1330                1335

Cys Ala Ala Ala Pro Cys Leu His Gly Gly Ser Cys Arg Pro Ala
1340                1345                1350

Pro Leu Ala Pro Phe Phe Arg Cys Ala Cys Ala Gln Gly Trp Thr
1355                1360                1365

Gly Pro Arg Cys Glu Ala Pro Ala Ala Ala Pro Glu Val Ser Glu
1370                1375                1380

Glu Pro Arg Cys Pro Arg Ala Ala Cys Gln Ala Lys Arg Gly Asp
1385                1390                1395

Gln Arg Cys Asp Arg Glu Cys Asn Ser Pro Gly Cys Gly Trp Asp
1400                1405                1410

Gly Gly Asp Cys Ser Leu Ser Val Gly Asp Pro Trp Arg Gln Cys
1415                1420                1425

Glu Ala Leu Gln Cys Trp Arg Leu Phe Asn Asn Ser Arg Cys Asp
1430                1435                1440

Pro Ala Cys Ser Ser Pro Ala Cys Leu Tyr Asp Asn Phe Asp Cys
1445                1450                1455

His Ala Gly Gly Arg Glu Arg Thr Cys Asn Pro Val Tyr Glu Lys
1460                1465                1470

Tyr Cys Ala Asp His Phe Ala Asp Gly Arg Cys Asp Gln Gly Cys
1475                1480                1485

Asn Thr Glu Glu Cys Gly Trp Asp Gly Leu Asp Cys Ala Ser Glu
1490                1495                1500

Val Pro Ala Leu Leu Ala Arg Gly Val Leu Val Leu Thr Val Leu
1505                1510                1515

Leu Pro Pro Glu Glu Leu Leu Arg Ser Ser Ala Asp Phe Leu Gln
1520                1525                1530

Arg Leu Ser Ala Ile Leu Arg Thr Ser Leu Arg Phe Arg Leu Asp
1535                1540                1545

Ala His Gly Gln Ala Met Val Phe Pro Tyr His Arg Pro Ser Pro
1550                1555                1560

Gly Ser Glu Pro Arg Ala Arg Arg Glu Leu Ala Pro Glu Val Ile
1565                1570                1575

Gly Ser Val Val Met Leu Glu Ile Asp Asn Arg Leu Cys Leu Gln
1580                1585                1590

Ser Pro Glu Asn Asp His Cys Phe Pro Asp Ala Gln Ser Ala Ala
1595                1600                1605

Asp Tyr Leu Gly Ala Leu Ser Ala Val Glu Arg Leu Asp Phe Pro
1610                1615                1620

Tyr Pro Leu Arg Asp Val Arg Gly Glu Pro Leu Glu Pro Pro Glu
1625                1630                1635

Pro Ser Val Pro Leu Leu Pro Leu Leu Val Ala Gly Ala Val Leu
1640                1645                1650

Leu Leu Val Ile Leu Val Leu Gly Val Met Val Ala Arg Arg Lys
1655                1660                1665

Arg Glu His Ser Thr Leu Trp Phe Pro Glu Gly Phe Ser Leu His
1670                1675                1680
```

```
Lys Asp Val Ala Ser Gly His Lys Gly Arg Arg Glu Pro Val Gly
    1685                1690                1695

Gln Asp Ala Leu Gly Met Lys Asn Met Ala Lys Gly Glu Ser Leu
    1700                1705                1710

Met Gly Glu Val Ala Thr Asp Trp Met Asp Thr Glu Cys Pro Glu
    1715                1720                1725

Ala Lys Arg Leu Lys Val Glu Glu Pro Gly Met Gly Ala Glu Glu
    1730                1735                1740

Ala Val Asp Cys Arg Gln Trp Thr Gln His His Leu Val Ala Ala
    1745                1750                1755

Asp Ile Arg Val Ala Pro Ala Met Ala Leu Thr Pro Pro Gln Gly
    1760                1765                1770

Asp Ala Asp Ala Asp Gly Met Asp Val Asn Val Arg Gly Pro Asp
    1775                1780                1785

Gly Phe Thr Pro Leu Met Leu Ala Ser Phe Cys Gly Gly Ala Leu
    1790                1795                1800

Glu Pro Met Pro Thr Glu Glu Asp Glu Ala Asp Asp Thr Ser Ala
    1805                1810                1815

Ser Ile Ile Ser Asp Leu Ile Cys Gln Gly Ala Gln Leu Gly Ala
    1820                1825                1830

Arg Thr Asp Arg Thr Gly Glu Thr Ala Leu His Leu Ala Ala Arg
    1835                1840                1845

Tyr Ala Arg Ala Asp Ala Ala Lys Arg Leu Leu Asp Ala Gly Ala
    1850                1855                1860

Asp Thr Asn Ala Gln Asp His Ser Gly Arg Thr Pro Leu His Thr
    1865                1870                1875

Ala Val Thr Ala Asp Ala Gln Gly Val Phe Gln Ile Leu Ile Arg
    1880                1885                1890

Asn Arg Ser Thr Asp Leu Asp Ala Arg Met Ala Asp Gly Ser Thr
    1895                1900                1905

Ala Leu Ile Leu Ala Ala Arg Leu Ala Val Glu Gly Met Val Glu
    1910                1915                1920

Glu Leu Ile Ala Ser His Ala Asp Val Asn Ala Val Asp Glu Leu
    1925                1930                1935

Gly Lys Ser Ala Leu His Trp Ala Ala Ala Val Asn Asn Val Glu
    1940                1945                1950

Ala Thr Leu Ala Leu Leu Lys Asn Gly Ala Asn Lys Asp Met Gln
    1955                1960                1965

Asp Ser Lys Glu Glu Thr Pro Leu Phe Leu Ala Ala Arg Glu Gly
    1970                1975                1980

Ser Tyr Glu Ala Ala Lys Leu Leu Leu Asp His Phe Ala Asn Arg
    1985                1990                1995

Glu Ile Thr Asp His Leu Asp Arg Leu Pro Arg Asp Val Ala Gln
    2000                2005                2010

Glu Arg Leu His Gln Asp Ile Val Arg Leu Leu Asp Gln Pro Ser
    2015                2020                2025

Gly Pro Arg Ser Pro Pro Gly Pro His Gly Leu Gly Pro Leu Leu
    2030                2035                2040

Cys Pro Pro Gly Ala Phe Leu Pro Gly Leu Lys Ala Ala Gln Ser
    2045                2050                2055

Gly Ser Lys Lys Ser Arg Arg Pro Pro Gly Lys Ala Gly Leu Gly
    2060                2065                2070

Pro Gln Gly Pro Arg Gly Arg Gly Lys Lys Leu Thr Leu Ala Cys
```

| | | | | | | | | | |
|---|---|---|---|---|---|---|---|---|---|
| | | 2075 | | | 2080 | | | 2085 | |

Pro Gly Pro Leu Ala Asp Ser Ser Val Thr Leu Ser Pro Val Asp
    2090                2095                2100

Ser Leu Asp Ser Pro Arg Pro Phe Gly Gly Pro Pro Ala Ser Pro
    2105                2110                2115

Gly Gly Phe Pro Leu Glu Gly Pro Tyr Ala Ala Ala Thr Ala Thr
    2120                2125                2130

Ala Val Ser Leu Ala Gln Leu Gly Gly Pro Gly Arg Ala Gly Leu
    2135                2140                2145

Gly Arg Gln Pro Pro Gly Gly Cys Val Leu Ser Leu Gly Leu Leu
    2150                2155                2160

Asn Pro Val Ala Val Pro Leu Asp Trp Ala Arg Leu Pro Pro Pro
    2165                2170                2175

Ala Pro Pro Gly Pro Ser Phe Leu Leu Pro Leu Ala Pro Gly Pro
    2180                2185                2190

Gln Leu Leu Asn Pro Gly Thr Pro Val Ser Pro Gln Glu Arg Pro
    2195                2200                2205

Pro Pro Tyr Leu Ala Val Pro Gly His Gly Glu Glu Tyr Pro Ala
    2210                2215                2220

Ala Gly Ala His Ser Ser Pro Pro Lys Ala Arg Phe Leu Arg Val
    2225                2230                2235

Pro Ser Glu His Pro Tyr Leu Thr Pro Ser Pro Glu Ser Pro Glu
    2240                2245                2250

His Trp Ala Ser Pro Ser Pro Pro Ser Leu Ser Asp Trp Ser Glu
    2255                2260                2265

Ser Thr Pro Ser Pro Ala Thr Ala Thr Gly Ala Met Ala Thr Thr
    2270                2275                2280

Thr Gly Ala Leu Pro Ala Gln Pro Leu Pro Leu Ser Val Pro Ser
    2285                2290                2295

Ser Leu Ala Gln Ala Gln Thr Gln Leu Gly Pro Gln Pro Glu Val
    2300                2305                2310

Thr Pro Lys Arg Gln Val Leu Ala
    2315                2320

<210> SEQ ID NO 11
<211> LENGTH: 8091
<212> TYPE: DNA
<213> ORGANISM: Homo sapiens

<400> SEQUENCE: 11

| | | |
|---|---|---|
| acgcggcgcg gaggctggcc cgggacgcgc ccggagccca gggaaggagg gaggagggga | 60 |
| gggtcgcggc cggccgccat ggggccgggg gcccgtggcc gccgccgccg ccgtcgcccg | 120 |
| atgtcgccgc caccgccacc gccacccgtg cgggcgctgc ccctgctgct gctgctagcg | 180 |
| gggccggggg ctgcagcccc ccttgcctg gacggaagcc cgtgtgcaaa tggaggtcgt | 240 |
| tgcacccagc tgccctcccg ggaggctgcc tgcctgtgcc cgcctggctg ggtgggtgag | 300 |
| cggtgtcagc tggaggaccc ctgtcactca ggcccctgtg ctggccgtgg tgtctgccag | 360 |
| agttcagtgg tggctggcac cgcccgattc tcatgccggt gccccgtgg cttccgaggc | 420 |
| cctgactgct ccctgccaga tccctgcctc agcagccctt gtgcccacgg tgcccgctgc | 480 |
| tcagtgggc ccgatggacg cttcctctgc tcctgcccac ctggctacca gggccgcagc | 540 |
| tgccgaagcg acgtggatga gtgccgggtg ggtgagccct gccgcatgg tgcacctgc | 600 |
| ctcaacacac ctggctcctt ccgctgccag tgtccagctg gctacacagg gccactatgt | 660 |

```
gagaacccg cggtgccctg tgcgccctca ccatgccgta acggggggcac ctgcaggcag    720
agtggcgacc tcacttacga ctgtgcctgt cttcctgggt ttgagggtca gaattgtgaa    780
gtgaacgtgg acgactgtcc aggacaccga tgtctcaatg gggggacatg cgtggatggc    840
gtcaacacct ataactgcca gtgccctcct gagtggacag gccagttctg cacggaggac    900
gtggatgagt gtcagctgca gcccaacgcc tgccacaatg ggggtacctg cttcaacacg    960
ctgggtggcc acagctgcgt gtgtgtcaat ggctggacag tgagagctg cagtcagaat    1020
atcgatgact gtgccacagc cgtgtgcttc catggggcca cctgccatga ccgcgtggct    1080
tctttctact gtgcctgccc catgggcaag actggcctcc tgtgtcacct ggatgacgcc    1140
tgtgtcagca cccctgcca cgaggatgct atctgtgaca caaatccggt gaacggccgg    1200
gccatttgca cctgtcctcc cggcttcacg ggtggggcat gtgaccagga tgtggacgag    1260
tgctctatcg cgccaaccc ctgcgagcac ttgggcaggt gcgtgaacac gcagggctcc    1320
ttcctgtgcc agtgcggtcg tggctacact ggacctcgct gtgagaccga tgtcaacgag    1380
tgtctgtcgg ggccctgccg aaaccaggcc acgtgcctcg accgcatagg ccagttcacc    1440
tgtatctgta tggcaggctt cacaggaacc tattgcgagg tggacattga cgagtgtcag    1500
agtagcccct gtgtcaacgg tgggtctgc aaggaccgag tcaatggctt cagctgcacc    1560
tgcccctcgg gcttcagcgg ctccacgtgt cagctggacg tggacgaatg cgccagcacg    1620
ccctgcagga atggcgccaa atgcgtggac cagcccgatg gctacgagtg ccgctgtgcc    1680
gagggctttg agggcacgct gtgtgatcgc aacgtggacg actgctccc tgacccatgc    1740
caccatggtc gctgcgtgga tggcatcgcc agcttctcat gtcctgtgc tcctggctac    1800
acgggcacac gctgcgagag ccaggtggac gaatgccgca gccagccctg ccgccatggc    1860
ggcaaatgcc tagacctggt ggacaagtac ctctgccgct gcccttctgg gaccacaggt    1920
gtgaactgcg aagtgaacat tgacgactgt gccagcaacc cctgcacctt ggagtctgc    1980
cgtgatggca tcaaccgcta cgactgtgtc tgccaacctg gcttcacagg gccccttgt    2040
aacgtggaga tcaatgagtg tgcttccagc ccatgcggcg agggaggttc ctgtgtggat    2100
ggggaaaatg gcttccgctg cctctgcccg cctggctcct gcccccact ctgcctcccc    2160
ccgagccatc cctgtgccca tgagccctgc agtcacggca tctgctatga tgcacctggc    2220
gggttccgct gtgtgtgtga gcctggctgg agtggccccc gctgcagcca gagcctggcc    2280
cgagacgcct gtgagtccca gccgtgcagg gccggtggga catgcagcag cgatggaatg    2340
ggtttccact gcacctgccc gcctggtgtc cagggacgtc agtgtgaact cctctcccc    2400
tgcacccga accctgtga gcatgggggc cgctgcgagt ctgcccctgg ccagctgcct    2460
gtctgctcct gccccagggg ctggcaaggc ccacgatgcc agcaggatgt ggacgagtgt    2520
gctggccccg caccctgtgg ccctcatggt atctgcacca acctggcagg gagtttcagc    2580
tgcacctgcc atggagggta cactggccct tcctgtgatc aggacatcaa tgactgtgac    2640
cccaacccat gcctgaacgg tggctcgtgc caagacggcg tgggctcctt ttcctgctcc    2700
tgcctccctg gtttcgccgg cccacgatgc gcccgcgatg tggatgagtg cctgagcaac    2760
ccctgcggcc cgggcacctg taccgaccac gtggcctcct tcacctgcac ctgcccgccg    2820
ggctacggag gcttccactg cgaacaggac ctgcccgact gcagcccag ctcctgcttc    2880
aatgcggga cctgtgtgga cggcgtgaac tcgttcagct gcctgtgccg tcccggctac    2940
acaggagccc actgccaaca tgaggcagac ccctgcctct cgcggccctg cctacacggg    3000
```

-continued

```
ggcgtctgca gcgccgccca ccctggcttc cgctgcacct gcctcgagag cttcacgggc   3060
ccgcagtgcc agacgctggt ggattggtgc agccgccagc cttgtcaaaa cgggggtcgc   3120
tgcgtccaga ctggggccta ttgcctttgt ccccctggat ggagcggacg cctctgtgac   3180
atccgaagct tgccctgcag ggaggccgca gcccagatcg gggtgcggct ggagcagctg   3240
tgtcaggcgg gtgggcagtg tgtggatgaa gacagctccc actactgcgt gtgcccagag   3300
ggccgtactg gtagccactg tgagcaggag gtggacccct gcttggccca gccctgccag   3360
catgggggga cctgccgtgg ctatatgggg ggctacatgt gtgagtgtct tcctggctac   3420
aatggtgata actgtgagga cgacgtggac gagtgtgcct cccagccctg ccagcacggg   3480
ggttcatgca ttgacctcgt ggcccgctat ctctgctcct gtcccccagg aacgctgggg   3540
gtgctctgcg agattaatga ggatgactgc ggcccaggcc caccgctgga ctcagggccc   3600
cggtgcctac acaatggcac ctgcgtggac ctggtgggtg gtttccgctg cacctgtccc   3660
ccaggataca ctggtttgcg ctgcgaggca gacatcaatg agtgtcgctc aggtgcctgc   3720
cacgcggcac acacccggga ctgcctgcag gacccaggcg gaggtttccg ttgcctttgt   3780
catgctggct tctcaggtcc tcgctgtcag actgtcctgt ctccctgcga gtcccagcca   3840
tgccagcatg gaggccagtg ccgtcctagc ccgggtcctg gggtgggct gaccttcacc   3900
tgtcactgtg cccagccgtt ctggggtccg cgttgcgagc gggtggcgcg ctcctgccgg   3960
gagctgcagt gcccggtggg cgtcccatgc cagcagacgc cccgcgggcc gcgctgcgcc   4020
tgcccccag ggttgtcggg accctcctgc cgcagcttcc cggggtcgcc gccgggggcc   4080
agcaacgcca gctgcgcggc cgccccctgt ctccacgggg gctcctgccg ccccgcgccg   4140
ctcgcgccct tcttccgctg cgcttgcgcg cagggctgga ccgggccgcg ctgcgaggcg   4200
cccgccgcgg cacccgaggt ctcggaggag ccgcggtgcc cgcgcgccgc ctgccaggcc   4260
aagcgcgggg accagcgctg cgaccgcgag tgcaacagcc caggctgcgg ctgggacggc   4320
ggcgactgct cgctgagcgt gggcgacccc tggcggcaat gcgaggcgct gcagtgctgg   4380
cgcctcttca acaacagccg ctgcgacccc gcctgcagct cgcccgcctg cctctacgac   4440
aacttcgact gccacgccgg tggccgcgag cgcacttgca acccggtgta cgagaagtac   4500
tgcgccgacc actttgccga cggccgctgc gaccagggct gcaacacgga ggagtgcggc   4560
tgggatgggc tggattgtgc cagcgaggtg ccggccctgc tggcccgcgg cgtgctggtg   4620
ctcacagtgc tgctgccgcc ggaggagcta ctgcgttcca gcgccgactt tctgcagcgg   4680
ctcagcgcca tcctgcgcac ctcgctgcgc ttccgcctgg acgcgcacgg ccaggccatg   4740
gtcttccctt accaccggcc tagtcctggc tccgaacccc gggcccgtcg ggagctggcc   4800
cccgaggtga tcggctcggt agtaatgctg gagattgaca accggctctg cctgcagtcg   4860
cctgagaatg atcactgctt ccccgatgcc cagagcgccg ctgactacct gggagcgttg   4920
tcagcggtgg agcgcctgga cttcccgtac ccactgcggg acgtgcgggg ggagccgctg   4980
gagcctccag aacccagcgt cccgctgctg ccactgctag tggcgggcgc tgtcttgctg   5040
ctggtcattc tcgtcctggg tgtcatggtg gcccggcgca agcgcgagca cagcaccctc   5100
tggttccctg agggcttctc actgcacaag gacgtggcct ctggtcacaa gggccggcgg   5160
gaacccgtgg gccaggacgc gctgggcatg aagaacatgg ccaagggtga gagcctgatg   5220
ggggaggtgg ccacagactg gatggacaca gagtgcccag aggccaagcg gctaaaggta   5280
gaggagccag gcatgggggc tgaggaggct gtggattgcc gtcagtggac tcaacaccat   5340
ctggttgctg ctgacatccg cgtggcacca gccatggcac tgacaccacc acagggcgac   5400
```

-continued

```
gcagatgctg atggcatgga tgtcaatgtg cgtggcccag atggcttcac ccgctaatg    5460
ctggcttcct tctgtggggg ggctctggag ccaatgccaa ctgaagagga tgaggcagat    5520
gacacatcag ctagcatcat ctccgacctg atctgccagg gggctcagct tggggcacgg    5580
actgaccgta ctggcgagac tgctttgcac ctggctgccc gttatgcccg tgctgatgca    5640
gccaagcggc tgctggatgc tggggcagac accaatgccc aggaccactc aggccgcact    5700
cccctgcaca cagctgtcac agccgatgcc cagggtgtct tccagattct catccgaaac    5760
cgctctacag acttggatgc ccgcatggca gatggctcaa cggcactgat cctggcggcc    5820
cgcctggcag tagagggcat ggtggaagag ctcatcgcca gccatgctga tgtcaatgct    5880
gtggatgagc ttgggaaatc agccttacac tgggctgcgg ctgtgaacaa cgtggaagcc    5940
actttggccc tgctcaaaaa tggagccaat aaggacatgc aggatagcaa ggaggagacc    6000
cccctattcc tggccgcccg cgagggcagc tatgaggctg ccaagctgct gttggaccac    6060
tttgccaacc gtgagatcac cgaccacctg acaggctgcc cgcggacgt agcccaggag    6120
agactgcacc aggacatcgt gcgcttgctg gatcaaccca gtgggccccg cagccccccc    6180
ggtccccacg gcctggggcc tctgctctgt cctccagggg ccttcctccc tggcctcaaa    6240
gcggcacagt cggggtccaa gaagagcagg aggcccccg gaaggcggg gctggggccg    6300
caggggcccc gggggcgggg caagaagctg acgctggcct gcccgggccc cctggctgac    6360
agctcggtca cgctgtcgcc cgtggactcg ctggactccc cgcggccttt cggtgggccc    6420
cctgcttccc ctggtggctt ccccttgag gggccctatg cagctgccac tgccactgca    6480
gtgtctctgg cacagcttgg tggcccaggc cgggcaggtc tagggcgcca gccccctgga    6540
ggatgtgtac tcagcctggg cctgctgaac cctgtggctg tgcccctcga ttgggcccgg    6600
ctgcccccac ctgccctcc aggcccctcg ttcctgctgc cactggcgcc gggacccag    6660
ctgctcaacc cagggacccc cgtctcccg caggagcggc cccgccctta cctggcagtc    6720
ccaggacatg gcgaggagta cccggtggct ggggcacaca gcagccccc aaaggcccgc    6780
ttcctgcggg ttcccagtga gcaccttac ctgaccccat ccccgaatc ccctgagcac    6840
tgggccagcc cctcacctcc ctccctctca gactggtccg aatccacgcc tagcccagcc    6900
actgccactg gggccatggc caccaccact ggggcactgc ctgcccagcc acttcccttg    6960
tctgttccca gctcccttgc tcaggcccag acccagctgg ggcccccagcc ggaagttacc    7020
cccaagaggc aagtgttggc ctgagacgct cgtcagttct tagatcttgg gggcctaaag    7080
agaccccgt cctgcctcct ttctttctct gtctcttcct tcctttttagt cttttttcatc    7140
ctcttctctt tccaccaacc ctcctgcatc cttgccttgc agcgtgaccg agataggtca    7200
tcagcccagg gcttcagtct tccttttattt ataatgggtg ggggctacca cccaccctct    7260
cagtcttgtg aagagtctgg gacctccttc ttccccactt ctctcttccc tcattccttt    7320
ctctctcctt ctgggcctctc atttccttac actctgacat gaatgaatta ttattatttt    7380
tcttttttctt tttttttta catttttgtat agaaacaaat tcatttaaac aaacttatta    7440
ttattatttt ttacaaaata tatatatgga gatgctccct cccctgtga acccccagt    7500
gcccccgtgg ggctgagtct gtgggcccat tcggccaagc tggattctgt gtacctagta    7560
cacaggcatg actgggatcc cgtgtaccga gtacacgacc caggtatgta ccaagtaggc    7620
acccttgggc gcaccactg gggccagggg tcggggagt gttgggagcc tcctccccac    7680
cccacctccc tcacttcact gcattccaga ttggacatgt tccatagcct tgctggggaa    7740
```

```
gggcccactg ccaactccct ctgccccagc cccaccttg gccatctccc tttgggaact    7800 aggggctgc tggtgggaaa tgggagccag ggcagatgta tgcattcctt tatgtccctg    7860
taaatgtggg actacaagaa gaggagctgc ctgagtggta ctttctcttc ctggtaatcc    7920
tctggcccag ccttatggca gaatagaggt attttaggc tatttttgta atatggcttc    7980
tggtcaaaat ccctgtgtag ctgaattccc aagccctgca ttgtacagcc ccccactccc    8040
ctcaccacct aataaaggaa tagttaacac tcaaaaaaaa aaaaaaaaaa a            8091
```

<210> SEQ ID NO 12
<211> LENGTH: 1532
<212> TYPE: PRT
<213> ORGANISM: Homo sapiens

<400> SEQUENCE: 12

```
Ala Pro Pro Cys Leu Asp Gly Ser Pro Cys Ala Asn Gly Gly Arg Cys
1               5                   10                  15

Thr Gln Leu Pro Ser Arg Glu Ala Ala Cys Leu Cys Pro Pro Gly Trp
            20                  25                  30

Val Gly Glu Arg Cys Gln Leu Glu Asp Pro Cys His Ser Gly Pro Cys
        35                  40                  45

Ala Gly Arg Gly Val Cys Gln Ser Ser Val Val Ala Gly Thr Ala Arg
    50                  55                  60

Phe Ser Cys Arg Cys Pro Arg Gly Phe Arg Gly Pro Asp Cys Ser Leu
65                  70                  75                  80

Pro Asp Pro Cys Leu Ser Ser Pro Cys Ala His Gly Ala Arg Cys Ser
                85                  90                  95

Val Gly Pro Asp Gly Arg Phe Leu Cys Ser Cys Pro Pro Gly Tyr Gln
            100                 105                 110

Gly Arg Ser Cys Arg Ser Asp Val Asp Glu Cys Arg Val Gly Glu Pro
        115                 120                 125

Cys Arg His Gly Gly Thr Cys Leu Asn Thr Pro Gly Ser Phe Arg Cys
    130                 135                 140

Gln Cys Pro Ala Gly Tyr Thr Gly Pro Leu Cys Glu Asn Pro Ala Val
145                 150                 155                 160

Pro Cys Ala Pro Ser Pro Cys Arg Asn Gly Gly Thr Cys Arg Gln Ser
                165                 170                 175

Gly Asp Leu Thr Tyr Asp Cys Ala Cys Leu Pro Gly Phe Glu Gly Gln
            180                 185                 190

Asn Cys Glu Val Asn Val Asp Asp Cys Pro Gly His Arg Cys Leu Asn
        195                 200                 205

Gly Gly Thr Cys Val Asp Gly Val Asn Thr Tyr Asn Cys Gln Cys Pro
    210                 215                 220

Pro Glu Trp Thr Gly Gln Phe Cys Thr Glu Asp Val Asp Glu Cys Gln
225                 230                 235                 240

Leu Gln Pro Asn Ala Cys His Asn Gly Gly Thr Cys Phe Asn Thr Leu
                245                 250                 255

Gly Gly His Ser Cys Val Cys Val Asn Gly Trp Thr Gly Glu Ser Cys
            260                 265                 270

Ser Gln Asn Ile Asp Asp Cys Ala Thr Ala Val Cys Phe His Gly Ala
        275                 280                 285

Thr Cys His Asp Arg Val Ala Ser Phe Tyr Cys Ala Cys Pro Met Gly
    290                 295                 300

Lys Thr Gly Leu Leu Cys His Leu Asp Asp Ala Cys Val Ser Asn Pro
305                 310                 315                 320
```

-continued

```
Cys His Glu Asp Ala Ile Cys Asp Thr Asn Pro Val Asn Gly Arg Ala
                325                 330                 335
Ile Cys Thr Cys Pro Pro Gly Phe Thr Gly Gly Ala Cys Asp Gln Asp
            340                 345                 350
Val Asp Glu Cys Ser Ile Gly Ala Asn Pro Cys Glu His Leu Gly Arg
        355                 360                 365
Cys Val Asn Thr Gln Gly Ser Phe Leu Cys Gln Cys Gly Arg Gly Tyr
    370                 375                 380
Thr Gly Pro Arg Cys Glu Thr Asp Val Asn Glu Cys Leu Ser Gly Pro
385                 390                 395                 400
Cys Arg Asn Gln Ala Thr Cys Leu Asp Arg Ile Gly Gln Phe Thr Cys
            405                 410                 415
Ile Cys Met Ala Gly Phe Thr Gly Thr Tyr Cys Glu Val Asp Ile Asp
        420                 425                 430
Glu Cys Gln Ser Ser Pro Cys Val Asn Gly Gly Val Cys Lys Asp Arg
    435                 440                 445
Val Asn Gly Phe Ser Cys Thr Cys Pro Ser Gly Phe Ser Gly Ser Thr
    450                 455                 460
Cys Gln Leu Asp Val Asp Glu Cys Ala Ser Thr Pro Cys Arg Asn Gly
465                 470                 475                 480
Ala Lys Cys Val Asp Gln Pro Asp Gly Tyr Glu Cys Arg Cys Ala Glu
            485                 490                 495
Gly Phe Glu Gly Thr Leu Cys Asp Arg Asn Val Asp Asp Cys Ser Pro
        500                 505                 510
Asp Pro Cys His His Gly Arg Cys Val Asp Gly Ile Ala Ser Phe Ser
    515                 520                 525
Cys Ala Cys Ala Pro Gly Tyr Thr Gly Thr Arg Cys Glu Ser Gln Val
530                 535                 540
Asp Glu Cys Arg Ser Gln Pro Cys Arg His Gly Gly Lys Cys Leu Asp
545                 550                 555                 560
Leu Val Asp Lys Tyr Leu Cys Arg Cys Pro Ser Gly Thr Thr Gly Val
            565                 570                 575
Asn Cys Glu Val Asn Ile Asp Asp Cys Ala Ser Asn Pro Cys Thr Phe
        580                 585                 590
Gly Val Cys Arg Asp Gly Ile Asn Arg Tyr Asp Cys Val Cys Gln Pro
    595                 600                 605
Gly Phe Thr Gly Pro Leu Cys Asn Val Glu Ile Asn Glu Cys Ala Ser
    610                 615                 620
Ser Pro Cys Gly Glu Gly Gly Ser Cys Val Asp Gly Glu Asn Gly Phe
625                 630                 635                 640
Arg Cys Leu Cys Pro Pro Gly Ser Leu Pro Pro Leu Cys Leu Pro Pro
            645                 650                 655
Ser His Pro Cys Ala His Glu Pro Cys Ser His Gly Ile Cys Tyr Asp
        660                 665                 670
Ala Pro Gly Gly Phe Arg Cys Val Cys Glu Pro Gly Trp Ser Gly Pro
    675                 680                 685
Arg Cys Ser Gln Ser Leu Ala Arg Asp Ala Cys Glu Ser Gln Pro Cys
    690                 695                 700
Arg Ala Gly Gly Thr Cys Ser Ser Asp Gly Met Gly Phe His Cys Thr
705                 710                 715                 720
Cys Pro Pro Gly Val Gln Gly Arg Gln Cys Glu Leu Leu Ser Pro Cys
            725                 730                 735
```

```
Thr Pro Asn Pro Cys Glu His Gly Gly Arg Cys Glu Ser Ala Pro Gly
            740                 745                 750

Gln Leu Pro Val Cys Ser Cys Pro Gln Gly Trp Gln Gly Pro Arg Cys
            755                 760                 765

Gln Gln Asp Val Asp Glu Cys Ala Gly Pro Ala Pro Cys Gly Pro His
            770                 775                 780

Gly Ile Cys Thr Asn Leu Ala Gly Ser Phe Ser Cys Thr Cys His Gly
785                 790                 795                 800

Gly Tyr Thr Gly Pro Ser Cys Asp Gln Asp Ile Asn Asp Cys Asp Pro
                805                 810                 815

Asn Pro Cys Leu Asn Gly Gly Ser Cys Gln Asp Gly Val Gly Ser Phe
            820                 825                 830

Ser Cys Ser Cys Leu Pro Gly Phe Ala Gly Pro Arg Cys Ala Arg Asp
            835                 840                 845

Val Asp Glu Cys Leu Ser Asn Pro Cys Gly Pro Gly Thr Cys Thr Asp
            850                 855                 860

His Val Ala Ser Phe Thr Cys Thr Cys Pro Pro Gly Tyr Gly Gly Phe
865                 870                 875                 880

His Cys Glu Gln Asp Leu Pro Asp Cys Ser Pro Ser Ser Cys Phe Asn
                885                 890                 895

Gly Gly Thr Cys Val Asp Gly Val Asn Ser Phe Ser Cys Leu Cys Arg
            900                 905                 910

Pro Gly Tyr Thr Gly Ala His Cys Gln His Glu Ala Asp Pro Cys Leu
            915                 920                 925

Ser Arg Pro Cys Leu His Gly Gly Val Cys Ser Ala Ala His Pro Gly
            930                 935                 940

Phe Arg Cys Thr Cys Leu Glu Ser Phe Thr Gly Pro Gln Cys Gln Thr
945                 950                 955                 960

Leu Val Asp Trp Cys Ser Arg Gln Pro Cys Gln Asn Gly Gly Arg Cys
                965                 970                 975

Val Gln Thr Gly Ala Tyr Cys Leu Cys Pro Pro Gly Trp Ser Gly Arg
            980                 985                 990

Leu Cys Asp Ile Arg Ser Leu Pro  Cys Arg Glu Ala Ala  Ala Gln Ile
            995                 1000                1005

Gly Val  Arg Leu Glu Gln Leu  Cys Gln Ala Gly Gly  Gln Cys Val
     1010                1015                1020

Asp Glu  Asp Ser Ser His Tyr  Cys Val Cys Pro Glu  Gly Arg Thr
     1025                1030                1035

Gly Ser  His Cys Glu Gln Glu  Val Asp Pro Cys Leu  Ala Gln Pro
     1040                1045                1050

Cys Gln His Gly Gly Thr Cys  Arg Gly Tyr Met Gly  Gly Tyr Met
     1055                1060                1065

Cys Glu Cys Leu Pro Gly Tyr  Asn Gly Asp Asn Cys  Glu Asp Asp
     1070                1075                1080

Val Asp  Glu Cys Ala Ser Gln  Pro Cys Gln His Gly  Gly Ser Cys
     1085                1090                1095

Ile Asp  Leu Val Ala Arg Tyr  Leu Cys Ser Cys Pro  Pro Gly Thr
     1100                1105                1110

Leu Gly  Val Leu Cys Glu Ile  Asn Glu Asp Asp Cys  Gly Pro Gly
     1115                1120                1125

Pro Pro  Leu Asp Ser Gly Pro  Arg Cys Leu His Asn  Gly Thr Cys
     1130                1135                1140

Val Asp  Leu Val Gly Gly Phe  Arg Cys Thr Cys Pro  Pro Gly Tyr
```

-continued

```
            1145                1150                1155
Thr Gly Leu Arg Cys Glu Ala Asp Ile Asn Glu Cys Arg Ser Gly
        1160                1165                1170
Ala Cys His Ala Ala His Thr Arg Asp Cys Leu Gln Asp Pro Gly
        1175                1180                1185
Gly Gly Phe Arg Cys Leu Cys His Ala Gly Phe Ser Gly Pro Arg
        1190                1195                1200
Cys Gln Thr Val Leu Ser Pro Cys Glu Ser Gln Pro Cys Gln His
        1205                1210                1215
Gly Gly Gln Cys Arg Pro Ser Pro Gly Pro Gly Gly Leu Thr
        1220                1225                1230
Phe Thr Cys His Cys Ala Gln Pro Phe Trp Gly Pro Arg Cys Glu
        1235                1240                1245
Arg Val Ala Arg Ser Cys Arg Glu Leu Gln Cys Pro Val Gly Val
        1250                1255                1260
Pro Cys Gln Gln Thr Pro Arg Gly Pro Arg Cys Ala Cys Pro Pro
        1265                1270                1275
Gly Leu Ser Gly Pro Ser Cys Arg Ser Phe Pro Gly Ser Pro Pro
        1280                1285                1290
Gly Ala Ser Asn Ala Ser Cys Ala Ala Pro Cys Leu His Gly
        1295                1300                1305
Gly Ser Cys Arg Pro Ala Pro Leu Ala Pro Phe Phe Arg Cys Ala
        1310                1315                1320
Cys Ala Gln Gly Trp Thr Gly Pro Arg Cys Glu Ala Pro Ala Ala
        1325                1330                1335
Ala Pro Glu Val Ser Glu Glu Pro Arg Cys Pro Arg Ala Ala Cys
        1340                1345                1350
Gln Ala Lys Arg Gly Asp Gln Arg Cys Asp Arg Glu Cys Asn Ser
        1355                1360                1365
Pro Gly Cys Gly Trp Asp Gly Gly Asp Cys Ser Leu Ser Val Gly
        1370                1375                1380
Asp Pro Trp Arg Gln Cys Glu Ala Leu Gln Cys Trp Arg Leu Phe
        1385                1390                1395
Asn Asn Ser Arg Cys Asp Pro Ala Cys Ser Ser Pro Ala Cys Leu
        1400                1405                1410
Tyr Asp Asn Phe Asp Cys His Ala Gly Gly Arg Glu Arg Thr Cys
        1415                1420                1425
Asn Pro Val Tyr Glu Lys Tyr Cys Ala Asp His Phe Ala Asp Gly
        1430                1435                1440
Arg Cys Asp Gln Gly Cys Asn Thr Glu Glu Cys Gly Trp Asp Gly
        1445                1450                1455
Leu Asp Cys Ala Ser Glu Val Pro Ala Leu Leu Ala Arg Gly Val
        1460                1465                1470
Leu Val Leu Thr Val Leu Leu Pro Pro Glu Glu Leu Leu Arg Ser
        1475                1480                1485
Ser Ala Asp Phe Leu Gln Arg Leu Ser Ala Ile Leu Arg Thr Ser
        1490                1495                1500
Leu Arg Phe Arg Leu Asp Ala His Gly Gln Ala Met Val Phe Pro
        1505                1510                1515
Tyr His Arg Pro Ser Pro Gly Ser Glu Pro Arg Ala Arg Arg
        1520                1525                1530

<210> SEQ ID NO 13
```

<211> LENGTH: 1533
<212> TYPE: PRT
<213> ORGANISM: Mus musculus

<400> SEQUENCE: 13

```
Ala Pro Pro Cys Leu Asp Gly Ser Pro Cys Ala Asn Gly Gly Arg Cys
1               5                   10                  15

Thr His Gln Gln Pro Ser Leu Glu Ala Ala Cys Leu Cys Leu Pro Gly
            20                  25                  30

Trp Val Gly Glu Arg Cys Gln Leu Glu Asp Pro Cys His Ser Gly Pro
        35                  40                  45

Cys Ala Gly Arg Gly Val Cys Gln Ser Ser Val Val Ala Gly Thr Ala
50                  55                  60

Arg Phe Ser Cys Arg Cys Leu Arg Gly Phe Gln Gly Pro Asp Cys Ser
65                  70                  75                  80

Gln Pro Asp Pro Cys Val Ser Arg Pro Cys Val His Gly Ala Pro Cys
                85                  90                  95

Ser Val Gly Pro Asp Gly Arg Phe Ala Cys Ala Cys Pro Pro Gly Tyr
            100                 105                 110

Gln Gly Gln Ser Cys Gln Ser Asp Ile Asp Glu Cys Arg Ser Gly Thr
        115                 120                 125

Thr Cys Arg His Gly Gly Thr Cys Leu Asn Thr Pro Gly Ser Phe Arg
130                 135                 140

Cys Gln Cys Pro Leu Gly Tyr Thr Gly Leu Leu Cys Glu Asn Pro Val
145                 150                 155                 160

Val Pro Cys Ala Pro Ser Pro Cys Arg Asn Gly Gly Thr Cys Arg Gln
                165                 170                 175

Ser Ser Asp Val Thr Tyr Asp Cys Ala Cys Leu Pro Gly Phe Glu Gly
            180                 185                 190

Gln Asn Cys Glu Val Asn Val Asp Asp Cys Pro Gly His Arg Cys Leu
        195                 200                 205

Asn Gly Gly Thr Cys Val Asp Gly Val Asn Thr Tyr Asn Cys Gln Cys
210                 215                 220

Pro Pro Glu Trp Thr Gly Gln Phe Cys Thr Glu Asp Val Asp Glu Cys
225                 230                 235                 240

Gln Leu Gln Pro Asn Ala Cys His Asn Gly Gly Thr Cys Phe Asn Leu
                245                 250                 255

Leu Gly Gly His Ser Cys Val Cys Val Asn Gly Trp Thr Gly Glu Ser
            260                 265                 270

Cys Ser Gln Asn Ile Asp Asp Cys Ala Thr Ala Val Cys Phe His Gly
        275                 280                 285

Ala Thr Cys His Asp Arg Val Ala Ser Phe Tyr Cys Ala Cys Pro Met
290                 295                 300

Gly Lys Thr Gly Leu Leu Cys His Leu Asp Asp Ala Cys Val Ser Asn
305                 310                 315                 320

Pro Cys His Glu Asp Ala Ile Cys Asp Thr Asn Pro Val Ser Gly Arg
                325                 330                 335

Ala Ile Cys Thr Cys Pro Pro Gly Phe Thr Gly Gly Ala Cys Asp Gln
            340                 345                 350

Asp Val Asp Glu Cys Ser Ile Gly Ala Asn Pro Cys Glu His Leu Gly
        355                 360                 365

Arg Cys Val Asn Thr Gln Gly Ser Phe Leu Cys Gln Cys Gly Arg Gly
370                 375                 380

Tyr Thr Gly Pro Arg Cys Glu Thr Asp Val Asn Glu Cys Leu Ser Gly
```

```
            385                 390                 395                 400
Pro Cys Arg Asn Gln Ala Thr Cys Leu Asp Arg Ile Gly Gln Phe Thr
                    405                 410                 415
Cys Ile Cys Met Ala Gly Phe Thr Gly Thr Tyr Cys Glu Val Asp Ile
                420                 425                 430
Asp Glu Cys Gln Ser Ser Pro Cys Val Asn Gly Val Cys Lys Asp
            435                 440                 445
Arg Val Asn Gly Phe Ser Cys Thr Cys Pro Ser Gly Phe Ser Gly Ser
        450                 455                 460
Met Cys Gln Leu Asp Val Asp Glu Cys Ala Ser Thr Pro Cys Arg Asn
465                 470                 475                 480
Gly Ala Lys Cys Val Asp Gln Pro Asp Gly Tyr Glu Cys Arg Cys Ala
                485                 490                 495
Glu Gly Phe Glu Gly Thr Leu Cys Glu Arg Asn Val Asp Cys Ser
            500                 505                 510
Pro Asp Pro Cys His His Gly Arg Cys Val Asp Gly Ile Ala Ser Phe
        515                 520                 525
Ser Cys Ala Cys Ala Pro Gly Tyr Thr Gly Ile Arg Cys Glu Ser Gln
    530                 535                 540
Val Asp Glu Cys Arg Ser Gln Pro Cys Arg Tyr Gly Gly Lys Cys Leu
545                 550                 555                 560
Asp Leu Val Asp Lys Tyr Leu Cys Arg Cys Pro Pro Gly Thr Thr Gly
                565                 570                 575
Val Asn Cys Glu Val Asn Ile Asp Asp Cys Ala Ser Asn Pro Cys Thr
            580                 585                 590
Phe Gly Val Cys Arg Asp Gly Ile Asn Arg Tyr Asp Cys Val Cys Gln
        595                 600                 605
Pro Gly Phe Thr Gly Pro Leu Cys Asn Val Glu Ile Asn Glu Cys Ala
    610                 615                 620
Ser Ser Pro Cys Gly Glu Gly Ser Cys Val Asp Gly Glu Asn Gly
625                 630                 635                 640
Phe His Cys Leu Cys Pro Pro Gly Ser Leu Pro Pro Leu Cys Leu Pro
                645                 650                 655
Ala Asn His Pro Cys Ala His Lys Pro Cys Ser His Gly Val Cys His
            660                 665                 670
Asp Ala Pro Gly Gly Phe Arg Cys Val Cys Glu Pro Gly Trp Ser Gly
        675                 680                 685
Pro Arg Cys Ser Gln Ser Leu Ala Pro Asp Ala Cys Glu Ser Gln Pro
    690                 695                 700
Cys Gln Ala Gly Gly Thr Cys Thr Ser Asp Gly Ile Gly Phe Arg Cys
705                 710                 715                 720
Thr Cys Ala Pro Gly Phe Gln Gly His Gln Cys Glu Val Leu Ser Pro
                725                 730                 735
Cys Thr Pro Ser Leu Cys Glu His Gly Gly His Cys Glu Ser Asp Pro
            740                 745                 750
Asp Arg Leu Thr Val Cys Ser Cys Pro Pro Gly Trp Gln Gly Pro Arg
        755                 760                 765
Cys Gln Gln Asp Val Asp Glu Cys Ala Gly Ala Ser Pro Cys Gly Pro
    770                 775                 780
His Gly Thr Cys Thr Asn Leu Pro Gly Asn Phe Arg Cys Ile Cys His
785                 790                 795                 800
Arg Gly Tyr Thr Gly Pro Phe Cys Asp Gln Asp Ile Asp Asp Cys Asp
                805                 810                 815
```

-continued

```
Pro Asn Pro Cys Leu His Gly Gly Ser Cys Gln Asp Gly Val Gly Ser
            820                 825                 830

Phe Ser Cys Ser Cys Leu Asp Gly Phe Ala Gly Pro Arg Cys Ala Arg
            835                 840                 845

Asp Val Asp Glu Cys Leu Ser Ser Pro Cys Gly Pro Gly Thr Cys Thr
850                 855                 860

Asp His Val Ala Ser Phe Thr Cys Ala Cys Pro Pro Gly Tyr Gly Gly
865                 870                 875                 880

Phe His Cys Glu Ile Asp Leu Pro Asp Cys Ser Pro Ser Ser Cys Phe
                885                 890                 895

Asn Gly Gly Thr Cys Val Asp Gly Val Ser Ser Phe Ser Cys Leu Cys
            900                 905                 910

Arg Pro Gly Tyr Thr Gly Thr His Cys Gln Tyr Glu Ala Asp Pro Cys
            915                 920                 925

Phe Ser Arg Pro Cys Leu His Gly Gly Ile Cys Asn Pro Thr His Pro
    930                 935                 940

Gly Phe Glu Cys Thr Cys Arg Glu Gly Phe Thr Gly Ser Gln Cys Gln
945                 950                 955                 960

Asn Pro Val Asp Trp Cys Ser Gln Ala Pro Cys Gln Asn Gly Gly Arg
                965                 970                 975

Cys Val Gln Thr Gly Ala Tyr Cys Ile Cys Pro Pro Gly Trp Ser Gly
            980                 985                 990

Arg Leu Cys Asp Ile Gln Ser Leu Pro Cys Thr Glu Ala Ala Ala Gln
            995                 1000                1005

Met Gly Val Arg Leu Glu Gln Leu Cys Gln Glu Gly Gly Lys Cys
    1010                1015                1020

Ile Asp Lys Gly Arg Ser His Tyr Cys Val Cys Pro Glu Gly Arg
    1025                1030                1035

Thr Gly Ser His Cys Glu His Glu Val Asp Pro Cys Thr Ala Gln
    1040                1045                1050

Pro Cys Gln His Gly Gly Thr Cys Arg Gly Tyr Met Gly Gly Tyr
    1055                1060                1065

Val Cys Glu Cys Pro Ala Gly Tyr Ala Gly Asp Ser Cys Glu Asp
    1070                1075                1080

Asn Ile Asp Glu Cys Ala Ser Gln Pro Cys Gln Asn Gly Gly Ser
    1085                1090                1095

Cys Ile Asp Leu Val Ala Arg Tyr Leu Cys Ser Cys Pro Pro Gly
    1100                1105                1110

Thr Leu Gly Val Leu Cys Glu Ile Asn Glu Asp Asp Cys Asp Leu
    1115                1120                1125

Gly Pro Ser Leu Asp Ser Gly Val Gln Cys Leu His Asn Gly Thr
    1130                1135                1140

Cys Val Asp Leu Val Gly Gly Phe Arg Cys Asn Cys Pro Pro Gly
    1145                1150                1155

Tyr Thr Gly Leu His Cys Glu Ala Asp Ile Asn Glu Cys Arg Pro
    1160                1165                1170

Gly Ala Cys His Ala Ala His Thr Arg Asp Cys Leu Gln Asp Pro
    1175                1180                1185

Gly Gly His Phe Arg Cys Val Cys His Pro Gly Phe Thr Gly Pro
    1190                1195                1200

Arg Cys Gln Ile Ala Leu Ser Pro Cys Glu Ser Gln Pro Cys Gln
    1205                1210                1215
```

His Gly Gly Gln Cys Arg His Ser Leu Gly Arg Gly Gly Gly Leu
1220                1225                1230

Thr Phe Thr Cys His Cys Val Pro Pro Phe Trp Gly Leu Arg Cys
1235                1240                1245

Glu Arg Val Ala Arg Ser Cys Arg Glu Leu Gln Cys Pro Val Gly
1250                1255                1260

Ile Pro Cys Gln Gln Thr Ala Arg Gly Pro Arg Cys Ala Cys Pro
1265                1270                1275

Pro Gly Leu Ser Gly Pro Ser Cys Arg Val Ser Arg Ala Ser Pro
1280                1285                1290

Ser Gly Ala Thr Asn Ala Ser Cys Ala Ser Ala Pro Cys Leu His
1295                1300                1305

Gly Gly Ser Cys Leu Pro Val Gln Ser Val Pro Phe Phe Arg Cys
1310                1315                1320

Val Cys Ala Pro Gly Trp Gly Gly Pro Arg Cys Glu Thr Pro Ser
1325                1330                1335

Ala Ala Pro Glu Val Pro Glu Pro Arg Cys Pro Arg Ala Ala
1340                1345                1350

Cys Gln Ala Lys Arg Gly Asp Gln Asn Cys Asp Arg Glu Cys Asn
1355                1360                1365

Thr Pro Gly Cys Gly Trp Asp Gly Gly Asp Cys Ser Leu Asn Val
1370                1375                1380

Asp Asp Pro Trp Arg Gln Cys Glu Ala Leu Gln Cys Trp Arg Leu
1385                1390                1395

Phe Asn Asn Ser Arg Cys Asp Pro Ala Cys Ser Ser Pro Ala Cys
1400                1405                1410

Leu Tyr Asp Asn Phe Asp Cys Tyr Ser Gly Gly Arg Asp Arg Thr
1415                1420                1425

Cys Asn Pro Val Tyr Glu Lys Tyr Cys Ala Asp His Phe Ala Asp
1430                1435                1440

Gly Arg Cys Asp Gln Gly Cys Asn Thr Glu Glu Cys Gly Trp Asp
1445                1450                1455

Gly Leu Asp Cys Ala Ser Glu Val Pro Ala Leu Leu Ala Arg Gly
1460                1465                1470

Val Leu Val Leu Thr Val Leu Leu Pro Pro Glu Glu Leu Leu Arg
1475                1480                1485

Ser Ser Ala Asp Phe Leu Gln Arg Leu Ser Ala Ile Leu Arg Thr
1490                1495                1500

Ser Leu Arg Phe Arg Leu Asp Ala Arg Gly Gln Ala Met Val Phe
1505                1510                1515

Pro Tyr His Arg Pro Ser Pro Gly Ser Glu Ser Arg Val Arg Arg
1520                1525                1530

<210> SEQ ID NO 14
<211> LENGTH: 1218
<212> TYPE: PRT
<213> ORGANISM: Homo sapiens

<400> SEQUENCE: 14

Met Arg Ser Pro Arg Thr Arg Gly Arg Ser Gly Arg Pro Leu Ser Leu
1               5                   10                  15

Leu Leu Ala Leu Leu Cys Ala Leu Arg Ala Lys Val Cys Gly Ala Ser
                20                  25                  30

Gly Gln Phe Glu Leu Glu Ile Leu Ser Met Gln Asn Val Asn Gly Glu
        35                  40                  45

-continued

```
Leu Gln Asn Gly Asn Cys Cys Gly Gly Ala Arg Asn Pro Gly Asp Arg
     50                  55                  60
Lys Cys Thr Arg Asp Glu Cys Asp Thr Tyr Phe Lys Val Cys Leu Lys
 65                  70                  75                  80
Glu Tyr Gln Ser Arg Val Thr Ala Gly Gly Pro Cys Ser Phe Gly Ser
                 85                  90                  95
Gly Ser Thr Pro Val Ile Gly Gly Asn Thr Phe Asn Leu Lys Ala Ser
            100                 105                 110
Arg Gly Asn Asp Arg Asn Arg Ile Val Leu Pro Phe Ser Phe Ala Trp
            115                 120                 125
Pro Arg Ser Tyr Thr Leu Leu Val Glu Ala Trp Asp Ser Ser Asn Asp
        130                 135                 140
Thr Val Gln Pro Asp Ser Ile Ile Glu Lys Ala Ser His Ser Gly Met
145                 150                 155                 160
Ile Asn Pro Ser Arg Gln Trp Gln Thr Leu Lys Gln Asn Thr Gly Val
                165                 170                 175
Ala His Phe Glu Tyr Gln Ile Arg Val Thr Cys Asp Asp Tyr Tyr Tyr
            180                 185                 190
Gly Phe Gly Cys Asn Lys Phe Cys Arg Pro Arg Asp Asp Phe Phe Gly
            195                 200                 205
His Tyr Ala Cys Asp Gln Asn Gly Asn Lys Thr Cys Met Glu Gly Trp
        210                 215                 220
Met Gly Pro Glu Cys Asn Arg Ala Ile Cys Arg Gln Gly Cys Ser Pro
225                 230                 235                 240
Lys His Gly Ser Cys Lys Leu Pro Gly Asp Cys Arg Cys Gln Tyr Gly
                245                 250                 255
Trp Gln Gly Leu Tyr Cys Asp Lys Cys Ile Pro His Pro Gly Cys Val
            260                 265                 270
His Gly Ile Cys Asn Glu Pro Trp Gln Cys Leu Cys Glu Thr Asn Trp
            275                 280                 285
Gly Gly Gln Leu Cys Asp Lys Asp Leu Asn Tyr Cys Gly Thr His Gln
        290                 295                 300
Pro Cys Leu Asn Gly Gly Thr Cys Ser Asn Thr Gly Pro Asp Lys Tyr
305                 310                 315                 320
Gln Cys Ser Cys Pro Glu Gly Tyr Ser Gly Pro Asn Cys Glu Ile Ala
                325                 330                 335
Glu His Ala Cys Leu Ser Asp Pro Cys His Asn Arg Gly Ser Cys Lys
            340                 345                 350
Glu Thr Ser Leu Gly Phe Glu Cys Glu Cys Ser Pro Gly Trp Thr Gly
            355                 360                 365
Pro Thr Cys Ser Thr Asn Ile Asp Asp Cys Ser Pro Asn Asn Cys Ser
        370                 375                 380
His Gly Gly Thr Cys Gln Asp Leu Val Asn Gly Phe Lys Cys Val Cys
385                 390                 395                 400
Pro Pro Gln Trp Thr Gly Lys Thr Cys Gln Leu Asp Ala Asn Glu Cys
                405                 410                 415
Glu Ala Lys Pro Cys Val Asn Ala Lys Ser Cys Lys Asn Leu Ile Ala
            420                 425                 430
Ser Tyr Tyr Cys Asp Cys Leu Pro Gly Trp Met Gly Gln Asn Cys Asp
            435                 440                 445
Ile Asn Ile Asn Asp Cys Leu Gly Gln Cys Gln Asn Asp Ala Ser Cys
        450                 455                 460
```

```
Arg Asp Leu Val Asn Gly Tyr Arg Cys Ile Cys Pro Gly Tyr Ala
465                 470                 475                 480

Gly Asp His Cys Glu Arg Asp Ile Asp Glu Cys Ala Ser Asn Pro Cys
            485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
            515                 520                 525

Cys Glu Pro Asn Pro Cys Gln Asn Gly Ala Gln Cys Tyr Asn Arg Ala
            530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Pro Cys Glu Val Ile Asp
            565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Gln
            595                 600                 605

Ser Gly Gly Lys Phe Thr Cys Asp Cys Asn Lys Gly Phe Thr Gly Thr
            610                 615                 620

Tyr Cys His Glu Asn Ile Asn Asp Cys Glu Ser Asn Pro Cys Arg Asn
625                 630                 635                 640

Gly Gly Thr Cys Ile Asp Gly Val Asn Ser Tyr Lys Cys Ile Cys Ser
            645                 650                 655

Asp Gly Trp Glu Gly Ala Tyr Cys Glu Thr Asn Ile Asn Asp Cys Ser
            660                 665                 670

Gln Asn Pro Cys His Asn Gly Gly Thr Cys Arg Asp Leu Val Asn Asp
            675                 680                 685

Phe Tyr Cys Asp Cys Lys Asn Gly Trp Lys Gly Lys Thr Cys His Ser
690                 695                 700

Arg Asp Ser Gln Cys Asp Glu Ala Thr Cys Asn Asn Gly Gly Thr Cys
705                 710                 715                 720

Tyr Asp Glu Gly Asp Ala Phe Lys Cys Met Cys Pro Gly Gly Trp Glu
            725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Glu Ser Phe Thr Cys
            755                 760                 765

Val Cys Lys Glu Gly Trp Glu Gly Pro Ile Cys Ala Gln Asn Thr Asn
            770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
            805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Arg Cys Val Cys Pro Pro
            835                 840                 845

Gly His Ser Gly Ala Lys Cys Gln Glu Val Ser Gly Arg Pro Cys Ile
            850                 855                 860

Thr Met Gly Ser Val Ile Pro Asp Gly Ala Lys Trp Asp Asp Asp Cys
865                 870                 875                 880

Asn Thr Cys Gln Cys Leu Asn Gly Arg Ile Ala Cys Ser Lys Val Trp
```

```
                        885                 890                 895
        Cys Gly Pro Arg Pro Cys Leu Leu His Lys Gly His Ser Glu Cys Pro
                    900                 905                 910

Ser Gly Gln Ser Cys Ile Pro Ile Leu Asp Asp Gln Cys Phe Val His
                    915                 920                 925

Pro Cys Thr Gly Val Gly Glu Cys Arg Ser Ser Leu Gln Pro Val
                930                 935                 940

Lys Thr Lys Cys Thr Ser Asp Ser Tyr Tyr Gln Asp Asn Cys Ala Asn
        945                 950                 955                 960

Ile Thr Phe Thr Phe Asn Lys Glu Met Met Ser Pro Gly Leu Thr Thr
                        965                 970                 975

Glu His Ile Cys Ser Glu Leu Arg Asn Leu Asn Ile Leu Lys Asn Val
                    980                 985                 990

Ser Ala Glu Tyr Ser Ile Tyr Ile Ala Cys Glu Pro Ser Pro Ser Ala
                    995                 1000                1005

Asn Asn Glu Ile His Val Ala Ile Ser Ala Glu Asp Ile Arg Asp
                1010                1015                1020

Asp Gly Asn Pro Ile Lys Glu Ile Thr Asp Lys Ile Ile Asp Leu
                1025                1030                1035

Val Ser Lys Arg Asp Gly Asn Ser Ser Leu Ile Ala Ala Val Ala
                1040                1045                1050

Glu Val Arg Val Gln Arg Arg Pro Leu Lys Asn Arg Thr Asp Phe
                1055                1060                1065

Leu Val Pro Leu Leu Ser Ser Val Leu Thr Val Ala Trp Ile Cys
                1070                1075                1080

Cys Leu Val Thr Ala Phe Tyr Trp Cys Leu Arg Lys Arg Arg Lys
                1085                1090                1095

Pro Gly Ser His Thr His Ser Ala Ser Glu Asp Asn Thr Thr Asn
                1100                1105                1110

Asn Val Arg Glu Gln Leu Asn Gln Ile Lys Asn Pro Ile Glu Lys
                1115                1120                1125

His Gly Ala Asn Thr Val Pro Ile Lys Asp Tyr Glu Asn Lys Asn
                1130                1135                1140

Ser Lys Met Ser Lys Ile Arg Thr His Asn Ser Glu Val Glu Glu
                1145                1150                1155

Asp Asp Met Asp Lys His Gln Gln Lys Ala Arg Phe Ala Lys Gln
                1160                1165                1170

Pro Ala Tyr Thr Leu Val Asp Arg Glu Glu Lys Pro Pro Asn Gly
                1175                1180                1185

Thr Pro Thr Lys His Pro Asn Trp Thr Asn Lys Gln Asp Asn Arg
                1190                1195                1200

Asp Leu Glu Ser Ala Gln Ser Leu Asn Arg Met Glu Tyr Ile Val
                1205                1210                1215

<210> SEQ ID NO 15
<211> LENGTH: 1034
<212> TYPE: PRT
<213> ORGANISM: Homo sapiens

<400> SEQUENCE: 15

Gln Phe Glu Leu Glu Ile Leu Ser Met Gln Asn Val Asn Gly Glu Leu
1               5                   10                  15

Gln Asn Gly Asn Cys Cys Gly Gly Ala Arg Asn Pro Gly Asp Arg Lys
            20                  25                  30
```

-continued

```
Cys Thr Arg Asp Glu Cys Asp Thr Tyr Phe Lys Val Cys Leu Lys Glu
         35                  40                  45

Tyr Gln Ser Arg Val Thr Ala Gly Gly Pro Cys Ser Phe Gly Ser Gly
 50                  55                  60

Ser Thr Pro Val Ile Gly Gly Asn Thr Phe Asn Leu Lys Ala Ser Arg
 65                  70                  75                  80

Gly Asn Asp Arg Asn Arg Ile Val Leu Pro Phe Ser Phe Ala Trp Pro
                 85                  90                  95

Arg Ser Tyr Thr Leu Leu Val Glu Ala Trp Asp Ser Ser Asn Asp Thr
            100                 105                 110

Val Gln Pro Asp Ser Ile Ile Glu Lys Ala Ser His Ser Gly Met Ile
        115                 120                 125

Asn Pro Ser Arg Gln Trp Gln Thr Leu Lys Gln Asn Thr Gly Val Ala
130                 135                 140

His Phe Glu Tyr Gln Ile Arg Val Thr Cys Asp Asp Tyr Tyr Tyr Gly
145                 150                 155                 160

Phe Gly Cys Asn Lys Phe Cys Arg Pro Arg Asp Asp Phe Phe Gly His
                165                 170                 175

Tyr Ala Cys Asp Gln Asn Gly Asn Lys Thr Cys Met Glu Gly Trp Met
            180                 185                 190

Gly Pro Glu Cys Asn Arg Ala Ile Cys Arg Gln Gly Cys Ser Pro Lys
        195                 200                 205

His Gly Ser Cys Lys Leu Pro Gly Asp Cys Arg Cys Gln Tyr Gly Trp
    210                 215                 220

Gln Gly Leu Tyr Cys Asp Lys Cys Ile Pro His Pro Gly Cys Val His
225                 230                 235                 240

Gly Ile Cys Asn Glu Pro Trp Gln Cys Leu Cys Glu Thr Asn Trp Gly
                245                 250                 255

Gly Gln Leu Cys Asp Lys Asp Leu Asn Tyr Cys Gly Thr His Gln Pro
            260                 265                 270

Cys Leu Asn Gly Gly Thr Cys Ser Asn Thr Gly Pro Asp Lys Tyr Gln
        275                 280                 285

Cys Ser Cys Pro Glu Gly Tyr Ser Gly Pro Asn Cys Glu Ile Ala Glu
    290                 295                 300

His Ala Cys Leu Ser Asp Pro Cys His Asn Arg Gly Ser Cys Lys Glu
305                 310                 315                 320

Thr Ser Leu Gly Phe Glu Cys Glu Cys Ser Pro Gly Trp Thr Gly Pro
                325                 330                 335

Thr Cys Ser Thr Asn Ile Asp Asp Cys Ser Pro Asn Asn Cys Ser His
            340                 345                 350

Gly Gly Thr Cys Gln Asp Leu Val Asn Gly Phe Lys Cys Val Cys Pro
        355                 360                 365

Pro Gln Trp Thr Gly Lys Thr Cys Gln Leu Asp Ala Asn Glu Cys Glu
    370                 375                 380

Ala Lys Pro Cys Val Asn Ala Lys Ser Cys Lys Asn Leu Ile Ala Ser
385                 390                 395                 400

Tyr Tyr Cys Asp Cys Leu Pro Gly Trp Met Gly Gln Asn Cys Asp Ile
                405                 410                 415

Asn Ile Asn Asp Cys Leu Gly Gln Cys Gln Asn Asp Ala Ser Cys Arg
            420                 425                 430

Asp Leu Val Asn Gly Tyr Arg Cys Ile Cys Pro Pro Gly Tyr Ala Gly
        435                 440                 445

Asp His Cys Glu Arg Asp Ile Asp Glu Cys Ala Ser Asn Pro Cys Leu
```

```
            450               455               460
Asn Gly Gly His Cys Gln Asn Glu Ile Asn Arg Phe Gln Cys Leu Cys
465                 470                 475                 480

Pro Thr Gly Phe Ser Gly Asn Leu Cys Gln Leu Asp Ile Asp Tyr Cys
                485                 490                 495

Glu Pro Asn Pro Cys Gln Asn Gly Ala Gln Cys Tyr Asn Arg Ala Ser
                500                 505                 510

Asp Tyr Phe Cys Lys Cys Pro Glu Asp Tyr Glu Gly Lys Asn Cys Ser
            515                 520                 525

His Leu Lys Asp His Cys Arg Thr Thr Pro Cys Glu Val Ile Asp Ser
        530                 535                 540

Cys Thr Val Ala Met Ala Ser Asn Asp Thr Pro Glu Gly Val Arg Tyr
545                 550                 555                 560

Ile Ser Ser Asn Val Cys Gly Pro His Gly Lys Cys Lys Ser Gln Ser
                565                 570                 575

Gly Gly Lys Phe Thr Cys Asp Cys Asn Lys Gly Phe Thr Gly Thr Tyr
                580                 585                 590

Cys His Glu Asn Ile Asn Asp Cys Glu Ser Asn Pro Cys Arg Asn Gly
        595                 600                 605

Gly Thr Cys Ile Asp Gly Val Asn Ser Tyr Lys Cys Ile Cys Ser Asp
        610                 615                 620

Gly Trp Glu Gly Ala Tyr Cys Glu Thr Asn Ile Asn Asp Cys Ser Gln
625                 630                 635                 640

Asn Pro Cys His Asn Gly Gly Thr Cys Arg Asp Leu Val Asn Asp Phe
                645                 650                 655

Tyr Cys Asp Cys Lys Asn Gly Trp Lys Gly Lys Thr Cys His Ser Arg
                660                 665                 670

Asp Ser Gln Cys Asp Glu Ala Thr Cys Asn Asn Gly Gly Thr Cys Tyr
            675                 680                 685

Asp Glu Gly Asp Ala Phe Lys Cys Met Cys Pro Gly Gly Trp Glu Gly
        690                 695                 700

Thr Thr Cys Asn Ile Ala Arg Asn Ser Ser Cys Leu Pro Asn Pro Cys
705                 710                 715                 720

His Asn Gly Gly Thr Cys Val Val Asn Gly Glu Ser Phe Thr Cys Val
                725                 730                 735

Cys Lys Glu Gly Trp Glu Gly Pro Ile Cys Ala Gln Asn Thr Asn Asp
                740                 745                 750

Cys Ser Pro His Pro Cys Tyr Asn Ser Gly Thr Cys Val Asp Gly Asp
            755                 760                 765

Asn Trp Tyr Arg Cys Glu Cys Ala Pro Gly Phe Ala Gly Pro Asp Cys
        770                 775                 780

Arg Ile Asn Ile Asn Glu Cys Gln Ser Ser Pro Cys Ala Phe Gly Ala
785                 790                 795                 800

Thr Cys Val Asp Glu Ile Asn Gly Tyr Arg Cys Val Cys Pro Pro Gly
                805                 810                 815

His Ser Gly Ala Lys Cys Gln Glu Val Ser Gly Arg Pro Cys Ile Thr
                820                 825                 830

Met Gly Ser Val Ile Pro Asp Gly Ala Lys Trp Asp Asp Cys Asn
            835                 840                 845

Thr Cys Gln Cys Leu Asn Gly Arg Ile Ala Cys Ser Lys Val Trp Cys
        850                 855                 860

Gly Pro Arg Pro Cys Leu Leu His Lys Gly His Ser Glu Cys Pro Ser
865                 870                 875                 880
```

```
Gly Gln Ser Cys Ile Pro Ile Leu Asp Asp Gln Cys Phe Val His Pro
                885                 890                 895

Cys Thr Gly Val Gly Glu Cys Arg Ser Ser Leu Gln Pro Val Lys
            900                 905                 910

Thr Lys Cys Thr Ser Asp Ser Tyr Tyr Gln Asp Asn Cys Ala Asn Ile
        915                 920                 925

Thr Phe Thr Phe Asn Lys Glu Met Met Ser Pro Gly Leu Thr Thr Glu
    930                 935                 940

His Ile Cys Ser Glu Leu Arg Asn Leu Asn Ile Leu Lys Asn Val Ser
945                 950                 955                 960

Ala Glu Tyr Ser Ile Tyr Ile Ala Cys Glu Pro Ser Pro Ser Ala Asn
                965                 970                 975

Asn Glu Ile His Val Ala Ile Ser Ala Glu Asp Ile Arg Asp Asp Gly
            980                 985                 990

Asn Pro Ile Lys Glu Ile Thr Asp  Lys Ile Ile Asp Leu  Val Ser Lys
        995                 1000                1005

Arg Asp  Gly Asn Ser Ser Leu  Ile Ala Ala Val Ala  Glu Val Arg
    1010                1015                1020

Val Gln  Arg Arg Pro Leu Lys  Asn Arg Thr Asp
1025                1030

<210> SEQ ID NO 16
<211> LENGTH: 1238
<212> TYPE: PRT
<213> ORGANISM: Homo sapiens

<400> SEQUENCE: 16

Met Arg Ala Gln Gly Arg Gly Arg Leu Pro Arg Arg Leu Leu Leu Leu
1               5                   10                  15

Leu Ala Leu Trp Val Gln Ala Ala Arg Pro Met Gly Tyr Phe Glu Leu
            20                  25                  30

Gln Leu Ser Ala Leu Arg Asn Val Asn Gly Glu Leu Leu Ser Gly Ala
        35                  40                  45

Cys Cys Asp Gly Asp Gly Arg Thr Thr Arg Ala Gly Gly Cys Gly His
    50                  55                  60

Asp Glu Cys Asp Thr Tyr Val Arg Val Cys Leu Lys Glu Tyr Gln Ala
65                  70                  75                  80

Lys Val Thr Pro Thr Gly Pro Cys Ser Tyr Gly His Gly Ala Thr Pro
                85                  90                  95

Val Leu Gly Gly Asn Ser Phe Tyr Leu Pro Pro Ala Gly Ala Ala Gly
            100                 105                 110

Asp Arg Ala Arg Ala Arg Ala Arg Ala Gly Gly Asp Gln Asp Pro Gly
        115                 120                 125

Leu Val Val Ile Pro Phe Gln Phe Ala Trp Pro Arg Ser Phe Thr Leu
    130                 135                 140

Ile Val Glu Ala Trp Asp Trp Asp Asn Asp Thr Thr Pro Asn Glu Glu
145                 150                 155                 160

Leu Leu Ile Glu Arg Val Ser His Ala Gly Met Ile Asn Pro Glu Asp
                165                 170                 175

Arg Trp Lys Ser Leu His Phe Ser Gly His Val Ala His Leu Glu Leu
            180                 185                 190

Gln Ile Arg Val Arg Cys Asp Glu Asn Tyr Tyr Ser Ala Thr Cys Asn
        195                 200                 205

Lys Phe Cys Arg Pro Arg Asn Asp Phe Phe Gly His Tyr Thr Cys Asp
```

```
            210                 215                 220
Gln Tyr Gly Asn Lys Ala Cys Met Asp Gly Trp Met Gly Lys Glu Cys
225                 230                 235                 240

Lys Glu Ala Val Cys Lys Gln Gly Cys Asn Leu Leu His Gly Gly Cys
                245                 250                 255

Thr Val Pro Gly Glu Cys Arg Cys Ser Tyr Gly Trp Gln Gly Arg Phe
                260                 265                 270

Cys Asp Glu Cys Val Pro Tyr Pro Gly Cys Val His Gly Ser Cys Val
            275                 280                 285

Glu Pro Trp Gln Cys Asn Cys Glu Thr Asn Trp Gly Gly Leu Leu Cys
            290                 295                 300

Asp Lys Asp Leu Asn Tyr Cys Gly Ser His His Pro Cys Thr Asn Gly
305                 310                 315                 320

Gly Thr Cys Ile Asn Ala Glu Pro Asp Gln Tyr Arg Cys Thr Cys Pro
                325                 330                 335

Asp Gly Tyr Ser Gly Arg Asn Cys Glu Lys Ala Glu His Ala Cys Thr
                340                 345                 350

Ser Asn Pro Cys Ala Asn Gly Gly Ser Cys His Glu Val Pro Ser Gly
                355                 360                 365

Phe Glu Cys His Cys Pro Ser Gly Trp Ser Gly Pro Thr Cys Ala Leu
            370                 375                 380

Asp Ile Asp Glu Cys Ala Ser Asn Pro Cys Ala Ala Gly Gly Thr Cys
385                 390                 395                 400

Val Asp Gln Val Asp Gly Phe Glu Cys Ile Cys Pro Glu Gln Trp Val
                405                 410                 415

Gly Ala Thr Cys Gln Leu Asp Ala Asn Glu Cys Glu Gly Lys Pro Cys
                420                 425                 430

Leu Asn Ala Phe Ser Cys Lys Asn Leu Ile Gly Gly Tyr Tyr Cys Asp
                435                 440                 445

Cys Ile Pro Gly Trp Lys Gly Ile Asn Cys His Ile Asn Val Asn Asp
            450                 455                 460

Cys Arg Gly Gln Cys Gln His Gly Gly Thr Cys Lys Asp Leu Val Asn
465                 470                 475                 480

Gly Tyr Gln Cys Val Cys Pro Arg Gly Phe Gly Arg His Cys Glu
                485                 490                 495

Leu Glu Arg Asp Glu Cys Ala Ser Ser Pro Cys His Ser Gly Gly Leu
                500                 505                 510

Cys Glu Asp Leu Ala Asp Gly Phe His Cys His Cys Pro Gln Gly Phe
            515                 520                 525

Ser Gly Pro Leu Cys Glu Val Asp Val Asp Leu Cys Glu Pro Ser Pro
            530                 535                 540

Cys Arg Asn Gly Ala Arg Cys Tyr Asn Leu Glu Gly Asp Tyr Tyr Cys
545                 550                 555                 560

Ala Cys Pro Asp Asp Phe Gly Gly Lys Asn Cys Ser Val Pro Arg Glu
                565                 570                 575

Pro Cys Pro Gly Gly Ala Cys Arg Val Ile Asp Gly Cys Gly Ser Asp
                580                 585                 590

Ala Gly Pro Gly Met Pro Gly Thr Ala Ala Ser Gly Val Cys Gly Pro
            595                 600                 605

His Gly Arg Cys Val Ser Gln Pro Gly Gly Asn Phe Ser Cys Ile Cys
            610                 615                 620

Asp Ser Gly Phe Thr Gly Thr Tyr Cys His Glu Asn Ile Asp Asp Cys
625                 630                 635                 640
```

```
Leu Gly Gln Pro Cys Arg Asn Gly Gly Thr Cys Ile Asp Glu Val Asp
                645                 650                 655

Ala Phe Arg Cys Phe Cys Pro Ser Gly Trp Glu Gly Glu Leu Cys Asp
            660                 665                 670

Thr Asn Pro Asn Asp Cys Leu Pro Asp Pro Cys His Ser Arg Gly Arg
            675                 680                 685

Cys Tyr Asp Leu Val Asn Asp Phe Tyr Cys Ala Cys Asp Asp Gly Trp
        690                 695                 700

Lys Gly Lys Thr Cys His Ser Arg Glu Phe Gln Cys Asp Ala Tyr Thr
705                 710                 715                 720

Cys Ser Asn Gly Gly Thr Cys Tyr Asp Ser Gly Asp Thr Phe Arg Cys
                725                 730                 735

Ala Cys Pro Pro Gly Trp Lys Gly Ser Thr Cys Ala Val Ala Lys Asn
            740                 745                 750

Ser Ser Cys Leu Pro Asn Pro Cys Val Asn Gly Gly Thr Cys Val Gly
            755                 760                 765

Ser Gly Ala Ser Phe Ser Cys Ile Cys Arg Asp Gly Trp Glu Gly Arg
        770                 775                 780

Thr Cys Thr His Asn Thr Asn Asp Cys Asn Pro Leu Pro Cys Tyr Asn
785                 790                 795                 800

Gly Gly Ile Cys Val Asp Gly Val Asn Trp Phe Arg Cys Glu Cys Ala
                805                 810                 815

Pro Gly Phe Ala Gly Pro Asp Cys Arg Ile Asn Ile Asp Glu Cys Gln
            820                 825                 830

Ser Ser Pro Cys Ala Tyr Gly Ala Thr Cys Val Asp Glu Ile Asn Gly
            835                 840                 845

Tyr Arg Cys Ser Cys Pro Pro Gly Arg Ala Gly Pro Arg Cys Gln Glu
        850                 855                 860

Val Ile Gly Phe Gly Arg Ser Cys Trp Ser Arg Gly Thr Pro Phe Pro
865                 870                 875                 880

His Gly Ser Ser Trp Val Glu Asp Cys Asn Ser Cys Arg Cys Leu Asp
                885                 890                 895

Gly Arg Arg Asp Cys Ser Lys Val Trp Cys Gly Trp Lys Pro Cys Leu
            900                 905                 910

Leu Ala Gly Gln Pro Glu Ala Leu Ser Ala Gln Cys Pro Leu Gly Gln
            915                 920                 925

Arg Cys Leu Glu Lys Ala Pro Gly Gln Cys Leu Arg Pro Pro Cys Glu
        930                 935                 940

Ala Trp Gly Glu Cys Gly Ala Glu Glu Pro Pro Ser Thr Pro Cys Leu
945                 950                 955                 960

Pro Arg Ser Gly His Leu Asp Asn Asn Cys Ala Arg Leu Thr Leu His
                965                 970                 975

Phe Asn Arg Asp His Val Pro Gln Gly Thr Thr Val Gly Ala Ile Cys
            980                 985                 990

Ser Gly Ile Arg Ser Leu Pro Ala Thr Arg Ala Val Ala Arg Asp Arg
        995                 1000                1005

Leu Leu Val Leu Leu Cys Asp Arg Ala Ser Ser Gly Ala Ser Ala
    1010                1015                1020

Val Glu Val Ala Val Ser Phe Ser Pro Ala Arg Asp Leu Pro Asp
    1025                1030                1035

Ser Ser Leu Ile Gln Gly Ala Ala His Ala Ile Val Ala Ala Ile
    1040                1045                1050
```

-continued

```
Thr Gln Arg Gly Asn Ser Ser Leu Leu Leu Ala Val Thr Glu Val
    1055                1060                1065

Lys Val Glu Thr Val Val Thr Gly Gly Ser Ser Thr Gly Leu Leu
    1070                1075                1080

Val Pro Val Leu Cys Gly Ala Phe Ser Val Leu Trp Leu Ala Cys
    1085                1090                1095

Val Val Leu Cys Val Trp Trp Thr Arg Lys Arg Lys Glu Arg
    1100                1105                1110

Glu Arg Ser Arg Leu Pro Arg Glu Glu Ser Ala Asn Asn Gln Trp
    1115                1120                1125

Ala Pro Leu Asn Pro Ile Arg Asn Pro Ile Glu Arg Pro Gly Gly
    1130                1135                1140

His Lys Asp Val Leu Tyr Gln Cys Lys Asn Phe Thr Pro Pro Pro
    1145                1150                1155

Arg Arg Ala Asp Glu Ala Leu Pro Gly Pro Ala Gly His Ala Ala
    1160                1165                1170

Val Arg Glu Asp Glu Glu Asp Glu Asp Leu Gly Arg Gly Glu Glu
    1175                1180                1185

Asp Ser Leu Glu Ala Glu Lys Phe Leu Ser His Lys Phe Thr Lys
    1190                1195                1200

Asp Pro Gly Arg Ser Pro Gly Arg Pro Ala His Trp Ala Ser Gly
    1205                1210                1215

Pro Lys Val Asp Asn Arg Ala Val Arg Ser Ile Asn Glu Ala Arg
    1220                1225                1230

Tyr Ala Gly Lys Glu
    1235

<210> SEQ ID NO 17
<211> LENGTH: 1054
<212> TYPE: PRT
<213> ORGANISM: Homo sapiens

<400> SEQUENCE: 17

Met Gly Tyr Phe Glu Leu Gln Leu Ser Ala Leu Arg Asn Val Asn Gly
1               5                   10                  15

Glu Leu Leu Ser Gly Ala Cys Cys Asp Gly Asp Gly Arg Thr Thr Arg
                20                  25                  30

Ala Gly Gly Cys Gly His Asp Glu Cys Asp Thr Tyr Val Arg Val Cys
            35                  40                  45

Leu Lys Glu Tyr Gln Ala Lys Val Thr Pro Thr Gly Pro Cys Ser Tyr
        50                  55                  60

Gly His Gly Ala Thr Pro Val Leu Gly Gly Asn Ser Phe Tyr Leu Pro
65                  70                  75                  80

Pro Ala Gly Ala Ala Gly Asp Arg Ala Arg Ala Arg Ala Arg Ala Gly
                85                  90                  95

Gly Asp Gln Asp Pro Gly Leu Val Val Ile Pro Phe Gln Phe Ala Trp
            100                 105                 110

Pro Arg Ser Phe Thr Leu Ile Val Glu Ala Trp Asp Trp Asp Asn Asp
        115                 120                 125

Thr Thr Pro Asn Glu Glu Leu Leu Ile Glu Arg Val Ser His Ala Gly
    130                 135                 140

Met Ile Asn Pro Glu Asp Arg Trp Lys Ser Leu His Phe Ser Gly His
145                 150                 155                 160

Val Ala His Leu Glu Leu Gln Ile Arg Val Arg Cys Asp Glu Asn Tyr
                165                 170                 175
```

```
Tyr Ser Ala Thr Cys Asn Lys Phe Cys Arg Pro Arg Asn Asp Phe Phe
            180                 185                 190

Gly His Tyr Thr Cys Asp Gln Tyr Gly Asn Lys Ala Cys Met Asp Gly
            195                 200                 205

Trp Met Gly Lys Glu Cys Lys Glu Ala Val Cys Lys Gln Gly Cys Asn
    210                 215                 220

Leu Leu His Gly Gly Cys Thr Val Pro Gly Glu Cys Arg Cys Ser Tyr
225                 230                 235                 240

Gly Trp Gln Gly Arg Phe Cys Asp Glu Cys Val Pro Tyr Pro Gly Cys
                245                 250                 255

Val His Gly Ser Cys Val Glu Pro Trp Gln Cys Asn Cys Glu Thr Asn
            260                 265                 270

Trp Gly Gly Leu Leu Cys Asp Lys Asp Leu Asn Tyr Cys Gly Ser His
        275                 280                 285

His Pro Cys Thr Asn Gly Gly Thr Cys Ile Asn Ala Glu Pro Asp Gln
        290                 295                 300

Tyr Arg Cys Thr Cys Pro Asp Gly Tyr Ser Gly Arg Asn Cys Glu Lys
305                 310                 315                 320

Ala Glu His Ala Cys Thr Ser Asn Pro Cys Ala Asn Gly Gly Ser Cys
                325                 330                 335

His Glu Val Pro Ser Gly Phe Glu Cys His Cys Pro Ser Gly Trp Ser
            340                 345                 350

Gly Pro Thr Cys Ala Leu Asp Ile Asp Glu Cys Ala Ser Asn Pro Cys
        355                 360                 365

Ala Ala Gly Gly Thr Cys Val Asp Gln Val Asp Gly Phe Glu Cys Ile
        370                 375                 380

Cys Pro Glu Gln Trp Val Gly Ala Thr Cys Gln Leu Asp Ala Asn Glu
385                 390                 395                 400

Cys Glu Gly Lys Pro Cys Leu Asn Ala Phe Ser Cys Lys Asn Leu Ile
                405                 410                 415

Gly Gly Tyr Tyr Cys Asp Cys Ile Pro Gly Trp Lys Gly Ile Asn Cys
            420                 425                 430

His Ile Asn Val Asn Asp Cys Arg Gly Gln Cys Gln His Gly Gly Thr
        435                 440                 445

Cys Lys Asp Leu Val Asn Gly Tyr Gln Cys Val Cys Pro Arg Gly Phe
450                 455                 460

Gly Gly Arg His Cys Glu Leu Glu Arg Asp Glu Cys Ala Ser Ser Pro
465                 470                 475                 480

Cys His Ser Gly Gly Leu Cys Glu Asp Leu Ala Asp Gly Phe His Cys
                485                 490                 495

His Cys Pro Gln Gly Phe Ser Gly Pro Leu Cys Glu Val Asp Val Asp
            500                 505                 510

Leu Cys Glu Pro Ser Pro Cys Arg Asn Gly Ala Arg Cys Tyr Asn Leu
        515                 520                 525

Glu Gly Asp Tyr Tyr Cys Ala Cys Pro Asp Asp Phe Gly Gly Lys Asn
        530                 535                 540

Cys Ser Val Pro Arg Glu Pro Cys Pro Gly Gly Ala Cys Arg Val Ile
545                 550                 555                 560

Asp Gly Cys Gly Ser Asp Ala Gly Pro Gly Met Pro Gly Thr Ala Ala
                565                 570                 575

Ser Gly Val Cys Gly Pro His Gly Arg Cys Val Ser Gln Pro Gly Gly
            580                 585                 590
```

-continued

```
Asn Phe Ser Cys Ile Cys Asp Ser Gly Phe Thr Gly Thr Tyr Cys His
        595                 600                 605
Glu Asn Ile Asp Asp Cys Leu Gly Gln Pro Cys Arg Asn Gly Gly Thr
610                 615                 620
Cys Ile Asp Glu Val Asp Ala Phe Arg Cys Phe Cys Pro Ser Gly Trp
625                 630                 635                 640
Glu Gly Glu Leu Cys Asp Thr Asn Pro Asn Asp Cys Leu Pro Asp Pro
                645                 650                 655
Cys His Ser Arg Gly Arg Cys Tyr Asp Leu Val Asn Asp Phe Tyr Cys
            660                 665                 670
Ala Cys Asp Asp Gly Trp Lys Gly Lys Thr Cys His Ser Arg Glu Phe
        675                 680                 685
Gln Cys Asp Ala Tyr Thr Cys Ser Asn Gly Gly Thr Cys Tyr Asp Ser
    690                 695                 700
Gly Asp Thr Phe Arg Cys Ala Cys Pro Pro Gly Trp Lys Gly Ser Thr
705                 710                 715                 720
Cys Ala Val Ala Lys Asn Ser Ser Cys Leu Pro Asn Pro Cys Val Asn
                725                 730                 735
Gly Gly Thr Cys Val Gly Ser Gly Ala Ser Phe Ser Cys Ile Cys Arg
            740                 745                 750
Asp Gly Trp Glu Gly Arg Thr Cys Thr His Asn Thr Asn Asp Cys Asn
        755                 760                 765
Pro Leu Pro Cys Tyr Asn Gly Gly Ile Cys Val Asp Gly Val Asn Trp
    770                 775                 780
Phe Arg Cys Glu Cys Ala Pro Gly Phe Ala Gly Pro Asp Cys Arg Ile
785                 790                 795                 800
Asn Ile Asp Glu Cys Gln Ser Ser Pro Cys Ala Tyr Gly Ala Thr Cys
                805                 810                 815
Val Asp Glu Ile Asn Gly Tyr Arg Cys Ser Cys Pro Pro Gly Arg Ala
            820                 825                 830
Gly Pro Arg Cys Gln Glu Val Ile Gly Phe Gly Arg Ser Cys Trp Ser
        835                 840                 845
Arg Gly Thr Pro Phe Pro His Gly Ser Ser Trp Val Glu Asp Cys Asn
850                 855                 860
Ser Cys Arg Cys Leu Asp Gly Arg Arg Asp Cys Ser Lys Val Trp Cys
865                 870                 875                 880
Gly Trp Lys Pro Cys Leu Leu Ala Gly Gln Pro Glu Ala Leu Ser Ala
                885                 890                 895
Gln Cys Pro Leu Gly Gln Arg Cys Leu Glu Lys Ala Pro Gly Gln Cys
            900                 905                 910
Leu Arg Pro Pro Cys Glu Ala Trp Gly Glu Cys Gly Ala Glu Glu Pro
        915                 920                 925
Pro Ser Thr Pro Cys Leu Pro Arg Ser Gly His Leu Asp Asn Asn Cys
    930                 935                 940
Ala Arg Leu Thr Leu His Phe Asn Arg Asp His Val Pro Gln Gly Thr
945                 950                 955                 960
Thr Val Gly Ala Ile Cys Ser Gly Ile Arg Ser Leu Pro Ala Thr Arg
                965                 970                 975
Ala Val Ala Arg Asp Arg Leu Leu Val Leu Leu Cys Asp Arg Ala Ser
            980                 985                 990
Ser Gly Ala Ser Ala Val Glu Val  Ala Val Ser Phe Ser  Pro Ala Arg
        995                 1000                 1005
Asp Leu  Pro Asp Ser Ser Leu  Ile Gln Gly Ala Ala  His Ala Ile
```

```
           1010                1015                1020

Val Ala Ala Ile Thr Gln Arg Gly Asn Ser Ser Leu Leu Leu Ala
    1025                1030                1035

Val Thr Glu Val Lys Val Glu Thr Val Val Thr Gly Gly Ser Ser
    1040                1045                1050

Thr

<210> SEQ ID NO 18
<211> LENGTH: 723
<212> TYPE: PRT
<213> ORGANISM: Homo sapiens

<400> SEQUENCE: 18

Met Gly Ser Arg Cys Ala Leu Ala Leu Ala Val Leu Ser Ala Leu Leu
1               5                   10                  15

Cys Gln Val Trp Ser Ser Gly Val Phe Glu Leu Lys Leu Gln Glu Phe
            20                  25                  30

Val Asn Lys Lys Gly Leu Leu Gly Asn Arg Asn Cys Cys Arg Gly Gly
        35                  40                  45

Ala Gly Pro Pro Cys Ala Cys Arg Thr Phe Phe Arg Val Cys Leu
    50                  55                  60

Lys His Tyr Gln Ala Ser Val Ser Pro Glu Pro Cys Thr Tyr Gly
65              70                  75                  80

Ser Ala Val Thr Pro Val Leu Gly Val Asp Ser Phe Ser Leu Pro Asp
                85                  90                  95

Gly Gly Gly Ala Asp Ser Ala Phe Ser Asn Pro Ile Arg Phe Pro Phe
            100                 105                 110

Gly Phe Thr Trp Pro Gly Thr Phe Ser Leu Ile Ile Glu Ala Leu His
        115                 120                 125

Thr Asp Ser Pro Asp Asp Leu Ala Thr Glu Asn Pro Glu Arg Leu Ile
    130                 135                 140

Ser Arg Leu Ala Thr Gln Arg His Leu Thr Val Gly Glu Glu Trp Ser
145                 150                 155                 160

Gln Asp Leu His Ser Ser Gly Arg Thr Asp Leu Lys Tyr Ser Tyr Arg
                165                 170                 175

Phe Val Cys Asp Glu His Tyr Tyr Gly Glu Gly Cys Ser Val Phe Cys
            180                 185                 190

Arg Pro Arg Asp Asp Ala Phe Gly His Phe Thr Cys Gly Glu Arg Gly
        195                 200                 205

Glu Lys Val Cys Asn Pro Gly Trp Lys Gly Pro Tyr Cys Thr Glu Pro
    210                 215                 220

Ile Cys Leu Pro Gly Cys Asp Glu Gln His Gly Phe Cys Asp Lys Pro
225                 230                 235                 240

Gly Glu Cys Lys Cys Arg Val Gly Trp Gln Gly Arg Tyr Cys Asp Glu
                245                 250                 255

Cys Ile Arg Tyr Pro Gly Cys Leu His Gly Thr Cys Gln Gln Pro Trp
            260                 265                 270

Gln Cys Asn Cys Gln Glu Gly Trp Gly Gly Leu Phe Cys Asn Gln Asp
        275                 280                 285

Leu Asn Tyr Cys Thr His His Lys Pro Cys Lys Asn Gly Ala Thr Cys
    290                 295                 300

Thr Asn Thr Gly Gln Gly Ser Tyr Thr Cys Ser Cys Arg Pro Gly Tyr
305                 310                 315                 320

Thr Gly Ala Thr Cys Glu Leu Gly Ile Asp Glu Cys Asp Pro Ser Pro
```

```
            325                 330                 335
Cys Lys Asn Gly Gly Ser Cys Thr Asp Leu Glu Asn Ser Tyr Ser Cys
            340                 345                 350

Thr Cys Pro Pro Gly Phe Tyr Gly Lys Ile Cys Glu Leu Ser Ala Met
            355                 360                 365

Thr Cys Ala Asp Gly Pro Cys Phe Asn Gly Gly Arg Cys Ser Asp Ser
            370                 375                 380

Pro Asp Gly Gly Tyr Ser Cys Arg Cys Pro Val Gly Tyr Ser Gly Phe
385                 390                 395                 400

Asn Cys Glu Lys Lys Ile Asp Tyr Cys Ser Ser Ser Pro Cys Ser Asn
            405                 410                 415

Gly Ala Lys Cys Val Asp Leu Gly Asp Ala Tyr Leu Cys Arg Cys Gln
            420                 425                 430

Ala Gly Phe Ser Gly Arg His Cys Asp Asp Asn Val Asp Asp Cys Ala
            435                 440                 445

Ser Ser Pro Cys Ala Asn Gly Gly Thr Cys Arg Asp Gly Val Asn Asp
            450                 455                 460

Phe Ser Cys Thr Cys Pro Pro Gly Tyr Thr Gly Arg Asn Cys Ser Ala
465                 470                 475                 480

Pro Val Ser Arg Cys Glu His Ala Pro Cys His Asn Gly Ala Thr Cys
            485                 490                 495

His Glu Arg Gly His Arg Tyr Val Cys Glu Cys Ala Arg Gly Tyr Gly
            500                 505                 510

Gly Pro Asn Cys Gln Phe Leu Leu Pro Glu Leu Pro Pro Gly Pro Ala
            515                 520                 525

Val Val Asp Leu Thr Glu Lys Leu Glu Gly Gln Gly Gly Pro Phe Pro
            530                 535                 540

Trp Val Ala Val Cys Ala Gly Val Ile Leu Val Leu Met Leu Leu Leu
545                 550                 555                 560

Gly Cys Ala Ala Val Val Val Cys Val Arg Leu Arg Leu Gln Lys His
            565                 570                 575

Arg Pro Pro Ala Asp Pro Cys Arg Gly Glu Thr Glu Thr Met Asn Asn
            580                 585                 590

Leu Ala Asn Cys Gln Arg Glu Lys Asp Ile Ser Val Ser Ile Ile Gly
            595                 600                 605

Ala Thr Gln Ile Lys Asn Thr Asn Lys Lys Ala Asp Phe His Gly Asp
            610                 615                 620

His Ser Ala Asp Lys Asn Gly Phe Lys Ala Arg Tyr Pro Ala Val Asp
625                 630                 635                 640

Tyr Asn Leu Val Gln Asp Leu Lys Gly Asp Asp Thr Ala Val Arg Asp
            645                 650                 655

Ala His Ser Lys Arg Asp Thr Lys Cys Gln Pro Gln Gly Ser Ser Gly
            660                 665                 670

Glu Glu Lys Gly Thr Pro Thr Thr Leu Arg Gly Gly Glu Ala Ser Glu
            675                 680                 685

Arg Lys Arg Pro Asp Ser Gly Cys Ser Thr Ser Lys Asp Thr Lys Tyr
            690                 695                 700

Gln Ser Val Tyr Val Ile Ser Glu Glu Lys Asp Glu Cys Val Ile Ala
705                 710                 715                 720

Thr Glu Val

<210> SEQ ID NO 19
<211> LENGTH: 528
```

```
<212> TYPE: PRT
<213> ORGANISM: Homo sapiens

<400> SEQUENCE: 19
```

| | | | | | | | | | | | | | | |
|---|---|---|---|---|---|---|---|---|---|---|---|---|---|---|
| Gln | Val | Trp | Ser | Ser | Gly | Val | Phe | Glu | Leu | Lys | Leu | Gln | Glu | Phe | Val |
| 1 | | | | 5 | | | | | 10 | | | | | 15 | |
| Asn | Lys | Lys | Gly | Leu | Leu | Gly | Asn | Arg | Asn | Cys | Cys | Arg | Gly | Gly | Ala |
| | | | 20 | | | | | 25 | | | | | 30 | | |
| Gly | Pro | Pro | Cys | Ala | Cys | Arg | Thr | Phe | Phe | Arg | Val | Cys | Leu | Lys | |
| | | 35 | | | | | 40 | | | | | 45 | | | |
| His | Tyr | Gln | Ala | Ser | Val | Ser | Pro | Glu | Pro | Cys | Thr | Tyr | Gly | Ser | |
| | 50 | | | | | 55 | | | | | 60 | | | | |
| Ala | Val | Thr | Pro | Val | Leu | Gly | Val | Asp | Ser | Phe | Ser | Leu | Pro | Asp | Gly |
| 65 | | | | | 70 | | | | 75 | | | | | 80 | |
| Gly | Gly | Ala | Asp | Ser | Ala | Phe | Ser | Asn | Pro | Ile | Arg | Phe | Pro | Phe | Gly |
| | | | | 85 | | | | | 90 | | | | | 95 | |
| Phe | Thr | Trp | Pro | Gly | Thr | Phe | Ser | Leu | Ile | Ile | Glu | Ala | Leu | His | Thr |
| | | | 100 | | | | | 105 | | | | | 110 | | |
| Asp | Ser | Pro | Asp | Asp | Leu | Ala | Thr | Glu | Asn | Pro | Glu | Arg | Leu | Ile | Ser |
| | | 115 | | | | | 120 | | | | | 125 | | | |
| Arg | Leu | Ala | Thr | Gln | Arg | His | Leu | Thr | Val | Gly | Glu | Glu | Trp | Ser | Gln |
| | 130 | | | | | 135 | | | | | 140 | | | | |
| Asp | Leu | His | Ser | Ser | Gly | Arg | Thr | Asp | Leu | Lys | Tyr | Ser | Tyr | Arg | Phe |
| 145 | | | | | 150 | | | | 155 | | | | | 160 | |
| Val | Cys | Asp | Glu | His | Tyr | Tyr | Gly | Glu | Gly | Cys | Ser | Val | Phe | Cys | Arg |
| | | | | 165 | | | | | 170 | | | | | 175 | |
| Pro | Arg | Asp | Asp | Ala | Phe | Gly | His | Phe | Thr | Cys | Gly | Glu | Arg | Gly | Glu |
| | | | 180 | | | | | 185 | | | | | 190 | | |
| Lys | Val | Cys | Asn | Pro | Gly | Trp | Lys | Gly | Pro | Tyr | Cys | Thr | Glu | Pro | Ile |
| | | 195 | | | | | 200 | | | | | 205 | | | |
| Cys | Leu | Pro | Gly | Cys | Asp | Glu | Gln | His | Gly | Phe | Cys | Asp | Lys | Pro | Gly |
| 210 | | | | | 215 | | | | | 220 | | | | | |
| Glu | Cys | Lys | Cys | Arg | Val | Gly | Trp | Gln | Gly | Arg | Tyr | Cys | Asp | Glu | Cys |
| 225 | | | | 230 | | | | | 235 | | | | | 240 | |
| Ile | Arg | Tyr | Pro | Gly | Cys | Leu | His | Gly | Thr | Cys | Gln | Gln | Pro | Trp | Gln |
| | | | | 245 | | | | | 250 | | | | | 255 | |
| Cys | Asn | Cys | Gln | Glu | Gly | Trp | Gly | Gly | Leu | Phe | Cys | Asn | Gln | Asp | Leu |
| | | | 260 | | | | | 265 | | | | | 270 | | |
| Asn | Tyr | Cys | Thr | His | His | Lys | Pro | Cys | Lys | Asn | Gly | Ala | Thr | Cys | Thr |
| | | 275 | | | | | 280 | | | | | 285 | | | |
| Asn | Thr | Gly | Gln | Gly | Ser | Tyr | Thr | Cys | Ser | Cys | Arg | Pro | Gly | Tyr | Thr |
| | 290 | | | | | 295 | | | | | 300 | | | | |
| Gly | Ala | Thr | Cys | Glu | Leu | Gly | Ile | Asp | Glu | Cys | Asp | Pro | Ser | Pro | Cys |
| 305 | | | | | 310 | | | | 315 | | | | | 320 | |
| Lys | Asn | Gly | Gly | Ser | Cys | Thr | Asp | Leu | Glu | Asn | Ser | Tyr | Ser | Cys | Thr |
| | | | | 325 | | | | | 330 | | | | | 335 | |
| Cys | Pro | Pro | Gly | Phe | Tyr | Gly | Lys | Ile | Cys | Glu | Leu | Ser | Ala | Met | Thr |
| | | | 340 | | | | | 345 | | | | | 350 | | |
| Cys | Ala | Asp | Gly | Pro | Cys | Phe | Asn | Gly | Gly | Arg | Cys | Ser | Asp | Ser | Pro |
| | | | 355 | | | | | 360 | | | | | 365 | | |
| Asp | Gly | Gly | Tyr | Ser | Cys | Arg | Cys | Pro | Val | Gly | Tyr | Ser | Gly | Phe | Asn |
| | 370 | | | | | 375 | | | | | 380 | | | | |
| Cys | Glu | Lys | Lys | Ile | Asp | Tyr | Cys | Ser | Ser | Ser | Pro | Cys | Ser | Asn | Gly |
| 385 | | | | | 390 | | | | | 395 | | | | | 400 |

Ala Lys Cys Val Asp Leu Gly Asp Ala Tyr Leu Cys Arg Cys Gln Ala
            405                 410                 415

Gly Phe Ser Gly Arg His Cys Asp Asp Asn Val Asp Cys Ala Ser
        420                 425                 430

Ser Pro Cys Ala Asn Gly Gly Thr Cys Arg Asp Gly Val Asn Asp Phe
        435                 440                 445

Ser Cys Thr Cys Pro Pro Gly Tyr Thr Gly Arg Asn Cys Ser Ala Pro
450                 455                 460

Val Ser Arg Cys Glu His Ala Pro Cys His Asn Gly Ala Thr Cys His
465                 470                 475                 480

Glu Arg Gly His Arg Tyr Val Cys Glu Cys Ala Arg Gly Tyr Gly Gly
                485                 490                 495

Pro Asn Cys Gln Phe Leu Leu Pro Glu Leu Pro Pro Gly Pro Ala Val
        500                 505                 510

Val Asp Leu Thr Glu Lys Leu Glu Gly Gln Gly Gly Pro Phe Pro Trp
        515                 520                 525

<210> SEQ ID NO 20
<211> LENGTH: 618
<212> TYPE: PRT
<213> ORGANISM: Homo sapiens

<400> SEQUENCE: 20

Met Val Ser Pro Arg Met Ser Gly Leu Leu Ser Gln Thr Val Ile Leu
1               5                   10                  15

Ala Leu Ile Phe Leu Pro Gln Thr Arg Pro Ala Gly Val Phe Glu Leu
            20                  25                  30

Gln Ile His Ser Phe Gly Pro Gly Pro Gly Pro Gly Ala Pro Arg Ser
        35                  40                  45

Pro Cys Ser Ala Arg Leu Pro Cys Arg Leu Phe Phe Arg Val Cys Leu
    50                  55                  60

Lys Pro Gly Leu Ser Glu Glu Ala Ala Glu Ser Pro Cys Ala Leu Gly
65                  70                  75                  80

Ala Ala Leu Ser Ala Arg Gly Pro Val Tyr Thr Glu Gln Pro Gly Ala
                85                  90                  95

Pro Ala Pro Asp Leu Pro Leu Pro Asp Gly Leu Leu Gln Val Pro Phe
            100                 105                 110

Arg Asp Ala Trp Pro Gly Thr Phe Ser Phe Ile Ile Glu Thr Trp Arg
        115                 120                 125

Glu Glu Leu Gly Asp Gln Ile Gly Gly Pro Ala Trp Ser Leu Leu Ala
    130                 135                 140

Arg Val Ala Gly Arg Arg Arg Leu Ala Ala Gly Gly Pro Trp Ala Arg
145                 150                 155                 160

Asp Ile Gln Arg Ala Gly Ala Trp Glu Leu Arg Phe Ser Tyr Arg Ala
                165                 170                 175

Arg Cys Glu Pro Pro Ala Val Gly Thr Ala Cys Thr Arg Leu Cys Arg
            180                 185                 190

Pro Arg Ser Ala Pro Ser Arg Cys Gly Pro Gly Leu Arg Pro Cys Ala
        195                 200                 205

Pro Leu Glu Asp Glu Cys Glu Ala Pro Leu Val Cys Arg Ala Gly Cys
    210                 215                 220

Ser Pro Glu His Gly Phe Cys Glu Gln Pro Gly Glu Cys Arg Cys Leu
225                 230                 235                 240

Glu Gly Trp Thr Gly Pro Leu Cys Thr Val Pro Val Ser Thr Ser Ser

```
                245                 250                 255
Cys Leu Ser Pro Arg Gly Pro Ser Ser Ala Thr Thr Gly Cys Leu Val
            260                 265                 270

Pro Gly Pro Gly Pro Cys Asp Gly Asn Pro Cys Ala Asn Gly Gly Ser
        275                 280                 285

Cys Ser Glu Thr Pro Arg Ser Phe Glu Cys Thr Cys Pro Arg Gly Phe
    290                 295                 300

Tyr Gly Leu Arg Cys Glu Val Ser Gly Val Thr Cys Ala Asp Gly Pro
305                 310                 315                 320

Cys Phe Asn Gly Gly Leu Cys Val Gly Ala Asp Pro Asp Ser Ala
            325                 330                 335

Tyr Ile Cys His Cys Pro Pro Gly Phe Gln Gly Ser Asn Cys Glu Lys
            340                 345                 350

Arg Val Asp Arg Cys Ser Leu Gln Pro Cys Arg Asn Gly Gly Leu Cys
            355                 360                 365

Leu Asp Leu Gly His Ala Leu Arg Cys Arg Cys Arg Ala Gly Phe Ala
370                 375                 380

Gly Pro Arg Cys Glu His Asp Leu Asp Asp Cys Ala Gly Arg Ala Cys
385                 390                 395                 400

Ala Asn Gly Gly Thr Cys Val Glu Gly Gly Ala His Arg Cys Ser
            405                 410                 415

Cys Ala Leu Gly Phe Gly Gly Arg Asp Cys Arg Glu Arg Ala Asp Pro
            420                 425                 430

Cys Ala Ala Arg Pro Cys Ala His Gly Gly Arg Cys Tyr Ala His Phe
            435                 440                 445

Ser Gly Leu Val Cys Ala Cys Ala Pro Gly Tyr Met Gly Ala Arg Cys
    450                 455                 460

Glu Phe Pro Val His Pro Asp Gly Ala Ser Ala Leu Pro Ala Ala Pro
465                 470                 475                 480

Pro Gly Leu Arg Pro Gly Asp Pro Gln Arg Tyr Leu Pro Pro Ala
            485                 490                 495

Leu Gly Leu Leu Val Ala Ala Gly Val Ala Gly Ala Ala Leu Leu Leu
                500                 505                 510

Val His Val Arg Arg Arg Gly His Ser Gln Asp Ala Gly Ser Arg Leu
        515                 520                 525

Leu Ala Gly Thr Pro Glu Pro Ser Val His Ala Leu Pro Asp Ala Leu
    530                 535                 540

Asn Asn Leu Arg Thr Gln Glu Gly Ser Gly Asp Gly Pro Ser Ser Ser
545                 550                 555                 560

Val Asp Trp Asn Arg Pro Glu Asp Val Asp Pro Gln Gly Ile Tyr Val
            565                 570                 575

Ile Ser Ala Pro Ser Ile Tyr Ala Arg Glu Val Ala Thr Pro Leu Phe
            580                 585                 590

Pro Pro Leu His Thr Gly Arg Ala Gly Gln Arg Gln His Leu Leu Phe
            595                 600                 605

Pro Tyr Pro Ser Ser Ile Leu Ser Val Lys
            610                 615

<210> SEQ ID NO 21
<211> LENGTH: 466
<212> TYPE: PRT
<213> ORGANISM: Homo sapiens

<400> SEQUENCE: 21
```

-continued

```
Ala Gly Val Phe Glu Leu Gln Ile His Ser Phe Gly Pro Gly Pro Gly
 1               5                  10                  15

Pro Gly Ala Pro Arg Ser Pro Cys Ser Ala Arg Leu Pro Cys Arg Leu
                20                  25                  30

Phe Phe Arg Val Cys Leu Lys Pro Gly Leu Ser Glu Glu Ala Ala Glu
            35                  40                  45

Ser Pro Cys Ala Leu Gly Ala Ala Leu Ser Ala Arg Gly Pro Val Tyr
        50                  55                  60

Thr Glu Gln Pro Gly Ala Pro Ala Pro Asp Leu Pro Leu Pro Asp Gly
 65                  70                  75                  80

Leu Leu Gln Val Pro Phe Arg Asp Ala Trp Pro Gly Thr Phe Ser Phe
                85                  90                  95

Ile Ile Glu Thr Trp Arg Glu Leu Gly Asp Gln Ile Gly Gly Pro
            100                 105                 110

Ala Trp Ser Leu Leu Ala Arg Val Ala Gly Arg Arg Leu Ala Ala
        115                 120                 125

Gly Gly Pro Trp Ala Arg Asp Ile Gln Arg Ala Gly Ala Trp Glu Leu
    130                 135                 140

Arg Phe Ser Tyr Arg Ala Arg Cys Glu Pro Pro Ala Val Gly Thr Ala
145                 150                 155                 160

Cys Thr Arg Leu Cys Arg Pro Arg Ser Ala Pro Ser Arg Cys Gly Pro
                165                 170                 175

Gly Leu Arg Pro Cys Ala Pro Leu Glu Asp Glu Cys Glu Ala Pro Leu
                180                 185                 190

Val Cys Arg Ala Gly Cys Ser Pro Glu His Gly Phe Cys Glu Gln Pro
                195                 200                 205

Gly Glu Cys Arg Cys Leu Glu Gly Trp Thr Gly Pro Leu Cys Thr Val
    210                 215                 220

Pro Val Ser Thr Ser Ser Cys Leu Ser Pro Arg Gly Pro Ser Ser Ala
225                 230                 235                 240

Thr Thr Gly Cys Leu Val Pro Gly Pro Gly Pro Cys Asp Gly Asn Pro
                245                 250                 255

Cys Ala Asn Gly Gly Ser Cys Ser Glu Thr Pro Arg Ser Phe Glu Cys
                260                 265                 270

Thr Cys Pro Arg Gly Phe Tyr Gly Leu Arg Cys Glu Val Ser Gly Val
                275                 280                 285

Thr Cys Ala Asp Gly Pro Cys Phe Asn Gly Gly Leu Cys Val Gly Gly
                290                 295                 300

Ala Asp Pro Asp Ser Ala Tyr Ile Cys His Cys Pro Pro Gly Phe Gln
305                 310                 315                 320

Gly Ser Asn Cys Glu Lys Arg Val Asp Arg Cys Ser Leu Gln Pro Cys
                325                 330                 335

Arg Asn Gly Gly Leu Cys Leu Asp Leu Gly His Ala Leu Arg Cys Arg
                340                 345                 350

Cys Arg Ala Gly Phe Ala Gly Pro Arg Cys Glu His Asp Leu Asp Asp
                355                 360                 365

Cys Ala Gly Arg Ala Cys Ala Asn Gly Gly Thr Cys Val Glu Gly Gly
                370                 375                 380

Gly Ala His Arg Cys Ser Cys Ala Leu Gly Phe Gly Gly Arg Asp Cys
385                 390                 395                 400

Arg Glu Arg Ala Asp Pro Cys Ala Ala Arg Pro Cys Ala His Gly Gly
                405                 410                 415

Arg Cys Tyr Ala His Phe Ser Gly Leu Val Cys Ala Cys Ala Pro Gly
```

```
                420         425           430
Tyr Met Gly Ala Arg Cys Glu Phe Pro Val His Pro Asp Gly Ala Ser
            435             440             445
Ala Leu Pro Ala Ala Pro Pro Gly Leu Arg Pro Gly Asp Pro Gln Arg
        450             455             460
Tyr Leu
465

<210> SEQ ID NO 22
<211> LENGTH: 685
<212> TYPE: PRT
<213> ORGANISM: Homo sapiens

<400> SEQUENCE: 22

Met Ala Ala Ser Arg Ser Ala Ser Gly Trp Ala Leu Leu Leu Leu
1               5                   10                  15
Val Ala Leu Trp Gln Gln Arg Ala Ala Gly Ser Gly Val Phe Gln Leu
                20                  25                  30
Gln Leu Gln Glu Phe Ile Asn Glu Arg Gly Val Leu Ala Ser Gly Arg
            35                  40                  45
Pro Cys Glu Pro Gly Cys Arg Thr Phe Arg Val Cys Leu Lys His
    50                  55                  60
Phe Gln Ala Val Val Ser Pro Gly Pro Cys Thr Phe Gly Thr Val Ser
65                  70                  75                  80
Thr Pro Val Leu Gly Thr Asn Ser Phe Ala Val Arg Asp Asp Ser Ser
                85                  90                  95
Gly Gly Gly Arg Asn Pro Leu Gln Leu Pro Phe Asn Phe Thr Trp Pro
            100                 105                 110
Gly Thr Phe Ser Leu Ile Ile Glu Ala Trp His Ala Pro Gly Asp Asp
        115                 120                 125
Leu Arg Pro Glu Ala Leu Pro Pro Asp Ala Leu Ile Ser Lys Ile Ala
    130                 135                 140
Ile Gln Gly Ser Leu Ala Val Gly Gln Asn Trp Leu Leu Asp Glu Gln
145                 150                 155                 160
Thr Ser Thr Leu Thr Arg Leu Arg Tyr Ser Tyr Arg Val Ile Cys Ser
                165                 170                 175
Asp Asn Tyr Tyr Gly Asp Asn Cys Ser Arg Leu Cys Lys Lys Arg Asn
            180                 185                 190
Asp His Phe Gly His Tyr Val Cys Gln Pro Asp Gly Asn Leu Ser Cys
        195                 200                 205
Leu Pro Gly Trp Thr Gly Glu Tyr Cys Gln Gln Pro Ile Cys Leu Ser
    210                 215                 220
Gly Cys His Glu Gln Asn Gly Tyr Cys Ser Lys Pro Ala Glu Cys Leu
225                 230                 235                 240
Cys Arg Pro Gly Trp Gln Gly Arg Leu Cys Asn Glu Cys Ile Pro His
                245                 250                 255
Asn Gly Cys Arg His Gly Thr Cys Ser Thr Pro Trp Gln Cys Thr Cys
            260                 265                 270
Asp Glu Gly Trp Gly Gly Leu Phe Cys Asp Gln Asp Leu Asn Tyr Cys
        275                 280                 285
Thr His His Ser Pro Cys Lys Asn Gly Ala Thr Cys Ser Asn Ser Gly
    290                 295                 300
Gln Arg Ser Tyr Thr Cys Thr Cys Arg Pro Gly Tyr Thr Gly Val Asp
305                 310                 315                 320
```

```
Cys Glu Leu Glu Leu Ser Glu Cys Asp Ser Asn Pro Cys Arg Asn Gly
            325                 330                 335

Gly Ser Cys Lys Asp Gln Glu Asp Gly Tyr His Cys Leu Cys Pro Pro
        340                 345                 350

Gly Tyr Tyr Gly Leu His Cys Glu His Ser Thr Leu Ser Cys Ala Asp
            355                 360                 365

Ser Pro Cys Phe Asn Gly Gly Ser Cys Arg Glu Arg Asn Gln Gly Ala
    370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Met Cys Arg Cys Arg Pro Gly Phe
            420                 425                 430

Thr Gly Thr Tyr Cys Glu Leu His Val Ser Asp Cys Ala Arg Asn Pro
        435                 440                 445

Cys Ala His Gly Gly Thr Cys His Asp Leu Glu Asn Gly Leu Met Cys
    450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly Leu Pro Pro Ser Phe Pro
        515                 520                 525

Trp Val Ala Val Ser Leu Gly Val Gly Leu Ala Val Leu Leu Val Leu
    530                 535                 540

Leu Gly Met Val Ala Val Ala Val Arg Gln Leu Arg Leu Arg Arg Pro
545                 550                 555                 560

Asp Asp Gly Ser Arg Glu Ala Met Asn Asn Leu Ser Asp Phe Gln Lys
                565                 570                 575

Asp Asn Leu Ile Pro Ala Ala Gln Leu Lys Asn Thr Asn Gln Lys Lys
            580                 585                 590

Glu Leu Glu Val Asp Cys Gly Leu Asp Lys Ser Asn Cys Gly Lys Gln
        595                 600                 605

Gln Asn His Thr Leu Asp Tyr Asn Leu Ala Pro Gly Pro Leu Gly Arg
    610                 615                 620

Gly Thr Met Pro Gly Lys Phe Pro His Ser Asp Lys Ser Leu Gly Glu
625                 630                 635                 640

Lys Ala Pro Leu Arg Leu His Ser Glu Lys Pro Glu Cys Arg Ile Ser
                645                 650                 655

Ala Ile Cys Ser Pro Arg Asp Ser Met Tyr Gln Ser Val Cys Leu Ile
            660                 665                 670

Ser Glu Glu Arg Asn Glu Cys Val Ile Ala Thr Glu Val
        675                 680                 685

<210> SEQ ID NO 23
<211> LENGTH: 503
<212> TYPE: PRT
<213> ORGANISM: Homo sapiens

<400> SEQUENCE: 23

Ser Gly Val Phe Gln Leu Gln Leu Gln Glu Phe Ile Asn Glu Arg Gly
1               5                   10                  15
```

Val Leu Ala Ser Gly Arg Pro Cys Glu Pro Gly Cys Arg Thr Phe Phe
            20                  25                  30

Arg Val Cys Leu Lys His Phe Gln Ala Val Val Ser Pro Gly Pro Cys
        35                  40                  45

Thr Phe Gly Thr Val Ser Thr Pro Val Leu Gly Thr Asn Ser Phe Ala
    50                  55                  60

Val Arg Asp Asp Ser Ser Gly Gly Arg Asn Pro Leu Gln Leu Pro
65                  70                  75                  80

Phe Asn Phe Thr Trp Pro Gly Thr Phe Ser Leu Ile Ile Glu Ala Trp
                85                  90                  95

His Ala Pro Gly Asp Asp Leu Arg Pro Glu Ala Leu Pro Pro Asp Ala
            100                 105                 110

Leu Ile Ser Lys Ile Ala Ile Gln Gly Ser Leu Ala Val Gly Gln Asn
        115                 120                 125

Trp Leu Leu Asp Glu Gln Thr Ser Thr Leu Thr Arg Leu Arg Tyr Ser
    130                 135                 140

Tyr Arg Val Ile Cys Ser Asp Asn Tyr Tyr Gly Asp Asn Cys Ser Arg
145                 150                 155                 160

Leu Cys Lys Lys Arg Asn Asp His Phe Gly His Tyr Val Cys Gln Pro
                165                 170                 175

Asp Gly Asn Leu Ser Cys Leu Pro Gly Trp Thr Gly Glu Tyr Cys Gln
            180                 185                 190

Gln Pro Ile Cys Leu Ser Gly Cys His Glu Gln Asn Gly Tyr Cys Ser
        195                 200                 205

Lys Pro Ala Glu Cys Leu Cys Arg Pro Gly Trp Gln Gly Arg Leu Cys
    210                 215                 220

Asn Glu Cys Ile Pro His Asn Gly Cys Arg His Gly Thr Cys Ser Thr
225                 230                 235                 240

Pro Trp Gln Cys Thr Cys Asp Glu Gly Trp Gly Gly Leu Phe Cys Asp
                245                 250                 255

Gln Asp Leu Asn Tyr Cys Thr His His Ser Pro Cys Lys Asn Gly Ala
            260                 265                 270

Thr Cys Ser Asn Ser Gly Gln Arg Ser Tyr Thr Cys Thr Cys Arg Pro
        275                 280                 285

Gly Tyr Thr Gly Val Asp Cys Glu Leu Glu Leu Ser Glu Cys Asp Ser
    290                 295                 300

Asn Pro Cys Arg Asn Gly Gly Ser Cys Lys Asp Gln Glu Asp Gly Tyr
305                 310                 315                 320

His Cys Leu Cys Pro Pro Gly Tyr Tyr Gly Leu His Cys Glu His Ser
                325                 330                 335

Thr Leu Ser Cys Ala Asp Ser Pro Cys Phe Asn Gly Gly Ser Cys Arg
            340                 345                 350

Glu Arg Asn Gln Gly Ala Asn Tyr Ala Cys Glu Cys Pro Pro Asn Phe
        355                 360                 365

Thr Gly Ser Asn Cys Glu Lys Lys Val Asp Arg Cys Thr Ser Asn Pro
    370                 375                 380

Cys Ala Asn Gly Gly Gln Cys Leu Asn Arg Gly Pro Ser Arg Met Cys
385                 390                 395                 400

Arg Cys Arg Pro Gly Phe Thr Gly Thr Tyr Cys Glu Leu His Val Ser
                405                 410                 415

Asp Cys Ala Arg Asn Pro Cys Ala His Gly Gly Thr Cys His Asp Leu
            420                 425                 430

```
Glu Asn Gly Leu Met Cys Thr Cys Pro Ala Gly Phe Ser Gly Arg Arg
            435                 440                 445

Cys Glu Val Arg Thr Ser Ile Asp Ala Cys Ala Ser Ser Pro Cys Phe
450                 455                 460

Asn Arg Ala Thr Cys Tyr Thr Asp Leu Ser Thr Asp Thr Phe Val Cys
465                 470                 475                 480

Asn Cys Pro Tyr Gly Phe Val Gly Ser Arg Cys Glu Phe Pro Val Gly
                485                 490                 495

Leu Pro Pro Ser Phe Pro Trp
            500

<210> SEQ ID NO 24
<211> LENGTH: 183
<212> TYPE: PRT
<213> ORGANISM: Homo sapiens

<400> SEQUENCE: 24

His Ser His Arg Asp Phe Gln Pro Val Leu His Leu Val Ala Leu Asn
1               5                   10                  15

Ser Pro Leu Ser Gly Gly Met Arg Gly Ile Arg Gly Ala Asp Phe Gln
            20                  25                  30

Cys Phe Gln Gln Ala Arg Ala Val Gly Leu Ala Gly Thr Phe Arg Ala
        35                  40                  45

Phe Leu Ser Ser Arg Leu Gln Asp Leu Tyr Ser Ile Val Arg Arg Ala
50                  55                  60

Asp Arg Ala Ala Val Pro Ile Val Asn Leu Lys Asp Glu Leu Leu Phe
65                  70                  75                  80

Pro Ser Trp Glu Ala Leu Phe Ser Gly Ser Glu Gly Pro Leu Lys Pro
                85                  90                  95

Gly Ala Arg Ile Phe Ser Phe Asp Gly Lys Asp Val Leu Arg His Pro
            100                 105                 110

Thr Trp Pro Gln Lys Ser Val Trp His Gly Ser Asp Pro Asn Gly Arg
        115                 120                 125

Arg Leu Thr Glu Ser Tyr Cys Glu Thr Trp Arg Thr Glu Ala Pro Ser
130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr Ala Ser Lys
            180

<210> SEQ ID NO 25
<211> LENGTH: 549
<212> TYPE: DNA
<213> ORGANISM: Homo sapiens

<400> SEQUENCE: 25
cacagccacc gcgacttcca gccggtgctc cacctggttg cgctcaacag cccccctgtca      60 ggcggcatgc ggggcatccg cggggccgac ttccagtgct tccagcaggc gcgggccgtg     120
gggctggcgg gcaccttccg cgccttcctg tcctcgcgcc tgcaggacct gtacagcatc     180
gtgcgccgtg ccgaccgcgc agccgtgccc atcgtcaacc tcaaggacga gctgctgttt     240
cccagctggg aggctctgtt ctcaggctct gagggtccgc tgaagcccgg ggcacgcatc     300
ttctcctttg acggcaagga cgtcctgagg caccccacct ggccccagaa gagcgtgtgg     360
```

```
catggctcgg accccaacgg gcgcaggctg accgagagct actgtgagac gtggcggacg    420
gaggctccct cggccacggg ccaggcctcc tcgctgctgg ggggcaggct cctggggcag    480
agtgccgcga gctgccatca cgcctacatc gtgctctgca ttgagaacag cttcatgact    540
gcctccaag                                                           549
```

<210> SEQ ID NO 26
<211> LENGTH: 259
<212> TYPE: PRT
<213> ORGANISM: Homo sapiens
<400> SEQUENCE: 26

```
Met Ser Glu Val Pro Val Ala Arg Val Trp Leu Val Leu Leu Leu Leu
1               5                   10                  15

Thr Val Gln Val Gly Val Thr Ala Gly Ala Pro Trp Gln Cys Ala Pro
            20                  25                  30

Cys Ser Ala Glu Lys Leu Ala Leu Cys Pro Pro Val Ser Ala Ser Cys
        35                  40                  45

Ser Glu Val Thr Arg Ser Ala Gly Cys Gly Cys Cys Pro Met Cys Ala
    50                  55                  60

Leu Pro Leu Gly Ala Ala Cys Gly Val Ala Thr Ala Arg Cys Ala Arg
65                  70                  75                  80

Gly Leu Ser Cys Arg Ala Leu Pro Gly Glu Gln Gln Pro Leu His Ala
                85                  90                  95

Leu Thr Arg Gly Gln Gly Ala Cys Val Gln Glu Ser Asp Ala Ser Ala
            100                 105                 110

Pro His Ala Ala Glu Ala Gly Ser Pro Glu Ser Pro Glu Ser Thr Glu
        115                 120                 125

Ile Thr Glu Glu Glu Leu Leu Asp Asn Phe His Leu Met Ala Pro Ser
    130                 135                 140

Glu Glu Asp His Ser Ile Leu Trp Asp Ala Ile Ser Thr Tyr Asp Gly
145                 150                 155                 160

Ser Lys Ala Leu His Val Thr Asn Ile Lys Lys Trp Lys Glu Pro Cys
                165                 170                 175

Arg Ile Glu Leu Tyr Arg Val Val Glu Ser Leu Ala Lys Ala Gln Glu
            180                 185                 190

Thr Ser Gly Glu Glu Ile Ser Lys Phe Tyr Leu Pro Asn Cys Asn Lys
        195                 200                 205

Asn Gly Phe Tyr His Ser Arg Gln Cys Glu Thr Ser Met Asp Gly Glu
    210                 215                 220

Ala Gly Leu Cys Trp Cys Val Tyr Pro Trp Asn Gly Lys Arg Ile Pro
225                 230                 235                 240

Gly Ser Pro Glu Ile Arg Gly Asp Pro Asn Cys Gln Ile Tyr Phe Asn
                245                 250                 255

Val Gln Asn
```

<210> SEQ ID NO 27
<211> LENGTH: 1660
<212> TYPE: DNA
<213> ORGANISM: Homo sapiens
<400> SEQUENCE: 27

```
ggtgcactag caaaacaaac ttattttgaa cactcagctc ctagcgtgcg gcgctgccaa     60
tcattaacct cctggtgcaa gtggcgcggc ctgtgccctt tataaggtgc gcgctgtgtc    120
cagcgagcat cggccaccgc catcccatcc agcgagcatc tgccgccgcg ccgccgccac    180
```

```
cctcccagag agcactggcc accgctccac catcacttgc ccagagtttg ggccaccgcc    240
cgccgccacc agcccagaga gcatcggccc ctgtctgctg ctcgcgcctg gagatgtcag    300
aggtccccgt tgctcgcgtc tggctggtac tgctcctgct gactgtccag gtcggcgtga    360
cagccggcgc tccgtggcag tgcgcgccct gctccgccga aagctcgcg ctctgcccgc     420 cggtgtccgc ctcgtgctcg gaggtcaccc ggtccgccgg ctgcggctgt tgcccgatgt    480
gcgccctgcc tctgggcgcc gcgtgcgcg tggcgactgc acgctgcgcc cggggactca     540
gttgccgcgc gctgccgggg gagcagcaac ctctgcacgc cctcacccgc ggccaaggcg    600
cctgcgtgca ggagtctgac gcctccgctc cccatgctgc agaggcaggg agccctgaaa    660
gcccagagag cacggagata actgaggagg agctcctgga taatttccat ctgatggccc    720
cttctgaaga ggatcattcc atcctttggg acgccatcag tacctatgat ggctcgaagg    780
ctctccatgt caccaacatc aaaaaatgga aggagccctg ccgaatagaa ctctacagag    840
tcgtagagag tttagccaag gcacaggaga tcaggaga agaaatttcc aaattttacc      900
tgccaaactg caacaagaat ggattttatc acagcagaca gtgtgagaca tccatggatg    960
gagaggcggg actctgctgg tgcgtctacc cttggaatgg gaagaggatc cctgggtctc    1020
cagagatcag gggagacccc aactgccaga tatattttaa tgtacaaaac tgaaaccaga    1080
tgaaataatg ttctgtcacg tgaaatattt aagtatatag tatatttata ctctagaaca    1140
tgcacattta tatatatatg tatatgtata tatatatagt aactactttt tatactccat    1200
acataacttg atatagaaag ctgtttattt attcactgta agtttatttt ttctacacag    1260
taaaaacttg tactatgtta ataacttgtc ctatgtcaat ttgtatatca tgaaacactt    1320
ctcatcatat tgtatgtaag taattgcatt tctgctcttc caaagctcct gcgtctgttt    1380
ttaaagagca tggaaaaata ctgcctagaa aatgcaaaat gaaataagag agagtagttt    1440
ttcagctagt ttgaaggagg acggttaact tgtatattcc accattcaca tttgatgtac    1500
atgtgtaggg aaagttaaaa gtgttgatta cataatcaaa gctacctgtg gtgatgttgc    1560
cacctgttaa aatgtacact ggatatgttg ttaaacacgt gtctataatg gaaacattta    1620
caataaatat tctgcatgga aatactgtta aaaaaaaaa                           1660
```

<210> SEQ ID NO 28
<211> LENGTH: 480
<212> TYPE: PRT
<213> ORGANISM: Homo sapiens

<400> SEQUENCE: 28

```
Met Gln Ile Pro Arg Ala Ala Leu Leu Pro Leu Leu Leu Leu Leu
1               5                   10                  15

Ala Ala Pro Ala Ser Ala Gln Leu Ser Arg Ala Gly Arg Ser Ala Pro
                20                  25                  30

Leu Ala Ala Gly Cys Pro Asp Arg Cys Glu Pro Ala Arg Cys Pro Pro
            35                  40                  45

Gln Pro Glu His Cys Glu Gly Gly Arg Ala Arg Asp Ala Cys Gly Cys
        50                  55                  60

Cys Glu Val Cys Gly Ala Pro Glu Gly Ala Cys Gly Leu Gln Glu
65                  70                  75                  80

Gly Pro Cys Gly Glu Gly Leu Gln Cys Val Val Pro Phe Gly Val Pro
                85                  90                  95

Ala Ser Ala Thr Val Arg Arg Arg Ala Gln Ala Gly Leu Cys Val Cys
                100                 105                 110
```

```
Ala Ser Ser Glu Pro Val Cys Gly Ser Asp Ala Asn Thr Tyr Ala Asn
        115                 120                 125

Leu Cys Gln Leu Arg Ala Ala Ser Arg Arg Ser Glu Arg Leu His Arg
    130                 135                 140

Pro Pro Val Ile Val Leu Gln Arg Gly Ala Cys Gly Gln Gly Gln Glu
145                 150                 155                 160

Asp Pro Asn Ser Leu Arg His Lys Tyr Asn Phe Ile Ala Asp Val Val
                165                 170                 175

Glu Lys Ile Ala Pro Ala Val Val His Ile Glu Leu Phe Arg Lys Leu
                180                 185                 190

Pro Phe Ser Lys Arg Glu Val Pro Val Ala Ser Gly Ser Gly Phe Ile
            195                 200                 205

Val Ser Glu Asp Gly Leu Ile Val Thr Asn Ala His Val Val Thr Asn
        210                 215                 220

Lys His Arg Val Lys Val Glu Leu Lys Asn Gly Ala Thr Tyr Glu Ala
225                 230                 235                 240

Lys Ile Lys Asp Val Asp Glu Lys Ala Asp Ile Ala Leu Ile Lys Ile
                245                 250                 255

Asp His Gln Gly Lys Leu Pro Val Leu Leu Gly Arg Ser Ser Glu
                260                 265                 270

Leu Arg Pro Gly Glu Phe Val Val Ala Ile Gly Ser Pro Phe Ser Leu
            275                 280                 285

Gln Asn Thr Val Thr Thr Gly Ile Val Ser Thr Thr Gln Arg Gly Gly
        290                 295                 300

Lys Glu Leu Gly Leu Arg Asn Ser Asp Met Asp Tyr Ile Gln Thr Asp
305                 310                 315                 320

Ala Ile Ile Asn Tyr Gly Asn Ser Gly Gly Pro Leu Val Asn Leu Asp
                325                 330                 335

Gly Glu Val Ile Gly Ile Asn Thr Leu Lys Val Thr Ala Gly Ile Ser
                340                 345                 350

Phe Ala Ile Pro Ser Asp Lys Ile Lys Lys Phe Leu Thr Glu Ser His
            355                 360                 365

Asp Arg Gln Ala Lys Gly Lys Ala Ile Thr Lys Lys Tyr Ile Gly
            370                 375                 380

Ile Arg Met Met Ser Leu Thr Ser Ser Lys Ala Lys Glu Leu Lys Asp
385                 390                 395                 400

Arg His Arg Asp Phe Pro Asp Val Ile Ser Gly Ala Tyr Ile Ile Glu
                405                 410                 415

Val Ile Pro Asp Thr Pro Ala Glu Ala Gly Leu Lys Glu Asn Asp
                420                 425                 430

Val Ile Ile Ser Ile Asn Gly Gln Ser Val Val Ser Ala Asn Asp Val
                435                 440                 445

Ser Asp Val Ile Lys Arg Glu Ser Thr Leu Asn Met Val Val Arg Arg
450                 455                 460

Gly Asn Glu Asp Ile Met Ile Thr Val Ile Pro Glu Glu Ile Asp Pro
465                 470                 475                 480

<210> SEQ ID NO 29
<211> LENGTH: 22
<212> TYPE: PRT
<213> ORGANISM: Artificial Sequence
<220> FEATURE:
<223> OTHER INFORMATION: positions 1-22 of (SEQ ID NO: 29) which
      correspond to the signal peptide
```

<400> SEQUENCE: 29

Met Gln Ile Pro Arg Ala Ala Leu Leu Pro Leu Leu Leu Leu Leu
1               5                   10                  15

Ala Ala Pro Ala Ser Ala
            20

<210> SEQ ID NO 30
<211> LENGTH: 161
<212> TYPE: PRT
<213> ORGANISM: Artificial Sequence
<220> FEATURE:
<223> OTHER INFORMATION: positions 204-364 (SEQ ID NO: 30) of SEQ ID NO:
      28 which correspond to a serine protease domain

<400> SEQUENCE: 30

Gly Ser Gly Phe Ile Val Ser Glu Asp Gly Leu Ile Val Thr Asn Ala
1               5                   10                  15

His Val Val Thr Asn Lys His Arg Val Lys Val Glu Leu Lys Asn Gly
            20                  25                  30

Ala Thr Tyr Glu Ala Lys Ile Lys Asp Val Asp Glu Lys Ala Asp Ile
        35                  40                  45

Ala Leu Ile Lys Ile Asp His Gln Gly Lys Leu Pro Val Leu Leu Leu
    50                  55                  60

Gly Arg Ser Ser Glu Leu Arg Pro Gly Glu Phe Val Val Ala Ile Gly
65                  70                  75                  80

Ser Pro Phe Ser Leu Gln Asn Thr Val Thr Thr Gly Ile Val Ser Thr
                85                  90                  95

Thr Gln Arg Gly Gly Lys Glu Leu Gly Leu Arg Asn Ser Asp Met Asp
            100                 105                 110

Tyr Ile Gln Thr Asp Ala Ile Ile Asn Tyr Gly Asn Ser Gly Gly Pro
        115                 120                 125

Leu Val Asn Leu Asp Gly Glu Val Ile Gly Ile Asn Thr Leu Lys Val
    130                 135                 140

Thr Ala Gly Ile Ser Phe Ala Ile Pro Ser Asp Lys Ile Lys Lys Phe
145                 150                 155                 160

Leu

<210> SEQ ID NO 31
<211> LENGTH: 2138
<212> TYPE: DNA
<213> ORGANISM: Homo sapiens

<400> SEQUENCE: 31
caatgggctg ggccgcgcgg ccgcgcgcac tcgcaccgc tgcccccgag gccctcctgc     60
actctccccg gcgccgctct ccggccctcg ccctgtccgc cgccaccgcc gccgccgcca    120
gagtcgccat gcagatcccg cgcgccgctc ttctcccgct gctgctgctg ctgctggcgg    180
cgcccgcctc ggcgcagctg tcccgggccg gccgctcggc gcctttggcc gccgggtgcc    240
cagaccgctg cgagccggcg cgctgcccgc cgcagccgga gcactgcgag ggcggccggg    300
cccgggacgc gtgcggctgc tgcgaggtgt gcggcgcgcc cgagggcgcc cgtgcggcc    360 tgcaggaggg cccgtgcggc gaggggctgc agtgcgtggt gccccttcggg gtgccagcct    420 cggccacggt gcggcggcgc gcgcaggccg gcctctgtgt gtgcgccagc agcgagccgg    480
tgtgcggcag cgacgccaac acctacgcca acctgtgcca gctgcgcgcc gccagccgcc    540
gctccgagag gctgcaccgg ccgccggtca tcgtcctgca gcgcggagcc tgcggccaag    600

```
ggcaggaaga tcccaacagt tgcgccata aatataactt tatcgcggac gtggtggaga      660
agatcgcccc tgccgtggtt catatcgaat tgtttcgcaa gcttccgttt tctaaacgag      720
aggtgccggt ggctagtggg tctgggttta ttgtgtcgga agatggactg atcgtgacaa      780
atgcccacgt ggtgaccaac aagcaccggg tcaaagttga gctgaagaac ggtgccactt      840
acgaagccaa aatcaaggat gtggatgaga aagcagacat cgcactcatc aaaattgacc      900
accagggcaa gctgcctgtc ctgctgcttg gccgctcctc agagctgcgg ccggagagt       960 tcgtggtcgc catcggaagc ccgttttccc ttcaaaacac agtcaccacc gggatcgtga     1020
gcaccaccca gcgaggcggc aaagagctgg ggctccgcaa ctcagacatg gactacatcc     1080
agaccgacgc catcatcaac tatggaaact cgggaggccc gttagtaaac ctggacggtg     1140
aagtgattgg aattaacact ttgaaagtga cagctggaat ctcctttgca atcccatctg     1200
ataagattaa aaagttcctc acggagtccc atgaccgaca ggccaaagga aaagccatca     1260
ccaagaagaa gtatattggt atccgaatga tgtcactcac gtccagcaaa gccaaagagc     1320
tgaaggaccg gcaccgggac ttcccagacg tgatctcagg agcgtatata attgaagtaa     1380
ttcctgatac cccagcagaa gctggtggtc tcaaggaaaa cgacgtcata atcagcatca     1440
atggacagtc cgtggtctcc gccaatgatg tcagcgacgt cattaaaagg gaaagcaccc     1500
tgaacatggt ggtccgcagg ggtaatgaag atatcatgat cacagtgatt cccgaagaaa     1560
ttgacccata ggcagaggca tgagctggac ttcatgtttc cctcaaagac tctcccgtgg     1620
atgacggatg aggactctgg gctgctggaa taggacactc aagacttttg actgccattt     1680
tgtttgttca gtggagactc cctggccaac agaatccttc ttgatagttt gcaggcaaaa     1740
caaatgtaat gttgcagatc cgcaggcaga agctctgccc ttctgtatcc tatgtatgca     1800
gtgtgctttt tcttgccagc ttgggccatt cttgcttaga cagtcagcat ttgtctcctc     1860
ctttaactga gtcatcatct tagtccaact aatgcagtcg atacaatgcg tagatagaag     1920
aagccccacg ggagccagga tgggactggt cgtgtttgtg cttttctcca agtcagcacc     1980
caaaggtcaa tgcacagaga ccccgggtgg gtgagcgctg gcttctcaaa cggccgaagt     2040
tgcctctttt aggaatctct ttggaattgg gagcacgatg actctgagtt tgagctatta     2100
aagtacttct tacacattgc aaaaaaaaaa aaaaaaaa                             2138
```

<210> SEQ ID NO 32
<211> LENGTH: 8089
<212> TYPE: DNA
<213> ORGANISM: Homo sapiens

<400> SEQUENCE: 32

```
gcggcgcgga ggctggcccg ggacgcgccc ggagcccagg gaaggaggga ggaggggagg       60
gtcgcggccg gccgccatgg ggccggggc ccgtggccgc cgccgccgcc gtcgcccgat      120
gtcgccgcca ccgccaccgc cacccgtgcg ggcgctgccc ctgctgctgc tgctagcggg      180
gccgggggct gcagccccc cttgcctgga cggaagcccg tgtgcaaatg gaggtcgttg      240
cacccagctg ccctcccggg aggctgcctg cctgtgcccg cctggctggg tgggtgagcg      300
gtgtcagctg gaggacccct gtcactcagg ccctgtgct ggccgtggtg tctgccagag      360
ttcagtggtg gctggcaccg cccgattctc atgccggtgc ccccgtggct tccgaggccc      420
tgactgctcc ctgccagatc cctgcctcag cagcccttgt gcccacggtg cccgctgctc      480 agtgggggccc gatggacgct tcctctgctc ctgcccacct ggctaccagg gccgcagctg      540
ccgaagcgac gtggatgagt gccgggtggg tgagccctgc cgccatggtg gcacctgcct      600
```

```
caacacacct ggctccttcc gctgccagtg tccagctggc tacacagggc cactatgtga    660
gaaccccgcg gtgccctgtg cacccctcac catgccgtaac gggggcacct gcaggcagag   720
tggcgacctc acttacgact gtgcctgtct tcctgggttt gagggtcaga attgtgaagt    780
gaacgtggac gactgtccag gacaccgatg tctcaatggg gggacatgcg tggatggcgt    840
caacacctat aactgccagt gccctcctga gtggacaggc cagttctgca cggaggacgt    900
ggatgagtgt cagctgcagc ccaacgcctg ccacaatggg ggtacctgct tcaacacgct    960
gggtggccac agctgcgtgt gtgtcaatgg ctggacaggc gagagctgca gtcagaatat   1020
cgatgactgt gccacagccg tgtgcttcca tggggccacc tgccatgacc gcgtggcttc   1080
tttctactgt gcctgcccca tgggcaagac tggcctcctg tgtcacctgg atgacgcctg   1140
tgtcagcaac ccctgccacg aggatgctat ctgtgacaca atccggtga acggccgggc    1200
catttgcacc tgtcctcccg gcttcacggg tggggcatgt gaccaggatg tggacgagtg   1260
ctctatcggc gccaaccccct gcgagcactt gggcaggtgc gtgaacacgc agggctcctt   1320
cctgtgccag tgcggtcgtg gctacactgg acctcgctgt gagaccgatg tcaacgagtg   1380
tctgtcgggg ccctgccgaa accaggccac gtgcctcgac cgcataggcc agttcacctg   1440
tatctgtatg gcaggcttca caggaaccta ttgcgaggtg acattgacg agtgtcagag    1500
tagcccctgt gtcaacggtg gggtctgcaa ggaccgagtc aatggcttca gctgcacctg   1560
cccctcgggc ttcagcggct ccacgtgtca gctggacgtg gacgaatgcg ccagcacgcc   1620
ctgcaggaat ggcgccaaat gcgtggacca gcccgatggc tacgagtgcc gctgtgccga   1680
gggctttgag ggcacgctgt gtgatcgcaa cgtggacgac tgctcccctg acccatgcca   1740
ccatggtcgc tgcgtggatg gcatcgccag cttctcatgt gcctgtgctc ctggctacac   1800
gggcacacgc tgcgagagcc aggtggacga atgccgcagc cagccctgcc gccatggcgg   1860
caaatgccta gacctggtgg acaagtacct ctgccgctgc ccttctggga ccacaggtgt   1920
gaactgcgaa gtgaacattg acgactgtgc cagcaacccc tgcacctttg gagtctgccg   1980
tgatggcatc aaccgctacg actgtgtctc ccaacctggc ttcacagggc ccctttgtaa   2040
cgtggagatc aatgagtgtg cttccagccc atgcggcgag gaggttcct gtgtggatgg    2100
ggaaaatggc ttccgctgcc tctgcccgcc tggctccttg ccccactct gcctcccccc    2160
gagccatccc tgtgcccatg agccctgcag tcacggcatc tgctatgatg cacctggcgg   2220
gttccgctgt gtgtgtgagc ctggctggag tggccccgc tgcagccaga gcctggcccg    2280
agacgcctgt gagtcccagc cgtgcagggc cggtgggaca tgcagcagcg atggaatggg   2340
tttccactgc acctgcccgc ctggtgtcca gggacgtcag tgtgaactcc tctcccctg    2400
cacccccgaac ccctgtgagc atgggggccg ctgcgagtct gccctggcc agctgcctgt   2460
ctgctcctgc ccccagggct ggcaaggccc acgatgccag caggatgtgg acgagtgtgc   2520
tggccccgca ccctgtggcc ctcatggtat ctgcaccaac ctggcaggga gtttcagctg   2580
cacctgccat ggagggtaca ctggcccttc ctgcgatcag acatcaatg actgtgaccc    2640
caacccatgc ctgaacggtg gctcgtgcca agacggcgtg ggctccttttt cctgctcctg   2700
cctccctggt ttcgccggcc cacgatgcgc ccgcgatgtg gatgagtgcc tgagcaaccc   2760
ctgcggcccg ggcacctgta ccgaccacgt ggcctccttc acctgcacct gccgccagg    2820
ctacggaggc ttccactgcg aacaggacct gcccgactgc agcccagct cctgcttcaa    2880
tggcgggacc tgtgtggacg gcgtgaactc gttcagctgc ctgtgccgtc ccggctacac   2940
```

```
aggagcccac tgccaacatg aggcagaccc ctgcctctcg cggccctgcc tacacgggggg    3000 cgtctgcagc gccgcccacc ctggcttccg ctgcacctgc ctcgagagct tcacgggccc    3060
gcagtgccag acgctggtgg attggtgcag ccgccagcct tgtcaaaacg ggggtcgctg    3120
cgtccagact ggggcctatt gcctttgtcc ccctggatgg agcggacgcc tctgtgacat    3180
ccgaagcttg ccctgcaggg aggccgcagc ccagatcggg gtgcggctgg agcagctgtg    3240
tcaggcgggt gggcagtgtg tggatgaaga cagctcccac tactgcgtgt gcccagaggg    3300
ccgtactggt agccactgtg agcaggaggt ggacccctgc ttggcccagc cctgccagca    3360
tggggggacc tgccgtggct atatggggggg ctacatgtgt gagtgtcttc ctggctacaa    3420
tggtgataac tgtgaggacg acgtggacga gtgtgcctcc cagccctgcc agcacggggg    3480
ttcatgcatt gacctcgtgg cccgctatct ctgctcctgt cccccaggaa cgctgggggt    3540
gctctgcgag attaatgagg atgactgcgg cccaggccca ccgctggact cagggccccg    3600
gtgcctacac aatggcacct gcgtggacct ggtgggtggt ttccgctgca cctgtccccc    3660
aggatacact ggtttgcgct gcgaggcaga catcaatgag tgtcgctcag gtgcctgcca    3720
cgcggcacac acccgggact gcctgcagga cccaggcgga ggtttccgtt gcctttgtca    3780
tgctggcttc tcaggtcctc gctgtcagac tgtcctgtct ccctgcgagt cccagccatg    3840
ccagcatgga ggccagtgcc gtcctagccc gggtcctggg ggtgggctga ccttcacctg    3900
tcactgtgcc cagccgttct gggggtccgcg ttgcgagcgg gtggcgcgct cctgccggga    3960
gctgcagtgc ccggtgggcg tcccatgcca gcagacgccc cgcgggccgc gctgcgcctg    4020 cccccccaggg ttgtcgggac cctcctgccg cagcttcccg gggtcgccgc cgggggccag    4080
caacgccagc tgcgcggccg cccccctgtct ccacggggggc tcctgccgcc ccgcgccgct    4140
cgcgcccttc ttccgctgcg cttgcgcgca gggctggacc gggccgcgct gcgaggcgcc    4200
cgccgcggca cccgaggtct cggaggagcc gcggtgcccg cgcgccgcct gccaggccaa    4260
gcgcggggac cagcgctgcg accgcgagtg caacagccca ggctgcggct gggacggcgg    4320
cgactgctcg ctgagcgtgg gcgacccctg gcggcaatgc gaggcgctgc agtgctggcg    4380
cctcttcaac aacagccgct gcgacccccgc ctgcagctcg cccgcctgcc tctacgacaa    4440
cttcgactgc cacgccggtg gccgcgagcg cacttgcaac ccggtgtacg agaagtactg    4500
cgccgaccac tttgccgacg gccgctgcga ccagggctgc aacacggagg agtgcggctg    4560
ggatgggctg gattgtgcca gcgaggtgcc ggccctgctg gcccgcggcg tgctggtgct    4620
cacagtgctg ctgccgccag aggagctact gcgttccagc gccgacttcc tgcagcggct    4680
cagcgccatc ctgcgcacct cgctgcgctt ccgcctggac gcgcacggcc aggccatggt    4740
cttcccttac caccggccta gtcctggctc cgaaccccgg gcccgtcggg agctggcccc    4800
cgaggtgatc ggctcggtag taatgctgga gattgacaac cggctctgcc tgcagtcgcc    4860
tgagaatgat cactgcttcc ccgatgccca gagcgccgct gactacctgg agcgttgtc    4920 agcggtggag cgcctggact tcccgtaccc actgcgggac gtgcgggggg agccgctgga    4980
gcctccagaa cccagcgtcc cgctgctgcc actgctagtg gcgggcgctg tcttgctgct    5040
ggtcattctc gtcctgggtg tcatggtggc ccggcgcaag cgcgagcaca gcaccctctg    5100
gttccctgag ggcttctcac tgcacaagga cgtggcctct ggtcacaagg gccggcggga    5160
acccgtgggc caggacgcgc tgggcatgaa gaacatggcc aagggtgaga gcctgatggg    5220 ggaggtggc acagactgga tggacacaga gtgcccagag gccaagcggc taaaggtaga    5280
ggagccaggc atgggggctg aggaggctgt ggattgccgt cagtggactc aacaccatct    5340
```

```
ggttgctgct gacatccgcg tggcaccagc catggcactg acaccaccac agggcgacgc   5400
agatgctgat ggcatggatg tcaatgtgcg tggcccagat ggcttcaccc cgctaatgct   5460
ggcttccttc tgtgggggg  ctctggagcc aatgccaact gaagaggatg aggcagatga   5520
cacatcagct agcatcatct ccgacctgat ctgccagggg gctcagcttg ggcacggac    5580
tgaccgtact ggcgagactg cttttgcacct ggctgcccgt tatgcccgtg ctgatgcagc  5640
caagcggctg ctggatgctg gggcagacac caatgcccag gaccactcag gccgcactcc   5700
cctgcacaca gctgtcacag ccgatgccca gggtgtcttc cagattctca tccgaaaccg   5760
ctctacagac ttggatgccc gcatggcaga tggctcaacg gcactgatcc tggcggcccg   5820
cctggcagta gagggcatgg tggaagagct catcgccagc catgctgatg tcaatgctgt   5880
ggatgagctt gggaaatcag ccttacactg ggctgcggct gtgaacaacg tggaagccac   5940
tttggccctg ctcaaaaatg gagccaataa ggacatgcag gatagcaagg aggagacccc   6000
cctattcctg gccgcccgcg agggcagcta tgaggctgcc aagctgctgt ggaccactt    6060
tgccaaccgt gagatcaccg accacctgga caggctgccg cgggacgtag cccaggagag   6120
actgcaccag gacatcgtgc gcttgctgga tcaacccagt gggccccgca gcccccccgg   6180
tccccacggc ctggggcctc tgctctgtcc tccagggccc ttcctccctg gcctcaaagc   6240
ggcacagtcg gggtccaaga agagcaggag gccccccggg aaggcgggc tggggccgca    6300
ggggccccgg gggcggggca agaagctgac gctggcctgc ccgggccccc tggctgacag   6360
ctcggtcacg ctgtcgcccg tggactcgct ggactcccg cggccttcg gtgggccccc     6420
tgcttcccct ggtggcttcc cccttgaggg gccctatgca gctgccactg ccactgcagt   6480
gtctctggca cagcttggtg gcccaggccg ggcgggtcta gggcgccagc ccctggagg    6540
atgtgtactc agcctgggcc tgctgaaccc tgtggctgtg cccctcgatt gggcccggct   6600
gcccccacct gcccctccag gcccctcgtt cctgctgcca ctggcgccgg accccagct    6660
gctcaaccca gggaccccg  tctccccgca ggagcggccc ccgccttacc tggcagtccc   6720
aggacatggc gaggagtacc cggcggctgg ggcacacagc agcccccaa aggcccgctt   6780
cctgcgggtt cccagtgagc acccttacct gaccccatcc cccgaatccc ctgagcactg   6840
ggccagcccc tcacctccct ccctctcaga ctggtccgaa tccacgccta gcccagccac   6900
tgccactggg gccatggcca ccaccactgg ggcactgcct gccagccac ttcccttgtc    6960
tgttcccagc tcccttgctc aggcccagac ccagctgggg cccagccgg aagttacccc    7020
caagaggcaa gtgttggcct gagacgctcg tcagttctta gatcttgggg gcctaaagag   7080
accccgtcc tgcctccttt ctttctctgt ctcttcctc cttttagtct tttcatcct      7140
cttctctttc caccaaccct cctgcatcct tgccttgcag cgtgaccgag ataggtcatc   7200
agcccagggc ttcagtcttc ctttatttat aatgggtggg ggctaccacc caccctctca   7260
gtcttgtgaa gagtctggga cctccttctt ccccacttct ctcttccctc attccttttct  7320
ctctccttct ggcctctcat ttccttacac tctgacatga atgaattatt attattttta  7380
tttttcttt  tttttttaca ttttgtatag aaacaaattc atttaaacaa acttattatt   7440
attatttttt acaaaatata tatatggaga tgctccctcc cctgtgaac  cccccagtgc   7500
ccccgtgggg ctgagtctgt gggcccattc ggccaagctg gattctgtgt acctagtaca   7560
caggcatgac tggatcccg  tgtaccgagt acacgaccca ggtatgtacc aagtaggcac   7620
ccttgggcgc acccactggg gccaggggtc ggggagtgt  tgggagcctc ctccccaccc   7680
```

```
cacctccctc acttcactgc attccagatg ggacatgttc catagccttg ctggggaagg    7740
gcccactgcc aactccctct gccccagccc caccccttggc catctccctt tgggaactag    7800
ggggctgctg gtgggaaatg ggagccaggg cagatgtatg cattcctttg tgtccctgta    7860
aatgtgggac tacaagaaga ggagctgcct gagtggtact ttctcttcct ggtaatcctc    7920
tggcccagcc tcatggcaga atagaggtat ttttaggcta tttttgtaat atggcttctg    7980
gtcaaaatcc ctgtgtagct gaattcccaa gccctgcatt gtacagcccc ccactcccct    8040
caccacctaa taaggaata gttaacactc aaaaaaaaaa aaaaaaaa                  8089
```

<210> SEQ ID NO 33
<211> LENGTH: 2321
<212> TYPE: PRT
<213> ORGANISM: Homo sapiens

<400> SEQUENCE: 33

```
Met Gly Pro Gly Ala Arg Gly Arg Arg Arg Arg Pro Met Ser
1               5                   10                  15

Pro Pro Pro Pro Pro Pro Val Arg Ala Leu Pro Leu Leu Leu Leu
                20                  25                  30

Leu Ala Gly Pro Ala Ala Ala Pro Pro Cys Leu Asp Gly Ser Pro
            35                  40                  45

Cys Ala Asn Gly Gly Arg Cys Thr Gln Leu Pro Ser Arg Glu Ala Ala
50                  55                  60

Cys Leu Cys Pro Pro Gly Trp Val Gly Glu Arg Cys Gln Leu Glu Asp
65                  70                  75                  80

Pro Cys His Ser Gly Pro Cys Ala Gly Arg Gly Val Cys Gln Ser Ser
                85                  90                  95

Val Val Ala Gly Thr Ala Arg Phe Ser Cys Arg Cys Pro Arg Gly Phe
            100                 105                 110

Arg Gly Pro Asp Cys Ser Leu Pro Asp Pro Cys Leu Ser Ser Pro Cys
        115                 120                 125

Ala His Gly Ala Arg Cys Ser Val Gly Pro Asp Gly Arg Phe Leu Cys
    130                 135                 140

Ser Cys Pro Pro Gly Tyr Gln Gly Arg Ser Cys Arg Ser Asp Val Asp
145                 150                 155                 160

Glu Cys Arg Val Gly Glu Pro Cys Arg His Gly Gly Thr Cys Leu Asn
                165                 170                 175

Thr Pro Gly Ser Phe Arg Cys Gln Cys Pro Ala Gly Tyr Thr Gly Pro
            180                 185                 190

Leu Cys Glu Asn Pro Ala Val Pro Cys Ala Pro Ser Pro Cys Arg Asn
        195                 200                 205

Gly Gly Thr Cys Arg Gln Ser Gly Asp Leu Thr Tyr Asp Cys Ala Cys
    210                 215                 220

Leu Pro Gly Phe Glu Gly Gln Asn Cys Glu Val Asn Val Asp Asp Cys
225                 230                 235                 240

Pro Gly His Arg Cys Leu Asn Gly Gly Thr Cys Val Asp Gly Val Asn
                245                 250                 255

Thr Tyr Asn Cys Gln Cys Pro Pro Glu Trp Thr Gly Gln Phe Cys Thr
            260                 265                 270

Glu Asp Val Asp Glu Cys Gln Leu Gln Pro Asn Ala Cys His Asn Gly
        275                 280                 285

Gly Thr Cys Phe Asn Thr Leu Gly Gly His Ser Cys Val Cys Val Asn
    290                 295                 300
```

```
Gly Trp Thr Gly Glu Ser Cys Ser Gln Asn Ile Asp Asp Cys Ala Thr
305                 310                 315                 320

Ala Val Cys Phe His Gly Ala Thr Cys His Asp Arg Val Ala Ser Phe
                325                 330                 335

Tyr Cys Ala Cys Pro Met Gly Lys Thr Gly Leu Leu Cys His Leu Asp
            340                 345                 350

Asp Ala Cys Val Ser Asn Pro Cys His Glu Asp Ala Ile Cys Asp Thr
        355                 360                 365

Asn Pro Val Asn Gly Arg Ala Ile Cys Thr Cys Pro Gly Phe Thr
370                 375                 380

Gly Gly Ala Cys Asp Gln Asp Val Asp Glu Cys Ser Ile Gly Ala Asn
385                 390                 395                 400

Pro Cys Glu His Leu Gly Arg Cys Val Asn Thr Gln Gly Ser Phe Leu
                405                 410                 415

Cys Gln Cys Gly Arg Gly Tyr Thr Gly Pro Arg Cys Glu Thr Asp Val
            420                 425                 430

Asn Glu Cys Leu Ser Gly Pro Cys Arg Asn Gln Ala Thr Cys Leu Asp
        435                 440                 445

Arg Ile Gly Gln Phe Thr Cys Ile Cys Met Ala Gly Phe Thr Gly Thr
450                 455                 460

Tyr Cys Glu Val Asp Ile Asp Glu Cys Gln Ser Ser Pro Cys Val Asn
465                 470                 475                 480

Gly Gly Val Cys Lys Asp Arg Val Asn Gly Phe Ser Cys Thr Cys Pro
                485                 490                 495

Ser Gly Phe Ser Gly Ser Thr Cys Gln Leu Asp Val Asp Glu Cys Ala
            500                 505                 510

Ser Thr Pro Cys Arg Asn Gly Ala Lys Cys Val Asp Gln Pro Asp Gly
        515                 520                 525

Tyr Glu Cys Arg Cys Ala Glu Gly Phe Glu Gly Thr Leu Cys Asp Arg
            530                 535                 540

Asn Val Asp Asp Cys Ser Pro Asp Pro Cys His His Gly Arg Cys Val
545                 550                 555                 560

Asp Gly Ile Ala Ser Phe Ser Cys Ala Cys Ala Pro Gly Tyr Thr Gly
                565                 570                 575

Thr Arg Cys Glu Ser Gln Val Asp Glu Cys Arg Ser Gln Pro Cys Arg
            580                 585                 590

His Gly Gly Lys Cys Leu Asp Leu Val Asp Lys Tyr Leu Cys Arg Cys
        595                 600                 605

Pro Ser Gly Thr Thr Gly Val Asn Cys Glu Val Asn Ile Asp Asp Cys
            610                 615                 620

Ala Ser Asn Pro Cys Thr Phe Gly Val Cys Arg Asp Gly Ile Asn Arg
625                 630                 635                 640

Tyr Asp Cys Val Cys Gln Pro Gly Phe Thr Gly Pro Leu Cys Asn Val
                645                 650                 655

Glu Ile Asn Glu Cys Ala Ser Ser Pro Cys Gly Glu Gly Gly Ser Cys
            660                 665                 670

Val Asp Gly Glu Asn Gly Phe Arg Cys Leu Cys Pro Pro Gly Ser Leu
        675                 680                 685

Pro Pro Leu Cys Leu Pro Pro Ser His Pro Cys Ala His Glu Pro Cys
            690                 695                 700

Ser His Gly Ile Cys Tyr Asp Ala Pro Gly Gly Phe Arg Cys Val Cys
705                 710                 715                 720

Glu Pro Gly Trp Ser Gly Pro Arg Cys Ser Gln Ser Leu Ala Arg Asp
```

```
            725                 730                 735
Ala Cys Glu Ser Gln Pro Cys Arg Ala Gly Gly Thr Cys Ser Ser Asp
                740                 745                 750
Gly Met Gly Phe His Cys Thr Cys Pro Pro Gly Val Gln Gly Arg Gln
                755                 760                 765
Cys Glu Leu Leu Ser Pro Cys Thr Pro Asn Pro Cys Glu His Gly Gly
            770                 775                 780
Arg Cys Glu Ser Ala Pro Gly Gln Leu Pro Val Cys Ser Cys Pro Gln
785                 790                 795                 800
Gly Trp Gln Gly Pro Arg Cys Gln Gln Asp Val Asp Glu Cys Ala Gly
                805                 810                 815
Pro Ala Pro Cys Gly Pro His Gly Ile Cys Thr Asn Leu Ala Gly Ser
                820                 825                 830
Phe Ser Cys Thr Cys His Gly Gly Tyr Thr Gly Pro Ser Cys Asp Gln
                835                 840                 845
Asp Ile Asn Asp Cys Asp Pro Asn Pro Cys Leu Asn Gly Gly Ser Cys
            850                 855                 860
Gln Asp Gly Val Gly Ser Phe Ser Cys Ser Cys Leu Pro Gly Phe Ala
865                 870                 875                 880
Gly Pro Arg Cys Ala Arg Asp Val Asp Glu Cys Leu Ser Asn Pro Cys
                885                 890                 895
Gly Pro Gly Thr Cys Thr Asp His Val Ala Ser Phe Thr Cys Thr Cys
                900                 905                 910
Pro Pro Gly Tyr Gly Gly Phe His Cys Glu Gln Asp Leu Pro Asp Cys
                915                 920                 925
Ser Pro Ser Ser Cys Phe Asn Gly Gly Thr Cys Val Asp Gly Val Asn
            930                 935                 940
Ser Phe Ser Cys Leu Cys Arg Pro Gly Tyr Thr Gly Ala His Cys Gln
945                 950                 955                 960
His Glu Ala Asp Pro Cys Leu Ser Arg Pro Cys Leu His Gly Gly Val
                965                 970                 975
Cys Ser Ala Ala His Pro Gly Phe Arg Cys Thr Cys Leu Glu Ser Phe
                980                 985                 990
Thr Gly Pro Gln Cys Gln Thr Leu Val Asp Trp Cys Ser Arg Gln Pro
            995                1000                1005
Cys Gln Asn Gly Gly Arg Cys Val Gln Thr Gly Ala Tyr Cys Leu
            1010                1015                1020
Cys Pro Pro Gly Trp Ser Gly Arg Leu Cys Asp Ile Arg Ser Leu
            1025                1030                1035
Pro Cys Arg Glu Ala Ala Ala Gln Ile Gly Val Arg Leu Glu Gln
            1040                1045                1050
Leu Cys Gln Ala Gly Gly Gln Cys Val Asp Glu Asp Ser Ser His
            1055                1060                1065
Tyr Cys Val Cys Pro Glu Gly Arg Thr Gly Ser His Cys Glu Gln
            1070                1075                1080
Glu Val Asp Pro Cys Leu Ala Gln Pro Cys Gln His Gly Gly Thr
            1085                1090                1095
Cys Arg Gly Tyr Met Gly Gly Tyr Met Cys Glu Cys Leu Pro Gly
            1100                1105                1110
Tyr Asn Gly Asp Asn Cys Glu Asp Asp Val Asp Glu Cys Ala Ser
            1115                1120                1125
Gln Pro Cys Gln His Gly Gly Ser Cys Ile Asp Leu Val Ala Arg
            1130                1135                1140
```

```
Tyr Leu Cys Ser Cys Pro Pro Gly Thr Leu Gly Val Leu Cys Glu
1145                1150                1155

Ile Asn Glu Asp Asp Cys Gly Pro Gly Pro Pro Leu Asp Ser Gly
1160                1165                1170

Pro Arg Cys Leu His Asn Gly Thr Cys Val Asp Leu Val Gly Gly
1175                1180                1185

Phe Arg Cys Thr Cys Pro Pro Gly Tyr Thr Gly Leu Arg Cys Glu
1190                1195                1200

Ala Asp Ile Asn Glu Cys Arg Ser Gly Ala Cys His Ala Ala His
1205                1210                1215

Thr Arg Asp Cys Leu Gln Asp Pro Gly Gly Gly Phe Arg Cys Leu
1220                1225                1230

Cys His Ala Gly Phe Ser Gly Pro Arg Cys Gln Thr Val Leu Ser
1235                1240                1245

Pro Cys Glu Ser Gln Pro Cys Gln His Gly Gly Gln Cys Arg Pro
1250                1255                1260

Ser Pro Gly Pro Gly Gly Gly Leu Thr Phe Thr Cys His Cys Ala
1265                1270                1275

Gln Pro Phe Trp Gly Pro Arg Cys Glu Arg Val Ala Arg Ser Cys
1280                1285                1290

Arg Glu Leu Gln Cys Pro Val Gly Val Pro Cys Gln Gln Thr Pro
1295                1300                1305

Arg Gly Pro Arg Cys Ala Cys Pro Pro Gly Leu Ser Gly Pro Ser
1310                1315                1320

Cys Arg Ser Phe Pro Gly Ser Pro Pro Gly Ala Ser Asn Ala Ser
1325                1330                1335

Cys Ala Ala Ala Pro Cys Leu His Gly Gly Ser Cys Arg Pro Ala
1340                1345                1350

Pro Leu Ala Pro Phe Phe Arg Cys Ala Cys Ala Gln Gly Trp Thr
1355                1360                1365

Gly Pro Arg Cys Glu Ala Pro Ala Ala Ala Pro Glu Val Ser Glu
1370                1375                1380

Glu Pro Arg Cys Pro Arg Ala Ala Cys Gln Ala Lys Arg Gly Asp
1385                1390                1395

Gln Arg Cys Asp Arg Glu Cys Asn Ser Pro Gly Cys Gly Trp Asp
1400                1405                1410

Gly Gly Asp Cys Ser Leu Ser Val Gly Asp Pro Trp Arg Gln Cys
1415                1420                1425

Glu Ala Leu Gln Cys Trp Arg Leu Phe Asn Asn Ser Arg Cys Asp
1430                1435                1440

Pro Ala Cys Ser Ser Pro Ala Cys Leu Tyr Asp Asn Phe Asp Cys
1445                1450                1455

His Ala Gly Gly Arg Glu Arg Thr Cys Asn Pro Val Tyr Glu Lys
1460                1465                1470

Tyr Cys Ala Asp His Phe Ala Asp Gly Arg Cys Asp Gln Gly Cys
1475                1480                1485

Asn Thr Glu Glu Cys Gly Trp Asp Gly Leu Asp Cys Ala Ser Glu
1490                1495                1500

Val Pro Ala Leu Leu Ala Arg Gly Val Leu Val Leu Thr Val Leu
1505                1510                1515

Leu Pro Pro Glu Glu Leu Leu Arg Ser Ser Ala Asp Phe Leu Gln
1520                1525                1530
```

```
Arg Leu Ser Ala Ile Leu Arg Thr Ser Leu Arg Phe Arg Leu Asp
    1535                1540                1545

Ala His Gly Gln Ala Met Val Phe Pro Tyr His Arg Pro Ser Pro
    1550                1555                1560

Gly Ser Glu Pro Arg Ala Arg Arg Glu Leu Ala Pro Glu Val Ile
    1565                1570                1575

Gly Ser Val Val Met Leu Glu Ile Asp Asn Arg Leu Cys Leu Gln
    1580                1585                1590

Ser Pro Glu Asn Asp His Cys Phe Pro Asp Ala Gln Ser Ala Ala
    1595                1600                1605

Asp Tyr Leu Gly Ala Leu Ser Ala Val Glu Arg Leu Asp Phe Pro
    1610                1615                1620

Tyr Pro Leu Arg Asp Val Arg Gly Glu Pro Leu Glu Pro Pro Glu
    1625                1630                1635

Pro Ser Val Pro Leu Leu Pro Leu Leu Val Ala Gly Ala Val Leu
    1640                1645                1650

Leu Leu Val Ile Leu Val Leu Gly Val Met Val Ala Arg Arg Lys
    1655                1660                1665

Arg Glu His Ser Thr Leu Trp Phe Pro Glu Gly Phe Ser Leu His
    1670                1675                1680

Lys Asp Val Ala Ser Gly His Lys Gly Arg Arg Glu Pro Val Gly
    1685                1690                1695

Gln Asp Ala Leu Gly Met Lys Asn Met Ala Lys Gly Glu Ser Leu
    1700                1705                1710

Met Gly Glu Val Ala Thr Asp Trp Met Asp Thr Glu Cys Pro Glu
    1715                1720                1725

Ala Lys Arg Leu Lys Val Glu Glu Pro Gly Met Gly Ala Glu Glu
    1730                1735                1740

Ala Val Asp Cys Arg Gln Trp Thr Gln His His Leu Val Ala Ala
    1745                1750                1755

Asp Ile Arg Val Ala Pro Ala Met Ala Leu Thr Pro Pro Gln Gly
    1760                1765                1770

Asp Ala Asp Ala Asp Gly Met Asp Val Asn Val Arg Gly Pro Asp
    1775                1780                1785

Gly Phe Thr Pro Leu Met Leu Ala Ser Phe Cys Gly Gly Ala Leu
    1790                1795                1800

Glu Pro Met Pro Thr Glu Glu Asp Glu Ala Asp Asp Thr Ser Ala
    1805                1810                1815

Ser Ile Ile Ser Asp Leu Ile Cys Gln Gly Ala Gln Leu Gly Ala
    1820                1825                1830

Arg Thr Asp Arg Thr Gly Glu Thr Ala Leu His Leu Ala Ala Arg
    1835                1840                1845

Tyr Ala Arg Ala Asp Ala Ala Lys Arg Leu Leu Asp Ala Gly Ala
    1850                1855                1860

Asp Thr Asn Ala Gln Asp His Ser Gly Arg Thr Pro Leu His Thr
    1865                1870                1875

Ala Val Thr Ala Asp Ala Gln Gly Val Phe Gln Ile Leu Ile Arg
    1880                1885                1890

Asn Arg Ser Thr Asp Leu Asp Ala Arg Met Ala Asp Gly Ser Thr
    1895                1900                1905

Ala Leu Ile Leu Ala Ala Arg Leu Ala Val Glu Gly Met Val Glu
    1910                1915                1920

Glu Leu Ile Ala Ser His Ala Asp Val Asn Ala Val Asp Glu Leu
```

```
            1925                1930                1935

Gly Lys Ser Ala Leu His Trp Ala Ala Ala Val Asn Asn Val Glu
        1940                1945                1950

Ala Thr Leu Ala Leu Leu Lys Asn Gly Ala Asn Lys Asp Met Gln
    1955                1960                1965

Asp Ser Lys Glu Glu Thr Pro Leu Phe Leu Ala Ala Arg Glu Gly
    1970                1975                1980

Ser Tyr Glu Ala Ala Lys Leu Leu Leu Asp His Phe Ala Asn Arg
    1985                1990                1995

Glu Ile Thr Asp His Leu Asp Arg Leu Pro Arg Asp Val Ala Gln
    2000                2005                2010

Glu Arg Leu His Gln Asp Ile Val Arg Leu Leu Asp Gln Pro Ser
    2015                2020                2025

Gly Pro Arg Ser Pro Pro Gly Pro His Gly Leu Gly Pro Leu Leu
    2030                2035                2040

Cys Pro Pro Gly Ala Phe Leu Pro Gly Leu Lys Ala Ala Gln Ser
    2045                2050                2055

Gly Ser Lys Lys Ser Arg Arg Pro Pro Gly Lys Ala Gly Leu Gly
    2060                2065                2070

Pro Gln Gly Pro Arg Gly Arg Gly Lys Lys Leu Thr Leu Ala Cys
    2075                2080                2085

Pro Gly Pro Leu Ala Asp Ser Ser Val Thr Leu Ser Pro Val Asp
    2090                2095                2100

Ser Leu Asp Ser Pro Arg Pro Phe Gly Gly Pro Pro Ala Ser Pro
    2105                2110                2115

Gly Gly Phe Pro Leu Glu Gly Pro Tyr Ala Ala Ala Thr Ala Thr
    2120                2125                2130

Ala Val Ser Leu Ala Gln Leu Gly Gly Pro Gly Arg Ala Gly Leu
    2135                2140                2145

Gly Arg Gln Pro Pro Gly Gly Cys Val Leu Ser Leu Gly Leu Leu
    2150                2155                2160

Asn Pro Val Ala Val Pro Leu Asp Trp Ala Arg Leu Pro Pro Pro
    2165                2170                2175

Ala Pro Pro Gly Pro Ser Phe Leu Leu Pro Leu Ala Pro Gly Pro
    2180                2185                2190

Gln Leu Leu Asn Pro Gly Thr Pro Val Ser Pro Gln Glu Arg Pro
    2195                2200                2205

Pro Pro Tyr Leu Ala Val Pro Gly His Gly Glu Glu Tyr Pro Val
    2210                2215                2220

Ala Gly Ala His Ser Ser Pro Pro Lys Ala Arg Phe Leu Arg Val
    2225                2230                2235

Pro Ser Glu His Pro Tyr Leu Thr Pro Ser Pro Glu Ser Pro Glu
    2240                2245                2250

His Trp Ala Ser Pro Ser Pro Pro Ser Leu Ser Asp Trp Ser Glu
    2255                2260                2265

Ser Thr Pro Ser Pro Ala Thr Ala Thr Gly Ala Met Ala Thr Thr
    2270                2275                2280

Thr Gly Ala Leu Pro Ala Gln Pro Leu Pro Leu Ser Val Pro Ser
    2285                2290                2295
```

```
-continued

Ser Leu Ala Gln Ala Gln Thr  Gln Leu Gly Pro Gln  Pro Glu Val
    2300            2305                 2310

Thr Pro Lys Arg Gln Val Leu  Ala
    2315            2320
```